United States Patent
Estrada et al.

(10) Patent No.: US 10,131,675 B2
(45) Date of Patent: Nov. 20, 2018

(54) TRICYCLIC DLK INHIBITORS AND USES THEREOF

(71) Applicant: Genentech, Inc., South San Francisco, CA (US)

(72) Inventors: Anthony Estrada, San Carlos, CA (US); Snahel Patel, Foster City, CA (US); Terry Kellar, Burlingame, CA (US); Malcolm Huestis, San Francisco, CA (US); Daniel Shore, San Francisco, CA (US); Michael Siu, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/699,095

(22) Filed: Sep. 8, 2017

(65) Prior Publication Data
US 2017/0369510 A1    Dec. 28, 2017

Related U.S. Application Data

(63) Continuation of application No. PCT/EP2016/054725, filed on Mar. 7, 2016.

(60) Provisional application No. 62/130,315, filed on Mar. 9, 2015.

(51) Int. Cl.
| | | |
|---|---|---|
| *C07D 498/14* | (2006.01) | |
| *C07D 491/14* | (2006.01) | |
| *C07D 519/00* | (2006.01) | |
| *A61K 31/5383* | (2006.01) | |
| *A61K 45/06* | (2006.01) | |
| *A61K 31/553* | (2006.01) | |

(52) U.S. Cl.
CPC ........ *C07D 498/14* (2013.01); *A61K 31/5383* (2013.01); *A61K 31/553* (2013.01); *A61K 45/06* (2013.01); *C07D 491/14* (2013.01); *C07D 519/00* (2013.01)

(58) Field of Classification Search
CPC .. C07D 498/14; C07D 519/00; C07D 491/14; A61K 31/5383; A61K 31/553; A61K 45/06
See application file for complete search history.

(56) References Cited

FOREIGN PATENT DOCUMENTS

| WO | 2012/082997 A1 | 6/2012 |
| WO | 2014/177524 A1 | 11/2014 |

OTHER PUBLICATIONS

Patel, S., "Selective Inhibitors of Dual Leucine Zipper Kinase (DLK, MAP3K12) with Activity in a Model of Alzheimer's Disease." Journal of medicinal chemistry 60.19 (2017): 8083-8102.*
Le Pichon, C. E., "Loss of dual leucine zipper kinase signaling is protective in animal models of neurodegenerative disease." Science translational medicine 9.403 (2017): eaag0394: 1-14.*

* cited by examiner

*Primary Examiner* — John M Mauro
(74) *Attorney, Agent, or Firm* — Jonathan Duffield

(57) ABSTRACT

The invention relates to compounds of formula (I) and salts thereof:

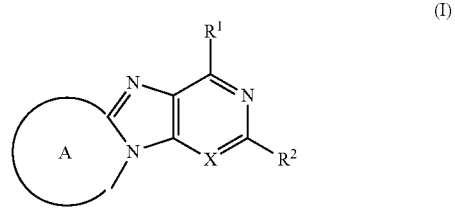

(I)

wherein ring A and $R^1$-$R^2$ have any of the values defined in the specification. The compounds and salts are useful for treating DLK mediated disorders. The invention also provides pharmaceutical compositions comprising a compound of formula (I), or a pharmaceutically acceptable salt thereof, as well as methods of using said compounds, salts, or compositions as DLK inhibitors and for treating neurodegeneration diseases and disorders.

34 Claims, No Drawings

TRICYCLIC DLK INHIBITORS AND USES THEREOF

RELATED APPLICATIONS

This application is a Continuation of International Application No. PCT/EP2016/054725, filed Mar. 7, 2016 claiming priority under 35 USC 119(e) to provisional application No. 62/130,315 filed Mar. 9, 2015, each of which are incorporated herein by reference in its entirety.

TECHNICAL FIELD OF THE INVENTION

The present invention relates to organic compounds useful for therapy and/or prophylaxis in a mammal, and in particular to inhibitors of dual leucine zipper-bearing kinase (DLK) useful for treating neurodegeneration diseases and disorders.

BACKGROUND OF THE INVENTION

Neuron or axon degeneration is a hallmark of many neurodegenerative diseases including for example, amyotrophic lateral sclerosis (ALS), glaucoma, Alzheimer's disease, and Parkinson's disease, as well as traumatic injury to the brain and spinal cord. Recent patent publication WO2011/050192, incorporated herein by reference, describes the role of the Dual Leucine Zipper Kinase (DLK), also referred to as MAP3K12, in neuronal cell death. Neurodegenerative diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age-related, and thus their incidence is increasing rapidly as population demographics change. There is a great need for the development of effective approaches for treating neurodegenerative diseases and nervous system injuries, including, for example, through the inhibitors of DLK in neurons.

SUMMARY OF THE INVENTION

One aspect includes a compound of formula (I), or a salt thereof:

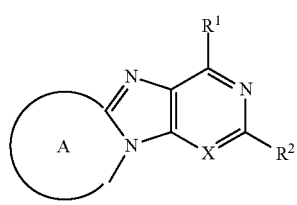

(I)

wherein:

A is a 6-10 membered heterocyclyl comprising one or more oxygen atoms, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-3}$alkenyl, $C_{2-6}$alkynyl, and $C_{3-6}$carbocyclyl;

X is N or CH;

$R^1$ is selected from the group consisting of hydrogen, —O—$R^d$, —N($R^d$)$_2$, a 3-12 membered carbocyclyl, and a 3-12 membered heterocyclyl, which 3-12 membered carbocyclyl and 3-12 membered heterocyclyl is optionally substituted with one or more groups independently selected from the group consisting of $C_{1-6}$alkyl, $C_{2-6}$alkenyl, $C_{2-6}$alkynyl, oxo, halo, —NO$_2$, —N($R^b$)$_2$, —CN, —C(O)—N($R^b$)$_2$, —O—$R^b$, —O—C(O)—$R^b$, —C(O)—$R^b$, —C(O)—O$R^b$, and —N($R^b$)—C(O)—$R^b$, wherein any $C_{1-6}$alkyl, $C_{2-6}$alkenyl, and $C_{2-6}$alkynyl, is optionally substituted with one or more groups independently selected from the group consisting of oxo, halo, —NO$_2$, —N($R^b$)$_2$, —CN, —C(O)—N($R^b$)$_2$, —O—$R^b$, —O—C(O)—$R^b$, —C(O)—$R^b$, —C(O)—O$R^b$, and —N($R^b$)—C(O)—$R^b$;

each $R^b$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl is optionally substituted with one or more groups independently selected from the group consisting of oxo, halo, —NO$_2$, —N($R^c$)$_2$, —CN, —C(O)—N($R^c$)$_2$, —O—$R^c$, —O—C(O)—$R^c$, —C(O)—$R^c$, —C(O)—O$R^c$, and —N($R^c$)—C(O)—$R^c$; or two $R^b$ are taken together with the nitrogen to which they are attached to form a 3-8 membered heterocyclyl that is optionally substituted with one or more groups independently selected from the group consisting of oxo, halo and $C_{1-3}$alkyl that is optionally substituted with one or more groups independently selected from the group consisting of oxo and halo;

each $R^c$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl is optionally substituted with one or more groups independently selected from the group consisting of oxo, halo, amino, hydroxy, $C_{1-6}$alkoxy, 3-12 membered carbocyclyl, 3-12 membered heterocyclyl, and $C_1$-$C_6$ alkyl that is optionally substituted with one or more groups independently selected from the group consisting of oxo and halo; or two $R^c$ are taken together with the nitrogen to which they are attached to form a 3-8 membered heterocyclyl that is optionally substituted with one or more groups independently selected from the group consisting of oxo, halo, and $C_{1-3}$alkyl that is optionally substituted with one or more groups independently selected from the group consisting of oxo and halo;

each $R^d$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl, is optionally substituted with one or more groups independently selected from the group consisting of oxo, halo, $C_{3-6}$carbocyclyl, —NO$_2$, —N($R^c$)$_2$, —CN, —C(O)—N($R^c$)$_2$, —O—$R^c$, —O—C(O)—$R^c$, —C(O)—$R^c$, —C(O)—O$R^c$, and —N($R^c$)—C(O)—$R^c$;

$R^2$ is a 3-12 membered heterocyclyl, which 3-12 membered heterocyclyl is optionally substituted with one or more groups independently selected from the group consisting of $C_{1-6}$alkyl, $C_{2-6}$alkenyl, $C_{2-6}$alkynyl, $C_{3-6}$carbocyclyl, oxo, halo, —NO$_2$, —N($R^e$)$_2$, —CN, —C(O)—N($R^e$)$_2$, —O—$R^e$, —O—C(O)—$R^e$, —C(O)—$R^e$, —C(O)—O$R^e$, and —N($R^e$)—C(O)—$R^e$, wherein any $C_{1-6}$alkyl, $C_{2-6}$alkenyl, $C_{3-6}$carbocyclyl, and $C_{2-6}$alkynyl, is optionally substituted with one or more groups independently selected from the group consisting of oxo, halo, —$NO_2$, —$N(R^e)_2$, —CN, —C(O)—$N(R^e)_2$, —O—$R^e$, —O—C(O)—$R^e$, —C(O)—$R^e$, —C(O)—$OR^e$, and —$N(R^e)$—C(O)—$R^e$;

each $R^e$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl is optionally substituted with one or more groups independently selected from the group consisting of oxo, halo, —$NO_2$, —$N(R^f)_2$, —CN, —C(O)—$N(R^f)_2$, —O—$R^f$, —O—C(O)—$R^f$, —C(O)—$R^f$, —C(O)—$OR^f$, —$N(R^f)$—C(O)—$R^f$, and $C_{3-6}$carbocyclyl that is optionally substituted with one or more groups independently selected from the group consisting of oxo, halo and $C_{1-3}$alkyl that is optionally substituted with one or more groups independently selected from the group consisting of oxo and halo; or two $R^e$ are taken together with the nitrogen to which they are attached to form a 3-8 membered heterocyclyl that is optionally substituted with one or more groups independently selected from the group consisting of oxo, halo and $C_{1-3}$alkyl that is optionally substituted with one or more groups independently selected from the group consisting of oxo and halo; and each $R^f$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl is optionally substituted with one or more groups independently selected from the group consisting of oxo, halo, amino, hydroxy, $C_{1-6}$alkoxy, 3-12 membered carbocyclyl, 3-12 membered heterocyclyl, and $C_1$-$C_6$ alkyl that is optionally substituted with one or more groups independently selected from the group consisting of oxo and halo; or two $R^f$ are taken together with the nitrogen to which they are attached to form a 3-8 membered heterocyclyl that is optionally substituted with one or more groups independently selected from the group consisting of oxo, halo and $C_{1-3}$alkyl that is optionally substituted with one or more groups independently selected from the group consisting of oxo and halo.

In another aspect the present invention provides for a pharmaceutical composition comprising a compound of formula (I) or any embodiment thereof and a pharmaceutically acceptable carrier, diluent or excipient.

In another aspect the present invention provides a method for inhibiting or preventing degeneration of a central nervous system (CNS) neuron or a portion thereof, the method comprising administering to the CNS neuron a compound of formula (I) or any embodiment thereof.

In another aspect the present invention provides a method for inhibiting or preventing degeneration of a central nervous system (CNS) neuron in a patient having or at risk of developing a neurodegenerative disease or condition comprising administering to said patient a therapeutically effective amount of a compound of formula (I) or any embodiment thereof, or a pharmaceutically acceptable salt thereof.

In another aspect the present invention provides a method for decreasing or preventing one or more symptoms of a neurodegenerative disease or condition in a patient suffering therefrom comprising administering to said patient a therapeutically effective amount of a compound of formula (I) or any embodiment thereof, or a pharmaceutically acceptable salt thereof.

In another aspect the present invention provides method for decreasing the progression of a neurodegenerative disease or condition in a patient suffering therefrom comprising administering to said patient a therapeutically effective amount of a compound of formula (I) or any embodiment thereof, or a pharmaceutically acceptable salt thereof.

In another aspect the present invention provides a compound of formula (I) or any embodiment thereof, or a pharmaceutically acceptable salt thereof for use in medical therapy.

In another aspect the present invention provides the use of a compound of formula (I) or any embodiment thereof, or a pharmaceutically acceptable salt thereof for the preparation of a medicament for inhibiting or preventing degeneration of a central nervous system (CNS) neuron in a patient having or at risk of developing a neurodegenerative disease or condition.

In another aspect the present invention provides use of a compound of formula (I) or any embodiment thereof, or a pharmaceutically acceptable salt thereof for the preparation of a medicament for decreasing or preventing one or more symptoms of a neurodegenerative disease or condition in a patient suffering therefrom.

In another aspect the present invention provides the use of a compound of formula (I) or any embodiment thereof, or a pharmaceutically acceptable salt thereof for the preparation of a medicament for decreasing the progression of a neurodegenerative disease or condition in a patient suffering therefrom.

In another aspect the present invention provides a compound of formula (I) or any embodiment thereof, or a pharmaceutically acceptable salt thereof for the therapeutic or prophylactic treatment of central nervous system (CNS) neuron degeneration.

In another aspect the present invention provides a compound of formula (I) or any embodiment thereof, or a pharmaceutically acceptable salt thereof for decreasing or preventing one or more symptoms of a neurodegenerative disease or condition in a patient suffering therefrom.

In another aspect the present invention provides a compound of formula (I) or any embodiment thereof, or a pharmaceutically acceptable salt thereof for decreasing the progression of a neurodegenerative disease or condition in a patient suffering therefrom.

In another aspect the present invention provides a compound of formula (I) or any embodiment thereof, or a pharmaceutically acceptable salt thereof for the therapeutic or prophylactic treatment of a neurodegenerative disease or condition.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula (I) include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula (I), wherein the independent replacement or enrichment of one or more hydrogen by deuterium or tritium, carbon by $^{13}$C- or $^{14}$C carbon, nitrogen by a $^{15}$N nitrogen, sulfur by a $^{33}$S, $^{34}$S or $^{36}$S sulfur, oxygen by a $^{17}$O or $^{18}$O oxygen, or fluorine by a $^{18}$F are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O.

The term "unsaturated", as used herein, means that a moiety has one or more units of unsaturation.

The term "carbocyclyl" used alone or as part of a larger moiety, refers to a saturated, partially unsaturated, or aromatic (e.g., aryl) ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocyclyl also includes cycloalkyl rings (e.g., saturated or partially unsaturated mono-, bi-, bridged-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{10}$, $C_1$-$C_5$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched radical represented by the formula —OR in which R is alkyl, alkenyl, alkynyl, heterocyclyl, or carbocyclyl. Alkoxy groups include, for example, methoxy, ethoxy, propoxy, isopropoxy, and cyclopropoxy.

The term "haloalkyl," as used herein, refers to an alkyl as defined herein that is substituted with one or more (e.g., 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted byone or more substituents described herein. A particular aryl is phenyl. In another embodiment aryl includes an aryl ring fused to one or more carbocyclic rings, such as indanyl, phthalimidyl, naphthimidyl, phenantriidinyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, pyrid-2-yl N-oxide, and pyrazolo[4,3-c]pyridinyl. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono-, bi- or tri-cyclic.

As used herein, the term "heterocyclyl" refers to a "carbocyclyl" as defined herein, wherein one or more (e.g., 1, 2, 3, or 4) carbon atoms have been replaced with a heteroatom (e.g., O, N, or S). In some embodiments, a heterocyclyl refers to a saturated ring system, such as a 3 to 12 membered saturated heterocyclyl ring system, or a 3 to 8 membered saturated heterocyclyl ring system. In some embodiments, a heterocyclyl refers to a 5 to 8 membered saturated heterocyclyl ring system. In some embodiments, a heterocyclyl refers to a 5 to 6 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein.

In one example, heterocyclyl includes 3-12 ring atoms and includes monocycles, bicycles, tricycles, bridged, and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxothiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazo[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5- triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "inhibitor" refers to a compound that binds to and inhibits DLK with measurable affinity and activity. In certain embodiments, an inhibitor has an $IC_{50}$ or binding constant of less about 20 µM, less than about 1 µM, less than about 500 nM, less than about 100 nM, or less than about 10 nM.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated. The identification of a specific salt of a compound of formula (I) herein is in no way limiting. The invention provides compounds of formula (I) as well as all salts thereof.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some embodiments, a therapeutically effective amount is an amount of a chemical entity described herein sufficient to significantly decrease or delay neuronal cell death.

The term "administering" as used herein includes contacting a neuron or portion thereof with a compound described herein. This includes administration of the compound to a subject in which the neuron or portion thereof is present, as well as introducing the inhibitor into a medium in which a neuron or portion thereof is cultured.

The term "patient" as used herein refers to any mammal, including humans, higher non-human primates, rodents, domestic and farm animals such as cow, horses, dogs and cats. In one embodiment, the patient is a human patient.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The phrases "preventing axon degeneration," "preventing neuron degeneration," "preventing CNS neuron degeneration," "inhibiting axon degeneration," "inhibiting neuron degeneration" and "inhibiting CNS neuron degeneration" as used herein include (i) the ability to inhibit or preserve axon or neuron degeration in patients diagnosed as having a neurodegenerative disease or risk of developing a neurodegenerative disease and (ii) the ability to inhibit or prevent further axon or neuron degeneration in patients who are already suffering from, or have symptoms of, a neurodegenerative disease. Preventing axon or neuron degeneration includes decreasing or inhibiting axon or neuron degeneration, which may be characterized by complete or partial inhibition or neuron or axon degeneration. This can be assessed, for example, by analysis of neurological function. The above-listed terms also include in vitro and ex vivo methods. Further, the phrases "preventing neuron degeneration" and "inhibiting neuron degeneration" include such inhibition with respect to the entire neuron or a portion thereof, such as the neuron cell body, axons and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease) in one or more symptoms of a disorder of the nervous system, a condition of the nervous system that is secondary to a disease, condition, or therapy having a primary effect outside of the nervous system; an injury to the nervous system caused by physical, mechanical or chemical trauma, pain; and ocular-related neurodegeneration; memory loss; or a psychiatric disorder (e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more compounds described herein.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the invention include cerebellar granule neurons, dorsal root ganglion neurons, and cortical neurons.

As used herein, "a" or "an" means one or more, unless clearly indicated otherwise. As used herein, "another" means at least a second or more.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

Should there be any discrepancy between a structure and its chemical name, the structure prevails.

Exemplary Values

In one embodiment the compound of formula (I) is selected from the group consisting of:

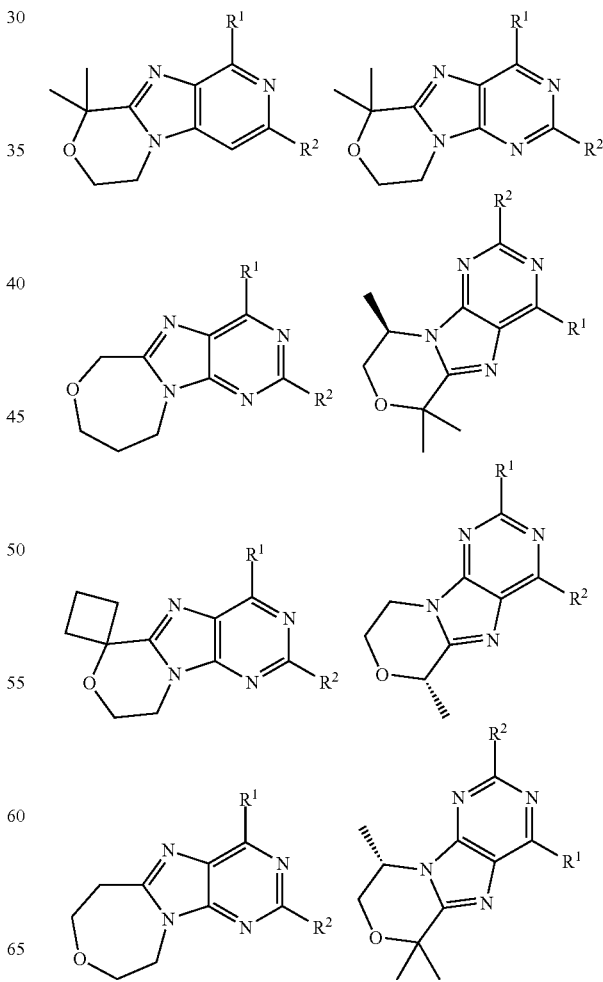

-continued
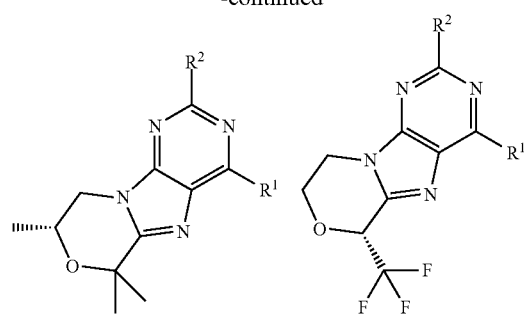
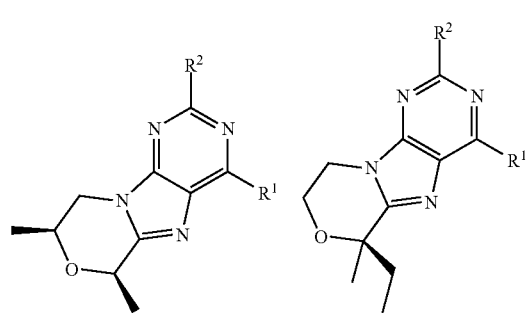
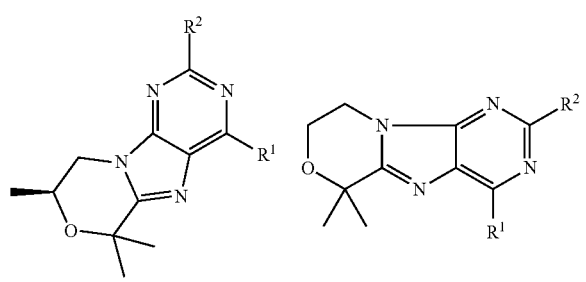
-continued
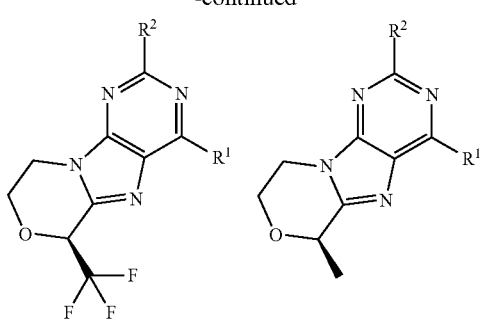
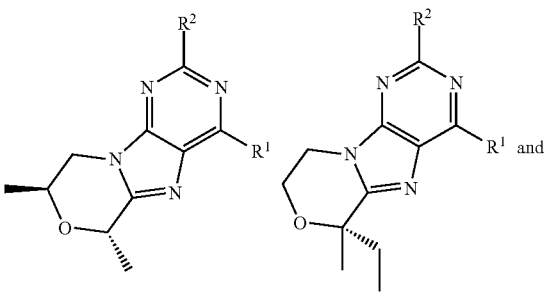
In one embodiment R¹ is selected from the group consisting of:
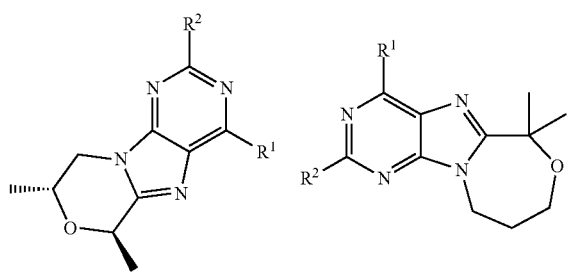
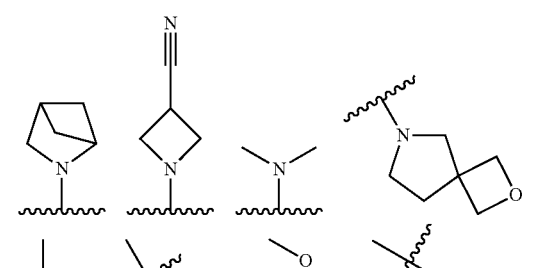
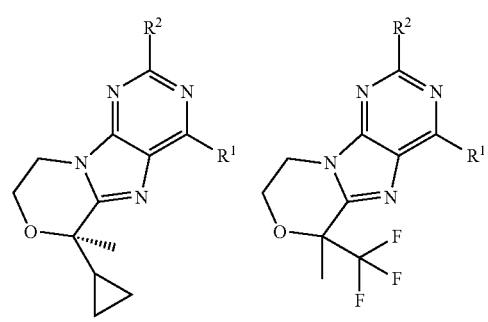
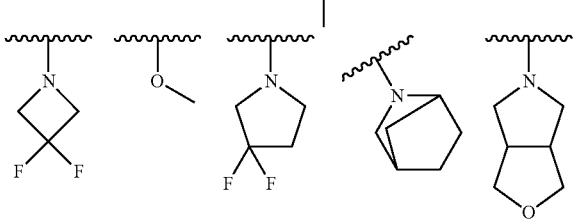

-continued
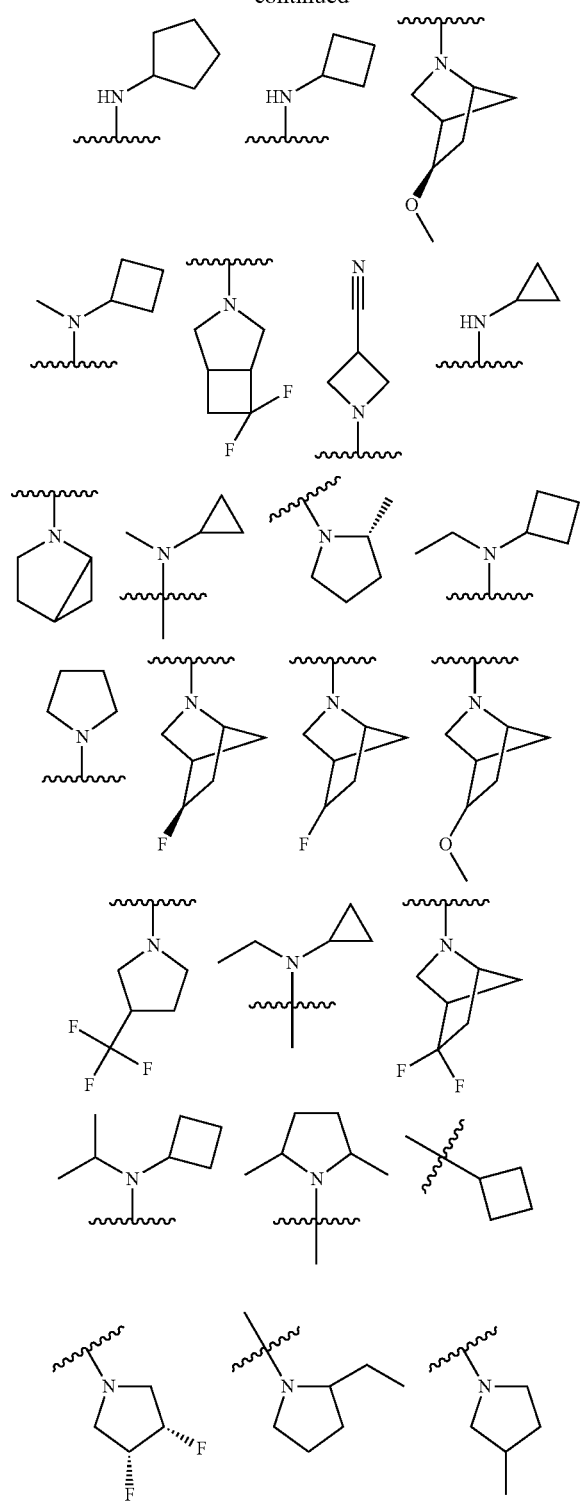
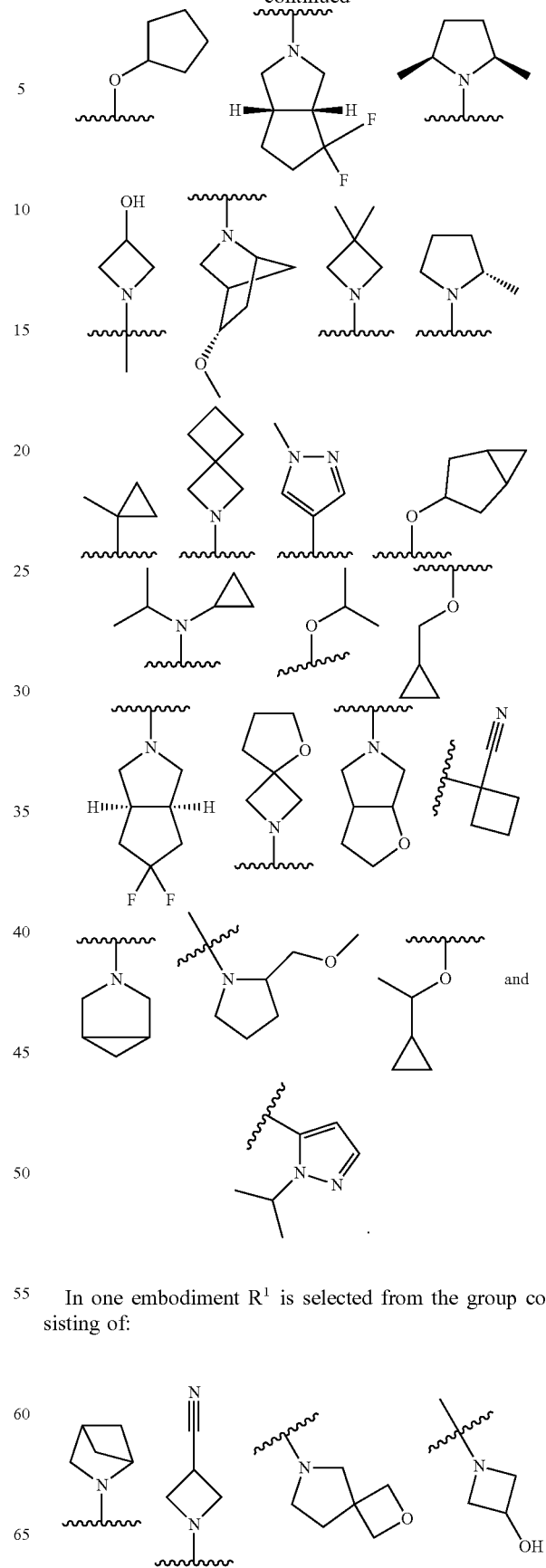
In one embodiment $R^1$ is selected from the group consisting of:

-continued
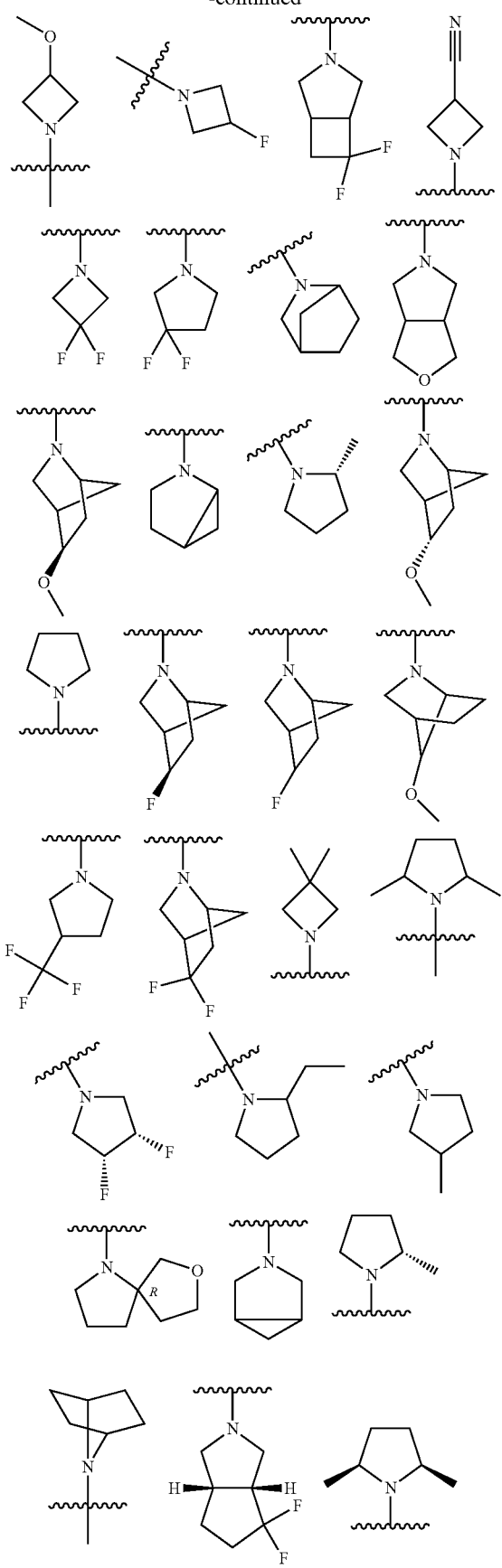
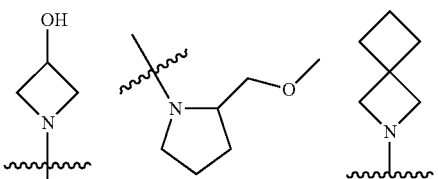
In one embodiment R¹ is selected from the group consisting of:
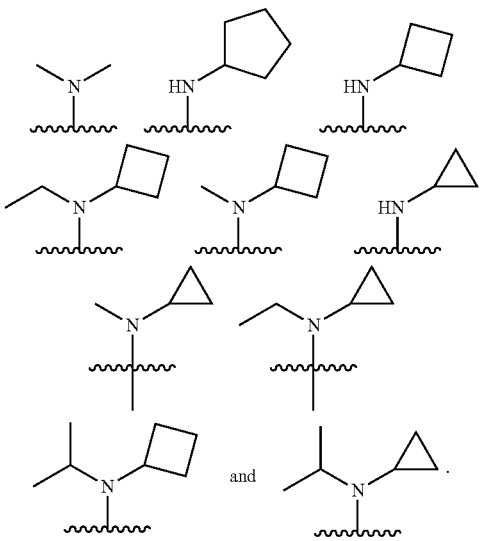
In one embodiment R¹ is selected from the group consisting of:
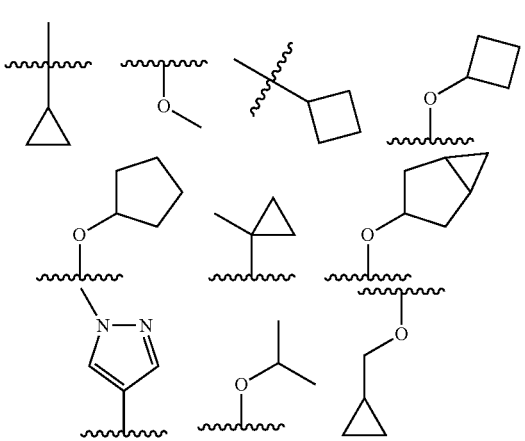

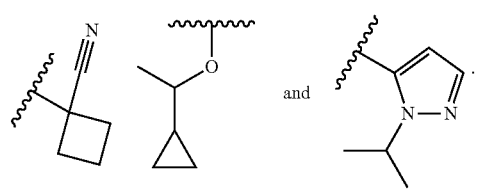
In one embodiment R² is selected from the group consisting of:
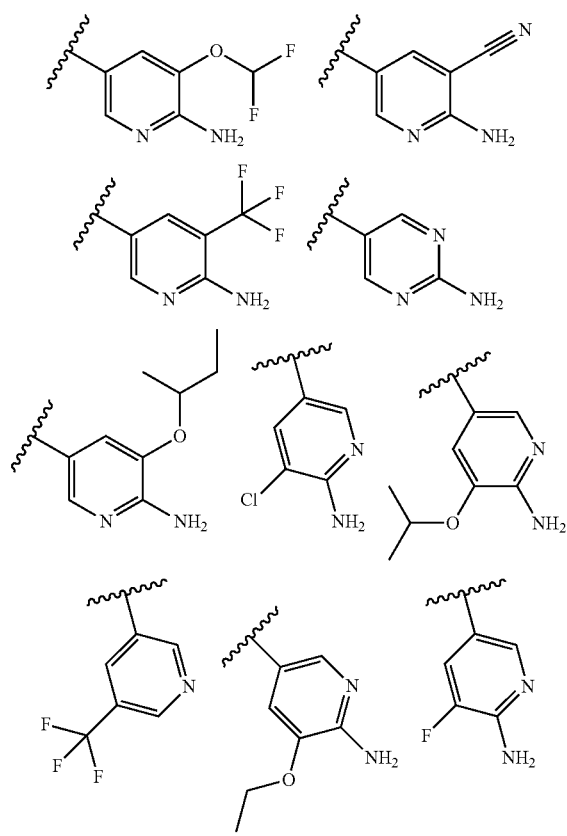
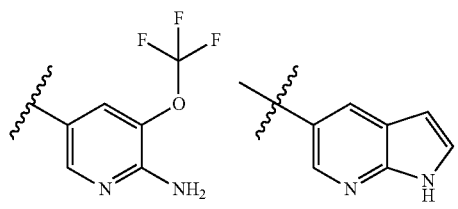
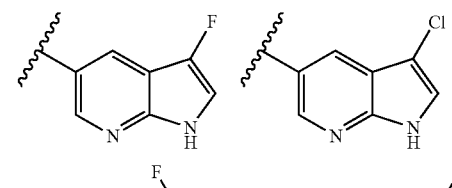
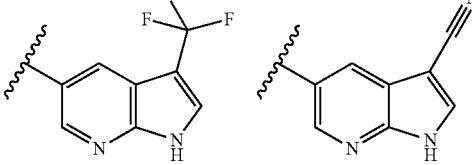
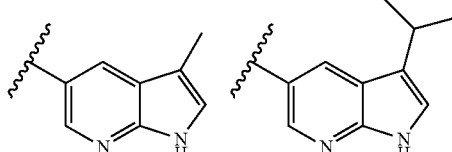
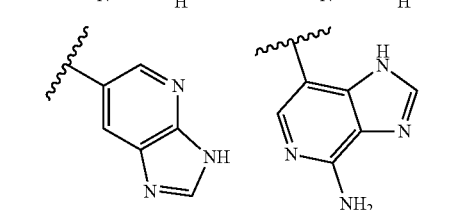
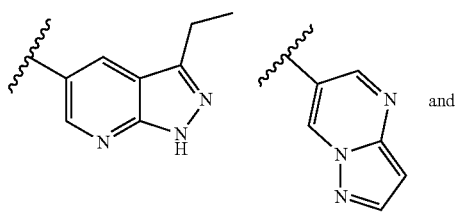
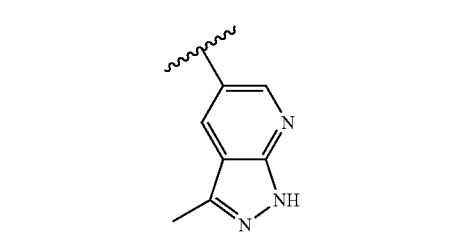
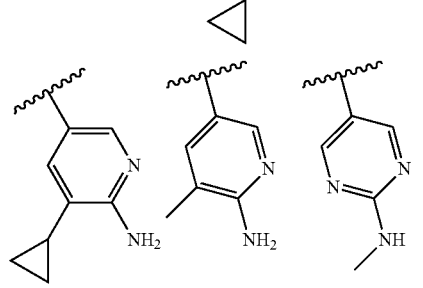
In one embodiment R² is selected from the group consisting of:
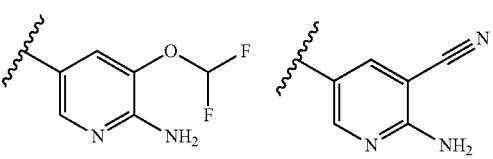

-continued
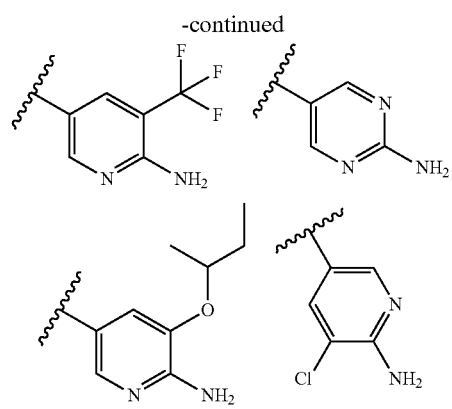
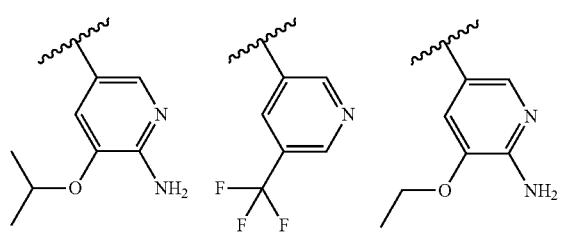
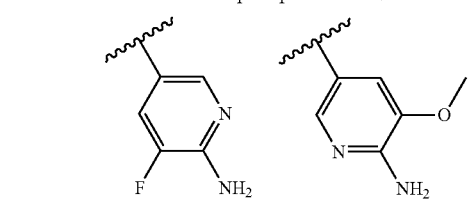
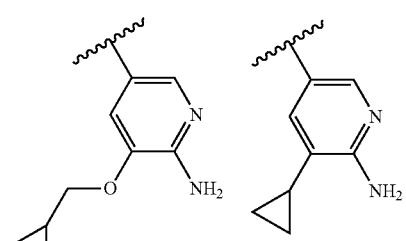
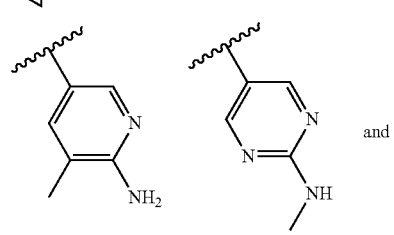
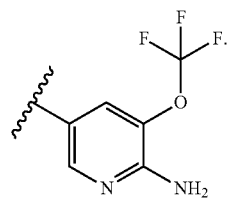
In one embodiment R² is selected from the group consisting of:
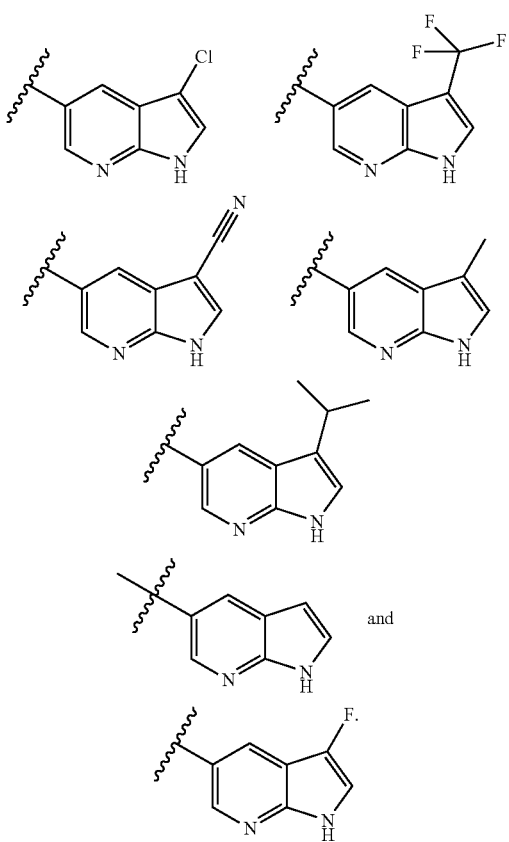
In one embodiment R² is selected from the group consisting of:
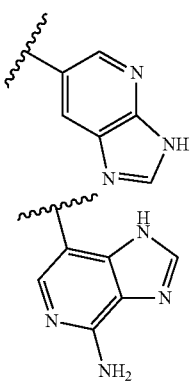
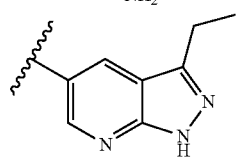
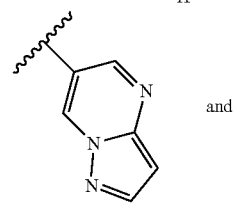

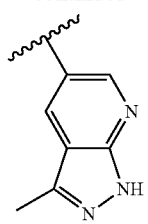

In one embodiment A is a 6-, 7-, or 8-membered heterocyclyl comprising one oxygen atom, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-6}$alkenyl, $C_{2-6}$alkynyl, and $C_{3-6}$carbocyclyl.

In one embodiment A is a 6-membered heterocyclyl comprising one oxygen atom, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-6}$alkenyl, $C_{2-6}$alkynyl, and $C_{3-6}$carbocyclyl.

In one embodiment A is a 7-membered heterocyclyl comprising one oxygen atom, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-6}$alkenyl, $C_{2-6}$alkynyl, and $C_{3-6}$carbocyclyl.

In one embodiment the compound is selected from the group consisting of:

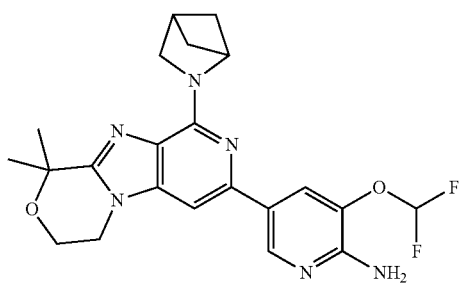

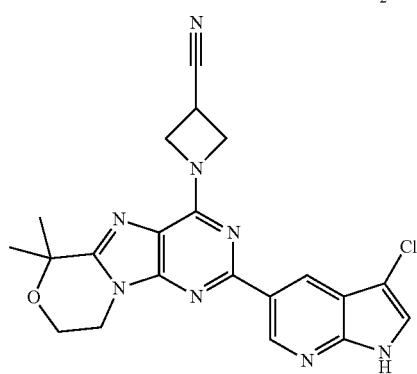

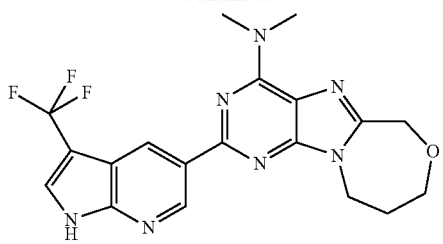

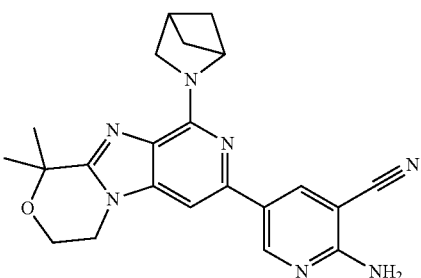

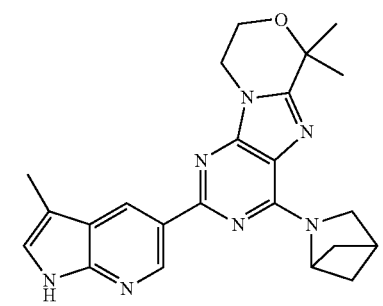

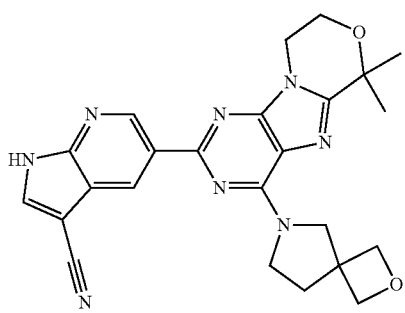

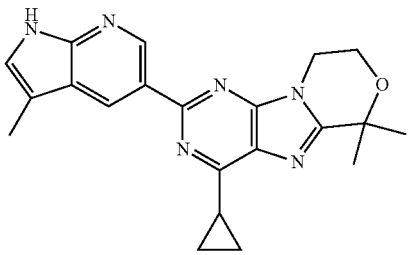

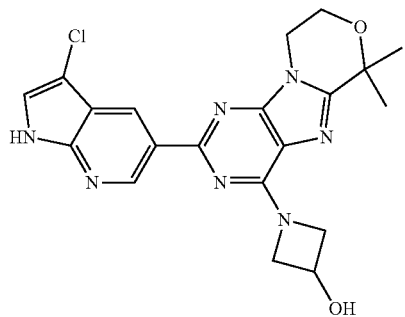

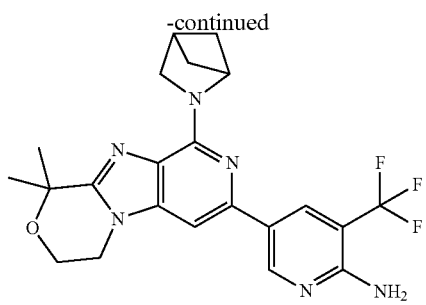
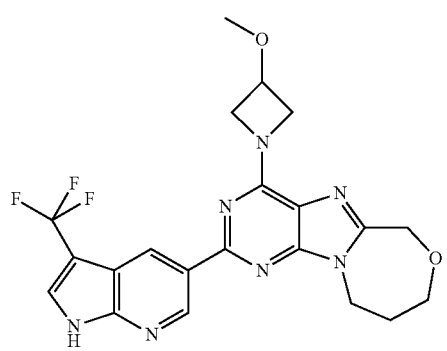
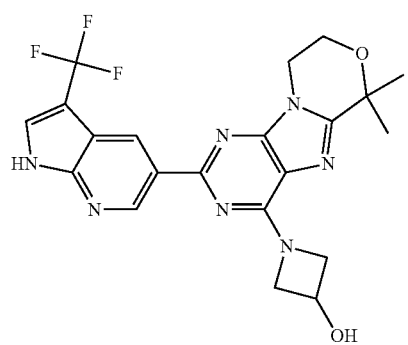
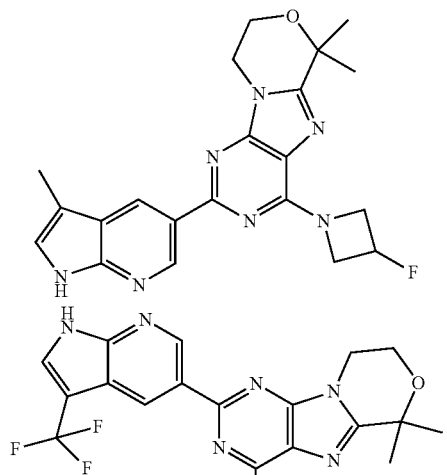
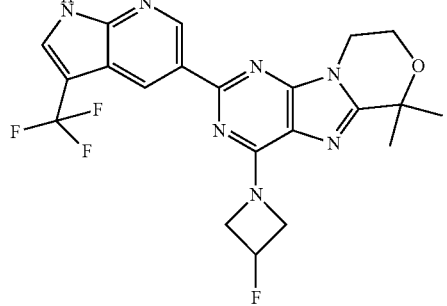
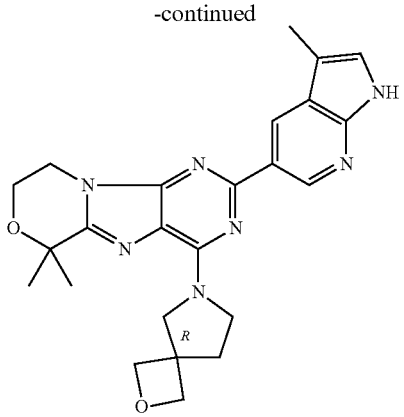
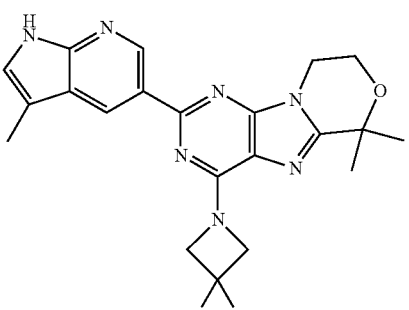
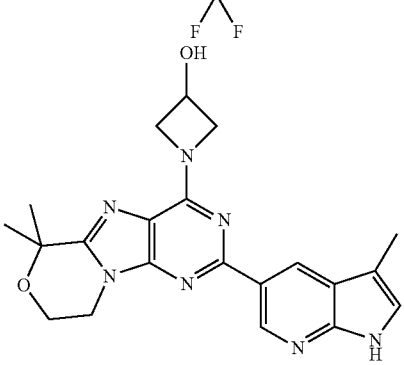
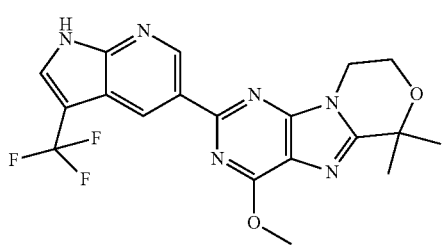
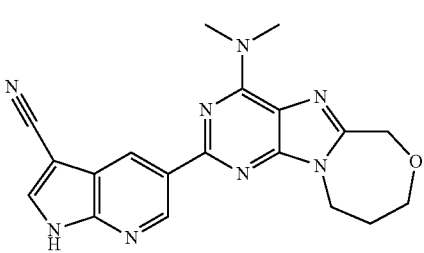

-continued
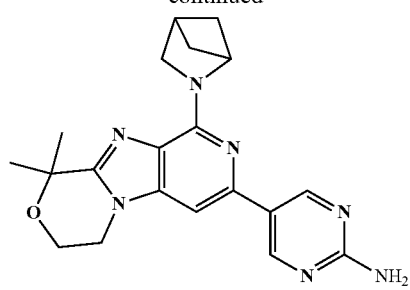
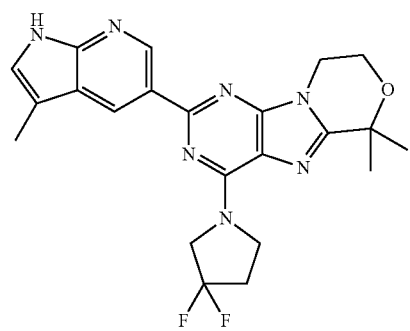
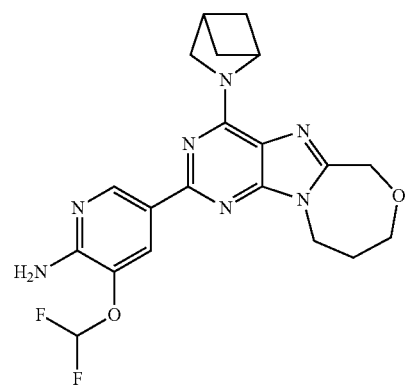
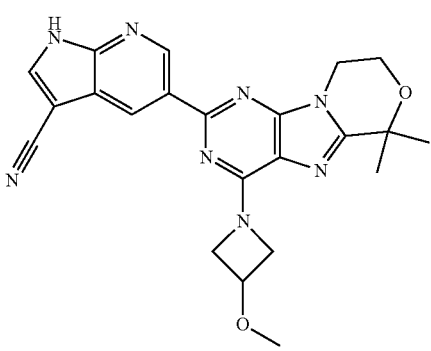
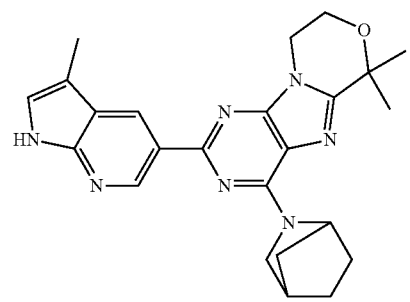
-continued
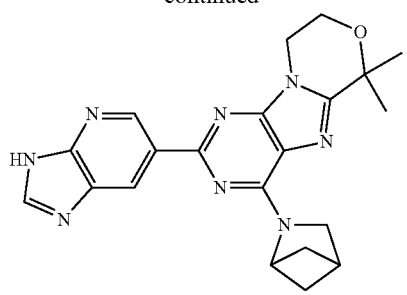
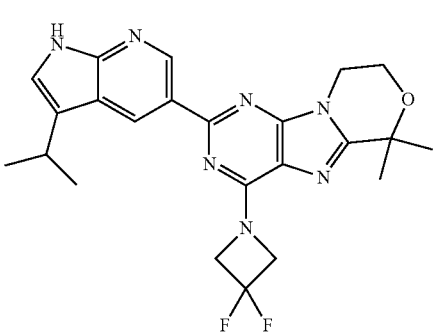
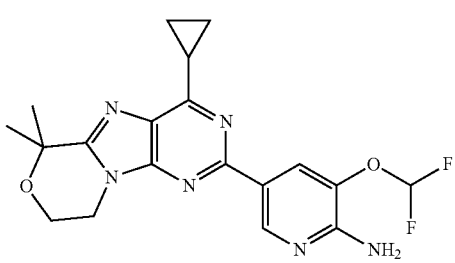
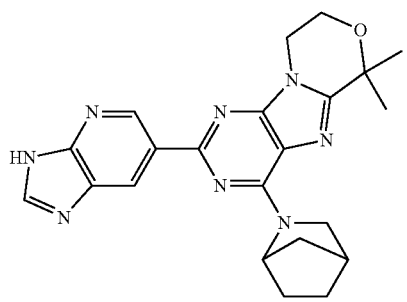
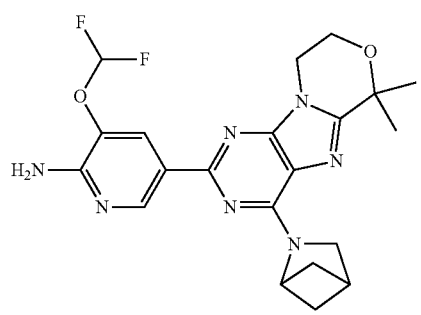

29
-continued
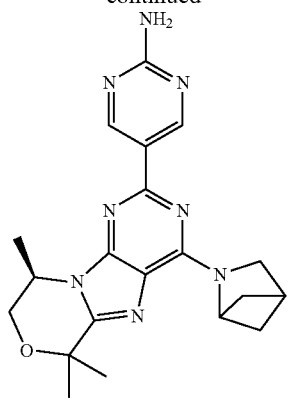
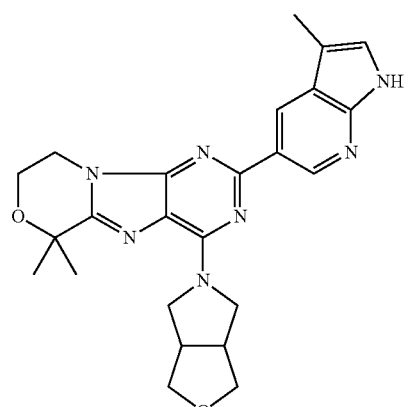
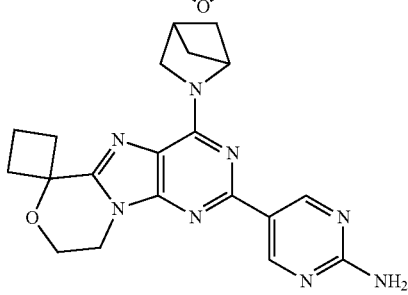
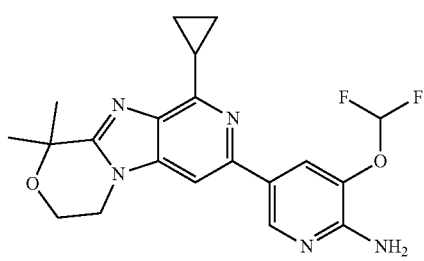
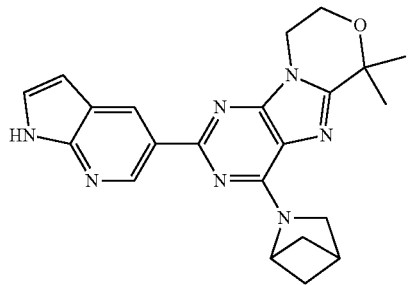
30
-continued
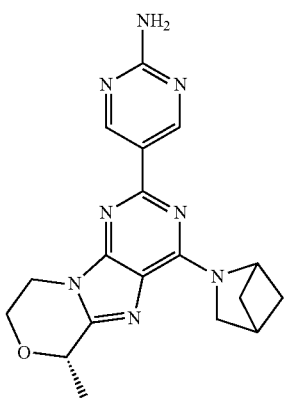
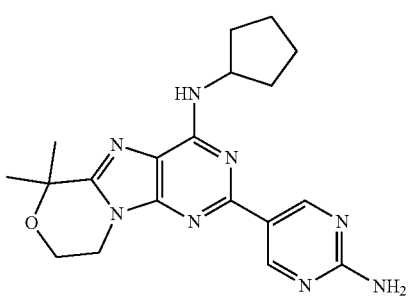
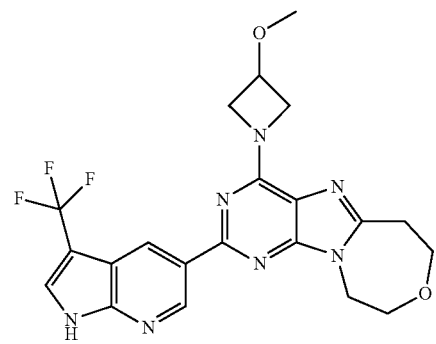
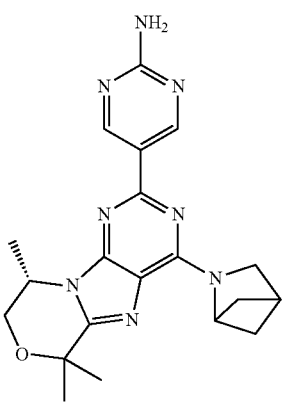

-continued
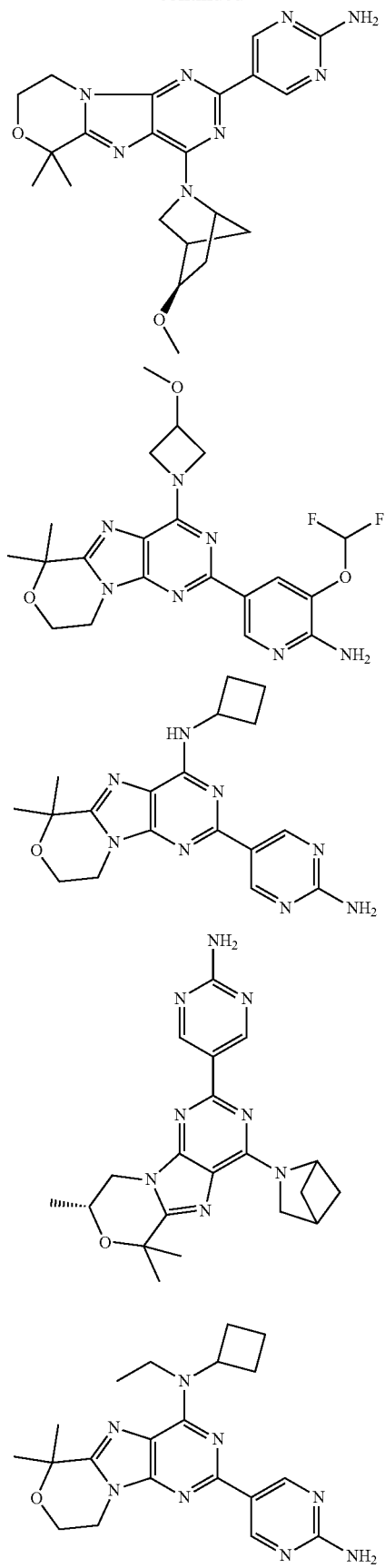
-continued
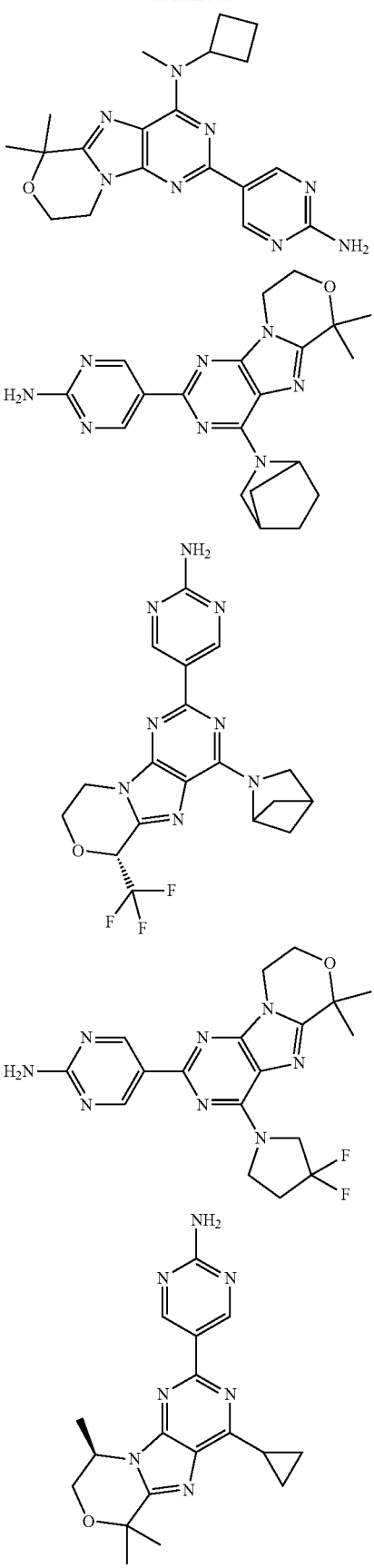

33
-continued
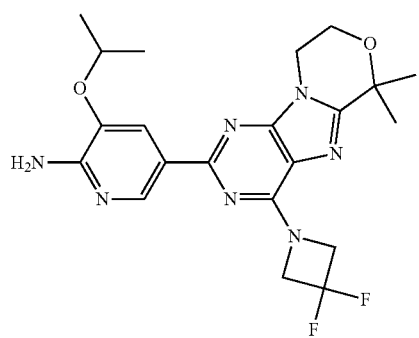
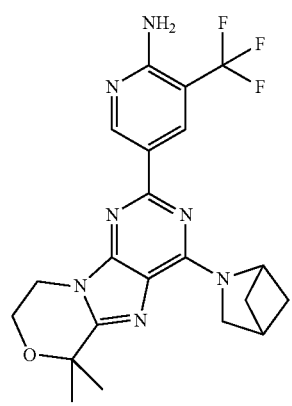
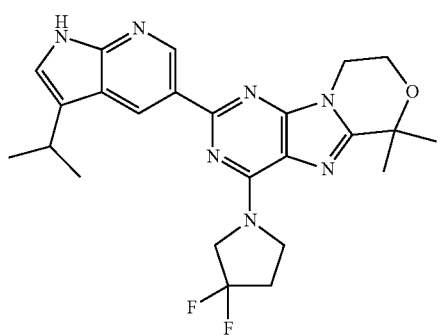
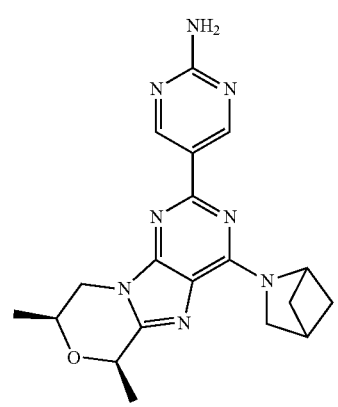
34
-continued
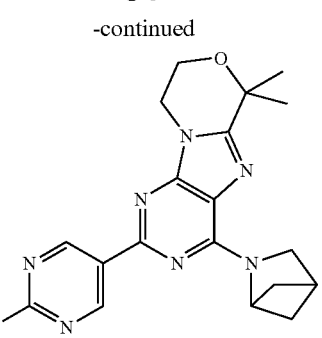
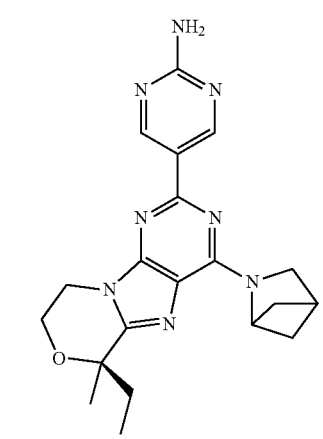
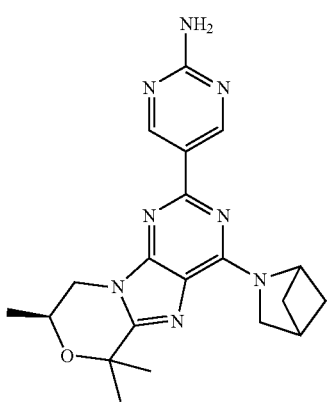
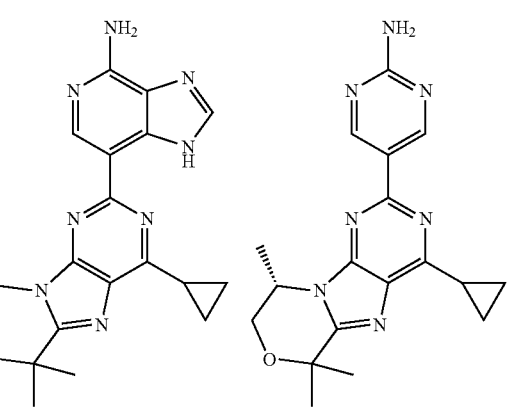

-continued
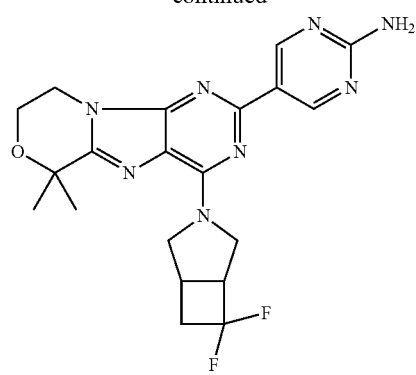
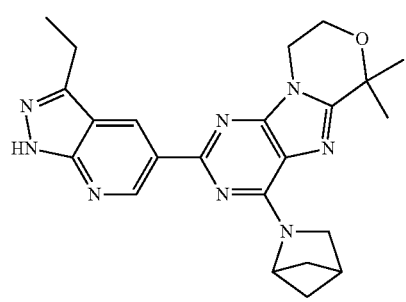
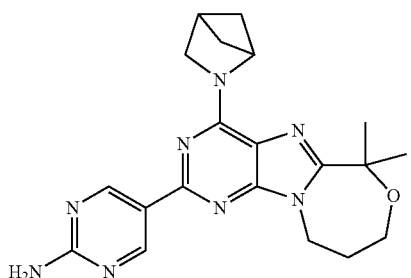
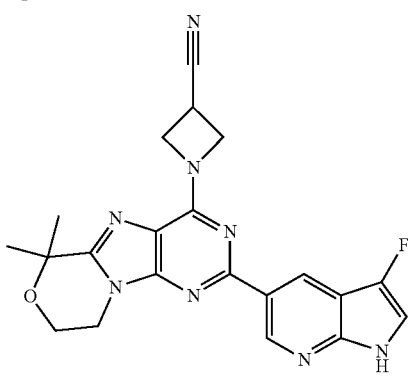
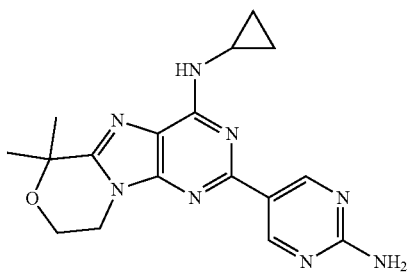
-continued
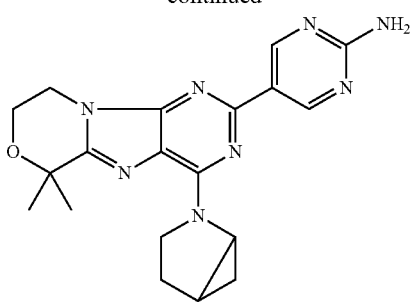
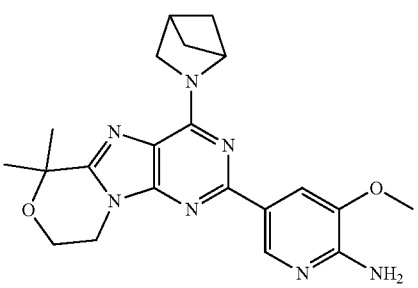
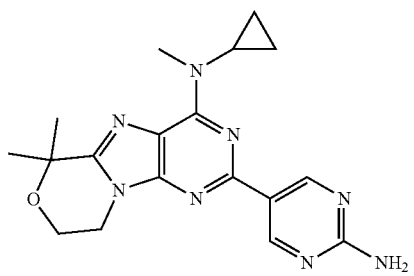
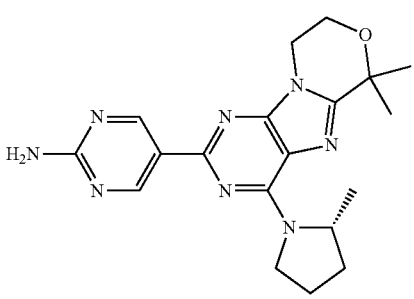
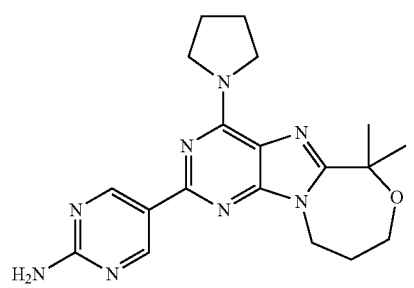

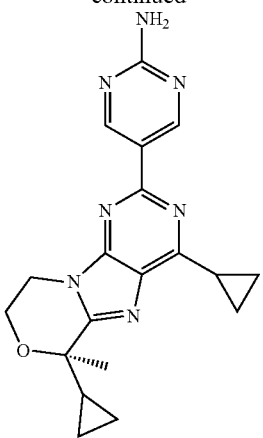
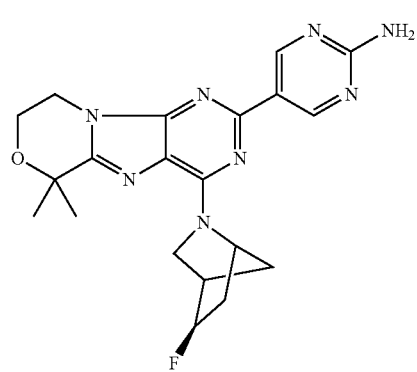
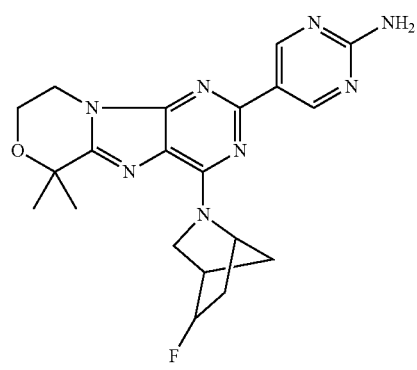
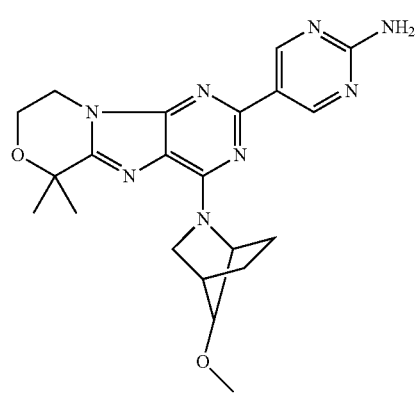
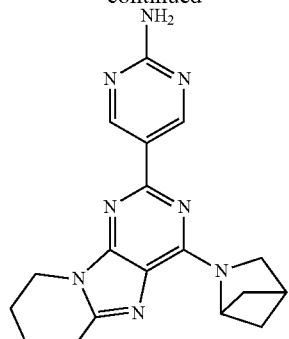
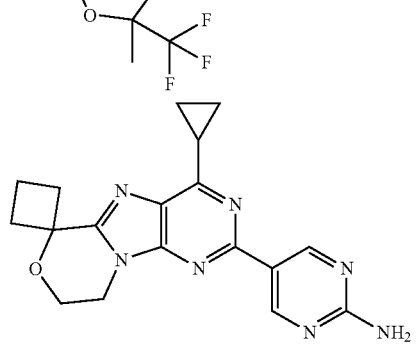
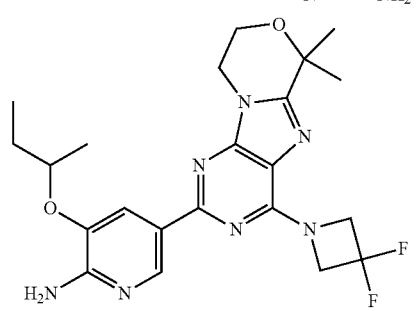
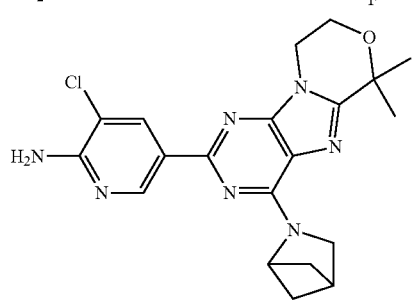
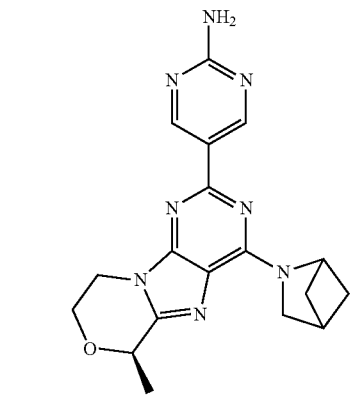

-continued
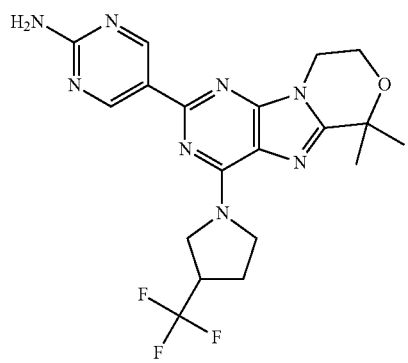
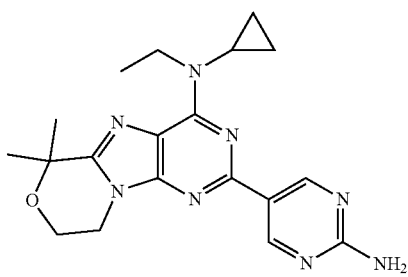
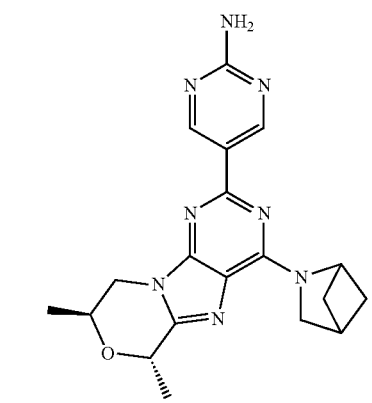
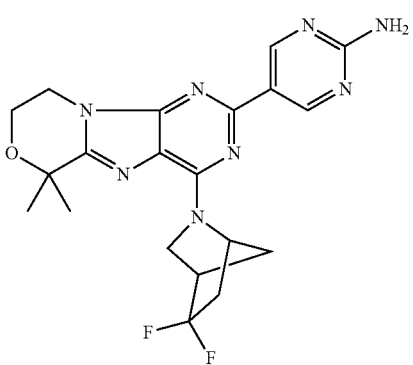
-continued
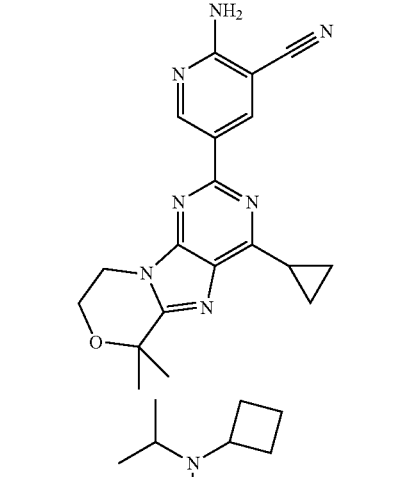
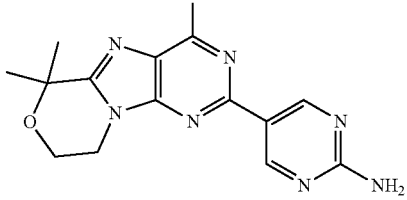
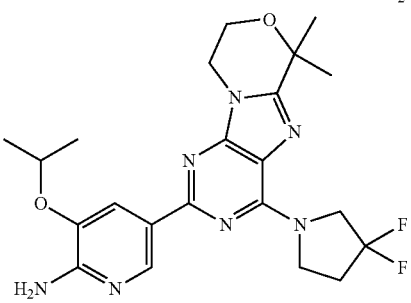
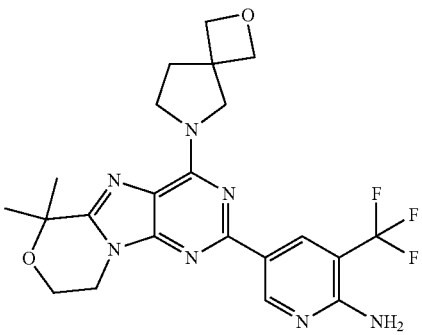
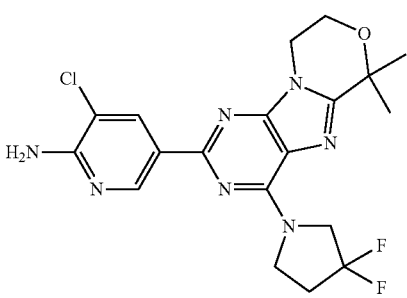

41
-continued
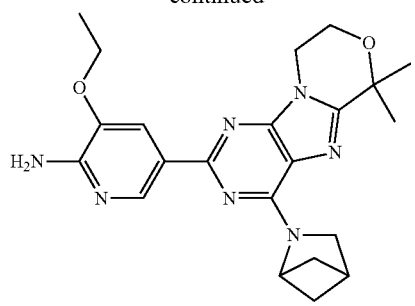
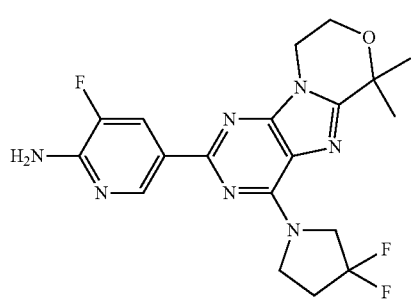
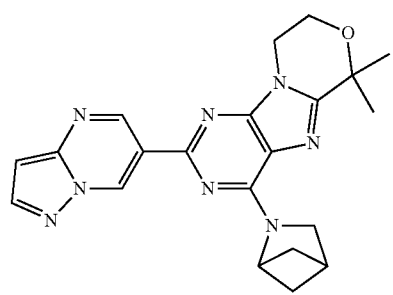
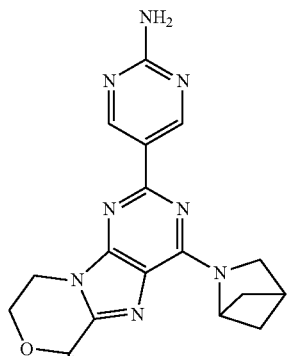
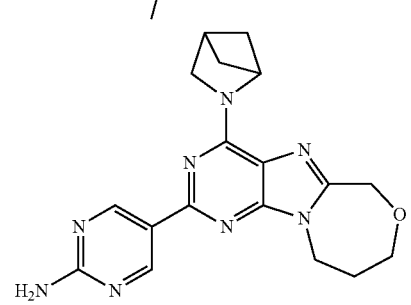
42
-continued
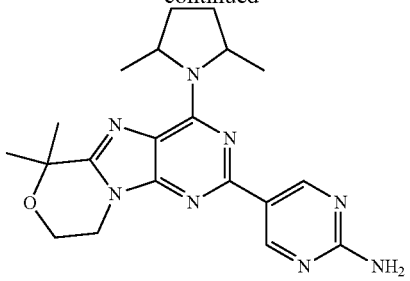
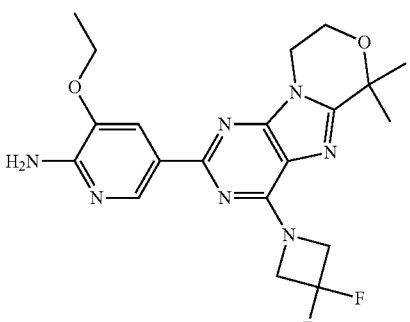
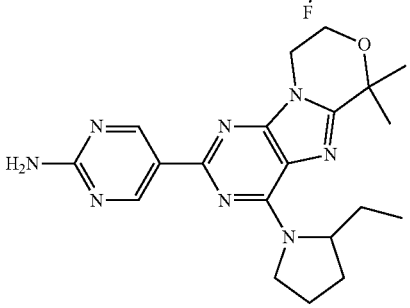
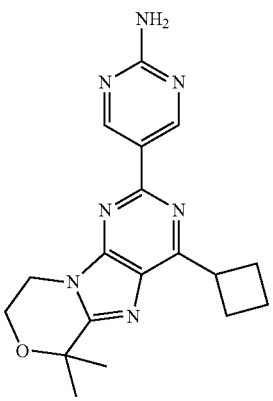
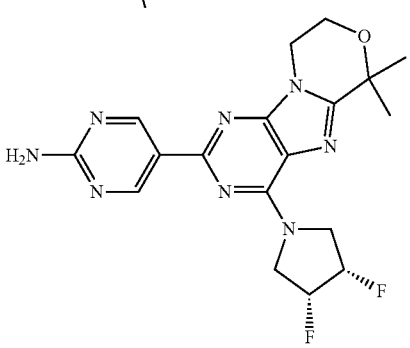

43
-continued
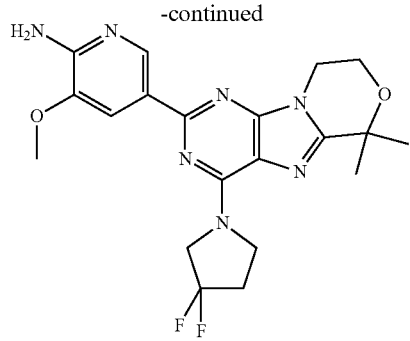
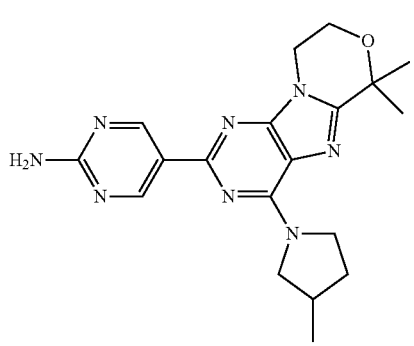
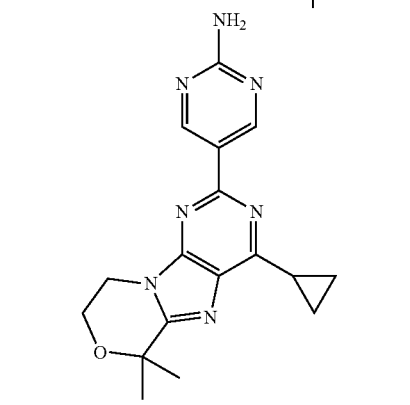
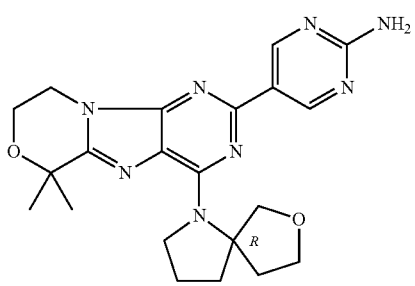
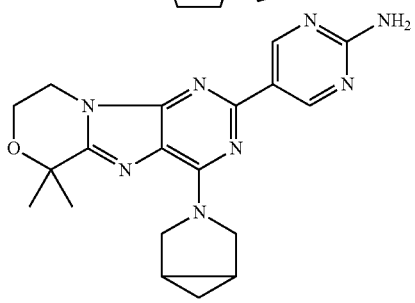
44
-continued
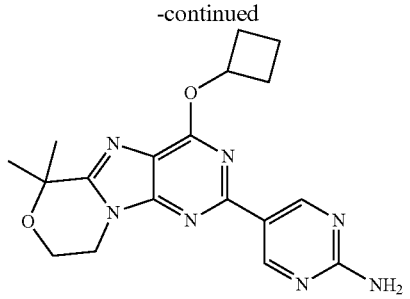
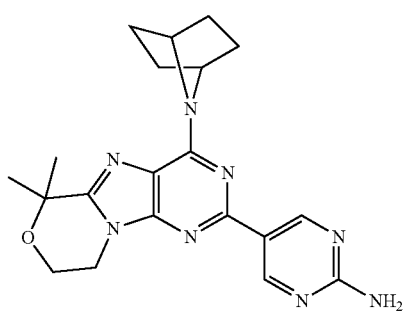
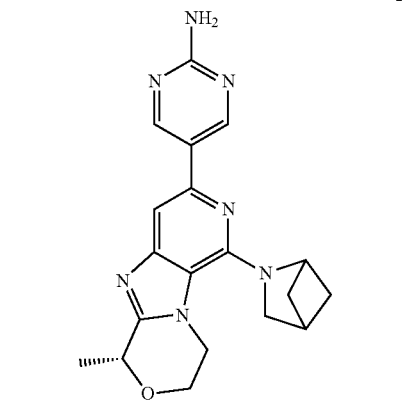
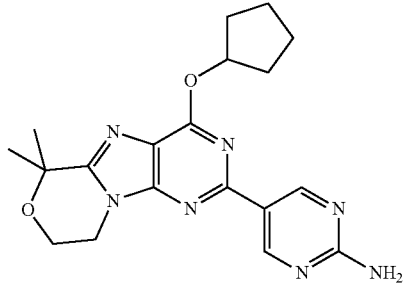
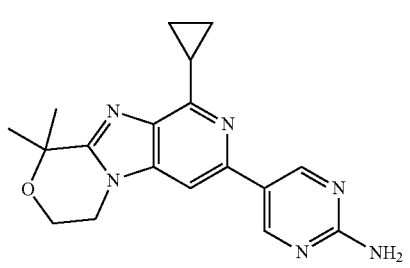

45
-continued
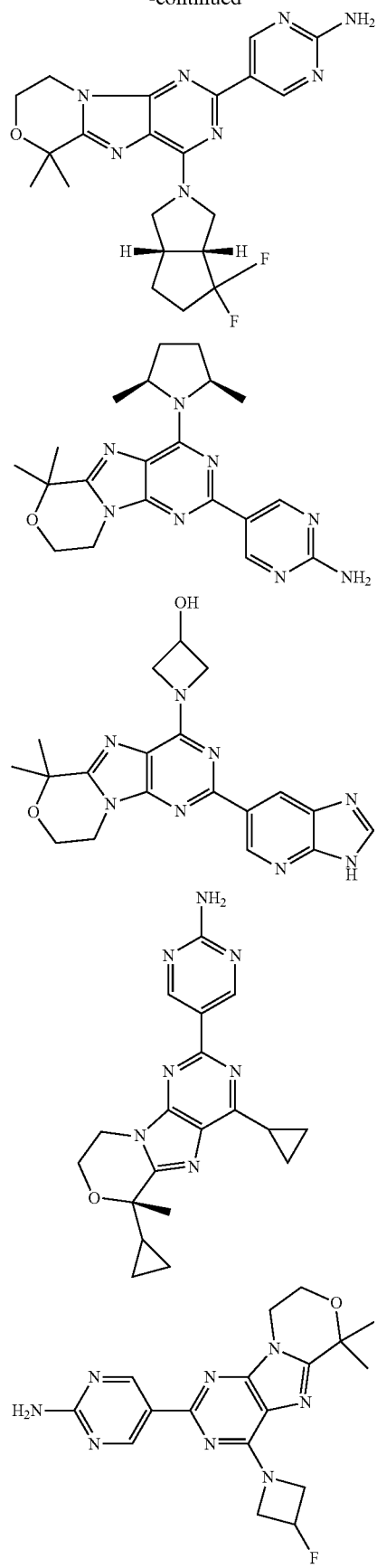
46
-continued
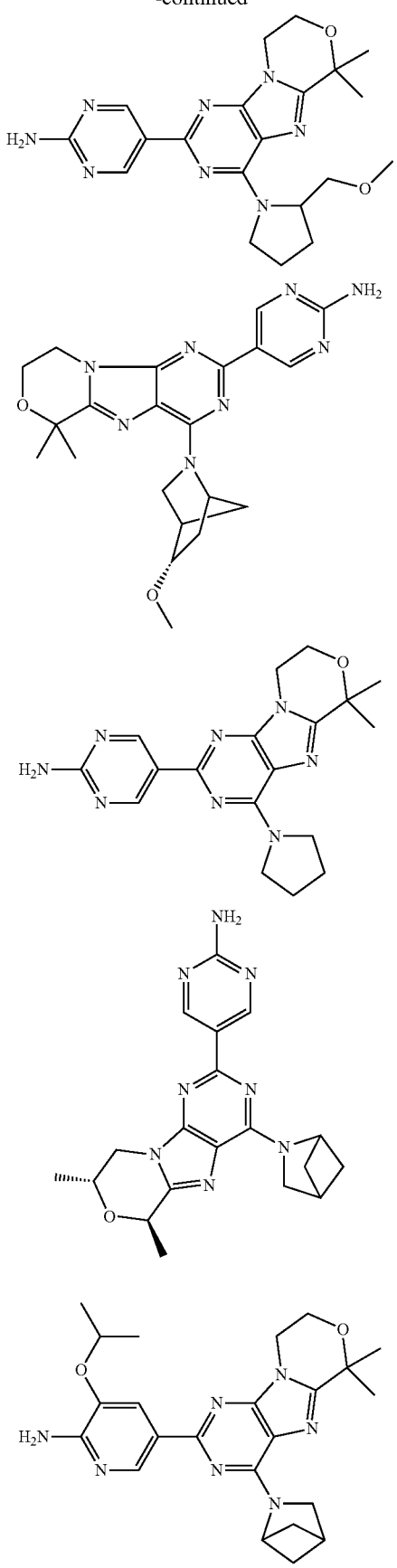

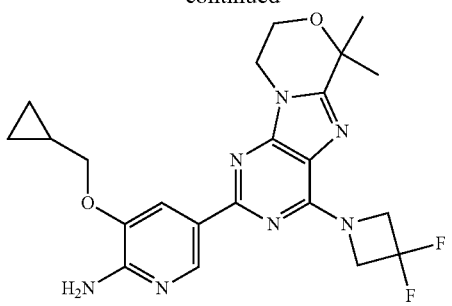
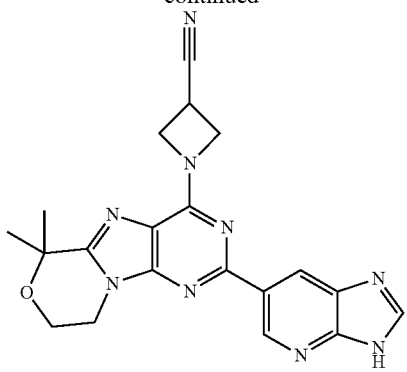
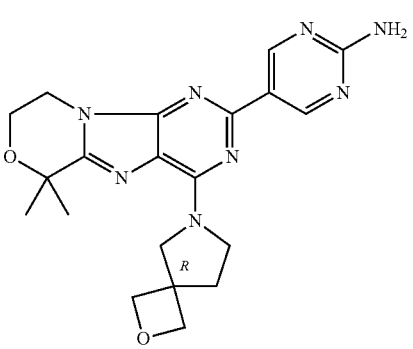
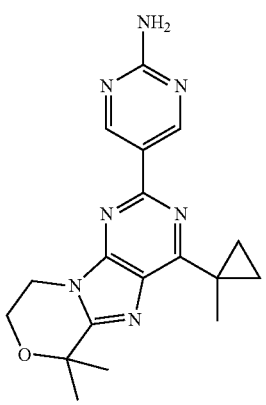
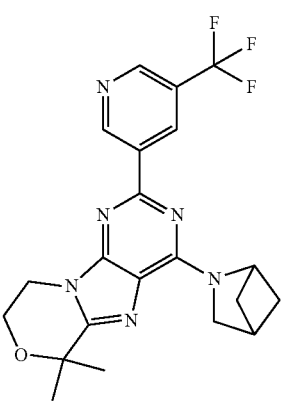

49
-continued
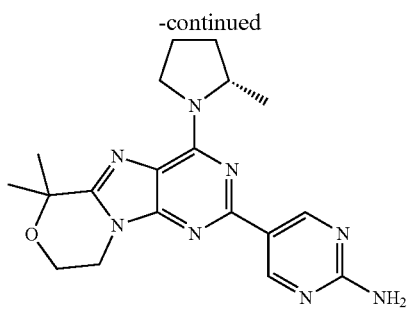
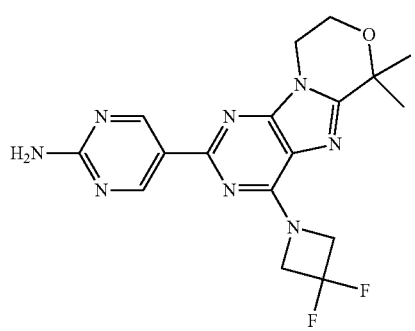
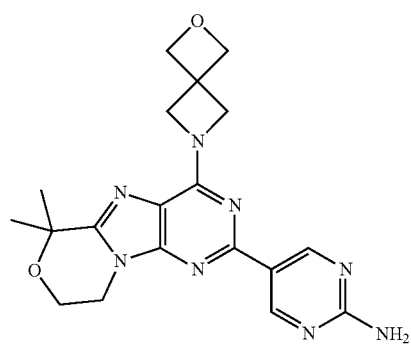
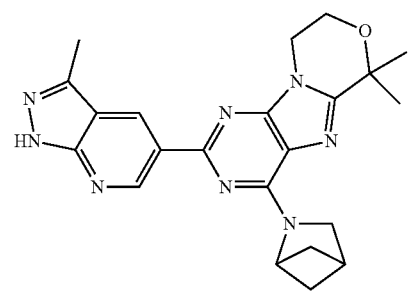
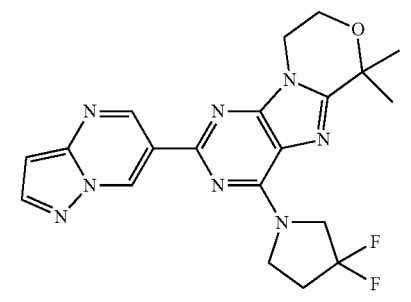
50
-continued
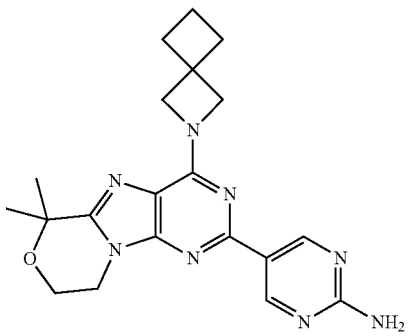
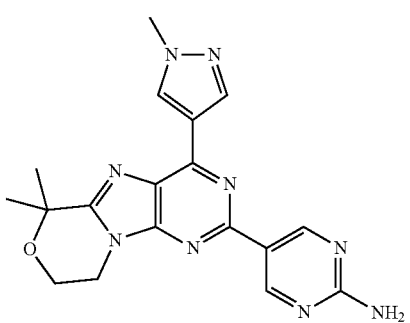
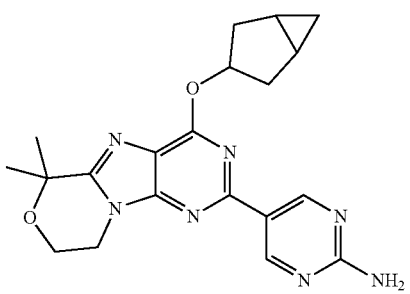
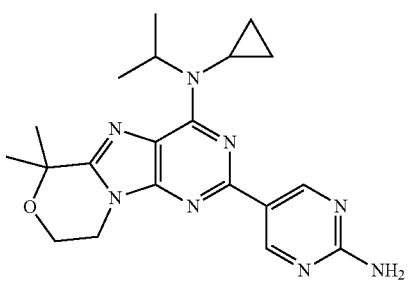
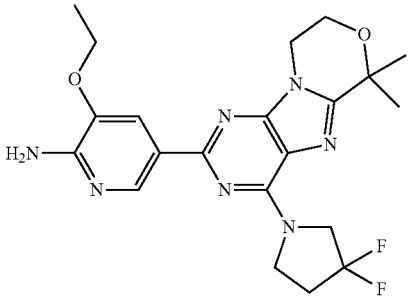

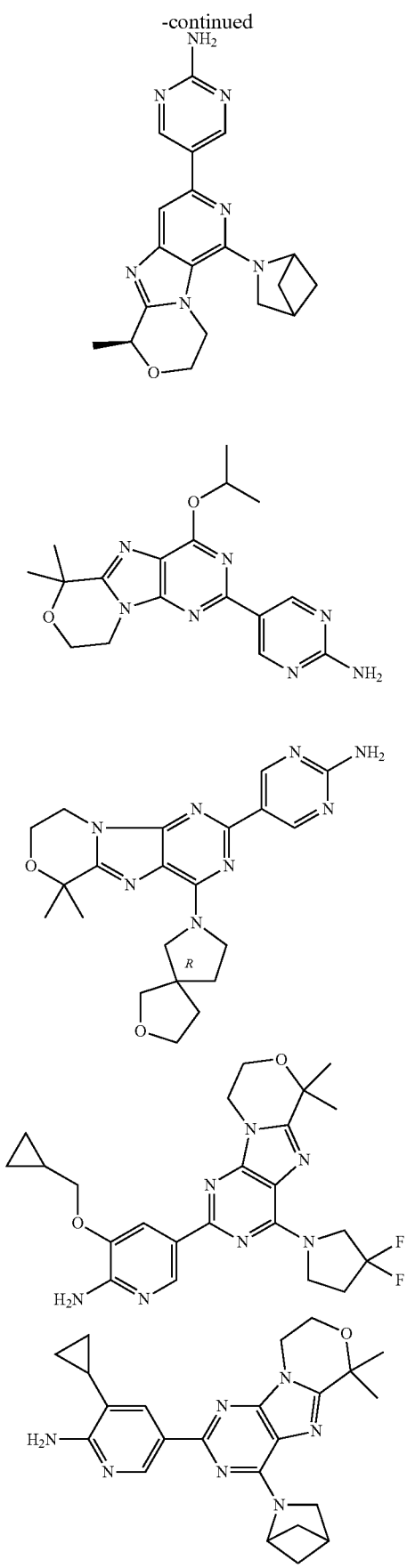

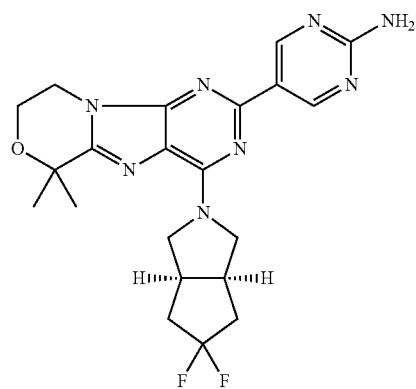
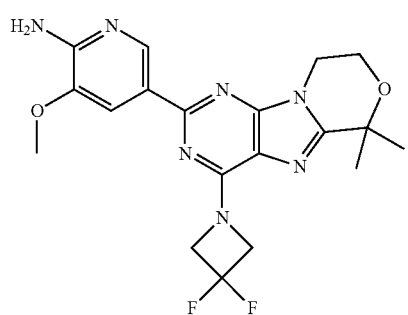
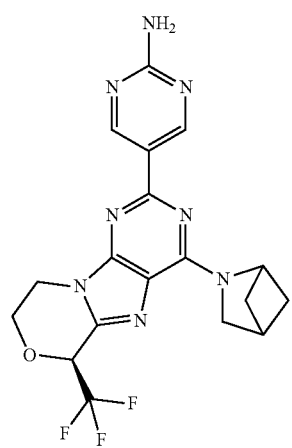
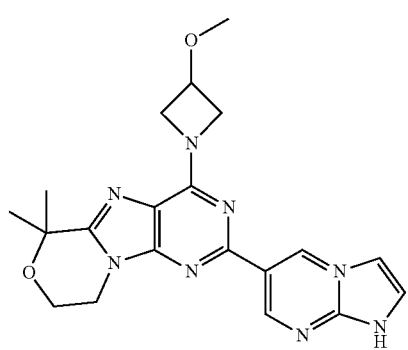
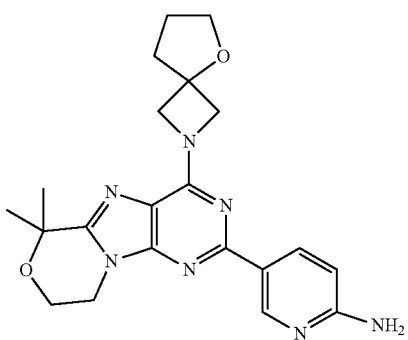
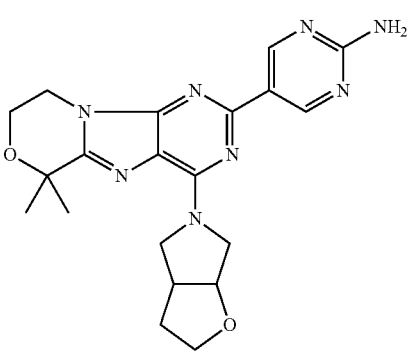
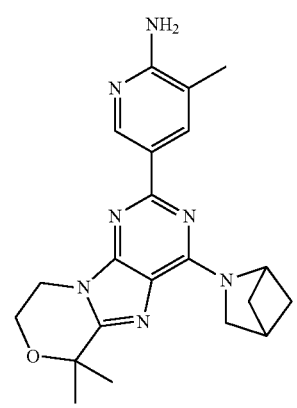
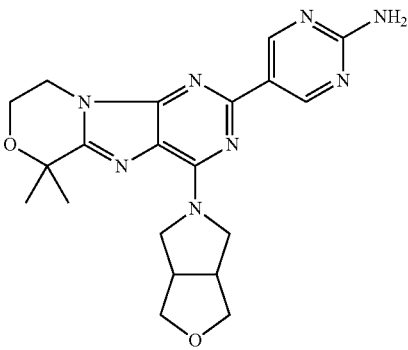

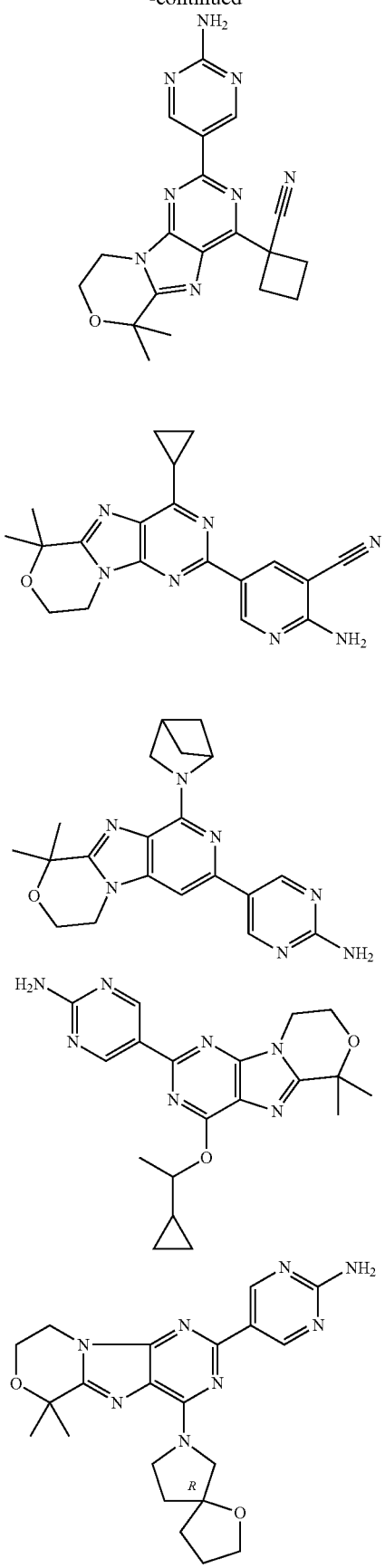
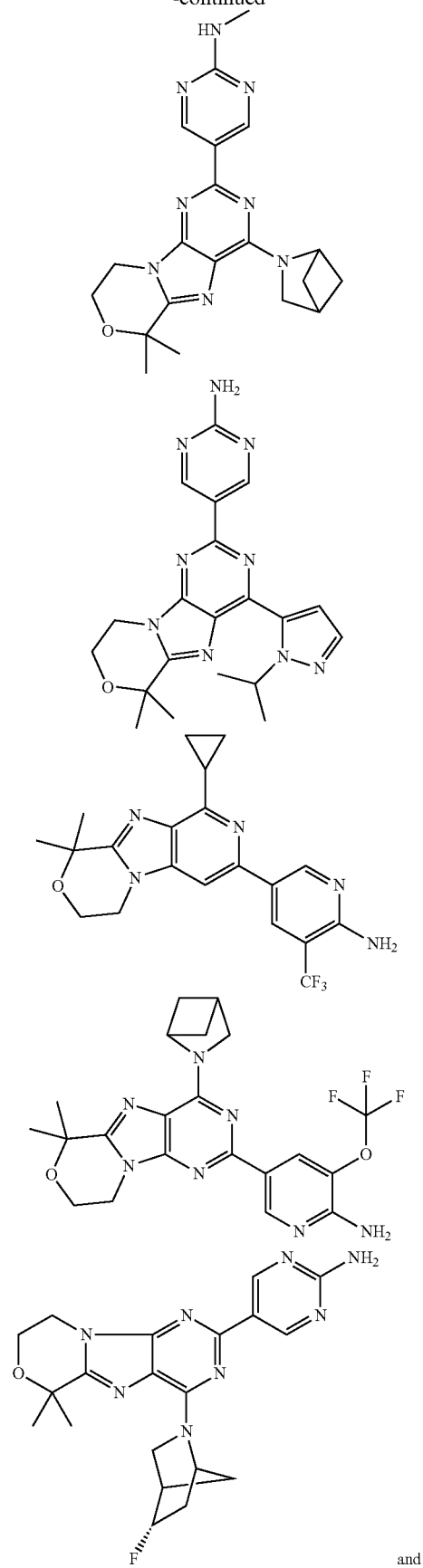

57
-continued
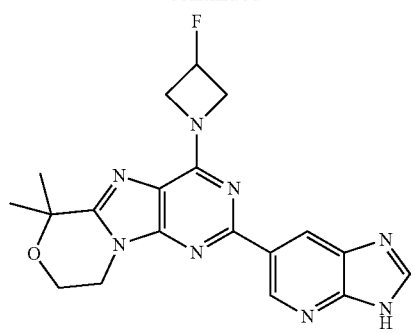
and salts thereof.
In one embodiment the compound is selected from the group consisting of:
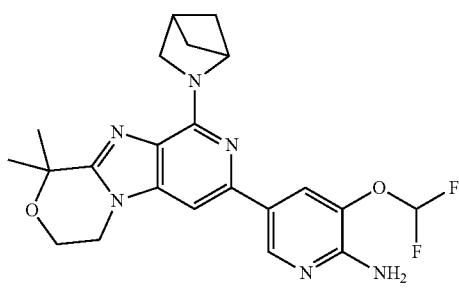
58
-continued
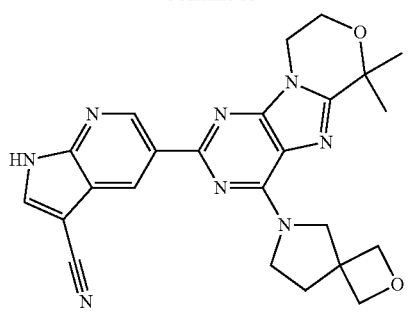
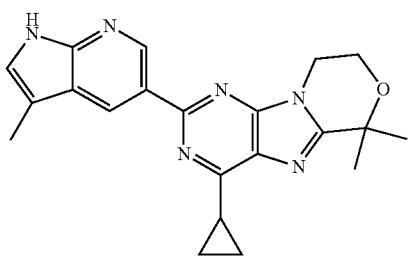
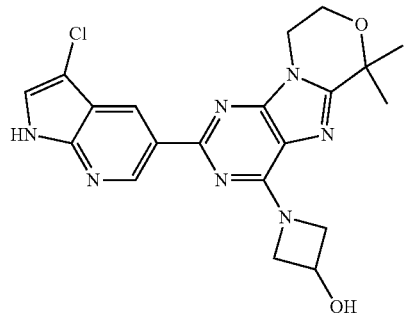
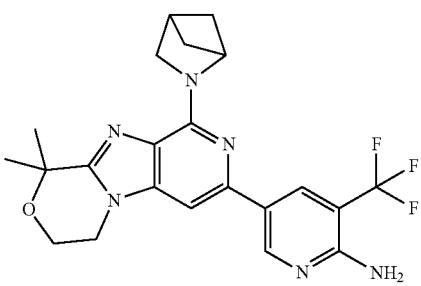
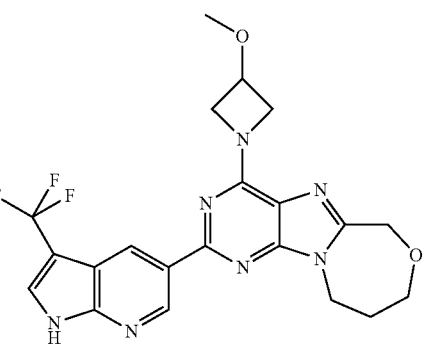

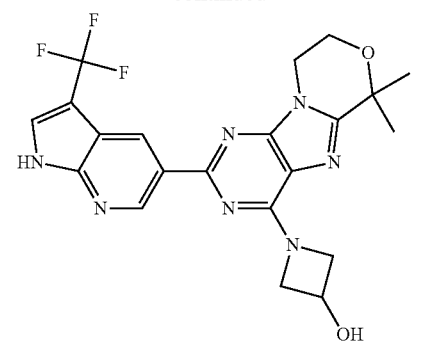
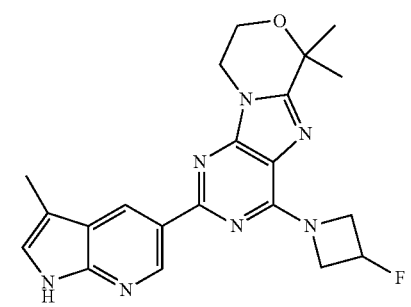
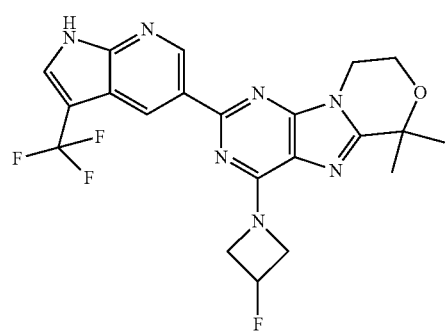
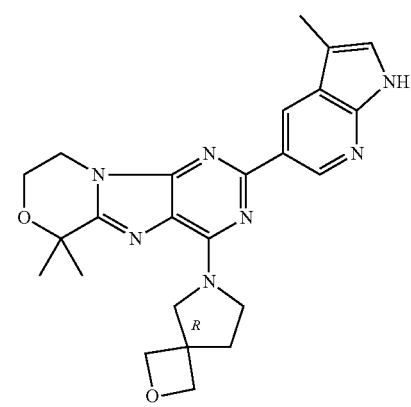
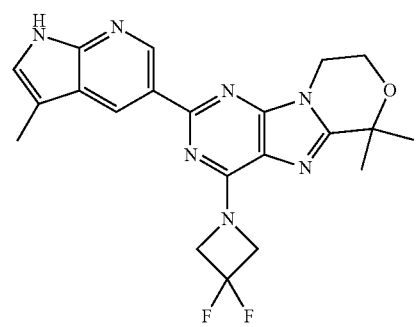
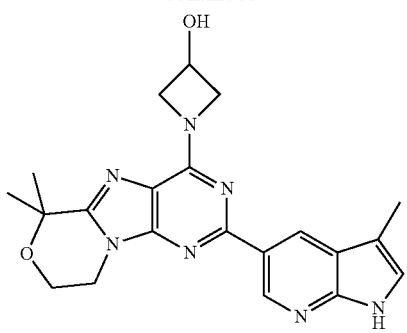
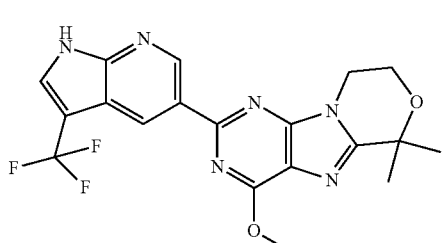
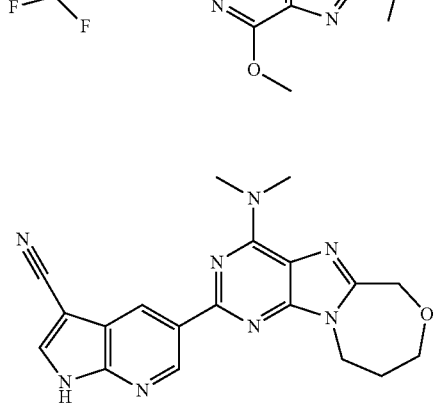
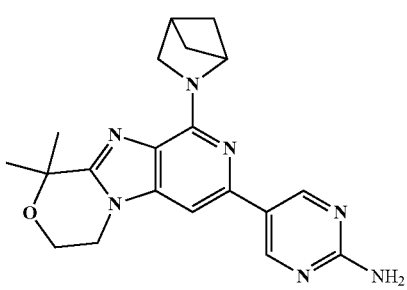
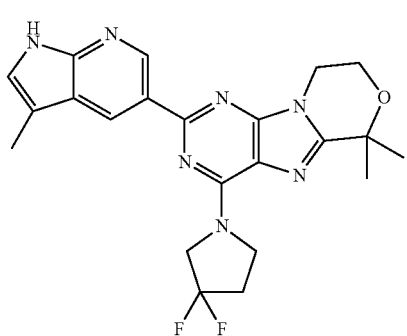

-continued
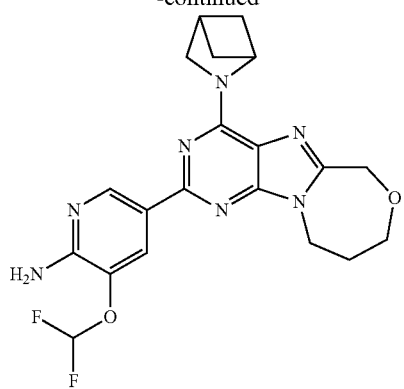
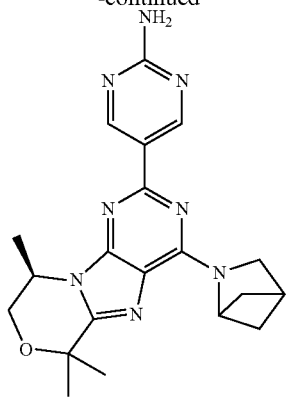
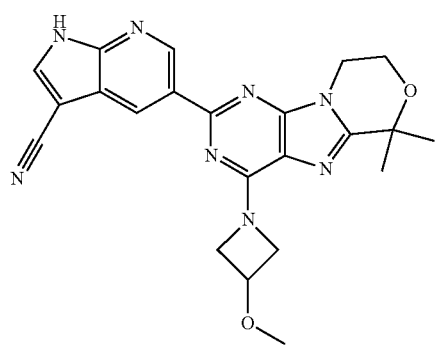
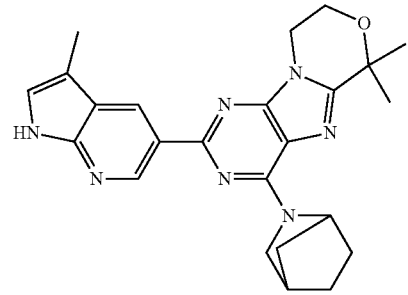
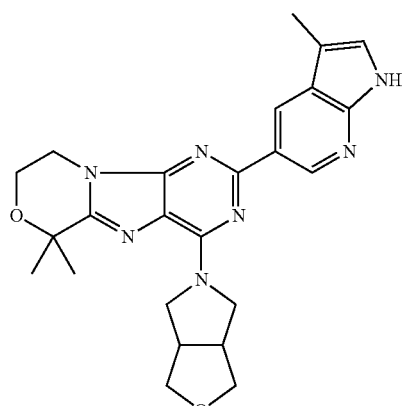
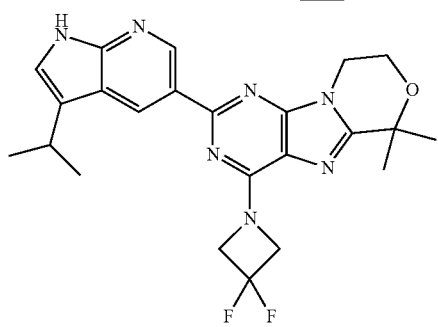
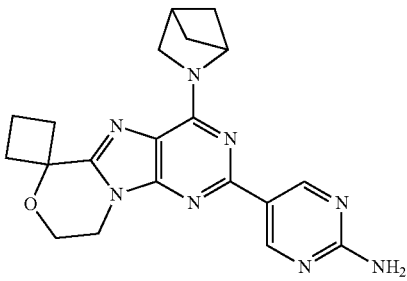
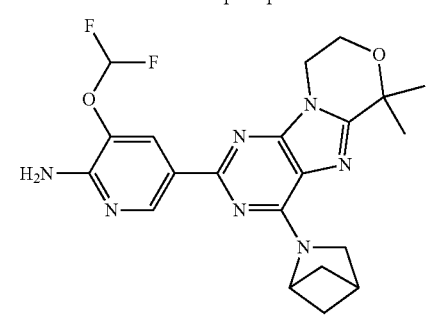
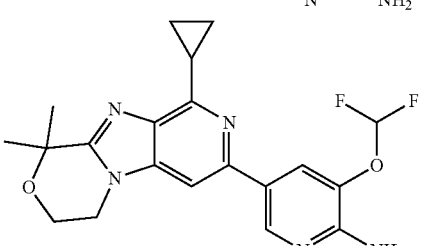
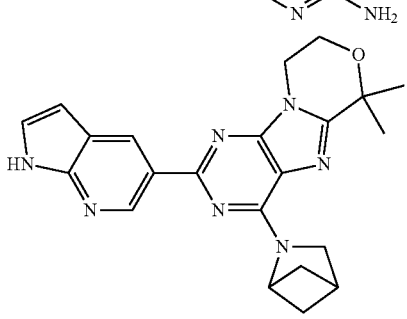

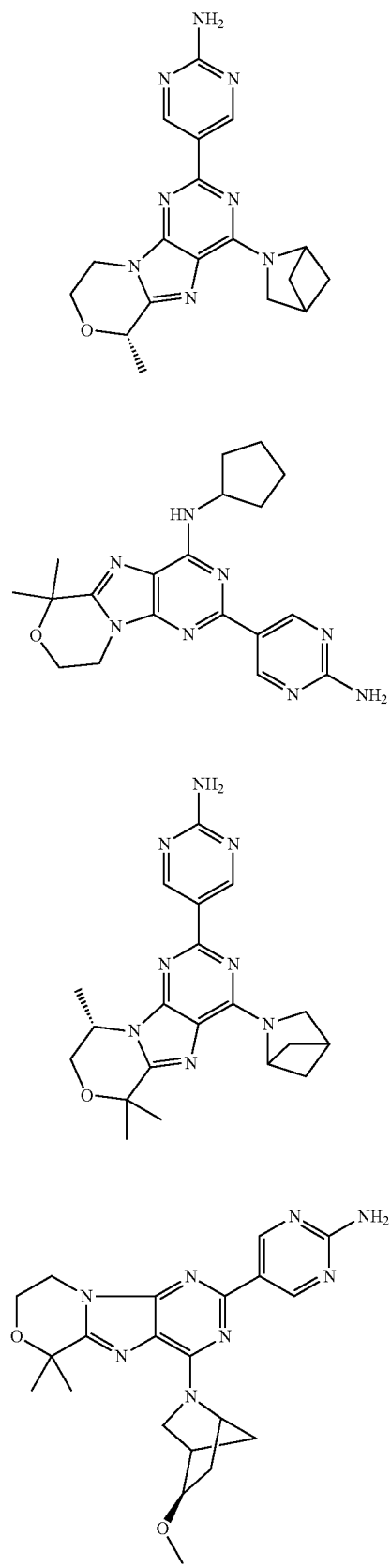
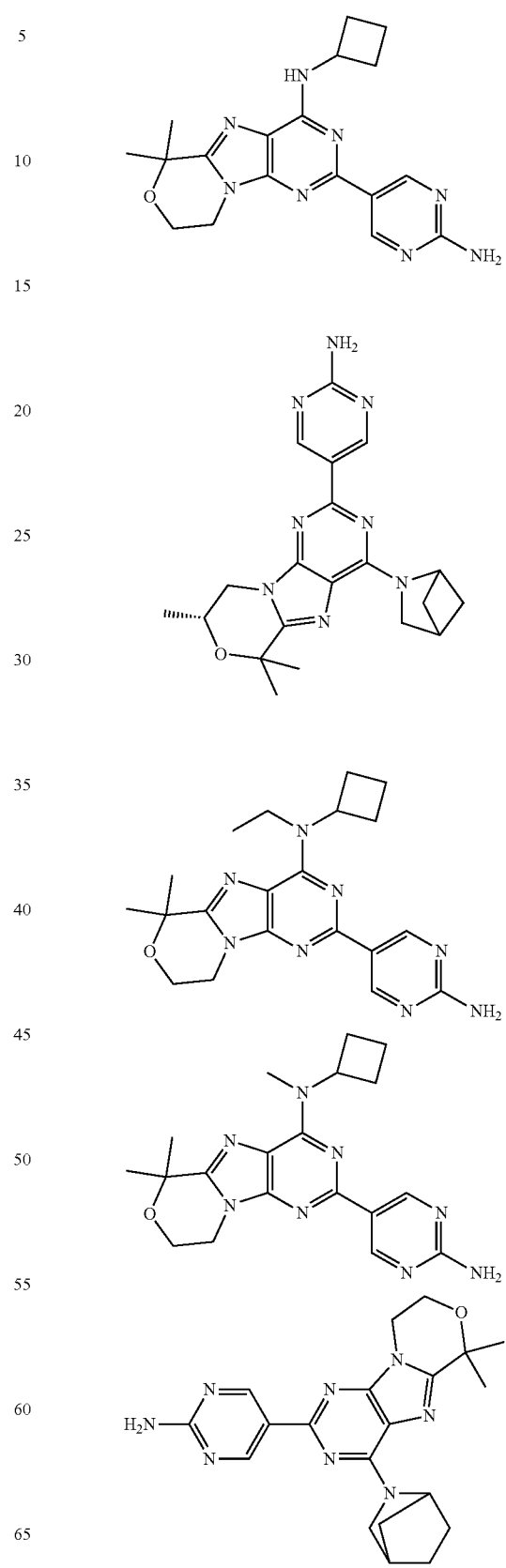

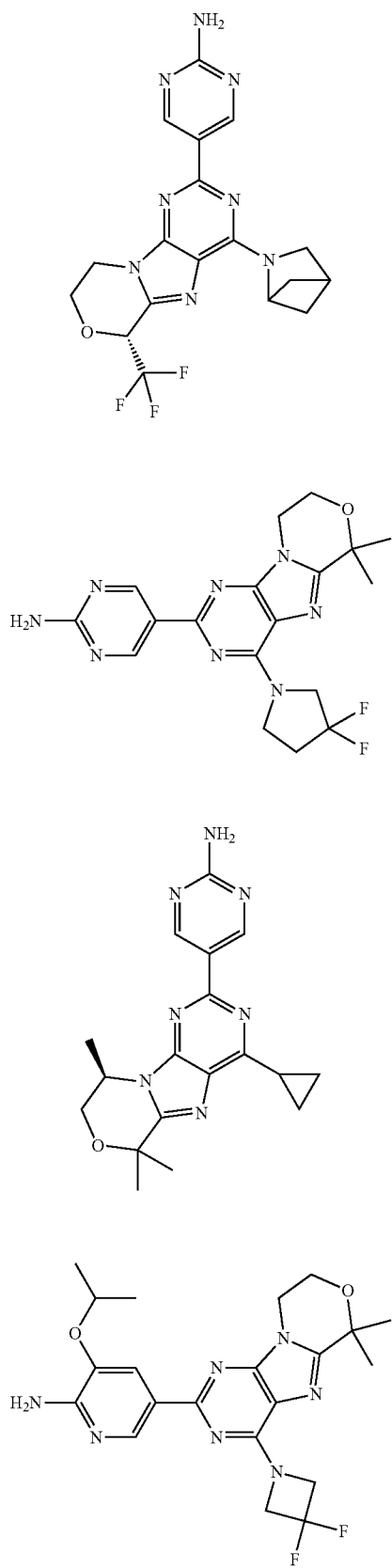
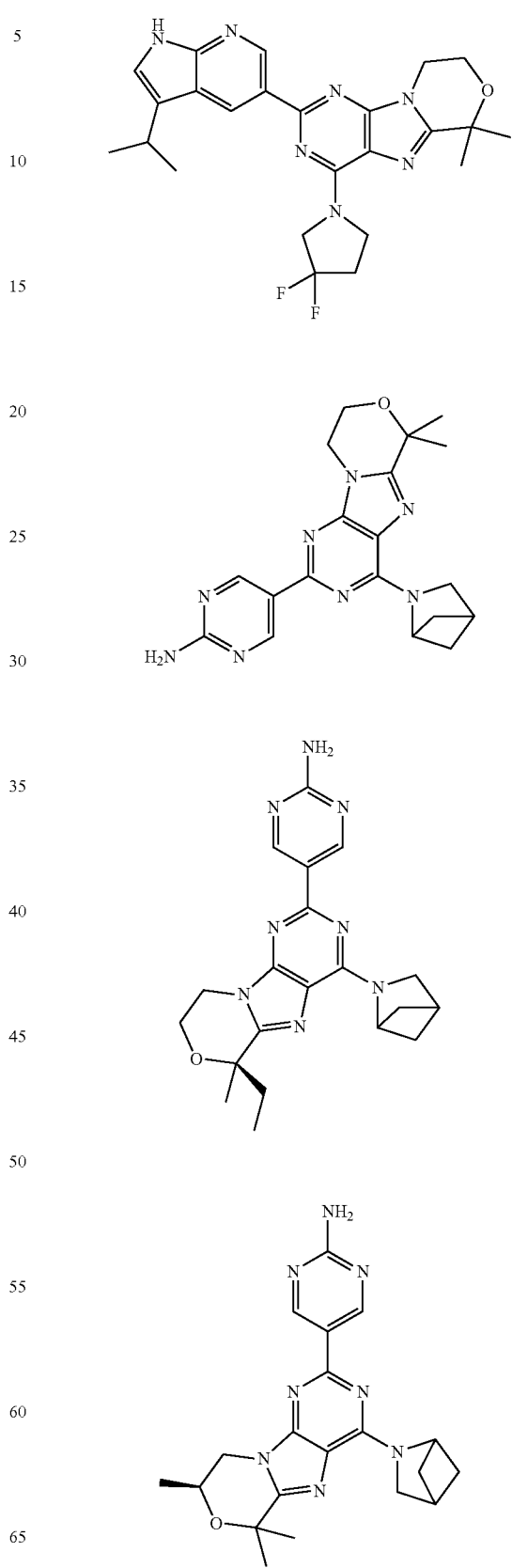

-continued
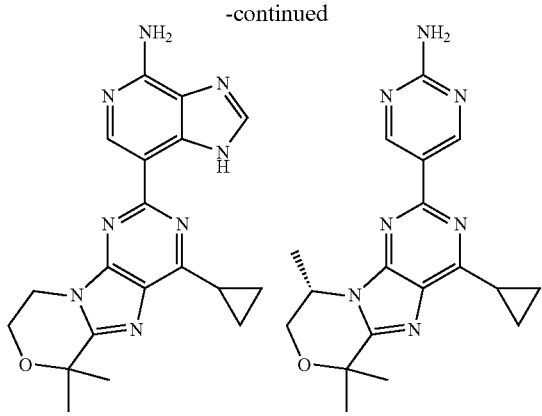
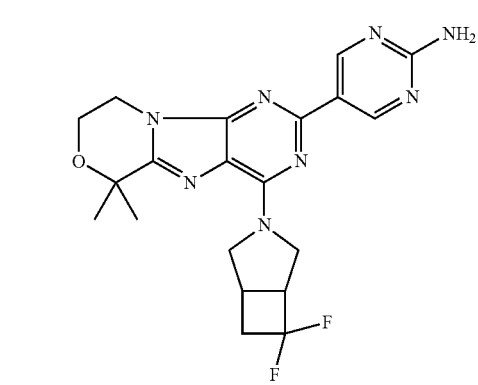
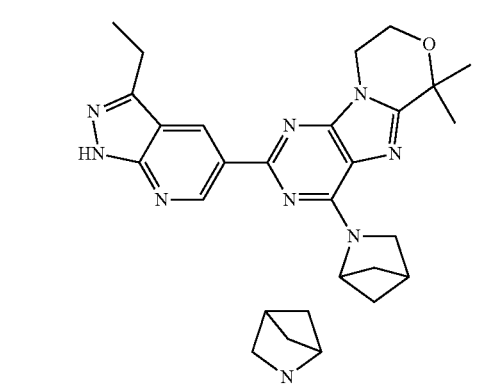
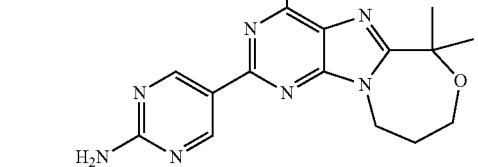
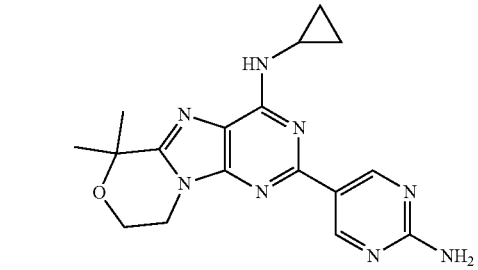
-continued
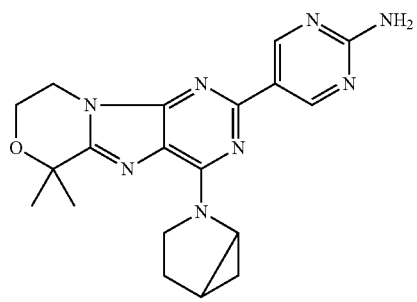
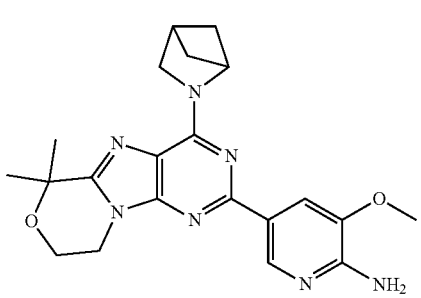
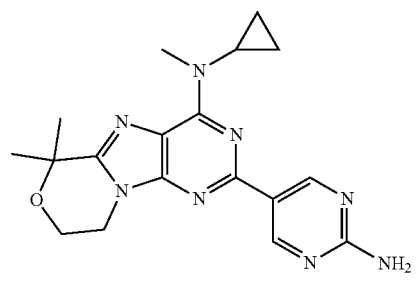
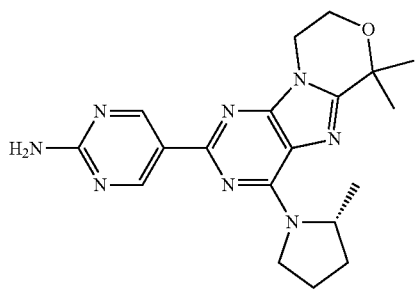
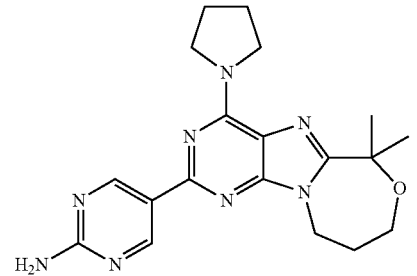

-continued
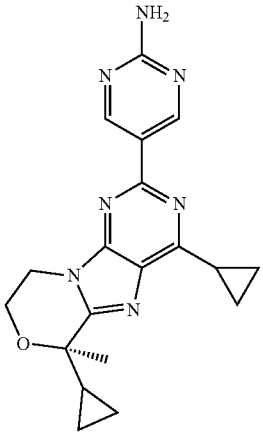
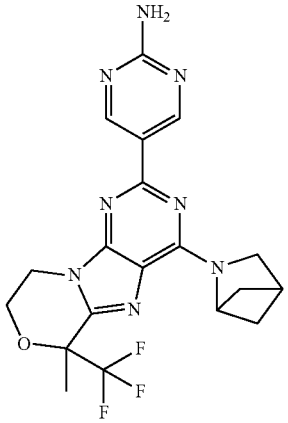
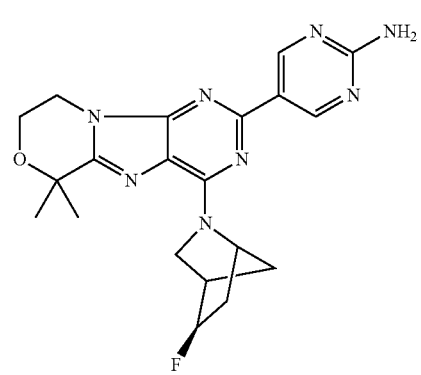
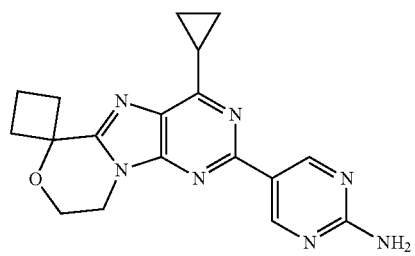
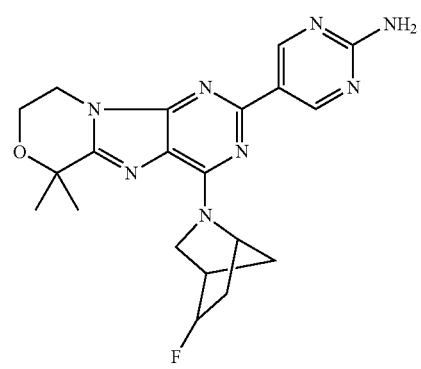
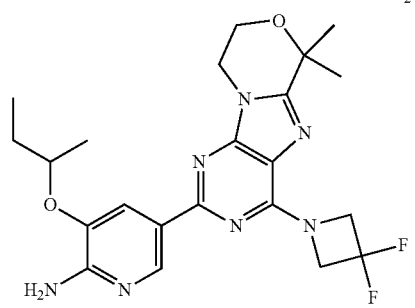
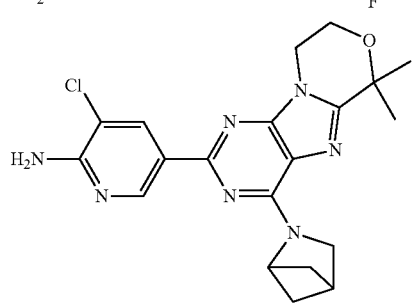
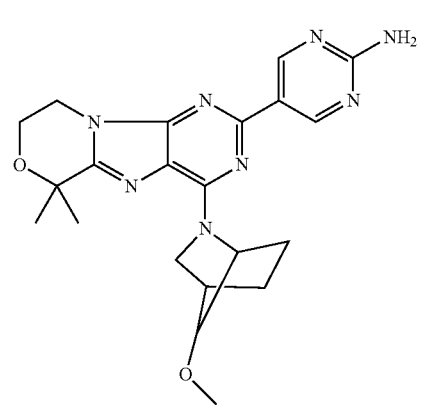
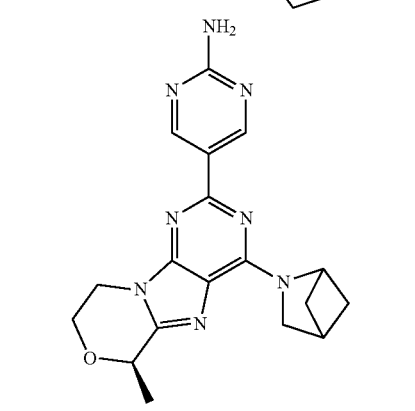

71
-continued
72
-continued
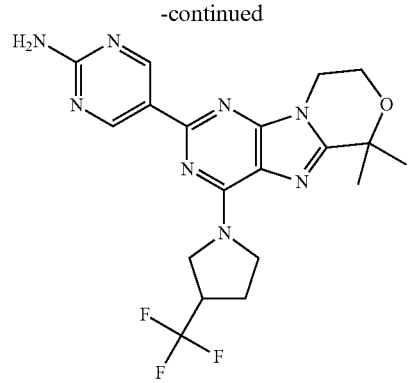
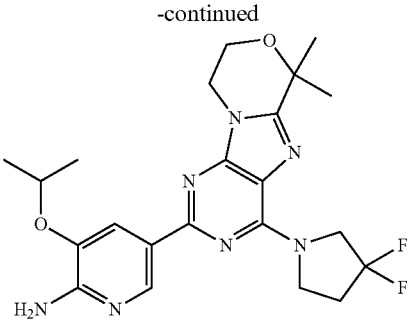
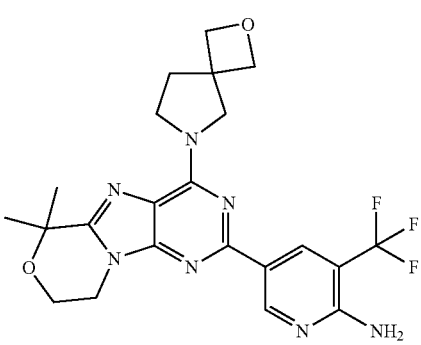
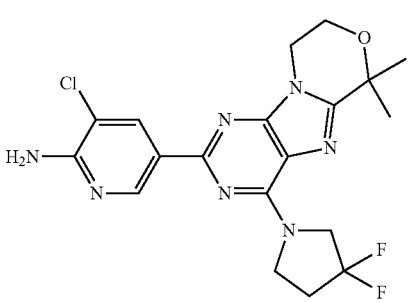
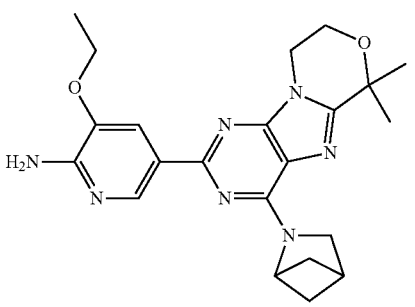
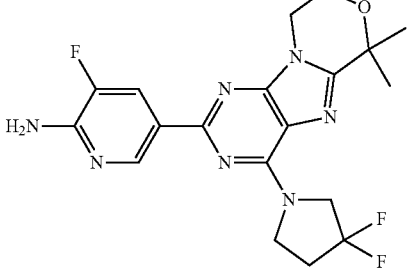

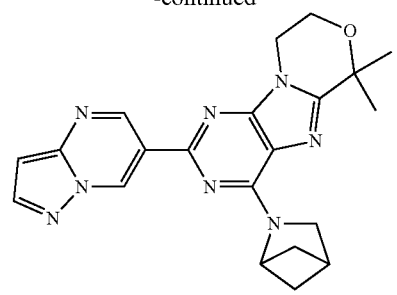
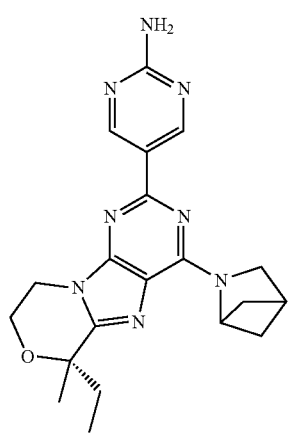
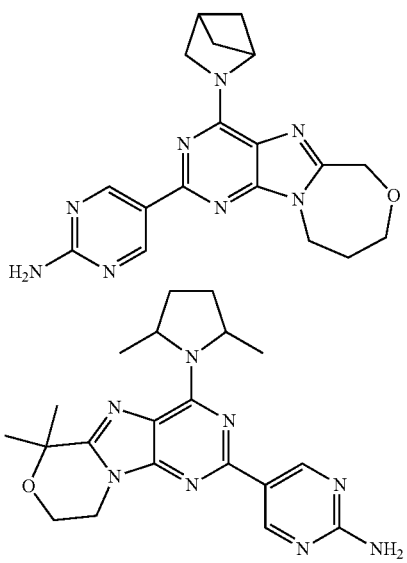
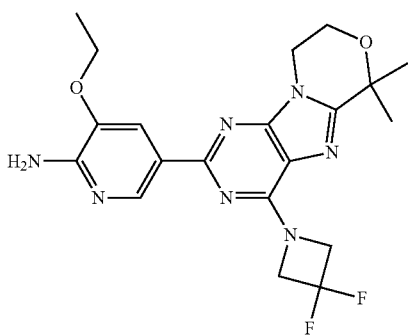
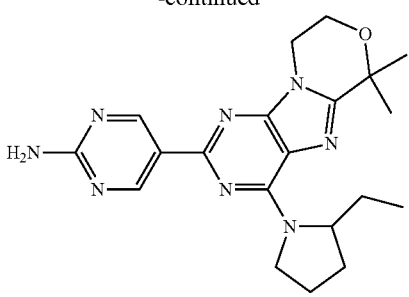
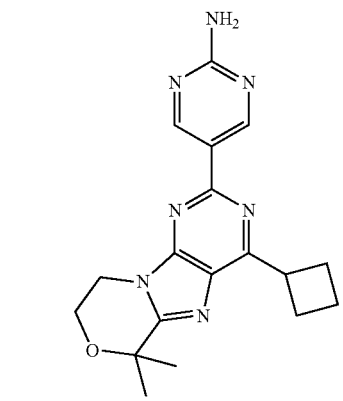
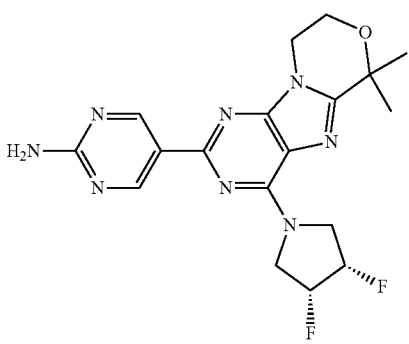
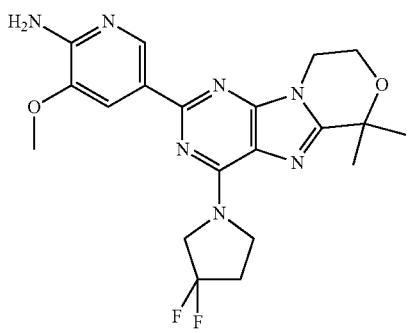
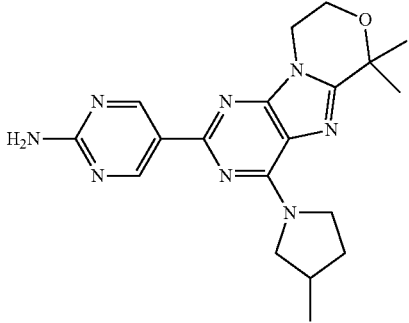

75
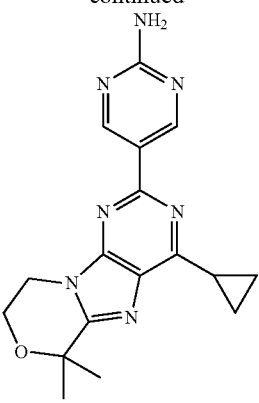
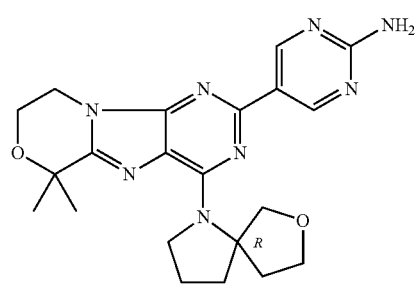
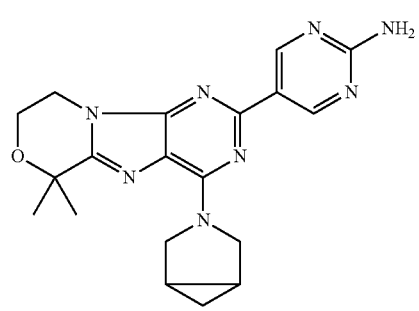
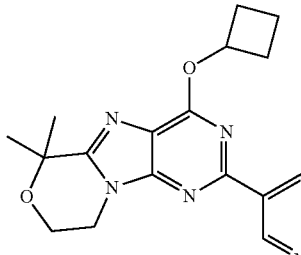
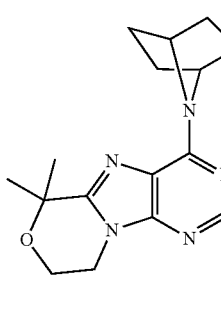
76
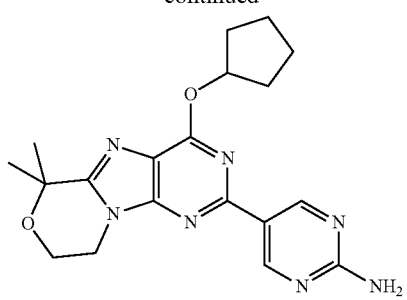
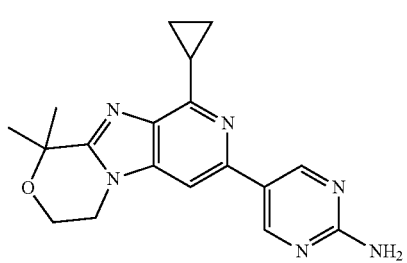
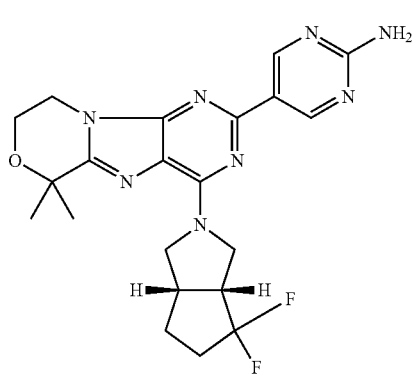
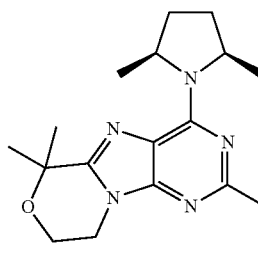
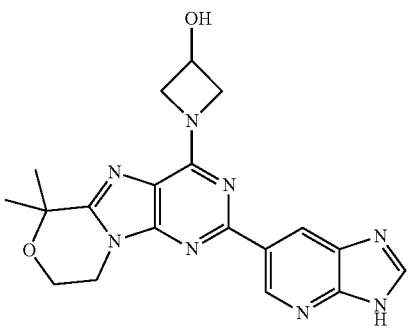

77
-continued
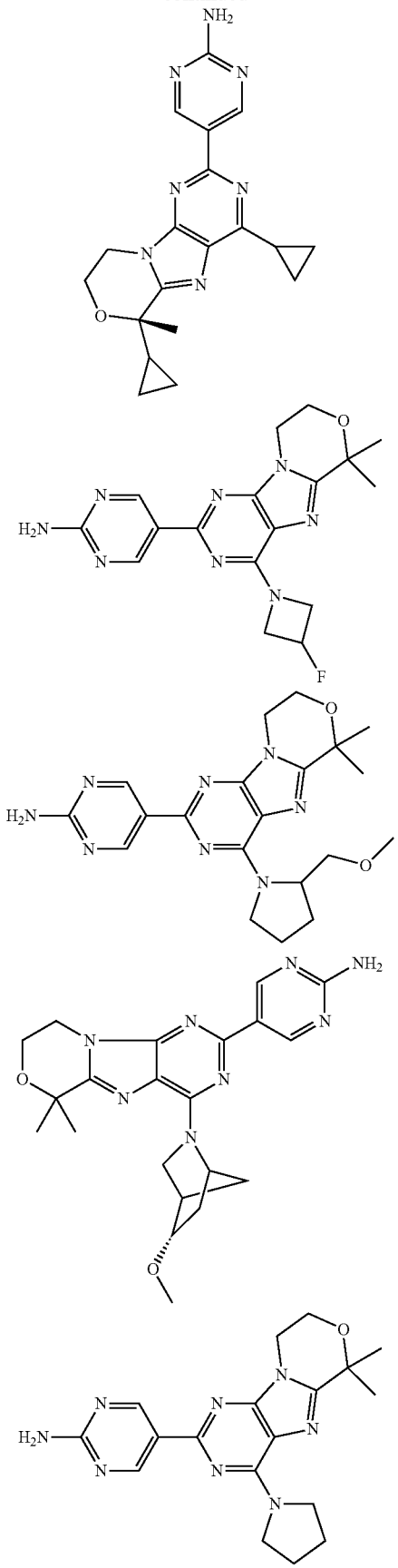
78
-continued
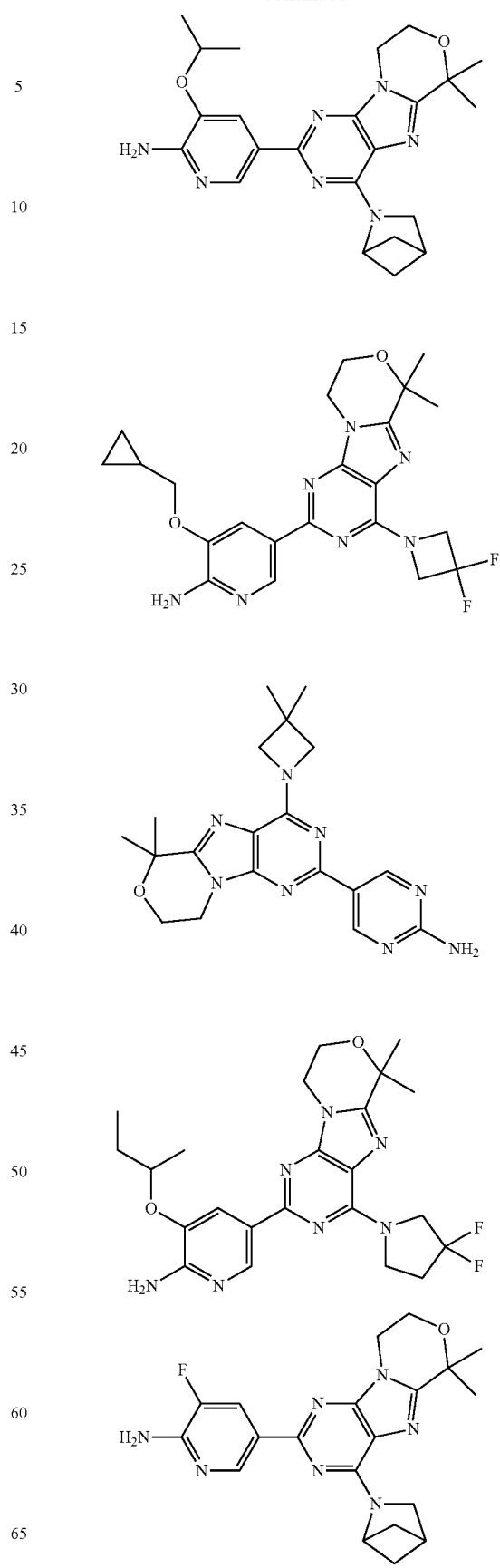

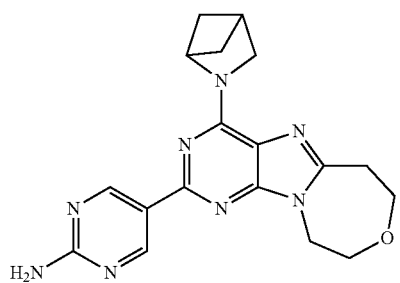
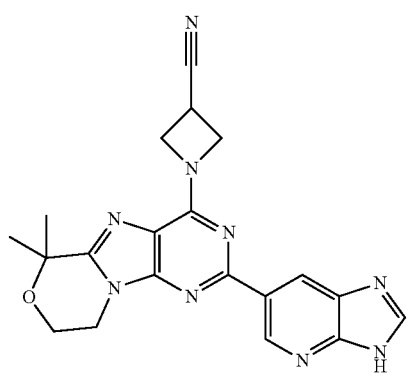
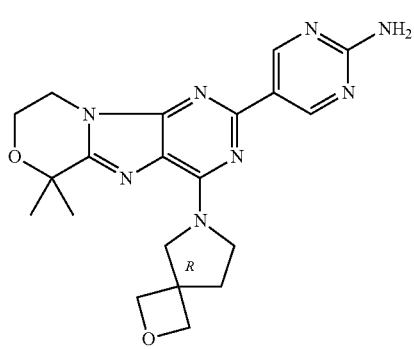
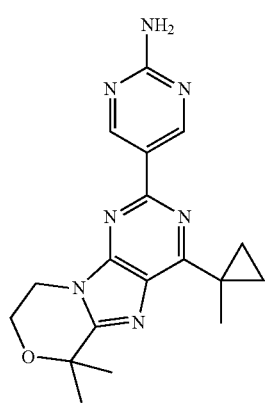
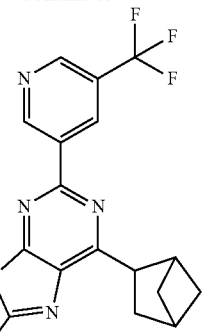
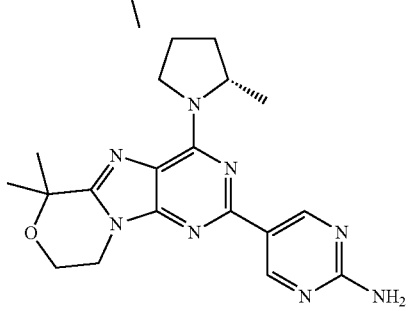
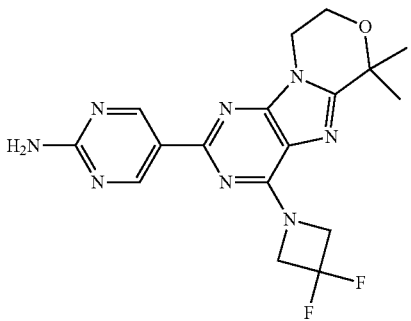
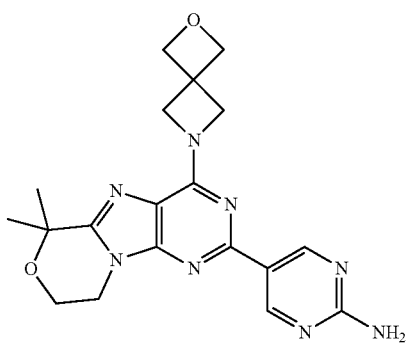
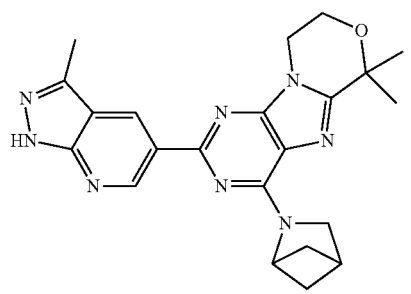

81
-continued
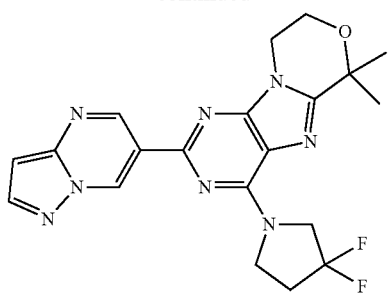
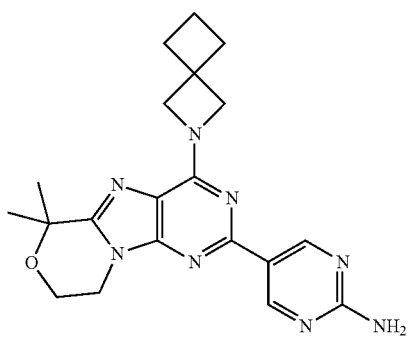
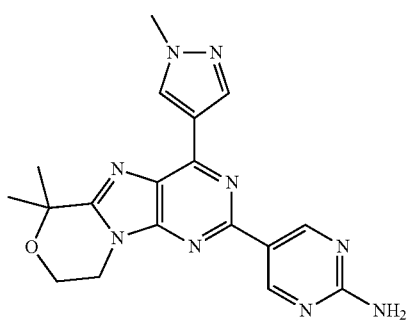
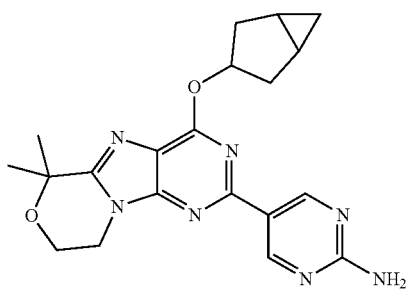
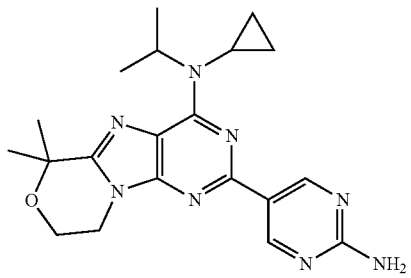
82
-continued
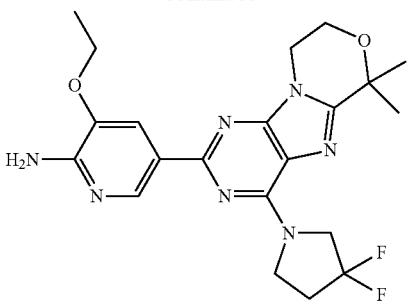
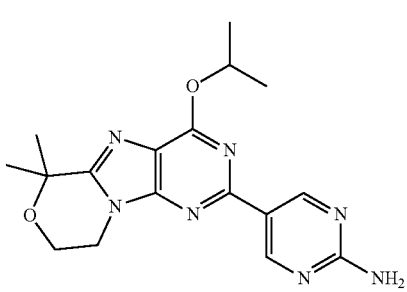
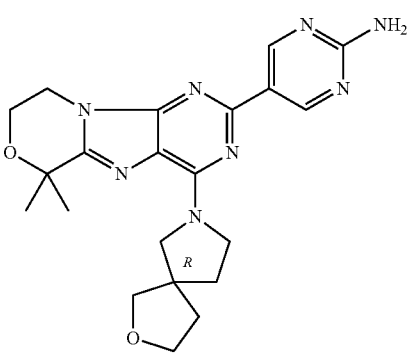
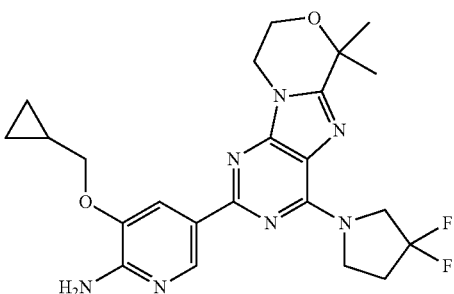
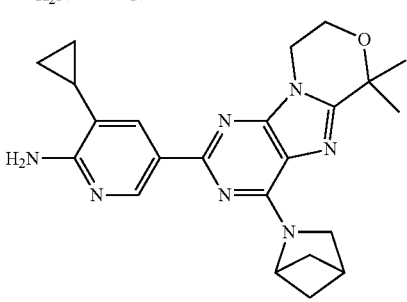

83
-continued
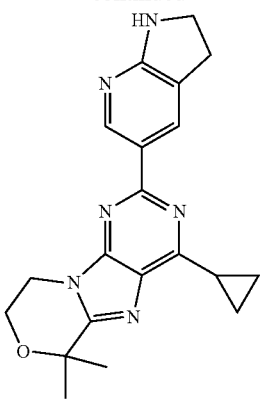
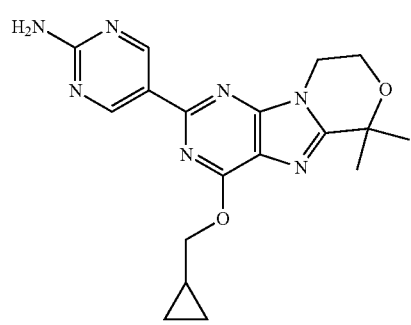
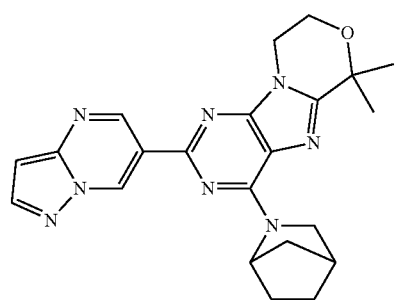
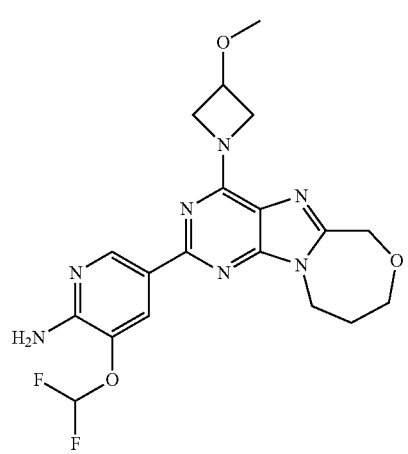
84
-continued
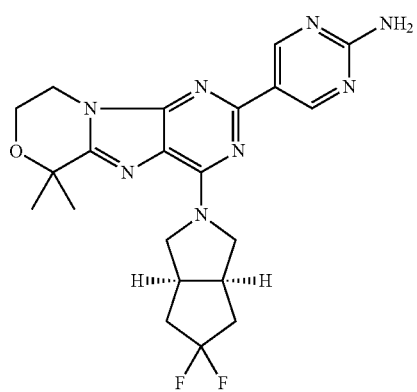
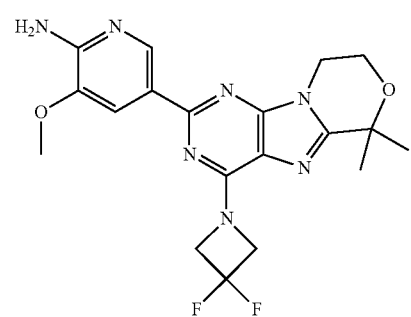
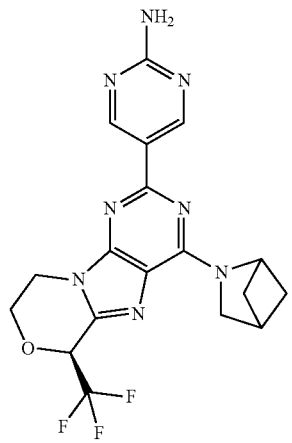
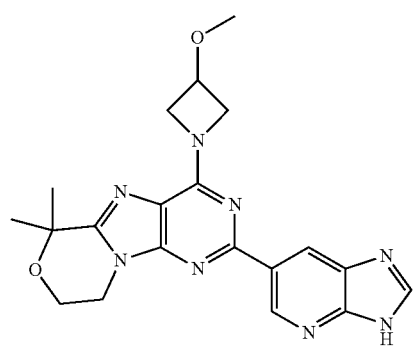

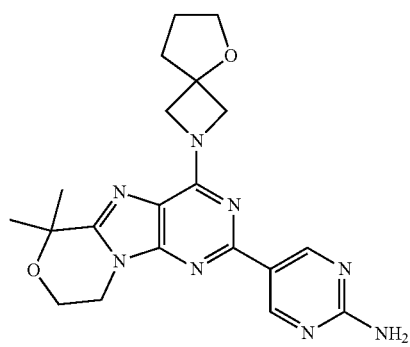
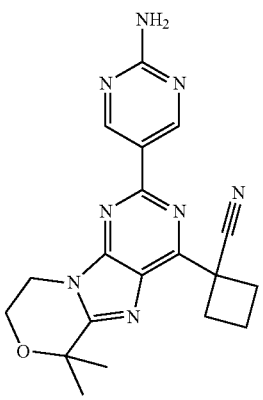
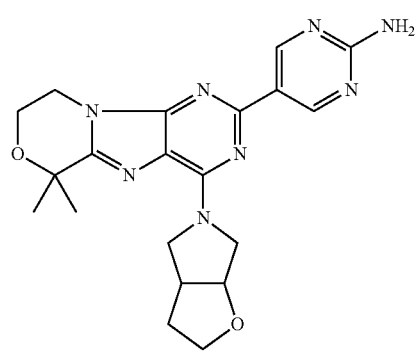
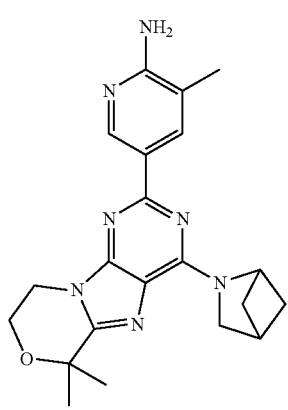
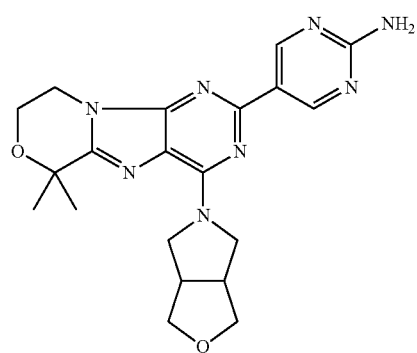
and

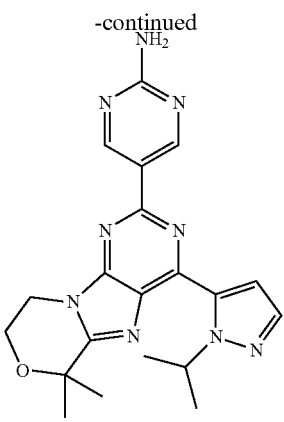

and salts thereof.

In certain embodiments the compound of formula (I) is a compound as described in the Examples herein, or a freebase or salt thereof.

Uses, Formulation and Administration

Pharmaceutically Acceptable Compositions

Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit DLK. In certain embodiments, the composition is formulated for administration to a patient in need thereof.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the composition comprising a compound of formula (I) or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragées, capsules, pills and granules of the compositions comprising a compound of formula (I) or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula (I) or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, and transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula (I) or salt thereof in the composition will also depend upon the particular compound in the composition.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds and compositions of the invention may be administered by any suitable means, including oral, topical (including buccal and sublingual), rectal, vaginal, transdermal, parenteral, subcutaneous, intraperitoneal, intrapulmonary, intradermal, intrathecal, epidural, intranasal, inhalation, via an implanted reservoir, and, if desired for local treatment, intralesional administration. Parenteral infusions include intramuscular, intravenous, intraarterial, intrasynovial, intrasternal, intrahepatic, intraperitoneal, intracranial, intracerebral, intraocular, intralesional or subcutaneous administration or infusion techniques.

The compositions comprising compounds of formula (I) any embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula (I) or any embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philidelphia, Pa.

Sustained-release preparations of a compound of the invention (e.g., compound of formula (I) or any embodiment thereof) can be prepared. Suitable examples of sustained-release preparations include semipermeable matrices of solid hydrophobic polymers containing a compound of formula (I) or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philidelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of formula (I) or any embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or an embodiment thereof is formulated in an acetate buffer, at pH 5. In another embodiment, the compounds of formula (I) or an embodiment thereof are sterile. The compound may be stored, for example, as a solid or amorphous composition, as a lyophilized formulation or as an aqueous solution.

Formulations of a compound of the invention (e.g., compound of formula (I) or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula (I) or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g., a phosphate buffer, adding a tonicifier, e.g., a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of formula (I) or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of formula (I)) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula (I) (or an embodiment thereof) to traverse the blood-brain barrier. Certain neurodegenerative diseases are associated with an increase in permeability of the blood-brain barrier, such that a compound of formula (I) (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula (I) (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula (I) (or an embodiment thereof) across the blood-brain barrier include, but are not limited to, encapsulating the a compound of formula (I) (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula (I) (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula (I) (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula (I) (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula (I) (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula (I) (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula (I) (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula (I) (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Indications and Methods of Treatment

In another aspect, the invention provides for methods of inhibiting the Dual Leucine Zipper Kinase (DLK) in an in vitro (e.g., a nerve graft or nerve transplant) or in vivo setting (e.g., in a patient) by contacting DLK present in an in vitro or in vivo setting with compounds of formula (I) or an embodiment thereof. In these methods of the invention, the inhibition of DLK signaling or expression with a compound of formula (I) or an embodiment thereof results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering one or more compounds of formula (I) or an embodiment thereof according to the methods of the invention can result in decrease in activity of kinase targets downstream of the DLK signalling cascade, e.g, (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compounds of the invention can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS dementia complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal deatchments, severe chemical burns of the eye, and iris atrophy.

Examples of types of pain that can be treated according to the methods of the invention include those associated with the following conditions: chronic pain, fibromyalgia, spinal pain, carpal tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine. Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells in vitro.

Accordingly, in another aspect, the invention provides for a method for inhibiting or preventing degeneration of a central nervous system (CNS) neuron or a portion thereof, the method comprising administering to the CNS neuron a compound of formula (I) or an embodiment thereof.

In one embodiment, of the method for inhibiting or preventing degeneration of a central nervous system neuron or a portion thereof, the administering to the CNS neuron is performed in vitro.

In another embodiment, of the method for inhibiting or preventing degeneration of a central nervous system neuron or a portion thereof, the method further comprises grafting or implanting the CNS neuron into a human patient after administration of the agent.

In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of said compound of formula (I) or an embodiment thereof in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits comprising combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the invention includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

EXEMPLIFICATION

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interferring groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated $CDCl_3$, $d_6$-DMSO, $CH_3OD$ or $d_6$-acetone solutions (reported in ppm), using tetramethylsilane (TMS) as the reference standard (0 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography—Mass Spectrometry (LCMS) experiments to performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute to determine retention times ($R_T$) and associated mass ions.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming feature ChemBioDraw Version 11.0 or from Accelrys' Pipeline Pilot IUPAC compound naming program.

Preparative Examples The following Preparative Examples illustrate the preparation of intermediate compounds that are useful for preparing compounds of formula (I). The novel intermediate compounds described herein, as well as the synthetic processes useful for preparing the intermediate compounds represent embodiments of the current invention.

Preparative Example 1

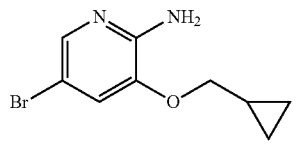 [SMILES: Nc1ncc(Br)cc1OCC1CC1]

Step 1:
5-bromo-3-(cyclopropylmethoxy)pyridin-2-amine

To a stirred solution of 2-amino-5-bromopyridine-3-ol (25 g, 132.9 mmol) in dichloromethane (150 mL) was added (bromomethyl)cyclopropane (35.88 g, 265.8 mmol), aliquat (7.5 g) and 40% aqueous sodium hydroxide (150 mL) at RT, followed by stirring for 16 h. The reaction mixture was diluted with water (500 mL) and extracted with dichloromethane (2×500 mL). The combined organic layers were concentrated to dryness in vacuo and the resulting residue was purified by column chromatography (silica gel, 100-200 mesh, 25% ethyl acetate in hexane) affording 5-bromo-3-(cyclopropylmethoxy)pyridin-2-amine as and off white solid (15 g, 47%): $^1$H NMR (300 MHz, DMSO-d6) δ 7.61 (s, 1H), 7.19 (s, 1H), 5.81 (s, 2H), 4-3.8 (m, 2H), 1.35-1.1 (m, 1H), 0.65-0.55 (m, 2H), 0.2-0.4 (m, 2H).

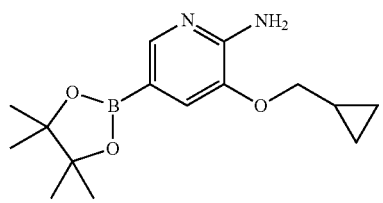 [SMILES: CC1(C)OB(c2cnc(N)c(OCC3CC3)c2)OC1(C)C]

Step 2: 3-(cyclopropylmethoxy)-5-(4,4,5,5-tetramethyl-1,3,2-dioxaborolan-2-yl)pyridin-2-amine To a stirred solution of 5-bromo-3-(cyclopropylmethoxy)pyridin-2-amine (10 g, 41.32 mmol) in 1,4-dioxane (120 mL) was added 4,4,4',4',5,5,5',5'-octamethyl-2,2'-bi(1,3,2-dioxaborolane) (11.54 g, 45.45 mmol), and potassium acetate (8.09 g, 82.64 mmol). The mixture was purged with argon gas for 15 min and tris(dibenzylideneacetone)dipalladium (756 mg, 0.82 mmol) and tricyclohexylphosphine (579 mg, 0.206 mmol) was added. The mixture was purged with argon gas for 15 min and the reaction mixture was stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-(cyclopropylmethoxy)-5-(4,4,5,5-tetramethyl-1,3,2-dioxaborolan-2-yl)pyridin-2-amine as a pale yellow solid (6.5 g, 54%): $^1$H NMR (300 MHz, DMSO-d6) δ 7.81 (s, 1H), 7.1 (s, 1H), 6 (s, 2H), 3.9-3.7 (m, 2H), 1.4-1.2 (m, 13H), 0.6-0.5 (m, 2H), 0.4-0.3 (m, 2H).

Preparative Example 2

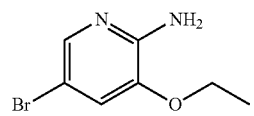

Step 1: 5-bromo-3-ethoxypyridin-2-amine

To a stirred solution of 2-amino-5-bromopyridine-3-ol (25 g, 132.9 mmol) in dichloromethane (150 mL) was added iodoethane (41.43 g, 265 mmol), aliquat (7.5 g) and 40% aqueous sodium hydroxide (150 mL) at RT, followed by stirring for 16 h. The reaction mixture was diluted with water (150 mL) and extracted with dichloromethane (2×300 mL). The combined organic layers were concentrated to dryness in vacuo and the resulting residue was purified by column chromatography (silica gel, 100-200 mesh, 20% ethyl acetate in hexane) affording 5-bromo-3-ethoxypyridin-2-amine as and off white solid (17 g, 59%): $^1$H NMR (300 MHz, DMSO-d6) δ 7.58 (s, 1H), 7.18 (s, 1H), 5.85 (s, 2H), 4.2-3.8 (m, 2H), 1.20-1.40 (m, 1H), 0.65-0.55 (m, 2H).

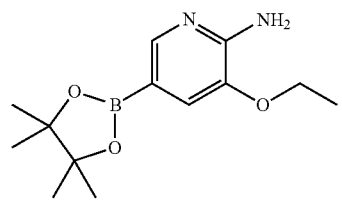 [SMILES: CCOc1cc(B2OC(C)(C)C(C)(C)O2)cnc1N]

Step 2: 3-ethoxy-5-(4,4,5,5-tetramethyl-1,3,2-dioxaborolan-2-yl)pyridin-2-amine

To a stirred solution of 5-bromo-3-ethoxypyridin-2-amine (12 g, 55.29 mmol) in 1,4-dioxane (120 mL) was added 4,4,4',4',5,5,5',5'-octamethyl-2,2'-bi(1,3,2-dioxaborolane) (15.44 g, 60.08 mmol), and potassium acetate (10.83 g, 110.58 mmol). The mixture was purged with argon gas for 15 min and tris(dibenzylideneacetone)dipalladium (1.0 g, 1.1 mmol) and tricyclohexylphosphine (775 mg, 2.76 mmol) was added. The mixture was purged with argon gas for 15 min and the reaction mixture was stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-(cyclopropylmethoxy)-5-(4,4,5,5-tetramethyl-1,3,2-dioxaborolan-2-yl)pyridin-2-amine as a of white solid (7.5 g, 51%): ¹H NMR (300 MHz, DMSO-d6) δ 7.80 (s, 1H), 7.0 (s, 1H), 6.05 (s, 2H), 4.1-3.9 (m, 2H), 1.4-1.2 (m, 15H).

Preparative Example 3

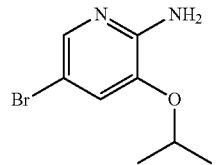

Step 1: 5-bromo-3-isopropoxypyridin-2-amine

To a stirred solution of 2-amino-5-bromopyridine-3-ol (25 g, 132.9 mmol) in dichloromethane (150 mL) was added 2-iodo-propane (45.15 g, 265.8 mmol), aliquat (7.5 g) and 40% aqueous sodium hydroxide (500 mL) at RT, followed by stirring for 16 h. The reaction mixture was diluted with water (150 mL) and extracted with dichloromethane (2×250 mL). The combined organic layers were concentrated to dryness in vacuo and the resulting residue was purified by column chromatography (silica gel, 100-200 mesh, 20% ethyl acetate in hexane) affording 5-bromo-3-isopropoxy-pyridin-2-amine as a pale yellow solid (15 g, 49%): ¹H NMR (300 MHz, Chloroform-d) δ 7.7 (s, 1H), 7.0 (s, 1H), 4.80-4.60 (s, 2H), 4.58-4.4 (m, 1H), 1.35 (s, 1H).

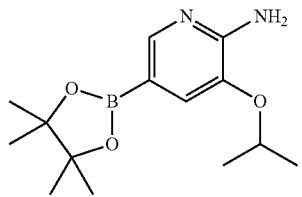 [SMILES: CC(C)Oc1cc(B2OC(C)(C)C(C)(C)O2)cnc1N]

Step 2: 3-isopropoxy-5-(4,4,5,5-tetramethyl-1,3,2-dioxaborolan-2-yl)pyridin-2-amine To a stirred solution of 5-bromo-3-isopropoxypyridin-2-amine (10 g, 43.29 mmol) in 1,4-dioxane (120 mL) was added 4,4,4',4',5,5,5',5'-octamethyl-2,2'-bi(1,3,2-dioxaborolane) (12.09 g, 47.61 mmol), and potassium acetate (8.48 g, 86.58 mmol). The mixture was purged with argon gas for 15 min and tris(dibenzylideneacetone)dipalladium (792 mg, 0.865 mmol) and tricyclohexylphosphine (605 mg, 2.16 mmol) was added. The mixture was purged with argon gas for 15 min, the reaction mixture was sealed and stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-isopropoxy-5-(4,4,5,5-tetramethyl-1,3,2-dioxaborolan-2-yl)pyridin-2-amine as a pale yellow solid (6 g, 50%): ¹H NMR (300 MHz, DMSO-d6) δ 7.80 (s, 1H), 7.0 (s, 1H), 6.0 (s, 2H), 4.6-4.4 (m, 1H), 1.4-1.2 (m, 18H).

Preparative Example 4

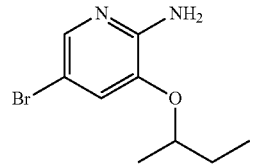

Step 1: 5-bromo-3-(sec-butoxy)pyridin-2-amine

To a stirred solution of 2-amino-5-bromopyridine-3-ol (25 g, 132.9 mmol) in dichloromethane (150 mL) was added 2-bromo butane (36.4 g, 265.8 mmol), aliquat (7.5 g) and 40% aqueous sodium hydroxide (500 mL) at RT, followed by stirring for 16 h. The reaction mixture was diluted with water (150 mL) and extracted with dichloromethane (2×250 mL). The combined organic layers were concentrated to dryness in vacuo and the resulting residue was purified by column chromatography (silica gel, 100-200 mesh, 20% ethyl acetate in hexane) affording 5-bromo-3-isopropoxy-pyridin-2-amine as a pale yellow solid (10 g, 30%): ¹H NMR (300 MHz, DMSO-d6) δ 7.58 (s, 1H), 7.2 (s, 1H), 5.80 (s, 2H), 4.50-4.30 (m, 1H), 1.80-1.40 (m, 2H), 1.30-1.15 (m, 3H), 1.0-0.8 (m, 3H).

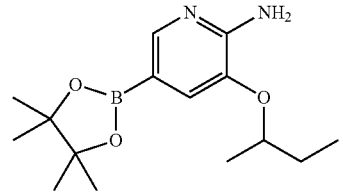 [SMILES: CCC(C)Oc1cc(B2OC(C)(C)C(C)(C)O2)cnc1N]

Step 2: 3-(sec-butoxy)-5-(4,4,5,5-tetramethyl-1,3,2-dioxaborolan-2-yl)pyridin-2-amine To a stirred solution of 5-bromo-3-(sec-butoxy)pyridin-2-amine (10 g, 40.98 mmol) in 1,4-dioxane (120 mL) was added 4,4,4',4',5,5,5',5'-octamethyl-2,2'-bi(1,3,2-dioxaborolane) (11.44 g, 45.08 mmol) and potassium acetate (8.03 g, 81.96 mmol). The mixture was purged with argon gas for 15 min and tris(dibenzylideneacetone)dipalladium (8.03 g, 81.96 mmol) and tricyclohexylphosphine (574 mg, 2.04 mmol) were added. The mixture was purged with argon gas for 15 min, the reaction mixture was sealed and stirred at 110° C. for 14 h. The reaction mixture was filtered through celite bed and washed with ethyl acetate (500 mL). The filtrate was concentrated to dryness in vacuo and the crude was crystallized (1:3, ethanol:water). The resulting solid was filtered and triturated with hexane, filtered and dried affording 3-isopropoxy-5-(4,4,5,5-tetramethyl-1,3,2-dioxaborolan-2-yl)pyridin-2-amine as a pale yellow solid (6.5 g, 54%): ¹H NMR (300 MHz, DMSO-d6) δ 7.80 (s, 1H), 7.0 (s, 1H), 6.0 (s, 2H), 4.2-4.4 (m, 1H), 1.8-1.5 (m, 2H), 1.4-1.15 (m, 15), 1.00-0.80 (m, 3).

Preparative Example 5

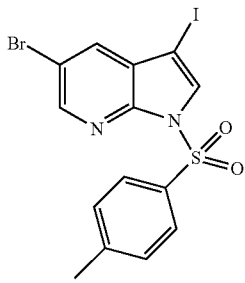 [SMILES: Cc1ccc(S(=O)(=O)n2cc(I)c3cc(Br)cnc32)cc1]

Step 1: 5-bromo-3-iodo-1-tosyl-1H-pyrrolo[2,3-b]pyridine

A stirred solution of sodium hydride (14.4 g, 0.36 mol) in tetrahydrofuran (800 mL) was added 5-bromo-3-iodo-1H-pyrrolo[2,3-b]pyridine (60 g, 0.186 mol) at 0° C. The reaction mixture was stirred for 0.5 h, 4-toluenesulfonyl chloride was added at 0° C., warmed to RT and stirred for 1 h. The reaction mixture was poured into ice water, the solid was filtered, washed with water, acetone and dried to give 5-bromo-3-iodo-1-tosyl-1H-pyrrolo[2,3-b]pyridine as a light yellow solid. (79 g, 88.8%): $^1$H NMR (DMSO-d6, 400 MHz): δ 8.642-8.647 (d, J=2 Hz, 1H), 8.375 (s, 1H), 8.158 (s, 1H), 8.119-8.124 (d, J=2 Hz, 2H), 7.559-7.579 (d, J=8 Hz, 2H), 2.654 (s, 3H).

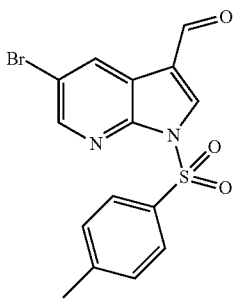 [SMILES: Cc1ccc(S(=O)(=O)n2cc(C=O)c3cc(Br)cnc32)cc1]

Step 2: 5-bromo-1-tosyl-1H-pyrrolo[2,3-b]pyridine-3-carbaldehyde

To a stirred solution of 5-bromo-3-iodo-1-tosyl-1H-pyrrolo[2,3-b]pyridine 3 (45 g, 0.094 mol) in tetrahydrofuran (600 mL), isopropylmagnesium bromide (103.75 mL, 0.103 mol) was added dropwise at 0° C. and the mixture was stirred for 0.5 h. N,N-dimethylformamide was added and stirred at RT for 2 h. The reaction was quenched with aqueous ammonium chloride, extracted with (3×1000 mL). The combined organic layers were washed with brine, dried over sodium sulfate and concentrated to dryness in vacuo. The resulting residue was purified by column chromatography (silica gel, 9% to 50% ethyl acetate in petroleum ether) affording 5-bromo-1-tosyl-1H-pyrrolo[2,3-b]pyridine-3-carbaldehyde as a white solid (48 g, 67.1%): $^1$H NMR (400 MHz, Chloroform-d): δ 10.010 (s, 1H), 8.665 (s, 1H), 8.518 (s, 1H), 8.379 (s, 1H), 8.114-8.135 (d, J=8.4 Hz, 2H), 7.330-7.351 (d, J=8.4 Hz, 2H), 2.170 (s, 3H).

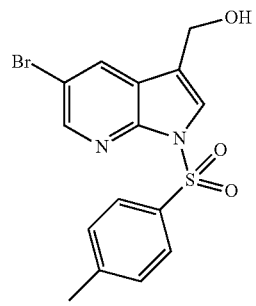 [SMILES: Cc1ccc(S(=O)(=O)n2cc(CO)c3cc(Br)cnc32)cc1]

Step 3: (5-bromo-1-tosyl-1H-pyrrolo[2,3-b]pyridin-3-yl)methanol

To a solution of 5-bromo-1-tosyl-1H-pyrrolo[2,3-b]pyridine-3-carbaldehyde (45 g, 0.12 mol) in methanol (600 mL) was added sodium borohydride at 0° C., and the mixture was stirred at RT overnight. The reaction mixture was quenched with aqueous ammonium chloride, and extracted with ethyl acetate (3×1000 mL). The combined organic layers were washed with brine, dried over sodium sulfate and concentrated to dryness in vacuo affording (5-bromo-1-tosyl-1H-pyrrolo[2,3-b]pyridin-3-yl)methanol as a white solid. (45 g, 99.5%): $^1$H NMR (400 MHz, Chloroform-d): δ 8.443-8.449 (d, J=2.4 Hz, 1H), 8.096 (s, 1H), 8.018-8.040 (d, J=8.8 Hz, 2H), 7.687 (s, 1H), 7.258-7.282 (d, J=8.8 Hz, 2H), 4.776-4.789 (d, J=5.2 Hz, 2H), 2.373 (s, 3H).

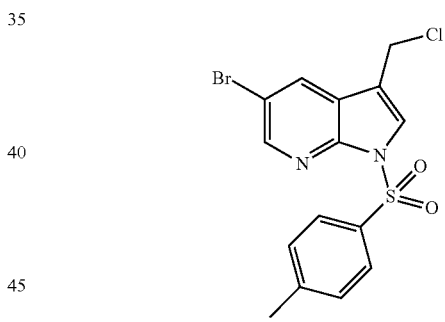

Step 4: 5-bromo-3-(chloromethyl)-1-tosyl-1H-pyrrolo[2,3-b]pyridine

To a solution of (5-bromo-1-tosyl-1H-pyrrolo[2,3-b]pyridin-3-yl)methanol (45 g, 0.12 mol) in dichloromethane (500 mL), thionyl chloride (28.1 g, 0.24 mol) was added at 0° C. and the mixture was stirred at RT for 0.5 h. The reaction mixture was quenched with water and adjusted to pH 8 with aqueous sodium carbonate. The resulting mixture was extracted with dichloromethane (3×800 mL). The combined organic layers were washed with brine, dried over sodium sulfate and concentrated to dryness in vacuo affording 5-bromo-3-(chloromethyl)-1-tosyl-1H-pyrrolo[2,3-b]pyridine as a white solid (47 g, 100%): $^1$H NMR (400 MHz, Chloroform-d), δ 8.471-8.477 (d, J=2.4 Hz, 1H), 8.101 (s, 1H), 8.044-8.065 (d, J=8.4 Hz, 2H), 7.765 (s, 1H), 7.283-7.303 (d, J=8.4 Hz, 2H), 4.680 (s, 2H), 2.383 (s, 3H).

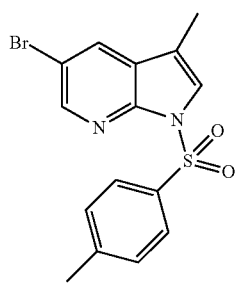 [SMILES: Cc1ccc(S(=O)(=O)n2cc(C)c3cc(Br)cnc32)cc1]

Step 5: 5-bromo-3-methyl-1-tosyl-1H-pyrrolo[2,3-b]pyridine

To a solution of 5-bromo-3-(chloromethyl)-1-tosyl-1H-pyrrolo[2,3-b]pyridine (47 g, 0.12 mol) in dimethyl sulfoxide (400 mL) was added sodium borohydride (8.97 g, 0.24 mol) and the mixture was stirred at 50° C. for 2 h. The reaction mixture was quenched with water and extracted with ethyl acetate (3×800 mL). The combined organic layers were washed with brine, dried over sodium sulfate and concentrated to dryness in vacuo. The resulting crude product was washed with ethyl acetate affording 5-bromo-3-methyl-1-tosyl-1H-pyrrolo[2,3-b]pyridine (35 g, 81.4%) as a white solid: $^1$H NMR (400 MHz, Chloroform-d), δ 8.424-8.429 (d, J=2 Hz, 1H), 7.995-8.016 (d, J=8.4 Hz, 2H), 7.889 (s, 1H), 7.477 (s, 1H), 7.248-7.260 (d, J=4.8 Hz, 2H), 2.366 (s, 3H), 2.217 (s, 3H).

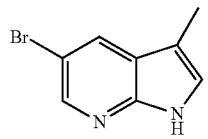

Step 6: 5-bromo-3-methyl-1H-pyrrolo[2,3-b]pyridine

To a solution of 5-bromo-3-methyl-1-tosyl-1H-pyrrolo[2,3-b]pyridine (35 g, 96.2 mmol) in methanol (200 mL) was added a solution of 6N sodium hydroxide (200 mL) and the mixture was heated at reflux for 2 h. The reaction mixture was concentrated in vacuo to remove methanol and adjusted to pH 7 with citric acid. The resulting solid was filtered, washed with water, dried to afford 5-bromo-3-methyl-1H-pyrrolo[2,3-b]pyridine as a yellow solid (20 g, 98.5%): $^1$H NMR (400 MHz, DMSO-d6), δ 11.462 (s, 1H), 8.134 (s, 1H), 8.045 (s, 1H), 7.210 (s, 1H), 2.135 (s, 3H).

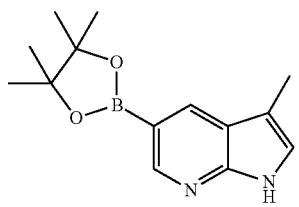 [SMILES: Cc1c[nH]c2ncc(B3OC(C)(C)C(C)(C)O3)cc12]

Step 7: 3-methyl-5-(4,4,5,5-tetramethyl-1,3,2-dioxaborolan-2-yl)-1H-pyrrolo[2,3-b]pyridine To a solution of 5-bromo-3-methyl-1H-pyrrolo[2,3-b]pyridine (20 g, 94.8 mmol) in N,N-dimethylformamide (200 mL) was added potassium acetate (27.9 g, 284.4 mmol) and 4,4,4',4',5,5,5',5'-octamethyl-2,2'-bi(1,3,2-dioxaborolane) (28.8 g, 113.74 mmol). The resulting mixture was degassed with nitrogen for 5 min, 1,1'-Bis(diphenylphosphino)ferrocene-palladium(II)dichloride (6.65 g, 9.48 mmol) was added and the mixture was degassed with nitrogen once more for 5 min. The reaction mixture was stirred overnight at 80-90° C. The reaction mixture was poured into water, extracted with (3×200 mL). The combined organic layers were washed with brine, dried over sodium sulfate and concentrated to dryness in vacuo. The resulting residue was purified by column chromatography (silica gel, 100-200 mesh, 9% to 50% ethyl acetate in petroleum ether) affording 3-methyl-5-(4,4,5,5-tetramethyl-1,3,2-dioxaborolan-2-yl)-1H-pyrrolo[2,3-b]pyridine as a white solid (10.5 g, 43%): $^1$H NMR (400 MHz, DMSO-d6), δ 11.360 (s, 1H), 8.371-8.375 (d, J=1.6 Hz, 1H), 8.097-8.100 (s, J=1.2 Hz, 2H), 7.17 (s, 1H), 3.296 (s, 3H), 1.245 (s, 12H).

Preparative Example 6

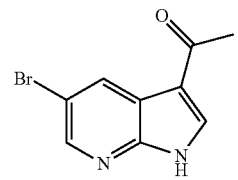

Step 1: 1-(5-bromo-1H-pyrrolo[2,3-b]pyridin-3-yl)ethanone

To a solution of 5-bromo-1H-pyrrolo[2,3-b]pyridine (30 g, 0.15 mol) and aluminium chloride (100 g, 0.75 mol) in dichloromethane (2000 mL) was added dropwise acetyl chloride (102 mL, 1.44 mol) over 1 h under nitrogen atmosphere at 0° C. The reaction mixture was warmed to RT and stirred overnight. Methanol (150 mL) was added dropwise at 0° C., and the resulting mixture was concentrated to dryness in vacuo. The resulting crude was dissolved in ice-water, basified with saturated sodium bicarbonate to pH 4-5 and extracted with ethyl acetated (3×3000 mL). The combined organic layer were washed with brine, dried over sodium sulfate and concentrated to dryness in vacuo affording crude 1-(5-bromo-1H-pyrrolo[2,3-b]pyridin-3-yl)ethanone as a yellow solid (330 g, 93% after 10 batch repeat) used for the next step without any further purification: $^1$H NMR (DMSO, 400 MHz): δ 12.675 (s, 1H), 8.537-8.543 (d, J=2.4 Hz, 1H), 8.506 (s, 1H), 8.371-8.377 (d, J=2.4 Hz, 1H), 2.445 (s, 3H).

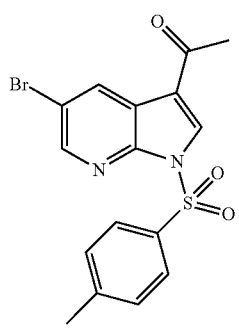 [SMILES: CC(=O)c1cn(S(=O)(=O)c2ccc(C)cc2)c2ncc(Br)cc12]

Step 2: 1-(5-bromo-1-tosyl-1H-pyrrolo[2,3-b]pyridin-3-yl)ethanone

To a solution of 1-(5-bromo-1H-pyrrolo[2,3-b]pyridin-3-yl)ethanone (50 g, 0.21 mol) in tetrahydrofuran (1400 mL) was added sodium hydride (8.8 g, 0.22 mol, 60%) at 0° C. After the mixture was stirred for 1 h at 0° C. a solution of 4-methylbenzene-1-sulfonyl chloride (48.3 g, 0.25 mol) in tetrahydrofuran (300 mL) was added dropwise at 0° C. The resulting mixture was warmed up to RT and stirred overnight. The reaction mixture was poured into ice water and extracted with ethyl acetate (3×1000 mL). The combined organic layers were washed with brine, dried over sodium sulfate and concentrated to dryness in vacuo affording crude 1-(5-bromo-1-tosyl-1H-pyrrolo[2,3-b]pyridin-3-yl)ethanone as yellow solid (75 g, yield: 90%), which was used for the next step without further purification: $^1$H NMR (400 MHz, DMSO-d6): δ 8.884 (s, 1H), 8.532-8.573 (m, 2H), 8.054-8.075 (d, J=12 Hz, 2H), 7.442-7.463 (d, J=8.4 Hz, 2H), 2.578 (s, 3H), 2.347 (s, 3H).

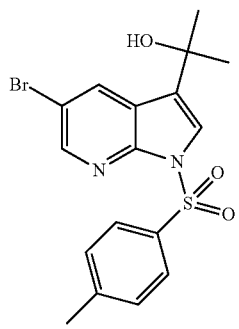 [SMILES: Cc1ccc(S(=O)(=O)n2cc(C(C)(C)O)c3cc(Br)cnc32)cc1]

Step 3: 2-(5-bromo-1-tosyl-1H-pyrrolo[2,3-b]pyridin-3-yl)propan-2-ol

To a solution of 1-(5-bromo-1-tosyl-1H-pyrrolo[2,3-b]pyridin-3-yl)ethanone (50 g, 0.13 mol) in tetrhydrofuran (1700 mL) was added dropwise methylmagnesium bromide (213 mL, 0.64 mol, 3M in ether) at 0° C. After addition the resulting mixture was stirred at 0° C. for 2 h. The mixture was poured into ice water and extracted with ethyl acetate (3×1000 mL). The combined organic layers were washed with brine, dried over sodium sulfate and concentrated to dryness in vacuo. The resulting residue was purified by column chromatography (silica gel, 100-200 mesh, 5% to 17% ethyl acetate in petroleum ether) affording 2-(5-bromo-1-tosyl-1H-pyrrolo[2,3-b]pyridin-3-yl)propan-2-ol as yellow solid (36 g, 69%). The yellow solid was used as is in the next step.

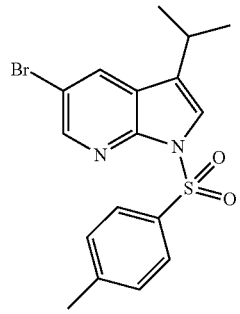 [SMILES: Cc1ccc(S(=O)(=O)n2cc(C(C)C)c3cc(Br)cnc32)cc1]

Step 4: 5-bromo-3-isopropyl-1-tosyl-1H-pyrrolo[2,3-b]pyridine

To a solution of 2-(5-bromo-1-tosyl-1H-pyrrolo[2,3-b]pyridin-3-yl)propan-2-ol (50 g, 0.122 mol) in dry dichloromethane (1000 mL) was added dropwise triethylsilane (42.6 g, 0.366 mol) and trifluoroacetic acid (71 g, 0.623 mol) at 0° C. The resulting mixture was warmed up to RT and stirred overnight. The mixture was poured into ice-water and basified with saturated sodium bicarbonate to pH 4~5 and extracted with dichloromethane (3×1000 mL). The combined organic layers were washed with brine, dried over sodium sulfate and concentrated to dryness in vacuo. The resulting residue was purified by column chromatography (silica gel, 100-200 mesh, 3% to 10% ethyl acetate in petroleum ether) affording 5-bromo-3-isopropyl-1-tosyl-1H-pyrrolo[2,3-b]pyridine (33.3 g, 69%): $^1$H NMR (400 MHz, Chloroform-d), δ 8.409-8.415 (d, J=2.4 Hz, 1H), 8.010-8.041 (m, 2H), 7.945-7.950 (d, J=2 Hz, 1H), 7.454-7.456 (d, J=0.8 Hz, 1H), 7.257-7.280 (m, 2H), 2.994-3.031 (m, 1H), 2.371 (s, 3H), 1.298-1.321 (dd, J=6.8 Hz, 6H).

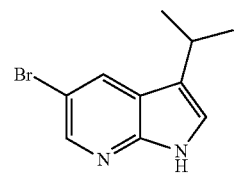

Step 5: 5-bromo-3-isopropyl-1H-pyrrolo[2,3-b]pyridine

To a solution of 5-bromo-3-isopropyl-1-tosyl-1H-pyrrolo[2,3-b]pyridine (30 g, 76.3 mmol) in methanol (1000 mL) was added a solution of 6N sodium hydroxide (600 mL) at RT. The resulting mixture was heated to reflux and stirred for 2 h. The mixture was concentrated in vacuo to remove methanol and residue was poured into ice water. The mixture was adjusted pH 5 by adding a saturated solution of critic acid and filtered. The filtered cake was dissolved in ethyl acetate, dried over sodium sulfate and concentrated to dryness in vacuo affording 5-bromo-3-isopropyl-1H-pyrrolo[2,3-b]pyridine (16.6 g, 91%), which was used for the next step without further purification.

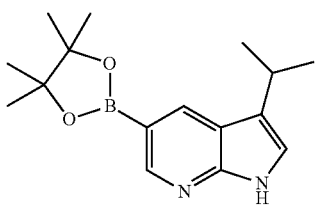 [SMILES: CC(C)c1c[nH]c2ncc(B3OC(C)(C)C(C)(C)O3)cc12]

Step 6: 3-isopropyl-5-(4,4,5,5-tetramethyl-1,3,2-dioxaborolan-2-yl)-1H-pyrrolo[2,3-b]pyridine To a solution of 5-bromo-3-isopropyl-1H-pyrrolo[2,3-b]pyridine (15 g, 62.7 mmol) in acetonitrile (350 mL) was added 4,4,4',4',5,5,5',5'-octamethyl-2,2'-bi(1,3,2-dioxaborolane) (20.6 g, 81.5 mmol), potassium acetate (30.7 g, 0.313 mol) and 1,1'-bis(diphenylphosphino)ferrocene-palladium (II)dichloride (3.75 g, 5.12 mmol) at ambient temperature under nitrogen atmosphere. The resulting mixture was heated to reflux under nitrogen atmosphere and stirred overnight. The resulting mixture was filtered and the filter cake was washed with ethyl acetate. The filtrate was concentrated to dryness in vacuo and the resulting residue was purified by column chromatography (silica gel, 100-200 mesh, 5% to 17% ethyl acetate in petroleum ether) affording 3-isopropyl-5-(4,4,5,5-tetramethyl-1,3,2-dioxaborolan-2-yl)-1H-pyrrolo[2,3-b]pyridine (12.2 g, yield: 33%, after 2 repeat batches): $^1$H NMR (400 MHz, Chloroform-d), δ: 10.500-11.100 (s, 1H), 8.702-8.709 (m, 1H), 8.401 (s, 1H), 7.097 (s, 1H), 3.211-3.212 (m, 1H), 1.359-1.391 (m, 18H).

Preparative Example 7

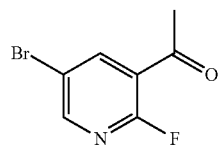

Step 1: 1-(5-bromo-2-fluoropyridin-3-yl)ethanone

To a solution of diisopropylamine (46.3 g, 458.4 mmol) in tetrahydrofuran (1000 mL) was added butyllithium (176 mL, 440 mmol, 2.5 M) at −78° C. under nitrogen. After addition, the reaction mixture was stirred for 30 min at −78° C. 5-bromo-2-fluoropyridine (86.7 g, 442.3 mmol) was added (keeping the temperature under −65° C.). After addition, the mixture was stirred for 1 h. N-methoxy-N-methylacetamide (50 g, 485.4 mmol) was added and stirred at −78° C. for 1 h. The reaction mixture was quenched with water (1000 mL), extracted with ethyl acetate (3×500 mL), washed with brine, dried over sodium sulfate and concentrated to dryness in vacuo. The resulting residue was purified by column chromatography (silica gel, 100-200 mesh, 0.5% ethyl acetate in petroleum ether) affording 1-(5-bromo-2-fluoropyridin-3-yl)ethanone (43 g, 44.6%): $^1$H NMR (400 MHz, Chloroform-d): δ 8.46-8.42 (m, 2H), 2.70 (s, 3H).

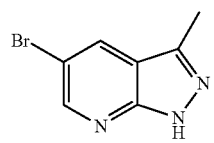

Step 2: 5-bromo-3-methyl-1H-pyrazolo[3,4-b]pyridine

To a solution of 1-(5-bromo-2-fluoropyridin-3-yl)ethanone (43 g, 197.2 mmol) in ethanol (500 mL) was added hydrazine monohydrate (34.8 g, 591.6 mmol, 85%) at RT. After addition, the reaction mixture was refluxed overnight. The reaction mixture was cooled to RT and concentrated to dryness in vacuo. The resulting residue was purified by column chromatography (silica gel, 100-200 mesh, 5% to 17% ethyl acetate in petroleum ether) affording 5-bromo-3-methyl-1H-pyrazolo[3,4-b]pyridine (35 g, 83.7%): $^1$H NMR (400 MHz, DMSO-d6): δ 13.42 (s, 1H), 8.51 (m, 2H), 2.54 (s, 3H).

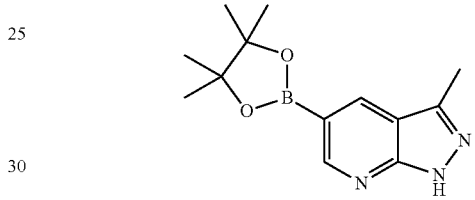

Step 3: 3-methyl-5-(4,4,5,5-tetramethyl-1,3,2-dioxaborolan-2-yl)-1H-pyrazolo[3,4-b]pyridine To a solution of 5-bromo-3-methyl-1H-pyrazolo[3,4-b]pyridine (25 g, 0.12 mol) in dimethylsulphoxide (500 mL) was added 4,4,4',4',5,5,5',5'-octamethyl-2,2'-bi(1,3,2-dioxaborolane) (46 g, 0.18 mmol) and potassium acetate (35.3 g, 0.36 mmol) and the mixture was degassed (3 times). To the reaction mixture was added 1,1'-bis(diphenylphosphino)ferrocene-palladium(II)dichloride (9.8 g, 0.012 mol) and the mixture was degassed (3 times). The reaction mixture was stirred at 100° C. under nitrogen for 4 h. The reaction mixture was cooled to RT and then poured in water (1000 mL) and ethyl acetate (500 mL). The bi-layered mixture was filtered through celite, the organic layer was washed with brine, dried over sodium sulfate and concentrated to dryness in vacuo. The resulting residue was purified by column chromatography (silica gel, 100-200 mesh, 5% to 6% ethyl acetate in petroleum ether) affording 3-methyl-5-(4,4,5,5-tetramethyl-1,3,2-dioxaborolan-2-yl)-1H-pyrazolo[3,4-b]pyridine (9 g, 28.95%): $^1$H NMR (400 MHz, Chloroform-d): δ 8.90 (s, 1H), 8.49 (s, 1H), 2.59 (s, 3H), 1.38 (s, 12H).

Preparative Example 8

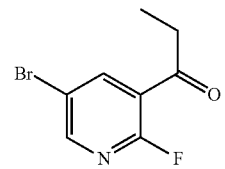

Step 1: 1-(5-bromo-2-fluoropyridin-3-yl)propan-1-one

To a solution of diisopropylamine (48.7 g, 482.1 mmol) in tetrahydrofuran (1000 mL) was added butyllithium (185.7 mL, 464.23 mmol, 2.5 M) at −78° C. under nitrogen. After addition, the reaction mixture was stirred for 30 min at −78° C. 5-bromo-2-fluoropyridine (70 g, 357.1 mmol) was added (keeping the temperature under −65° C.). After addition, the mixture was stirred for 1 h. N-methoxy-N-methylpropionamide (45.95 g, 392.8 mmol) was added and stirred at −78° C. for 1 h. The reaction mixture was quenched with water (1000 mL), extracted with ethyl acetate (3×500 mL), washed with brine, dried over sodium sulfate and concentrated to dryness in vacuo. The resulting residue was purified by column chromatography (silica gel, 100-200 mesh, 0.5% ethyl acetate in petroleum ether) affording 1-(5-bromo-2-fluoropyridin-3-yl)propan-1-one (36 g, 43.47%): $^1$H NMR (400 MHz, Chloroform-d): δ 8.42 (s, 2H), 3.04 (m, 2H), 1.23 (m. 3H).

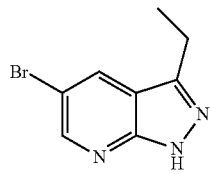

Step 2: 5-bromo-3-ethyl-1H-pyrazolo[3,4-b]pyridine

To a solution of 1-(5-bromo-2-fluoropyridin-3-yl)propan-1-one (36 g, 155.2 mmol) in ethanol (400 mL) was added hydrazine monohydrate (27.4 g, 456.8 mmol, 85%) at RT. After addition, the reaction mixture was refluxed overnight. The reaction mixture was cooled to RT and concentrated to dryness in vacuo. The resulting residue was purified by column chromatography (silica gel, 100-200 mesh, 5% to 17% ethyl acetate in petroleum ether) affording 5-bromo-3-ethyl-1H-pyrazolo[3,4-b]pyridine (27 g 77%): $^1$H NMR (400 MHz, Chloroform-d): δ 8.62 (s, 1H), 8.27 (s, 1H), 3.06-2.98 (m, 2H), 1.42 (m, 3H).

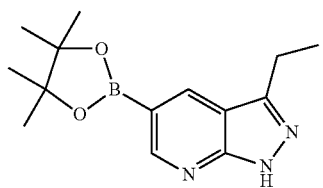 [SMILES: CCc1n[nH]c2ncc(B3OC(C)(C)C(C)(C)O3)cc12]

Step 3: 3-ethyl-5-(4,4,5,5-tetramethyl-1,3,2-dioxaborolan-2-yl)-1H-pyrazolo[3,4-b]pyridine To a solution of 5-bromo-3-ethyl-1H-pyrazolo[3,4-b]pyridine (27 g, 0.12 mol) in dimethylsulphoxide (500 mL) was added 4,4,4',4',5,5,5',5'-octamethyl-2,2'-bi(1,3,2-dioxaborolane) (46 g, 0.18 mmol) and potassium acetate (35.3 g, 0.36 mmol) and the mixture was degassed (3 times). To the reaction mixture was added 1,1'-bis(diphenylphosphino)ferrocene-palladium(II)dichloride (9.8 g, 0.012 mol) and the mixture was degassed (3 times). The reaction mixture was stirred at 100° C. under nitrogen for 4 h. The reaction mixture was cooled to RT and then poured in water (1000 mL) and ethyl acetate (500 mL). The bi-layered mixture was filtered through celite, the organic layer was washed with brine, dried over sodium sulfate and concentrated to dryness in vacuo. The resulting residue was purified by column chromatography (silica gel, 100-200 mesh, 5% to 6% ethyl acetate in petroleum ether) affording 3-ethyl-5-(4,4,5,5-tetramethyl-1,3,2-dioxaborolan-2-yl)-1H-pyrazolo[3,4-b]pyridine (13.4 g, 40.9%): $^1$H NMR (400 MHz, Chloroform-d): δ 8.96 (s, 1H), 8.52 (s, 1H), 3.05-3.00 (q, 2H), 1.45-1.41 (m, 3H) 1.38 (s, 12H).

Preparative Example 9

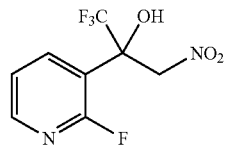 [SMILES: O=[N+]([O-])CC(O)(c1cccnc1F)C(F)(F)F]

Step 1: 1,1,1-trifluoro-2-(2-fluoropyridin-3-yl)-3-nitropropan-2-ol

To a solution of freshly prepared lithium diisopropylamide (42.5 g, 0.55 mol) in tetrahydrofuran (1200 mL) at −75° C. was added 2-fluoropyridine (45 g, 0.46 mol) and the mixture was stirred for 4 h at this temperature. To the resulting stirred suspension, ethyl trifluoroacetate (91.4 g, 0.64 mol) was added while ensuring the temperature did not rise above −45° C. The reaction mixture was warmed to RT., nitromethane (56.1 g, 0.92 mol) was added, and the reaction was stirred overnight. The solution was poured into 2N aqueous hydrochloric acid (6 L), and the mixture was extracted with ethyl acetate (3×500 mL). The combined organic layers were washed with brine, dried over sodium sulfate and concentrated to dryness in vacuo. The resulting residue was triturated with petroleum ether, and the product was collected by suction filtration to give 1,1,1-trifluoro-2-(2-fluoropyridin-3-yl)-3-nitropropan-2-ol (100 g, 85%): $^1$H NMR (400 MHz, DMSO-d6): δ 8.22-8.35 (m, 3H), 7.47-7.51 (m, 1H), 5.65 (d, J=13.2 Hz, 1H), 5.11 (d, J=13.2 Hz, 1H).

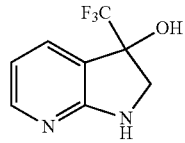 [SMILES: OC1(C(F)(F)F)CNc2ncccc21]

Step 2: 3-(trifluoromethyl)-2,3-dihydro-1H-pyrrolo[2,3-b]pyridin-3-ol 1,1,1-trifluoro-2-(2-fluoropyridin-3-yl)-3-nitropropan-2-ol (25 g, 98.4 mmol) was dissolved in ethanol (600 mL) and stirred under hydrogen (1 atm) with nickel catalyst (20 g). After theoretical consumption of hydrogen, the solution was filtered, the filtrate was refluxed for 48 h, triethylamine (11.5 g, 0.11 mol) was added, and reflux was continued overnight. The reaction mixture was allowed to cool and concentrated to dryness in vacuo. The resulting residue was dissolved in dichloromethane and washed with a solution of aqueous saturated sodium carbonate. The aqueous phase was extracted with dichloromethane (3×500 mL) and the combined organic layers were dried over sodium sulfate and concentrated to dryness in vacuo. The resulting residue was triturated with dichloromethane and the crystalline product was collected by suction filtration and washed with dichloromethane to give 3-(trifluoromethyl)-2,3-dihydro-1H-pyrrolo[2,3-b]pyridin-3-ol (15.4 g, 77%): $^1$H NMR (400 MHz, Chloroform-d): δ 7.98 (s, 1H), 7.62 (s, 1H), 6.65 (s, 1H), 4.74 (s, 1H), 3.91-3.95 (m, 1H), 3.65 (d, J=3.2 Hz, 1H).

Step 3: 3-(trifluoromethyl)-1H-pyrrolo[2,3-b]pyridine

To a solution of 3-(trifluoromethyl)-2,3-dihydro-1H-pyrrolo[2,3-b]pyridin-3-ol (84 g, 0.411 mol) in dichloromethane (1500 mL) was added pyridine (32.4 g, 0.82 mmol), thionyl chloride (97.5 g, 0.82 mmol) and the reaction was stirred for 2 h. Ice was added and the reaction was neutralized to pH 5.7 with aqueous sodium hydroxide solution. The mixture was extracted with dichloromethane (2×500 mL), the combined organic layers were washed with water, dried over sodium sulfate and concentrated to dryness in vacuo to yield tan crystals. The crude product was triturated with petroleum ether for 15 min, and the crystals were collected by suction filtration affording 3-(trifluoromethyl)-1H-pyrrolo[2,3-b]pyridine (65 g, 80%): $^1$H NMR (400 MHz, Chloroform-d), δ12.52 (s, 1H), 8.43 (t, J=3.6 Hz, 1H), 8.12-8.14 (m, 1H), 7.77 (s, 1H), 7.24-7.27 (m, 1H).

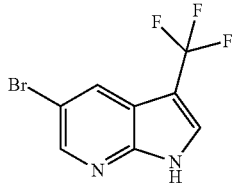 [SMILES: FC(F)(F)c1c[nH]c2ncc(Br)cc12]

Step 4: 5-bromo-3-(trifluoromethyl)-1H-pyrrolo[2,3-b]pyridine

To dry dichloromethane (200 mL) cooled to −5° C. was added dropwise bromine (36.2 g, 0.2 mol) over a period of 1 h. After a solution of 3-(trifluoromethyl)-1H-pyrrolo[2,3-b]pyridine (25 g, 0.13 mol) and pyridine (17 mL) in dichloromethane (500 mL) was added dropwise and the reaction mixture was stirred 0° C. for 45 min. The reaction mixture was poured into saturated aqueous sodium bicarbonate and sodium thiosulfate, extracted with ethyl acetate (3×1000 mL), the organic layer was washed with brine, dried over sodium sulfate, and concentrated to dryness in vacuo. The resulting residue was re-crystallized (8:1, ethyl acetate: petroleum ether) to afford 5-bromo-3-(trifluoromethyl)-1H-pyrrolo[2,3-b]pyridine (7.55 g, 21%): $^1$H NMR (400 MHz, DMSO-d6), δ12.76 (s, 1H), 8.44 (s, 1H), 8.23 (m, 2H).

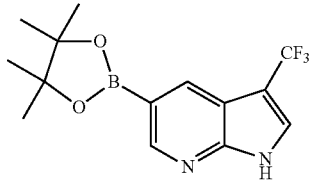 [SMILES: CC1(C)OB(c2cnc3[nH]cc(C(F)(F)F)c3c2)OC1(C)C]

Step 5: 5-(4,4,5,5-tetramethyl-1,3,2-dioxaborolan-2-yl)-3-(trifluoromethyl)-1H-pyrrolo[2,3-b]pyridine To a solution of 5-bromo-3-(trifluoromethyl)-1H-pyrrolo[2,3-b]pyridine (19 g, 72.3 mmol) in 1,4-dioxane (400 mL) was added potassium acetate (21.27 g, 220 mmol) and 4,4,4',4',5,5,5',5'-octamethyl-2,2'-bi(1,3,2-dioxaborolane) (21.9 g, 86.7 mmol). The resulting mixture was degassed with nitrogen for 5 times, 1,1'-bis(diphenylphosphino)ferrocene-palladium(II)dichloride (5.3 g, 7.23 mmol) was added and the mixture was degassed again. The reaction mixture was stirred at 80-90° C. and overnight. The reaction mixture was poured into water, extracted with ethyl acetate (3×500 mL), washed with brine, dried over sodium sulphate and concentrated to dryness in vacuo. The resulting residue was purified by column chromatography (silica gel, 100-200 mesh, 10% to 20% ethyl acetate in petroleum ether) affording 5-(4,4,5,5-tetramethyl-1,3,2-dioxaborolan-2-yl)-3-(trifluoromethyl)-1H-pyrrolo[2,3-b]pyridine (11.1 g, 49%): $^1$H NMR (400 MHz, DMSO-d6), δ12.62 (s, 1H), 8.58 (s, 1H), 8.21 (s, 1H), 8.18 (s, 1H), 1.31 (s, 12H).

Preparative Example 10

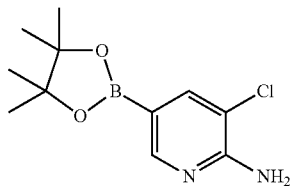 [SMILES: CC1(C)OB(c2cnc(N)c(Cl)c2)OC1(C)C]

Step 1: 3-chloro-5-(4,4,5,5-tetramethyl-1,3,2-dioxaborolan-2-yl)pyridin-2-amine

To a solution of 5-bromo-3-chloro-pyridin-2-ylamine (2.0 g, 9.64 mmol) in 1,4-dioxane (20 mL) were added 4,4,4',4',5,5,5',5'-octamethyl-2,2'-bi(1,3,2-dioxaborolane) (2.94 g, 11.57 mmol), potassium acetate (2.84 g, 28.92 mmol) and 1,1'-bis(diphenylphosphino)ferrocene-palladium(II)dichloride (705 mg, 0.96 mmol). The reaction mixture was purged with nitrogen for 2 min and heated to 100° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in hexane) affording 3-chloro-5-(4,4,5,5-tetramethyl-1,3,2-dioxaborolan-2-yl)pyridin-2-amine (2.0 g, 84%): $^1$H NMR (400 MHz, Chloroform-d) δ 8.32 (d, J=1.6 Hz, 1H), 7.84 (d, J=1.6 Hz, 1H), 5.09 (s, 2H), 1.32 (s, 12H).

Preparative Example 11

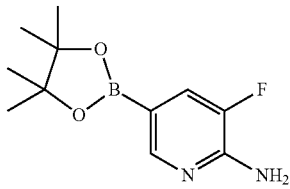

Step 1: 3-fluoro-5-(4,4,5,5-tetramethyl-1,3,2-dioxaborolan-2-yl)pyridin-2-amine

To a solution of 5-bromo-3-fluoro-pyridin-2-ylamine (1.9 g, 9.95 mmol) in 1,4-dioxane (20 mL) were added 4,4,4',4',5,5,5',5'-octamethyl-2,2'-bi(1,3,2-dioxaborolane) (3.03 g, 11.94 mmol), potassium acetate (2.93 g, 29.84 mmol) and 1,1'-bis(diphenylphosphino)ferrocene-palladium(II)dichloride (728 mg, 0.99 mmol). The reaction mixture was purged with nitrogen for 2 min and heated to 100° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in hexane) affording 3-fluoro-5-(4,4,5,5-tetramethyl-1,3,2-dioxaborolan-2-yl)pyridin-2-amine (2.0 g, 84%): $^1$H NMR (400 MHz, Chloroform-d) δ 8.20 (t, J=1.2 Hz, 1H), 7.84 (dd, J=11.2 Hz 1.2 Hz, 1H), 4.89 (s, 2H), 1.32 (s, 12H).

Preparative Example 12

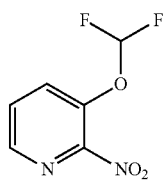

Step 1: 3-(difluoromethoxy)-2-nitropyridine

To a stirred solution of 2-nitropyridin-3-ol (5 g, 35.69 mmol) and sodium 2,2-dichloro-2-fluoroacetate (8.16 g, 53.53 mmol) in N,N-dimethylmethanamide (20 mL) and water (15 mL) was added potassium carbonate (9.86 g, 71.38 mmol) slowly. The reaction mixture was heated to 105° C. for 20 h. After cooling down the reaction mixture was diluted with water (150 mL), and the mixture was extracted with ethyl acetate (3×50 mL). The combined organic layers were dried over sodium sulfate and concentrated to dryness in vacuo affording 3-(difluoromethoxy)-2-nitropyridine (5 g, 74%). The residue was used in next step directly without further purification. $^1$H NMR (400 MHz, DMSO-d6) δ 8.48 (dd, J$_1$=4.4 Hz, J$_2$=1.2 Hz, 1H), 8.18 (dd, J$_1$=4.4 Hz, J$_2$=0.8 Hz, 1H), 7.95-7.91 (m, 1H), 7.45 (t, J=72.0 Hz, 1H).

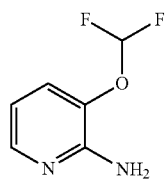 [SMILES: O=[N+]([O-])c1ncccc1OC(F)F]

Step 2: 3-(difluoromethoxy)pyridin-2-amine

To a stirred solution of 3-(difluoromethoxy)-2-nitropyridine (5 g, 2.63 mmol) and ammonium chloride (4.22 g, 78.9 mmol) in ethanol (40 mL) and water (30 mL) was added iron powder (7.34 g, 131.51 mmol). The reaction mixture was heated to 90° C. for 1 h. After cooling down the reaction mixture was filtered and the solid was washed with ethyl acetate. The mother liquid was concentrated to dryness in vacuo. The residue was diluted with water and extracted with ethyl acetate (3×70 mL). The combined organic layers were dried over sodium sulfate and concentrated to dryness in vacuo affording 3-(difluoromethoxy)pyridin-2-amine (2.3 g, 55%). The residue was used in next step directly without further purification. $^1$H NMR (400 MHz, DMSO-d6) δ 7.90 (dd, J$_1$=4.8 Hz, J$_2$=1.6 Hz, 1H), 7.28 (dd, J$_1$=8.0 Hz, J$_2$=0.8 Hz, 1H), 7.07 (t, J=74.0 Hz, 1H), 6.53 (dd, J$_1$=8.0 Hz, J$_2$=0.8 Hz, 1H), 6.01 (s, 2H).

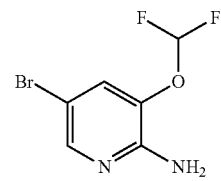 [SMILES: Nc1ncc(Br)cc1OC(F)F]

Step 3: 5-bromo-3-(difluoromethoxy)pyridin-2-amine

To a solution of 3-(difluoromethoxy)pyridin-2-amine (2.3 g, 14.36 mmol) in acetonitrile (15 mL) was added N-bromosuccinimide (2.61 g, 14.65 mmol) over 3 min at 0° C. The reaction mixture was stirred at the same temperature for another 20 min and subsequently concentrated to dryness in vacuo. The resulting viscous mass was diluted with water and extracted with ethyl acetate (3×60 mL). The combined organic layers were dried over sodium sulfate and concentrated to dryness in vacuo. The resulting residue was purified by column chromatography (silica gel, 100-200 mesh, 20% ethyl acetate in hexane) affording 5-bromo-3-(difluoromethoxy)pyridin-2-amine (3.2 g, 93%): $^1$H NMR (400 MHz, DMSO-d6) δ 7.89 (s, 1H), 7.51 (s, 1H), 7.16 (t, J=73.6 Hz, 1H), 6.34 (s, 2H).

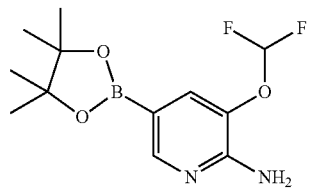 [SMILES: CC1(C)OB(c2cnc(N)c(OC(F)F)c2)OC1(C)C]

Step 4: 3-(difluoromethoxy)-5-(4,4,5,5-tetramethyl-1,3,2-dioxaborolan-2-yl)pyridin-2-amine To a solution of 5-bromo-3-(difluoromethoxy)pyridin-2-amine (3.2 g, 13.39 mmol) in 1,4-dioxane (60 mL) were added 4,4,4',4',5,5,5',5'-octamethyl-2,2'-bi(1,3,2-dioxaborolane) (3.74 g, 14.73 mmol), tricyclohexylphosphine (525 mg, 1.87 mmol), potassium acetate (3.28 g, 33.47 mmol) and tris(dibenzylideneacetone)dipalladium(0) (490 mg, 0.53 mmol). The reaction mixture was purged with nitrogen for 2 min and heated to 110° C. for 16 h and subsequently concentrated to dryness in vacuo. The resulting viscous mass was diluted with water and extracted with ethyl acetate (3×75 mL). The combined organic layers were dried over sodium sulfate and concentrated to dryness in vacuo. The resulting residue was purified by column chromatography (silica gel, 100-200 mesh, 25% ethyl acetate in hexane) affording 3-(difluoromethoxy)-5-(4,4,5,5-tetramethyl-1,3,2-dioxaborolan-2-yl)pyridin-2-amine (1.3 g, 34%): $^1$H NMR (400 MHz, DMSO-d6) δ 8.03 (s, 1H), 7.33 (s, 1H), 7.11 (t, J=73.6 Hz, 1H), 6.44 (s, 2H), 1.25 (s, 12H).

Preparative Example 13

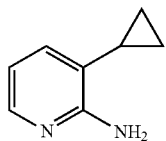

Step 1: 3-cyclopropylpyridin-2-amine

To a solution of 3-bromopyridin-2-amine (10.0 g, 58.13 mmol) in toluene (100 mL) and water (10 mL) were added cyclopropylboronic acid (6.49 g, 75.57 mmol), tricyclohexylphosphine (1.63 g, 5.81 mmol), tri-potassium phosphate trihydrate (54 g, 0.2 mol) and palladium(II) acetate (652 mg, 2.91 mmol). The reaction mixture was purged with nitrogen for 2 min and heated to 90° C. for 16 h and subsequently concentrated to dryness in vacuo. The resulting viscous mass was diluted with water and extracted with ethyl acetate (3×150 mL). The combined organic layers were dried over sodium sulfate and concentrated to dryness in vacuo. The resulting residue was purified by column chromatography (silica gel, 100-200 mesh, 10% to 30% ethyl acetate in hexane) affording 3-cyclopropylpyridin-2-amine (7.0 g, 90%): $^1$H NMR (400 MHz, Chloroform-d) δ 7.93-7.91 (m, 1H), 7.24-7.21 (m, 1H), 6.59-6.56 (m, 1H), 4.76 (s, 2H), 1.63-1.57 (m, 1H), 0.92-0.87 (m, 2H), 0.59-0.57 (m, 2H).

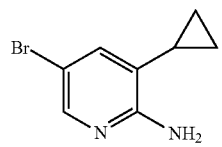

Step 2: 5-bromo-3-cyclopropylpyridin-2-amine

To a solution of 3-cyclopropylpyridin-2-amine (7.0 g, 52.17 mmol) in acetonitrile (100 mL) was added N-bromosuccinimide (9.75 g, 54.78 mmol). The reaction mixture was stirred at 25° C. for 30 min and subsequently concentrated to dryness in vacuo. The resulting viscous mass was diluted with water and extracted with ethyl acetate (3×100 mL). The combined organic layers were dried over sodium sulfate and concentrated to dryness in vacuo. The resulting residue was purified by column chromatography (silica gel, 100-200 mesh, 10% ethyl acetate in hexane) affording 5-bromo-3-cyclopropylpyridin-2-amine (9.5 g, 86%): $^1$H NMR (400 MHz, Chloroform-d) δ 7.94 (s, 1H), 7.31 (s, 1H), 4.85 (s, 2H), 1.62-1.55 (m, 1H), 0.95-0.90 (m, 2H), 0.60-0.56 (m, 2H).

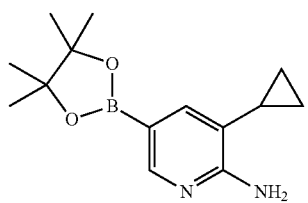 [SMILES: CC1(C)OB(c2cnc(N)c(C3CC3)c2)OC1(C)C]

Step 3: 3-cyclopropyl-5-(4,4,5,5-tetramethyl-1,3,2-dioxaborolan-2-yl)pyridin-2-amine To a solution of 5-bromo-3-cyclopropylpyridin-2-amine (2.13 g, 10 mmol) in 1,4-dioxane (60 mL) were added 4,4,4',4',5,5,5',5'-octamethyl-2,2'-bi(1,3,2-dioxaborolane) (2.8 g, 11 mmol), tricyclohexylphosphine (140 mg, 0.5 mmol), potassium acetate (1.96 g, 20 mmol) and tris(dibenzylideneacetone)dipalladium(0) (183 mg, 0.2 mmol). The reaction mixture was purged with nitrogen for 2 min and heated to 110° C. for 16 h and subsequently concentrated to dryness in vacuo. The resulting viscous mass was diluted with water and extracted with ethyl acetate (3×75 mL). The combined organic layers were dried over sodium sulfate and concentrated to dryness in vacuo. The resulting residue was purified by column chromatography (silica gel, 100-200 mesh, ethyl acetate) affording 3-cyclopropyl-5-(4,4,5,5-tetramethyl-1,3,2-dioxaborolan-2-yl)pyridin-2-amine (1.5 g, 57%): $^1$H NMR (400 MHz, Chloroform-d) δ 8.16 (s, 1H), 7.59 (s, 1H), 6.14 (s, 2H), 1.55-1.47 (m, 1H), 1.27 (s, 12H), 0.89-0.87 (m, 2H), 0.59-0.57 (m, 2H).

Preparative Example 14

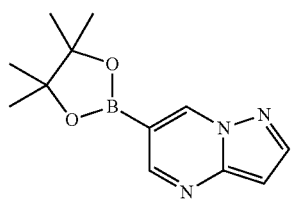 [SMILES: CC1(C)OB(c2cnc3ccnn3c2)OC1(C)C]

Step 1: 6-(4,4,5,5-tetramethyl-1,3,2-dioxaborolan-2-yl)pyrazolo[1,5-a]pyrimidine To a solution of 6-bromopyrazolo[1,5-a]pyrimidine (1.5 g, 7.57 mmol) in 1,4-dioxane (20 mL) were added 4,4,4',4',5,5,5',5'-octamethyl-2,2'-bi(1,3,2-dioxaborolane) (2.12 g, 8.33 mmol), potassium acetate (1.48 g, 15.14 mmol) and 1,1'-bis(diphenylphosphino)ferrocene-palladium(II)dichloride (553 mg, 0.76 mmol). The reaction mixture was purged with nitrogen for 2 min and heated to 100° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in hexane) affording 6-(4,4,5,5-tetramethyl-1,3,2-dioxaborolan-2-yl)pyrazolo[1,5-a]pyrimidine (1.0 g, 54%): $^1$H NMR (400 MHz, Chloroform-d) δ 8.99 (s, 1H), 8.69 (s, 1H), 8.15 (d, J=2.4 Hz, 1H), 6.67 (d, J=2.4 Hz, 1H), 1.42 (s, 12H).

Preparative Example 15

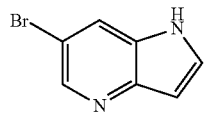

Step 1: 6-bromo-1H-pyrrolo[3,2-b]pyridine

To a solution of 5-bromo-2-methyl-3-nitropyridine (1.58 g, 7.28 mmol) in N,N-dimethylmethanamide (10 mL) was added N,N-dimethylformamide dimethyl acetal (1.65 mL, 12.37 mmol). The reaction mixture was heated to 100° C. for 1 h and subsequently concentrated to dryness in vacuo. The residue was dissolved in acetic acid (20 mL), and iron powder (1.22 g, 21.8 mmol) was added. The reaction mixture was purged with nitrogen for 2 min and heated to 100° C. for 20 h. After cooling down, the reaction mixture was diluted with methanol and filtered. The precipitate was washed with methanol. The mother liquid and the washing were concentrated to dryness in vacuo. The resulting viscous mass was diluted with aqueous sodium carbonate and extracted with ethyl acetate (2×60 mL). The combined organic layers were dried over sodium sulfate and concentrated to dryness in vacuo. The resulting residue was purified by column chromatography (silica gel, 100-200 mesh, 25% ethyl acetate in hexane) affording 6-bromo-1H-pyrrolo[3,2-b]pyridine (820 mg, 60%): $^1$H NMR (400 MHz, DMSO-d6) δ 11.48-11.45 (m, 1H), 8.36 (d, J=2 Hz, 1H), 8.02-8.00 (m, 1H), 7.69-7.66 (m, 1H), 6.59-6.56 (m, 1H).

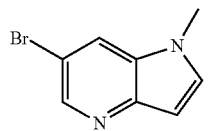

Step 2: 6-bromo-1-methyl-1H-pyrrolo[3,2-b]pyridine

To a solution of 6-bromo-1H-pyrrolo[3,2-b]pyridine (1.0 g, 5 mmol) in N,N-dimethylmethanamide (10 mL) was added sodium hydride (400 mg, 10 mmol, 60% in mineral oil) under ice-bath. The mixture was stirred for 1 h at the same temperature, and iodomethane (852 mg, 6 mmol) was added. The reaction mixture was stirred at 25° C. for another 2 h and then quenched with methanol. The mixture was concentrated to dryness in vacuo. The residue was purified by column chromatography (silica gel, 100-200 mesh, 20% ethyl acetate in hexane) affording 6-bromo-1-methyl-1H-pyrrolo[3,2-b]pyridine (1 g 95%): $^1$H NMR (400 MHz, Chloroform-d) δ 8.47 (d, J=2 Hz, 1H), 7.75-7.74 (m, 1H), 7.25-7.23 (m, 1H), 6.65-6.63 (m, 1H), 3.76 (s, 3H).

Preparative Example 16

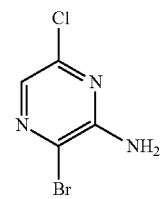

Step 1: 3-bromo-6-chloropyrazin-2-amine

To a solution of 6-chloropyrazin-2-amine (20 g, 154.44 mmol) in dichloromethane (400 mL) was added N-bromosuccinimide (28.86 g, 162.16 mmol) portion wise. The reaction mixture was stirred at 25° C. for 16 h and subsequently concentrated to dryness in vacuo. The resulting residue was purified by column chromatography (silica gel, 100-200 mesh, 20% ethyl acetate in hexane) affording 3-bromo-6-chloropyrazin-2-amine (4.2 g, 13%): $^1$H NMR (400 MHz, DMSO-d6) δ 7.63 (s, 1H), 7.23 (br, 2H).

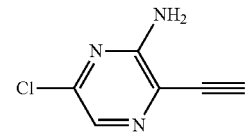

Step 2: 6-chloro-3-ethynylpyrazin-2-amine

To a solution of 3-bromo-6-chloropyrazin-2-amine (4.2 g, 20.15 mmol) and ethynyltrimethylsilane (3.96 g, 40.31 mmol) in triethylamine (100 mL) were added bis(triphenylphosphine)palladium(II) dichloride (1.41 g, 2.01 mmol) and copper(I) iodide (380 mg, 2.01 mmol). The reaction mixture was purged with nitrogen for 2 min and stirred at 25° C. for 3 h. The reaction mixture was concentrated to dryness in vacuo. The resulting residue was purified by column chromatography (silica gel, 100-200 mesh, 30% ethyl acetate in hexane) affording 6-chloro-3-ethynylpyrazin-2-amine (3.0 g, 97%): $^1$H NMR (400 MHz, DMSO-d6) δ 7.76 (s, 1H), 7.09 (br, 2H), 4.72 (s, 1H).

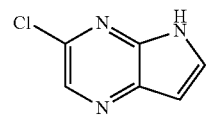

Step 3: 3-chloro-5H-pyrrolo[2,3-b]pyrazine

To a solution of 6-chloro-3-ethynylpyrazin-2-amine (3.0 g, 19.53 mmol) in 1-methyl-2-pyrrolidone (80 mL) was added potassium tert-butoxide (4.38 g, 39.06 mmol). The resulting mixture was heated to 80° C. for 16 h and diluted with water (100 mL). The mixture was extracted with ethyl acetate (3×300 mL). The combined organic layers were dried over sodium sulfate and concentrated to dryness in vacuo. The resulting residue was purified by column chromatography (silica gel, 100-200 mesh, 50% ethyl acetate in hexane) affording 3-chloro-5H-pyrrolo[2,3-b]pyrazine (2.0 g, 67%). LCMS (ESI, 10-80AB/2 min): retention time=0.683 min, m/z 153.8 [M+H]$^+$.

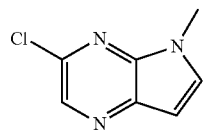

Step 4: 3-chloro-5-methyl-5H-pyrrolo[2,3-b]pyrazine

To a mixture of 3-chloro-5H-pyrrolo[2,3-b]pyrazine (2.0 g, 13.02 mmol) and potassium hydroxide (1.46 g, 26.04 mmol) in N,N-dimethylmethanamide (40 mL) was added iodomethane (3.70 g, 26.04 mmol). The reaction mixture was stirred at 25° C. for 3 h and diluted with water (50 mL). The mixture was extracted with ethyl acetate (3×100 mL). The combined organic layers were dried over sodium sulfate and concentrated to dryness in vacuo. The resulting residue was purified by column chromatography (silica gel, 100-200 mesh, 40% ethyl acetate in hexane) affording 3-chloro-5-methyl-5H-pyrrolo[2,3-b]pyrazine (2.0 g, 92%): $^1$H NMR (400 MHz, DMSO-d6) δ 8.47 (s, 1H), 7.94 (d, J=3.6 Hz, 1H), 6.72 (d, J=3.6 Hz, 1H), 3.82 (s, 3H).

Preparative Example 17

Step 1: 3,3,5-tribromo-1H-pyrrolo[2,3-b]pyridin-2(3H)-one

To a solution of 7-azaindole (20 g, 169.3 mmol) in tert-butanol (1000 mL) and water (1000 mL) was added bromine (86 mL, 1.69 mol) dropwise at 25° C. The reaction mixture was stirred at 25° C. for 16 h. The organic solvent was removed in vacuo and the aqueous suspension was treated with aqueous sodium bicarbonate to pH 8. The mixture was filtered and the filter cake was washed with water. The filter cake was dried in vacuo to afford 3,3,5-tribromo-1H-pyrrolo[2,3-b]pyridin-2(3H)-one (51 g, 81%): $^1$H NMR (400 MHz, Chloroform-d) δ 9.67 (s, 1H), 8.30 (d, J=2 Hz, 1H), 7.96 (d, J=2 Hz, 1H).

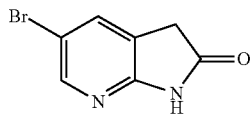

Step 2: 5-bromo-1H-pyrrolo[2,3-b]pyridin-2(3H)-one

To a solution of 3,3,5-tribromo-1H-pyrrolo[2,3-b]pyridin-2(3H)-one (20 g, 53.93 mmol) in acetic acid (150 mL) was added zinc dust (17.64 g, 269.67 mmol). The reaction mixture was stirred at RT for 5 h and subsequently concentrated to dryness in vacuo. The residue was diluted with ethyl acetate (200 mL) and washed with water. The organic layer was dried over anhydrous sodium sulfate and filtered. The filtrate was concentrated to dryness in vacuo to afford 5-bromo-1H-pyrrolo[2,3-b]pyridin-2(3H)-one (4.6 g, 40%): $^1$H NMR (400 MHz, DMSO-d6) δ 11.15 (s, 1H), 8.16 (s, 1H), 7.77 (s, 1H), 3.58 (s, 2H).

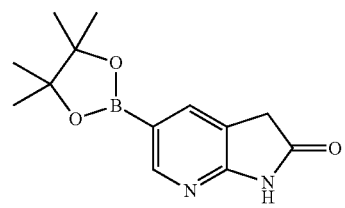 [SMILES: CC1(C)OB(c2cnc3c(c2)CC(=O)N3)OC1(C)C]

Step 3: 5-(4,4,5,5-tetramethyl-1,3,2-dioxaborolan-2-yl)-1H-pyrrolo[2,3-b]pyridin-2(3H)-one To a solution of 5-bromo-1H-pyrrolo[2,3-b]pyridin-2 (3H)-one (3 g, 14.08 mmol) in 1,4-dioxane (60 mL) were added 4,4,4',4',5,5,5',5'-octamethyl-2,2'-bi(1,3,2-dioxaborolane) (4.29 g, 16.9 mmol), potassium acetate (2.07 g, 21.12 mmol) and 1,1'-bis(diphenylphosphino)ferrocene-palladium (II)dichloride (1.02 g, 1.41 mmol). The reaction mixture was purged with nitrogen for 2 min and heated to 110° C. for 1 h. After cooling down the mixture was filtered and the solid was washed with ethyl acetate. The mother liquid was diluted with methanol and the precipitate was filtered and dried in vacuo to afford 5-(4,4,5,5-tetramethyl-1,3,2-dioxaborolan-2-yl)-1H-pyrrolo[2,3-b]pyridin-2(3H)-one (1.1 g, 30%): $^1$H NMR (400 MHz, DMSO-d6) δ 11.14 (s, 1H), 8.29 (s, 1H), 7.68 (s, 1H), 3.54 (s, 2H), 1.29 (s, 12H).

Preparative Example 18

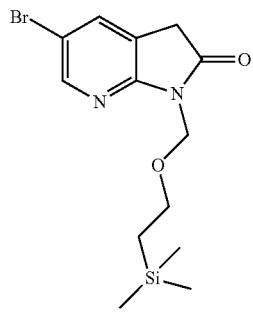 [SMILES: C[Si](C)(C)CCOCN1C(=O)Cc2cc(Br)cnc21]

Step 1: 5-bromo-1-((2-(trimethylsilyl)ethoxy)methyl)-1H-pyrrolo[2,3-b]pyridin-2(3H)-one To a stirred solution of 5-bromo-1H-pyrrolo[2,3-b]pyridin-2(3H)-one (8.52 g, 40 mmol) in tetrahydrofuran (100 mL) and N,N-dimethylmethanamide (100 mL) was added sodium hydride (1.6 g, 40 mmol, 60% in mineral oil) under nitrogen at 0° C., and the reaction mixture was stirred at the same temperature for 30 min. (2-(chloromethoxy)ethyl)trimethylsilane (8.67 g, 52 mmol) was added dropwise into the reaction mixture. The resulting solution was stirred at RT for 24 h. The reaction mixture was poured into ice-water (1000 mL) and extracted four times with ethyl acetate. The combined organic phases were washed with saturated sodium bicarbonate, water, brine, dried over sodium sulfate and concentrated to dryness in vacuo. The resulting residue was purified by column chromatography (silica gel, 100-200 mesh, 40% ethyl acetate in hexane) affording 5-bromo-1-((2-(trimethylsilyl)ethoxy)methyl)-1H-pyrrolo[2,3-b]pyridin-2(3H)-one (6.5 g, 47%): $^1$H NMR (400 MHz, DMSO-d6) δ 8.27 (m, 1H), 7.88 (m, 1H), 5.04 (s, 2H), 3.72 (s, 2H), 3.59-3.55 (m, 2H), 0.86-0.82 (m, 2H), −0.08 (s, 9H).

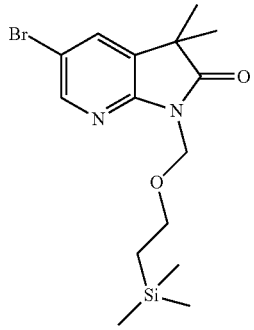 [SMILES: CC1(C)C(=O)N(COCC[Si](C)(C)C)c2ncc(Br)cc21]

Step 2: 5-bromo-3,3-dimethyl-1-((2-(trimethylsilyl)ethoxy)methyl)-1H-pyrrolo[2,3-b]pyridin-2(3H)-one To a stirred solution of 5-bromo-1-((2-(trimethylsilyl)ethoxy)methyl)-1H-pyrrolo[2,3-b]pyridin-2(3H)-one (6.4 g, 18.64 mmol) in N,N-dimethylmethanamide (50 mL), was added cesium carbonate (18.22 g, 56 mmol) and slow addition of iodomethane (2.84 mL, 56 mmol). The reaction mixture was stirred at 25° C. for 1 h and quenched with water. The mixture was extracted with ethyl acetate (3×60 mL). The combined organic layers were dried over sodium sulfate and concentrated to dryness in vacuo. The resulting residue was purified by column chromatography (silica gel, 100-200 mesh, 15% ethyl acetate in hexane) affording 5-bromo-3,3-dimethyl-1-((2-(trimethylsilyl)ethoxy)methyl)-1H-pyrrolo[2,3-b]pyridin-2(3H)-one (5.0 g, 72%): $^1$H NMR (400 MHz, DMSO-d6) δ 8.28 (s, 1H), 8.10 (s, 1H), 5.06 (s, 2H), 3.55 (t, J=8.0 Hz, 2H), 1.33 (s, 6H), 0.82 (t, J=8.0 Hz, 2H), −0.10 (s, 9H).

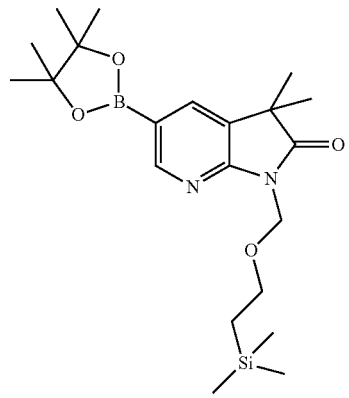 [SMILES: CC1(C)C(=O)N(COCC[Si](C)(C)C)c2ncc(B3OC(C)(C)C(C)(C)O3)cc21]

Step 3: 3,3-dimethyl-5-(4,4,5,5-tetramethyl-1,3,2-dioxaborolan-2-yl)-1-((2-(trimethylsilyl)ethoxy)methyl)-1H-pyrrolo[2,3-b]pyridin-2(3H)-one To a solution of 5-bromo-3,3-dimethyl-1-((2-(trimethylsilyl)ethoxy)methyl)-1H-pyrrolo[2,3-b]pyridin-2(3H)-one (1.4 g, 3.77 mmol) in 1,4-dioxane (20 mL) were added 4,4,4',4',5,5,5',5'-octamethyl-2,2'-bi(1,3,2-dioxaborolane) (1.05 g, 4.15 mmol), potassium acetate (1.11 g, 11.31 mmol) and 1,1'-bis(diphenylphosphino)ferrocene-palladium(II)dichloride (138 mg, 0.19 mmol). The reaction mixture was purged with nitrogen for 2 min and heated to 90° C. for 4 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 10% ethyl acetate in hexane) affording 3,3-dimethyl-5-(4,4,5,5-tetramethyl-1,3,2-dioxaborolan-2-yl)-1-((2-(trimethylsilyl)ethoxy)methyl)-1H-pyrrolo[2,3-b]pyridin-2(3H)-one (1.1 g, 70%): $^1$H NMR (400 MHz, DMSO-d6) δ 8.38 (s, 1H), 7.93 (s, 1H), 5.10 (s, 2H), 3.56 (t, J=8.0 Hz, 2H), 1.33 (s, 6H), 1.30 (s, 12H), 0.82 (t, J=8.0 Hz, 2H), −0.09 (s, 9H).

Preparative Example 19

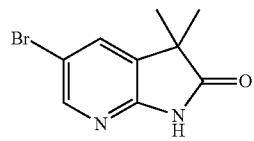

Step 1: 5-bromo-3,3-dimethyl-1H-pyrrolo[2,3-b]pyridin-2(3H)-one

To a solution of 5-bromo-3,3-dimethyl-1-((2-(trimethylsilyl)ethoxy)methyl)-1H-pyrrolo[2,3-b]pyridin-2(3H)-one (1.11 g, 3 mmol) in dichlormethane (20 mL) was added trifluoroacetic acid (5 mL). The reaction mixture was stirred at 25° C. for 2 h and subsequently concentrated to dryness in vacuo. The resulting viscous mass was diluted with methanol (10 mL) and ammonium hydroxide (10 mL). The mixture was stirred at 25° C. for 30 min and subsequently concentrated to dryness in vacuo affording crude 5-bromo- 3,3-dimethyl-1H-pyrrolo[2,3-b]pyridin-2(3H)-one. The crude residue was used without further purification.

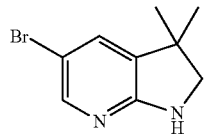

Step 2: 5-bromo-3,3-dimethyl-2,3-dihydro-1H-pyrrolo[2,3-b]pyridine

To a solution of 5-bromo-3,3-dimethyl-1H-pyrrolo[2,3-b]pyridin-2(3H)-one (2 g, 8.3 mmol) in tetrahydrofuran (5 mL) was added borane-tetrahydrofuran complex (83 mL, 83 mmol, 1 M solution). The reaction mixture was heated to 80° C. for 16 h and quenched with methanol carefully. The mixture was concentrated to dryness in vacuo. The resulting viscous mass was purified by column chromatography (silica gel, 100-200 mesh, 30% ethyl acetate in hexane) affording 5-bromo-3,3-dimethyl-2,3-dihydro-1H-pyrrolo[2,3-b]pyridine (1.1 g, 59%): $^1$H NMR (400 MHz, Chloroform-d) δ 7.86 (s, 1H), 7.23 (s, 1H), 3.36 (s, 2H), 1.31 (s, 6H).

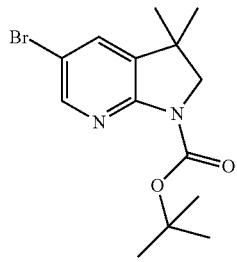 [SMILES: CC(C)(C)OC(=O)N1CC(C)(C)c2cc(Br)cnc21]

Step 3: tert-butyl 5-bromo-3,3-dimethyl-2,3-dihydro-1H-pyrrolo[2,3-b]pyridine-1-carboxylate To a solution of 5-bromo-3,3-dimethyl-2,3-dihydro-1H-pyrrolo[2,3-b]pyridine (500 mg, 2.2 mmol) in tetrahydrofuran (10 mL) was added lithium bis(trimethylsilyl)azanide (2 M, in terahydrofuran, 1.32 mL, 2.64 mmol) at −10° C. The reaction mixture was stirred at the same temperature for 30 min and di-tert-butyl-dicarbonate (576 mg, 2.64 mmol) was added dropwise. The reaction mixture was stirred at 25° C. for 1 h and quenched with aqueous ammonium chloride. The mixture was extracted with ethyl acetate (2×50 mL). The combined organic layers were dried over sodium sulfate and concentrated to dryness in vacuo. The resulting residue was purified by column chromatography (silica gel, 100-200 mesh, 10% ethyl acetate in hexane) affording tert-butyl 5-bromo-3,3-dimethyl-2,3-dihydro-1H-pyrrolo[2,3-b]pyridine-1-carboxylate (400 mg, 56%): $^1$H NMR (400 MHz, Chloroform-d) δ 8.26 (s, 1H), 7.43 (s, 1H), 3.72 (s, 2H), 1.55 (s, 3H), 1.31 (s, 6H).

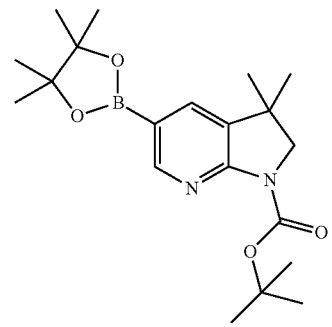 [SMILES: CC(C)(C)OC(=O)N1CC(C)(C)c2cc(B3OC(C)(C)C(C)(C)O3)cnc21]

Step 4: tert-butyl 3,3-dimethyl-5-(4,4,5,5-tetramethyl-1,3,2-dioxaborolan-2-yl)-2,3-dihydro-1H-pyrrolo[2,3-b]pyridine-1-carboxylate To a solution of tert-butyl 5-bromo-3,3-dimethyl-2,3-dihydro-1H-pyrrolo[2,3-b]pyridine-1-carboxylate (400 mg, 1.22 mmol) in 1,4-dioxane (10 mL) were added 4,4,4',4',5,5,5',5'-octamethyl-2,2'-bi(1,3,2-dioxaborolane) (403 mg, 1.59 mmol), potassium acetate (359 mg, 3.66 mmol) and 1,1'-bis(diphenylphosphino)ferrocene-palladium(II)dichloride (88 mg, 0.12 mmol). The reaction mixture was purged with nitrogen for 2 min and heated to 100° C. for 10 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 10% ethyl acetate in hexane) affording: tert-butyl 3,3-dimethyl-5-(4,4,5,5-tetramethyl-1,3,2-dioxaborolan-2-yl)-2,3-dihydro-1H-pyrrolo[2,3-b]pyridine-1-carboxylate (200 mg, 44%): $^1$H NMR (400 MHz, DMSO-d6) δ 8.32 (s, 1H), 7.71 (s, 1H), 3.65 (s, 2H), 1.49 (s, 9H), 1.29 (s, 12H), 1.16 (s, 6H).

Preparative Example 20

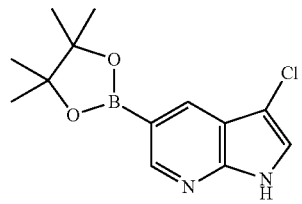 [SMILES: CC1(C)OB(c2cnc3[nH]cc(Cl)c3c2)OC1(C)C]

Step 1: 3-chloro-5-(4,4,5,5-tetramethyl-1,3,2-dioxaborolan-2-yl)-1H-pyrrolo[2,3-b]pyridine To a solution of 5-bromo-3-chloro-1H-pyrrolo[2,3-b]pyridine (1.0 g, 4.32 mmol) in 1,4-dioxane (20 mL) was added 4,4,4',4',5,5,5',5'-octamethyl-2,2'-bi(1,3,2-dioxaborolane) (1.32 g, 5.18 mmol), potassium acetate (1.27 g, 12.96 mmol) and 1,1'-bis(diphenylphosphino)ferrocene-palladium(II)dichloride (315 mg, 0.43 mmol). The reaction mixture was purged with nitrogen for 2 min and heated to 100° C. for 2 h and subsequently concentrated to dryness in vacuo. The resulting viscous mass was diluted with water and extracted with ethyl acetate (2×50 mL). The combined organic layers were dried over sodium sulfate and concentrated to dryness Preparative Example 21

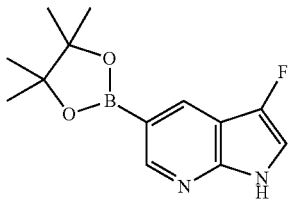 [SMILES: CC1(C)OB(c2cnc3[nH]cc(F)c3c2)OC1(C)C]

Step 1: 3-fluoro-5-(4,4,5,5-tetramethyl-1,3,2-dioxaborolan-2-yl)-1H-pyrrolo[2,3-b]pyridine To a solution of 5-bromo-3-fluoro-1H-pyrrolo[2,3-b]pyridine (1.0 g, 4.65 mmol) in 1,4-dioxane (20 mL) was added 4,4,4',4',5,5,5',5'-octamethyl-2,2'-bi(1,3,2-dioxaborolane) (1.77 g, 6.98 mmol), potassium acetate (1.37 g, 13.95 mmol) and 1,1'-bis(diphenylphosphino)ferrocene-palladium(II)dichloride (340 mg, 0.46 mmol). The reaction mixture was purged with nitrogen for 2 min and heated to 100° C. for 2 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 100-200 mesh, 30% ethyl acetate in petroleum ether) affording 3-fluoro-5-(4,4,5,5-tetramethyl-1,3,2-dioxaborolan-2-yl)-1H-pyrrolo[2,3-b]pyridine (240 mg, 20%): $^1$H NMR (400 MHz, Chloroform-d) δ 11.44 (m, 1H), 8.73 (d, J=1.6 Hz, 1H), 8.46 (d, J=1.2 Hz, 1H), 7.10 (m, 1H), 1.39 (s, 12H).

Preparative Example 22

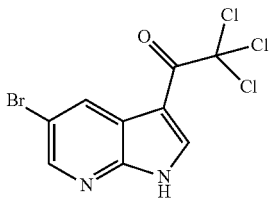 [SMILES: O=C(c1c[nH]c2ncc(Br)cc12)C(Cl)(Cl)Cl]

Step 1: 1-(5-bromo-1H-pyrrolo[2,3-b]pyridin-3-yl)-2,2,2-trichloroethanone

To a suspension of aluminum trichloride (4.06 g, 30.45 mmol) in dichloromethane (200 mL) was added 5-bromo-1H-pyrrolo[2,3-b]pyridine (2 g, 10.15 mmol) at 0° C. The resulting mixture was stirred for 3 h at the same temperature. After this period 2,2,2-trichloroacetyl chloride (1.13 mL, 10.15 mmol) was added dropwise. After addition, the mixture was stirred at 25° C. for 16 h. The reaction mixture was poured onto ice, the resulting solid was collected by filtration and dried in vacuo to give 1-(5-bromo-1H-pyrrolo[2,3-b]pyridin-3-yl)-2,2,2-trichloroethanone (2.5 g, 72%). The solid was used without further purification: MS (ESI+) m/z: 343 [M+3]$^+$.

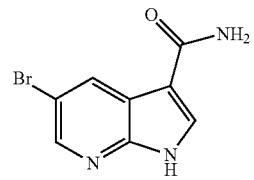 [SMILES: NC(=O)c1c[nH]c2ncc(Br)cc12]

Step 2: 5-bromo-1H-pyrrolo[2,3-b]pyridine-3-carboxamide

A mixture of 1-(5-bromo-1H-pyrrolo[2,3-b]pyridin-3-yl)-2,2,2-trichloroethanone (2.5 g, 7.3 mmol) in a 4M solution of ammonia in tetrahydrofuran (80 mL) was stirred at 100° C. for 16 h in a sealed vessel. After cooling down, the mixture filtered and the solid was dried to give 5-bromo-1H-pyrrolo[2,3-b]pyridine-3-carboxamide (1.6 g, 91%). The solid was used without further purification.

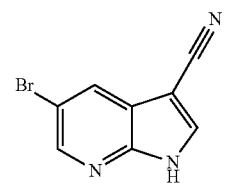 [SMILES: N#Cc1c[nH]c2ncc(Br)cc12]

Step 3: 5-bromo-1H-pyrrolo[2,3-b]pyridine-3-carbonitrile

To the suspension of 5-bromo-1H-pyrrolo[2,3-b]pyridine-3-carboxamide (1.5 g, 6.3 mmol) and triethylamine (8.7 mL, 63 mmol) in acetonitrile (60 mL) was added trifluoroacetic anhydride (2.6 mL, 19 mmol) dropwise at 0° C. After addition, the mixture was stirred for another 20 min and subsequently concentrated to dryness in vacuo. The resulting residue was purified by flash column chromatography (silica gel, 100-200 mesh, 10% ethyl acetate in hexane) to give 5-bromo-1H-pyrrolo[2,3-b]pyridine-3-carbonitrile (1 g, 72%). The residue was used as is in the next step.

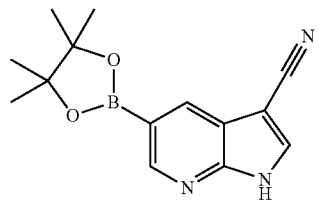 [SMILES: CC1(C)OB(c2cnc3[nH]cc(C#N)c3c2)OC1(C)C]

Step 4: 5-(4,4,5,5-tetramethyl-1,3,2-dioxaborolan-2-yl)-1H-pyrrolo[2,3-b]pyridine-3-carbonitrile To a solution of 5-bromo-1H-pyrrolo[2,3-b]pyridine-3-carbonitrile (700 mg, 3.15 mmol) in 1,4-dioxane (40 mL)

were added 4,4,4',4',5,5,5',5'-octamethyl-2,2'-bi(1,3,2-dioxaborolane) (1.2 g, 4.73 mmol), potassium acetate (930 mg, 9.46 mmol) and 1,1'-bis(diphenylphosphino)ferrocene-palladium(II)dichloride (100 mg, 0.14 mmol). The reaction mixture was purged with nitrogen for 2 min and heated to 80° C. for 10 h and subsequently concentrated to dryness in vacuo. The residue was diluted with ethyl acetate (60 mL), filtered and the filtrate was washed with brine (60 mL). The organic layer was dried over sodium sulfate, filtered and concentrated to dryness in vacuo. The residue was purified by flash column chromatography (silica gel, 100-200 mesh, ethyl acetate) to afford 5-(4,4,5,5-tetramethyl-1,3,2-dioxaborolan-2-yl)-1H-pyrrolo[2,3-b]pyridine-3-carbonitrile (400 mg, 47%): $^{1}$H NMR (400 MHz, DMSO-d6) δ 12.93 (s, 1H), 8.58 (s, 1H), 8.46 (s, 1H), 8.24 (s, 1H), 1.30 (s, 12H).

Preparative Example 23

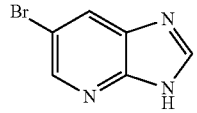

Step 1: 6-bromo-3H-imidazo[4,5-b]pyridine

A solution of 5-bromopyridine-2,3-diamine (10.0 g, 53.0 mmol) in formic acid (96%, 100 mL) was heated to reflux for 10 h and subsequently concentrated to dryness in vacuo. The residue was taken up in water and the title compound was collected as a solid by filtration, washed with water (2×30 mL) and dried to afford 6-bromo-3H-imidazo[4,5-b]pyridine (10.0 g, 95%): $^{1}$H NMR (400 MHz, methanol-d4) δ 8.46 (s, 1H), 8.40 (s, 1H), 8.21 (s, 1H).

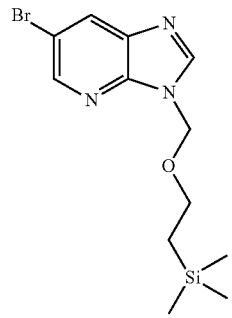 [SMILES: C[Si](C)(C)CCOCn1cnc2cc(Br)cnc21]

Step 2: 6-bromo-3-((2-(trimethylsilyl)ethoxy)methyl)-3H-imidazo[4,5-b]pyridine

To a solution of 6-bromo-3H-imidazo[4,5-b]pyridine (8.0 g, 40.6 mmol) in tetrahydrofuran (100 mL) at 0° C. was added sodium hydride (2.4 g, 60% in mineral oil, 60.9 mmol) and the reaction was stirred at 0° C. for 1 h. (2-(chloromethoxy)ethyl)trimethylsilane (7.4 g, 44.67 mmol) was added and the reaction was stirred at RT for 5 h. The reaction was quenched with water (100 mL) and extracted with ethyl acetate (3×100 mL). The combined organic layers were washed with brine (100 mL), dried over magnesium sulfate and concentrated to dryness in vacuo. The residue was purified by column chromatography (silica gel, 200-300 mesh, 20% ethyl acetate in hexane) affording 6-bromo-3-((2-(trimethylsilyl)ethoxy)methyl)-3H-imidazo [4,5-b]pyridine (8.3 g, 62%): $^{1}$HNMR (400 MHz, Chloroform-d) δ 8.51 (d, J=2.0 Hz, 1H), 8.27 (d, J=2.0 Hz, 1H), 8.23 (s, 1H), 5.70 (s, 2H), 3.65 (t, J=8.0 Hz, 2H), 0.97 (t, J=8.0 Hz, 2H), 0.00 (s, 9H).

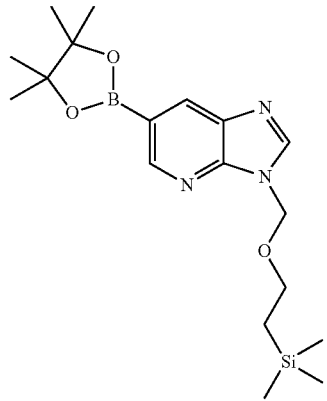

Step 3: 6-(4,4,5,5-tetramethyl-1,3,2-dioxaborolan-2-yl)-3-((2-(trimethylsilyl)ethoxy)methyl)-3H-imidazo[4,5-b]pyridine To a solution of 6-bromo-3-((2-(trimethylsilyl)ethoxy)methyl)-3H-imidazo[4,5-b]pyridine (9.2 g, 28 mmol) in 1,4-dioxane (100 mL) was added 4,4,4',4',5,5,5',5'-octamethyl-2,2'-bi(1,3,2-dioxaborolane) (14.3 g, 56 mmol), potassium acetate (5.5 g, 56 mmol) and 1,1'-bis(diphenylphosphino)ferrocene-palladium(II)dichloride (4.1 g, 5 mmol). The reaction mixture was purged with nitrogen for 2 min and heated to 95° C. for 16 h and subsequently concentrated to dryness in vacuo. The resulting viscous mass was diluted with water and extracted with ethyl acetate (2×50 mL). The combined organic layers were dried over sodium sulfate and concentrated to dryness in vacuo. The resulting residue was purified by column chromatography (silica gel, 200-300 mesh, 25% ethyl acetate in petroleum ether) affording 6-(4,4,5,5-tetramethyl-1,3,2-dioxaborolan-2-yl)-3-((2-(trimethylsilyl)ethoxy)methyl)-3H-imidazo[4,5-b]pyridine (8.6 g, 82%): $^{1}$HNMR (400 MHz, DMSO-d6) δ 8.76 (s, 1H), 8.71 (d, J=0.8 Hz, 1H), 8.35 (d, J=0.8 Hz, 1H), 5.77 (s, 2H), 3.68 (t, J=8.0 Hz, 2H), 1.44 (s, 12H), 0.93 (t, J=8.0 Hz, 2H), 0.00 (s, 9H).

Examples

Example 1

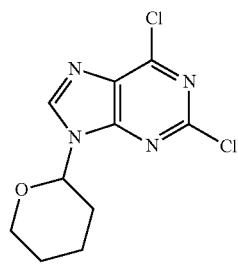 [SMILES: Clc1nc(Cl)c2ncn(C3CCCCO3)c2n1]

Step 1: 2,6-dichloro-9-(tetrahydro-2H-pyran-2-yl)-9H-purine

To a stirred solution of 2,6-dichlor-9H-purine (50 g, 264.5 mmol) in ethyl acetate (500 mL), was added p-toluenesulfonic acid (1.36 g, 7.935 mmol) and slow addition of 3,4-dihydro-2H-pyran (55.6 g, 661.2 mmol). The reaction mixture was heated at reflux for 2 h, cooled to RT and concentrated to dryness in vacuo. The resulting residue was purified by column chromatography (silica gel, 100-200 mesh, 50% ethyl acetate in hexane) affording 2,6-dichloro-9-(tetrahydro-2H-pyran-2-yl)-9H-purine as a cream solid (65 g, 90%): $^1$H NMR (400 MHz, Chloroform-d) δ 8.33 (s, 1H), 5.77 (1H, dd, J=10.5, 2.6), 4.24-4.14 (1H, m), 3.86-3.71 (m, 1H), 2.21-1.65 (m, 6H).

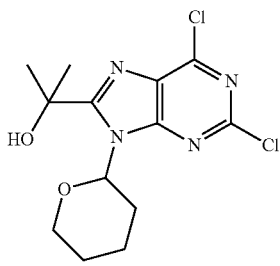 [SMILES: CC(C)(O)c1nc2c(Cl)nc(Cl)nc2n1C1CCCCO1]

Step 2: 2-(2,6-dichloro-9-(tetrahydro-2H-pyran-2-yl)-9H-purin-8-yl)propan-2-ol To a solution of 2,6-dichloro-9-(tetrahydro-2H-pyran-2-yl)-9H-purine (65 g, 238 mmol) cooled to −78° C. in dry tetrahydrofuran (1000 mL) was added drop wise a 2M solution of lithium diisopropylamide in tetrahydrofuran (234 mL, 477.8 mmol). After addition was completed, the resulting solution was stirred at −78° C. for 90 min, acetone (17.5 mL, 716.7 mmol) was added and the reaction mixture was stirred at −78° C. for another 30 min. The reaction mixture was quenched with saturated ammonium chloride and the aqueous layer extracted with ethyl acetate (2×300 mL). The combined organic layers were dried over sodium sulfate and concentrated to dryness in vacuo. The resulting residue was purified by column chromatography (silica gel, 100-200 mesh, 50% ethyl acetate in hexane) affording 2-(2,6-dichloro-9-(tetrahydro-2H-pyran-2-yl)-9H-purin-8-yl)propan-2-ol (40 g, 50%): $^1$H NMR (400 MHz, DMSO-d6) δ 6.41 (dd, J=11.2, 2.3 Hz, 1H), 6.13 (s, 1H), 4.10 (dd, J=11.2, 3.5 Hz, 1H), 3.68-3.54 (m, 1H), 2.97-2.82 (m, 1H), 2.10-1.95 (m, 1H), 1.89-1.51 (m, 10H).

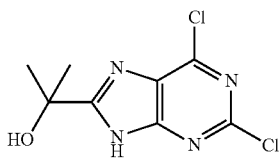

Step 3: 2-(2,6-dichloro-9H-purin-8-yl)propan-2-ol

To a stirred solution of 2-(2,6-dichloro-9-(tetrahydro-2H-pyran-2-yl)-9H-purin-8-yl)propan-2-ol (40 g, 120.8 mmol) in methanol (300 mL) was added p-toluenesulfonic acid (50 mg, 2.93 mmol) and the resulting mixture was heated to reflux for 2 h. The reaction mixture was concentrated in vacuo leaving behind a viscous mass which was diluted with dichloromethane (50 mL), the resulting precipitate was filtered and washed with dichloromethane affording 2-(2,6-dichloro-9H-purin-8-yl)propan-2-ol (22 g, 73%): $^1$H NMR (400 MHz, DMSO-d6) 1.58 (s, 6H).

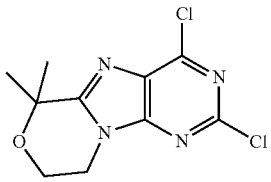 [SMILES: CC1(C)OCCn2c1nc1c(Cl)nc(Cl)nc12]

Step 4: 2,4-dichloro-6,6-dimethyl-8,9-dihydro-6H-[1,4]oxazino[4,3-e]purine

To a solution of 2-(2,6-dichloro-9H-purin-8-yl)propan-2-ol (22 g, 89.06 mmol) in acetonitrile (300 mL) was added cesium carbonate (87 g, 267.2 mmol), and 1,2-dibromoethane (23.7 mL, 267.2 mmol) in a seal tube. The reaction mixture was heated to 80° C. for 16 h and subsequently concentrated to dryness in vacuo. The resulting viscous mass was diluted with water and extracted with ethyl acetate (2×300 mL). The combined organic layers were dried over sodium sulfate and concentrated to dryness in vacuo. The resulting residue was purified by column chromatography (silica gel, 100-200 mesh, 10% ethyl acetate in hexane) affording 2,4-dichloro-6,6-dimethyl-8,9-dihydro-6H-[1,4]oxazino[4,3-e]purine (12 g, 50%): $^1$H NMR (400 MHz, DMSO-d6) δ 4.28-4.18 (m, 2H), 4.17-4.12 (m, 2H), 1.63 (s, 6H).

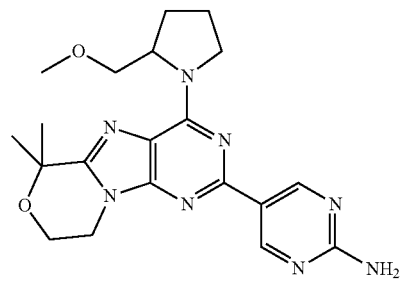 [SMILES: COCC1CCCN1c1nc(-c2cnc(N)nc2)nc2c1nc1n2CCOC1(C)C]

Step 5: 5-(4-(2-(methoxymethyl)pyrrolidin-1-yl)-6,6-dimethyl-8,9-dihydro-6H-[1,4]oxazino[4,3-e]purin-2-yl)pyrimidin-2-amine To a solution of 2,4-dichloro-6,6-dimethyl-8,9-dihydro-6H-[1,4]oxazino[4,3-e]purine (100 mg, 0.37 mmol) in N,N-dimethylformaldehyde (1.5 mL) was added 2-(methoxymethyl)pyrrolidine (51 mg, 0.44 mmol) and N,N-diisopropylethylamine (0.193 mL, 1.11 mmol). The reaction mixture was shaken at 40° C. for 16 h and concentrated to dryness in vacuo. The crude was redissolved in a 1:1 mixture of acetonitrile:1M potassium carbonate (4 mL) and transferred to a microwave vial equipped with a stirbar. To the solution was added 5-(4,4,5,5-tetramethyl-1,3,2-dioxaborolan-2-yl)pyrimidin-2-amine (121.4 mg, 0.55 mmol), 1,1′-bis(diphenylphosphino)ferrocene-palladium(II)dichloride (13.4 mg, 0.018 mmol) and the mixture was microwaved at 120° C. for 10 min. The reaction mixture was diluted with 10 mL water and extracted with ethyl acetate (3×15 ml). The combined organic layers were dried over magnesium sulfate, filtered and concentrated to dryness in vacuo. This crude material was purified by RP-HPLC affording 5-(4-(2-(methoxymethyl)pyrrolidin-1-yl)-6,6-dimethyl-8,9-dihydro-6H-[1,4]oxazino[4,3-e]purin-2-yl)pyrimidin-2-amine (78 mg, 52%): $^1$H NMR (DMSO-d6) δ: 9.08 (s, 2H), 6.98 (s, 2H), 4.17-4.02 (m, 4H), 3.66 (s, 2H), 3.33 (s, 3H), 3.17 (d, J=5.2 Hz, 2H), 2.03-1.98 (m, 4H), 1.98-1.93 (m, 1H), 1.58 (s, 6H)

Using a procedure similar to that described in Example 1, when following compounds were prepared.

| Ex | Structure | $^1$H NMR | MS (m/z) |
|---|---|---|---|
| 2 | 5-[1-(3-Fluoro-azetidin-1-yl)-8,8-dimethyl-5,6-dihydro-8H-7-oxa-2,4,4b,9-tetraaza-fluoren-3-yl]-pyrimidin-2-ylamine | $^1$H NMR (400 MHz, DMSO-d6) δ: 9.08 (s, 2H), 7.02 (s, 2H), 4.81-4.69 (m, 2H), 4.52-4.35 (m, 2H), 4.2-4.07 (m, 4H), 1.58 (s, 6H) | 371 |
| 3 | 1-(2-Aza-bicyclo[2.2.1]hex-2-yl)-8,8-dimethyl-3-(3-methyl-1H-pyrrolo[2,3-b]pyridin-5-yl)-5,6-dihydro-8H-7-oxa-2,4,4b,9-tetraaza-fluorene | $^1$H NMR (400 MHz, DMSO-d6) δ: 11.39 (s, 1H), 9.28 (d, J = 2.0 Hz, 1H), 8.82 (d, J = 2.0 Hz, 1H), 7.26 (s, 1H), 5.75 (s, 1H), 4.24-4.10 (m, 4H), 3.85 (s, 2H), 3.09-3.00 (m, 1H), 2.33 (s, 3H), 2.11 (s, 2H), 1.61 (s, 6H), 1.52-1.41 (m, 2H) | 416 |
| 4 | 1-(3-Fluoro-azetidin-1-yl)-8,8-dimethyl-3-(3-methyl-1H-pyrrolo[2,3-b]pyridin-5-yl)-5,6-dihydro-8H-7-oxa-2,4,4b,9-tetraaza-fluorene | $^1$H NMR (400 MHz, DMSO-d6) δ: 11.41 (s, 1H), 9.26 (d, J = 2.0 Hz, 1H), 8.79 (d, J = 2.0 Hz, 1H), 7.26 (s, 1H), 5.73-5.49 (m, 1H), 4.87-4.70 (m, 2H), 4.54-4.39 (m, 2H), 4.21 (t, J = 4.9 Hz, 2H), 4.13 (t, J = 4.9 Hz, 2H), 2.33 (s, 3H), 1.60 (s, 6H) | 408 |

| Ex | Structure | ¹H NMR | MS (m/z) |
|---|---|---|---|
| 5 | 5-[1-(3-Aza-bicyclo[3.1.0]hex-3-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.08 (s, 2H), 6.97 (s, 2H), 4.76-4.23 (m, 2H), 4.16-4.00 (m, 4H), 3.90-3.48 (m, 2H), 1.72 (d, J = 11.6 Hz, 2H), 1.58 (s, 6H), 0.83-0.70 (m, 1H), 0.21-0.10 (m, 1H) | 379 |
| 6 | 5-[1-(5,5-Dimethyl-hexahydro-cyclopenta[c]pyrrol-2-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 6.98 (s, 2H), 4.30-4.05 (m, 6H), 3.97-2.81 (m, 2H), 3.03-2.88 (m, 2H), 2.44-2.27 (m, 2H), 2.21-2.03 (m, 2H), 1.58 (s, 6H) | 443 |
| 7 | 5-[1-(2-Aza-bicyclo[3.1.0]hex-2-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 6.98 (s, 2H), 4.20-4.01 (m, 4H), 2.21-2.12 (m, 1H), 2.09-1.99 (m 1H), 1.79-1.69 (m, 1H), 1.58 (s, 6H), 0.84-0.76 (m, 1H), 0.69-0.64 (m, 1H) | 379 |

-continued

| Ex | Structure | ¹H NMR | MS (m/z) |
|---|---|---|---|
| 8 | 5-[8,8-Dimethyl-1-(2-oxa-6-aza-spiro[3.4]oct-6-yl)-5,6-hydro-8H-7-oxa-2,4,4b,9-tetraaza-fluoren-3-yl]-pyrimidin-2-ylamine | ¹H NMR (400 MHz, DMSO-d6) δ: 9.11 (s, 2H), 6.98 (s, 2H), 4.64 (d, J = 6.1 Hz, 2H), 4.56 (d, J = 6.1 Hz, 2H), 4.18-3.93 (m, 4H), 2.28 (s, 2H), 1.59 (s, 6H) | 409 |
| 9 | 5-[1-(7-Methoxy-7-aza-bicyclo[2.2.1]hept-2-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.08 (s, 2H), 6.97 (s, 2H), 5.45 (s, 1H), 4.20-4.04 (m, 4H), 3.88 (s, 1H), 3.70-3.63 (m, 1H), 3.52-3.43 (m, 1H), 3.34 (s, 3H), 1.91 (d, J = 12.0 Hz, 1H), 1.82 (d, J = 13.9 Hz, 1H), 1.57 (s, 6H), 1.44 (d, J = 11.4 Hz, 1H) | 423 |
| 10 | 5-[1-(6,6-Difluoro-3-aza-bicyclo[3.2.0]hept-3-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 7.02 (s, 2H), 4.20-4.03 (m, 4H), 2.44-2.25 (m, 1H), 2.19-1.94 (m, 7H), 1.59 (s, 6H) | 429 |

| Ex | Structure | ¹H NMR | MS (m/z) |
|---|---|---|---|
| 11 | 5-[1-(5,5-Difluoro-2-aza-bicyclo[2.2.1]hept-2-yl)-8,8-dimethyl-5,6-dimethyl-8H-7-oxa-2,4,4b,9-tetraaza-fluoren-3-yl]-pyrimidin-2-ylamine | ¹H NMR (400 MHz, DMSO-d6) δ: 9.11 (s, 2H), 7.01 (s, 2H), 4.20-4.08 (m, 4H), 3.67-3.47 (m, 4H), 2.92-2.81 (m, 2H), 2.36-2.18 (m, 2H), 1.59 (s, 6H) | 429 |
| 12 | 5-[8,8-Dimethyl-1-(2-oxa-7-aza-spiro[4.4]non-7-yl)-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 7.03 (s, 2H), 4.16-4.07 (m, 4H), 4.06-3.94 (m, 2H) 3.87-3.76 (m, 4H), 3.70-3.57 (m, 2H), 2.09-1.87 (m, 4H), 1.58 (s, 6H) | 423 |
| 13 | 5-[8,8-Dimethyl-1-(tetrahydro-furo[3,4-c]pyrrol-5-yl)-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 6.99 (s, 2H), 4.18-4.04 (m, 8H), 3.90-3.53 (m, 4H), 3.11-3.01 (m, 2H), 1.58 (s, 6H) | 409 |

| Ex | Structure | ¹H NMR | MS (m/z) |
|---|---|---|---|
| 14 | 5-[1-(Hexahydro-furo[2,3-c]pyrrol-5-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 7.03 (s, 2H), 4.58 (t, J = 5.4 Hz, 1H), 4.31 (s, 2H), 4.12 (d, J = 4.1 Hz, 4H), 3.85 (p, J = 7.8 Hz, 3H), 3.74 (td, J = 8.0, 5.0 Hz, 1H), 3.07-2.99 (m, 1H), 2.20-2.06 (m, 1H), 1.92-1.80 (m, 1H), 1.59 (s, 6H) | 409 |
| 15 | (±)-5-(4-((cis)-4,4-difluorohexahydrocyclopenta[c]-pyrrol-2(1H)-yl)-6,6-dimethyl-8,9-dihydro-6H-[1,4]oxazino[4,3-e]purin-2-yl)pyrimidin-2-amine | ¹H NMR (400 MHz, DMSO-d6) δ: 9.10 (s, 2H), 6.99 (s, 2H), 4.23-4.06 (m, 5H), 3.15-3.03 (m, 3H), 1.59 (s, 6H) | 443 |
| 16 | 5-[8,8-Dimethyl-1-(7-oxa-1-aza-spiro[4.4]non-1-yl)-5,6-dihydro-8H-7-oxa-2,4,4b,9-tetraaza-fluoren-3-yl]-pyrimidin-2-ylamine | ¹H NMR (400 MHz, DMSO-d6) δ: 9.13 (s, 2H), 6.96 (s, 2H), 4.58 (d, J = 8.0 Hz, 1H), 4.29-4.06 (m, 7H), 3.88-3.81 (m, 1H), 3.43 (d, J = 8.0 Hz, 1H), 3.18-3.05 (m, 1H), 2.11-2.03 (m, 2H), 2.01-1.88 (m, 2H), 1.72-1.62 (m, 1H), 1.57 (s, 6H) | 423 |

-continued

| Ex | Structure | $^1$H NMR | MS (m/z) |
|---|---|---|---|
| 17 | 5-[1-(5-Fluoro-2-aza-bicyclo[2.2.1]hept-2-yl)-8,8-dimethyl-5,6-dihydro-8H-7-oxa-2,4,4b,9-tetraaza-fluoren-3-yl]-pyrimidin-2-ylamine | $^1$H NMR (400 MHz, DMSO-d6) δ: 9.10 (s, 2H), 5.62-4.93 (m, 2H), 7.01 (s, 2H), 4.35-3.53 (m, 6H), 3.09-2.90 (m, 1H), 2.28-2.15 (m, 1H), 2.00-1.67 (m, 2H), 1.58 (s, 6H) | 411 |
| 18 | 5-(8,8-Dimethyl-1-pyrrolidin-1-yl-5,6-dihydro-8H-7-oxa-2,4,4b,9-tetraaza-fluoren-3-yl)-pyrimidin-2-ylamine | | 367 |
| 19 | 1-(2-Aza-bicyclo[2.1.1]hex-2-yl)-8,8-dimethyl-3-(3-methyl-1H-pyrazolo[3,4-b]pyridin-5-yl)-5,6-dihydro-8H-7-oxa-2,4,4b,9-tetraaza-fluorene | $^1$H NMR (400 MHz, DMSO-d6) δ: 13.29 (s, 1H), 9.54 (s, 1H), 9.02 (s, 1H), 5.85-5.80 (m, 1H), 4.24-4.10 (m, 4H), 3.88-3.83 (m, 2H), 3.08-2.99 (m, 1H), 2.58 (s, 3H), 212 (s, 2H), 1.61 (s, 6H), 1.51-1.44 (m, 2H) | 417 |

-continued

| Ex | Structure | ¹H NMR | MS (m/z) |
|---|---|---|---|
| 20 | 1-(2-Aza-bicyclo[2.1.1]hex-2-yl)-3-(3-ethyl-1H-pyrazolo[3,4-b]pyridin-5-yl)-8,8-dimethyl-5,6-dihydro-8H-7-oxa-2,4,4b,9-tetraaza-fluorene | ¹H NMR (400 MHz, DMSO-d6) δ: 13.30 (s, 1H), 9.54 (s, 1H), 9.04 (s, 1H), 5.83 (s, 1H), 4.24-4.10 (m, 4H), 3.88-3.83 (m, 2H), 3.07-2.96 (m, 3H), 2.14-2.09 (m, 2H), 1.61 (s, 6H), 1.53-1.44 (m, 2H), 1.37 (t, J = 7.6 Hz, 3H) | 431 |
| 21 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-3-ethoxy-pyridin-2-ylamine | ¹H NMR (400 MHz, DMSO-d6) δ: 8.59 (d, J = 1.8 Hz, 1H), 7.87 (d, J = 1.8 Hz, 1H), 5.97 (s, 2H), 5.72 (s, 1H), 4.17-4.07 (m, 6H), 3.81-3.76 (m, 2H), 3.04-2.96 (m, 1H), 2.11-2.05 (m, 2H), 1.58 (s, 6H), 1.49-1.37 (m, 5H) | 422 |
| 22 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-3-isopropoxy-pyridin-2-ylamine | ¹H NMR (400 MHz, DMSO-d6) δ: 8.58 (s, 1H), 7.90 (s, 1H), 5.91 (s, 2H), 4.68-4.57 (m, 1H), 4.17-4.06 (m, 4H), 3.80-3.75 (m, 2H), 3.04-2.96 (m, 1H), 2.11-2.05 (m, 2H), 1.58 (s, 6H), 1.47-1.41 (m, 2H), 1.34 (d, J = 6.0 Hz, 6H) | 436 |

-continued

| Ex | Structure | ¹H NMR | MS (m/z) |
|---|---|---|---|
| 23 | 1-(2-Aza-bicyclo[2.1.1]hex-2-yl)-8,8-dimethyl-3-(1H-pyrrolo[2,3-b]pyridin-5-yl)-5,6-dihydro-8H-7-oxa-2,4,4b,9-tetraaza-fluorene | 1H NMR (400 MHz, DMSO-d6) δ: δ: 11.73 (s, 1H), 9.30 (s, 1H), 8.90 (d, J =1.9 Hz, 1H), 7.53-7.47 (m, 1H), 6.60-6.54 (m, 1H), , 4.23-4.11 (m, 4H), 3.87-3.82 (m, 2H), 3.30-3.25 (m, 1H), 3.08-2.99 (m, 1H), 2.14-2.09 (m, 2H), 1.61 (s, 6H), 1.53-1.42 (m, 2H) | 402 |
| 24 | 5-[1-(2-Ethyl-pyrrolidin-1-yl)-8,8-dimethyl-5,6-dihydro-8H-7-oxa-2,4,4b,9-tetraaza-fluoren-3-yl]-pyrimidin-2-ylamine | 1H NMR (400 MHz, DMSO-d6) δ: 9.08 (s, 2H), 6.95 (s, 2H), 4.14-4.02 (m, 4H), 3.20-3.14 (m, 2H), 2.00-1.95 (m, 4H), 1.87-1.82 (m, 2H), 1.58 (s, 6H), 1.43-1.38 (m, 1H), 0.96 (t, J = 7.3 Hz, 3H) | 395 |
| 25 | 8,8-Dimethyl-3-(3-methyl-1H-pyrrolo[2,3-b]pyridin-5-yl)-1-(tetrahydro-furo[3,4-c]pyrrol-5-yl)-5,6-dihydro-8H-7-oxa-2,4,4b,9-tetraaza-fluorene | ¹H NMR (400 MHz, DMSO-d6) δ: 11.40 (s, 1H), 9.29 (d, J = 2.0 Hz, 1H), 8.81 (d, J = 2.0 Hz, 1H), 7.26 (s, 1H), 4.24-4.10 (m, 6H), 3.93-3.85 (m, 2H), 3.69-3.61 (m, 2H), 3.13-3.06 (m, 2H), 2.35-2.33 (m, 3H), 1.61 (s, 6H) | 446 |

-continued

| Ex | Structure | ¹H NMR | MS (m/z) |
|---|---|---|---|
| 26 | 5-[8,8-Dimethyl-1-((R)-2-methyl-pyrrolidin-1-yl)-5,6-dihydro-8H-7-oxa-2,4,4b,9-tetraaza-fluoren-3-yl]-pyrimidin-2-ylamine | ¹H NMR (400 MHz, DMSO-d6) δ: 9.09 (s, 2H), 6.96 (s, 2H), 4.14-4.09 (m, 4H), 2.10-2.05 (m, 2H), 1.99-1.94 (m, 2H), 1.76-1.71 (m, 1H), 1.58 (s, 6H), 1.32-1.27 (m, 3H), 1.09-1.04 (m, 1H) | 381 |
| 27 | 5-[8,8-Dimethyl-1-(3-methyl-pyrrolidin-1-yl)-5,6-dihydro-8H-7-oxa-2,4,4b,9-tetraaza-fluoren-3-yl]-pyrimidin-2-ylamine | ¹H NMR (400 MHz, DMSO-d6) δ: 9.09 (s, 2H), 6.96 (s, 2H), 4.32-4.27 (m, 1H), 4.17-4.06 (m, 4H), 3.97-3.92 (m, 2H), 2.39-2.34 (m, 1H), 2.14-2.09 (m, 1H), 1.58 (s, 6H), 1.12 (d, J = 6.6 Hz, 3H) | 381 |
| 28 | 5-[8,8-Dimethyl-1-(3-trifluoromethyl-pyrrolidin-1-yl)-5,6-dihydro-8H-7-oxa-2,4,4b,9-tetraaza-fluoren-3-yl]-pyrimidin-2-ylamine | ¹H NMR (400 MHz, DMSO-d6) δ: 9.11 (s, 2H), 7.00 (s, 2H), 4.24-4.19 (m, 2H), 4.19-4.08 (m, 4H), 2.36-2.29 (m, 2H), 2.21-2.12 (m, 1H), 1.59 (s, 6H) | 435 |

| Ex | Structure | ¹H NMR | MS (m/z) |
|---|---|---|---|
| 29 | 5-[1-(cis-3,4-Difluoro-pyrrolidin-1-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.12 (s, 2H), 7.02 (s, 2H), 5.61-5.50 (m, 1H), 5.48-5.37 (m, 1H), 4.20-4.08 (m, 4H), 1.60 (s, 6H) | 403 |
| 30 | 8,8-Dimethyl-3-(3-methyl-1H-pyrrolo[2,3-b]pyridin-5-yl)-1-(2-oxa-6-aza-spiro[3.4]oct-6-yl)-5,6-dihydro-8H-7-oxa-2,4,4b,9-tetraaza-fluorene | 1H NMR (400 MHz, DMSO-d6) δ: 11.40 (s, 1H), 9.30 (d, J = 2.0 Hz, 1H), 8.82 (d, J = 2.0 Hz, 1H), 7.26 (s, 1H), 4.68 (d, J = 6.1 Hz, 2H), 4.58 (d, J = 6.1 Hz, 2H), 4.25-4.10 (m, 4H), 2.37-2.27 (m, 5H), 1.62 (s, 6H) | 446 |
| 31 | 5-[1-(3,3-Dimethyl-azetidin-1-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.06 (s, 2H), 6.98 (s, 2H), 4.16-4.05 (m, 8H), 1.56 (s, 6H), 1.33 (s, 6H) | 381 |

-continued

| Ex | Structure | ¹H NMR | MS (m/z) |
|---|---|---|---|
| 32 | 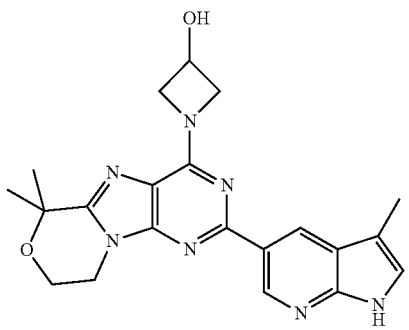 [SMILES: Cc1c[nH]c2ncc(-c3nc(N4CC(O)C4)c4nc5n(c4n3)CCOC5(C)C)cc12]

1-[8,8-Dimethyl-3-(3-methyl-1H-pyrrolo[2,3-b]pyridin-5-yl)-5,6-dihydro-8H-7-oxa-2,4,4b,9-tetraaza-fluoren-1-yl]-azetidin-3-ol | ¹H NMR (400 MHz, DMSO-d6) δ: 11.39 (s, 1H), 9.25 (d, J = 2.0 Hz, 1H), 8.78 (d, J = 1.9 Hz, 1H), 7.25 (s, 1H), 5.75 (d, J = 5.7 Hz, 1H), 4.73-4.60 (m, 3H), 4.23-4.09 (m, 6H), 2.32 (s, 3H), 1.59 (s, 6H) | 406 |
| 33 | 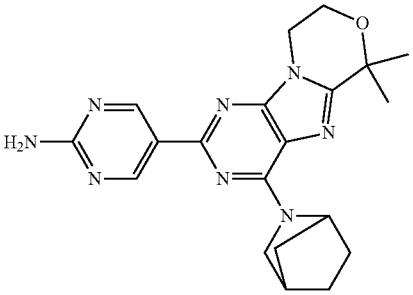 [SMILES: CC1(C)OCCn2c1nc1c(N3CC4CCC3C4)nc(-c3cnc(N)nc3)nc12]

5-[1-(2-Aza-bicyclo[2.2.1]hept-2-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.08 (s, 2H), 6.96 (s, 2H), 4.13-4.08 (m, 5H), 3.90-3.37 (m, 1H), 1.75-1.68 (m, 3H), 1.58 (s, 7H), 1.45-1.40 (m, 2H) | 393 |
| 34 | 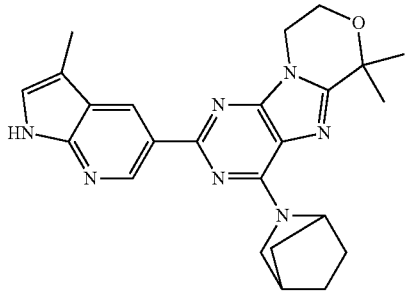 [SMILES: Cc1c[nH]c2ncc(-c3nc(N4CC5CCC4C5)c4nc5n(c4n3)CCOC5(C)C)cc12]

1-(2-Aza-bicyclo[2.2.1]hept-2-yl)-8,8-dimethyl-3-(3-methyl-1H-pyrrolo[2,3-b]pyridin-5-yl)-5,6-dihydro-8H-7-oxa-2,4,4b,9-tetraaza-fluorene | ¹H NMR (400 MHz, DMSO-d6) δ: 11.37 (s, 1H), 9.26 (d, J = 2.0 Hz, 1H), 8.79 (d, J = 1.9 Hz, 1H), 7.25 (s, 1H), 4.21-4.10 (m, 4H), 4.05-3.31 (m, 1H), 2.73-2.62 (m, 2H), 2.32 (s, 3H), 1.85-1.80 (m, 1H), 1.77-1.72 (m, 2H), 1.60 (s, 6H), 1.48-1.43 (m, 1H) | 430 |

| Ex | Structure | ¹H NMR | MS (m/z) |
|---|---|---|---|
| 35 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-3-chloro-pyridin-2-ylamine | ¹H NMR (400 MHz, DMSO-d6) δ: 8.90 (d, J = 1.9 Hz, 1H), 8.38 (s, 1H), 6.62 (s, 2H), 4.17-4.07 (m, 4H), 3.80-3.75 (m, 2H), 3.03-2.97 (m, 1H), 2.11-2.05 (m, 2H), 1.58 (s, 6H), 1.47-1.41 (m, 2H) | 412 |
| 36 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-3-fluoro-pyridin-2-ylamine | ¹H NMR (400 MHz, DMSO-d6) δ: 8.79 (s, 1H), 8.10 (dd, J = 12.6, 1.8 Hz, 1H), 6.54 (s, 2H), 4.16-4.07 (m, 4H), 3.80-3.75 (m, 2H), 3.04-2.96 (m, 1H), 2.11-2.05 (m, 2H), 1.58 (s, 6H), 1.49-1.40 (m, 2H) | 396 |
| 37 | 1-(2-Aza-bicyclo[2.2.1]hept-2-yl)-8,8-dimethyl-3-pyrazolo[1,5-a]pyrimidin-6-yl-5,6-dihydro-8H-7-oxa-2,4,4b,9-tetraaza-fluorene | ¹H NMR (400 MHz, DMSO-d6) δ: 9.63 (s, 1H), 9.44 (s, 1H), 8.31 (d, J = 2.4 Hz, 1H), 6.80 (d, J = 2.3 Hz, 1H), 4.21-4.12 (m, 4H), 4.03-3.39 (m, 2H), 2.74-2.69 (m, 1H), 1.92-1.66 (m, 3H), 1.64-1.56 (m, 8H), 1.47-1.42 (m, 1H) | 417 |

| Ex | Structure | ¹H NMR | MS (m/z) |
|---|---|---|---|
| 38 | 1-(2-Aza-bicyclo[2.1.1]hex-2-yl)-8,8-dimethyl-3-pyrazolo[1,5-a]pyrimidin-6-yl-5,6-dihydro-8H-7-oxa-2,4,4b,9-tetraaza-fluorene | 1H NMR (400 MHz, DMSO-d6) δ: 9.66 (s, 1H), 9.46 (s, 1H), 8.32 (d, J = 2.3 Hz, 1H), 6.81 (d, J = 2.2 Hz, 1H), 4.24-4.10 (m, 4H), 3.86-3.81 (m, 2H), 3.07-3.00 (m, 1H), 2.15-2.10 (m, 2H), 1.61 (s, 6H), 1.50-1.45 (m, 2H) | 403 |
| 39 | 1-[8,8-Dimethyl-3-(3-trifluoromethyl-1H-pyrrolo[2,3-b]pyridin-5-yl)-5,6-dihydro-8H-7-oxa-2,4,4b,9-tetraaza-fluoren-1-yl]-azetidin-3-ol | ¹H NMR (400 MHz, DMSO-d6) δ: 12.64 (s, 1H), 9.41 (d, J = 1.9 Hz, 1H), 8.91 (s, 1H), 8.21 (d, J = 9.7 Hz, 1H), 5.77 (d, J = 5.9 Hz, 1H), 4.73-4.62 (m, 3H), 4.24-4.09 (m, 6H), 1.59 (s, 6H) | 460 |
| 40 | 1-[3-(3-Chloro-1H-pyrrolo[2,3-b]pyridin-5-yl)-8,8-dimethyl-5,6-dihydro-8H-7-oxa-2,4,4b,9-tetraaza-fluoren-1-yl]-azetidin-3-ol | No NMR due to <5 mg registered | 426 |

| Ex | Structure | ¹H NMR | MS (m/z) |
|---|---|---|---|
| 41 | 5-[1-(3-Methoxy-azetidin-1-yl)-8,8-dimethyl-5,6-dihydro-8H-7-oxa-2,4,4b,9-tetraaza-fluoren-3-yl]-1H-pyrrolo[2,3-b]pyridin-3-carbonitrile | ¹H NMR (400 MHz, DMSO-d6) δ: 12.95 (s, 1H), 9.42 (d, J = 2.0 Hz, 1H), 8.91 (s, 1H), 8.49 (d, J = 3.0 Hz, 1H), 4.80-4.33 (m, 3H), 4.35-3.99 (m, 6H), 1.60 (s, 6H) | 431 |
| 42 | 5-[8,8-Dimethyl-1-(2-oxa-6-aza-spiro[3.4]oct-6-yl)-5,6-dihydro-8H-7-oxa-2,4,4b,9-tetraaza-fluoren-3-yl]-1H-pyrrolo[2,3-b]pyridin-3-carbonitrile | ¹H NMR (400 MHz, DMSO-d6) δ: 12.95 (s, 1H), 9.46 (d, J = 1.9 Hz, 1H), 8.93 (d, J = 2.0 Hz, 1H), 8.49 (s, 1H), 4.82-4.42 (m, 4H), 4.40-3.93 (m, 4H), 2.32 (d, J = 6.2 Hz, 2H), 1.61 (s, 6H) | 457 |
| 43 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-3-difluoromethoxy-pyridin-2-ylamine | ¹H NMR (400 MHz, DMSO-d6) δ: 8.84 (s, 1H), 8.16 (s, 1H), 6.43 (s, 2H), 4.17-3.99 (m, 4H), 3.78 (s, 2H), 3.05-2.96 (m, 1H), 2.11-2.04 (m, 2H), 1.58 (s, 6H), 1.47-1.41 (m, 2H) | 444 |

| Ex | Structure | ¹H NMR | MS (m/z) |
|---|---|---|---|
| 44 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-3-cyclopropyl-pyridin-2-ylamine | ¹H NMR (400 MHz, DMSO-d6) δ: 8.79 (s, 1H), 8.10 (s, 1H), 6.54 (s, 2H), 5.72 (s, 1H), 4.18-4.06 (m, 4H), 3.80-3.75 (m, 2H), 3.05-2.96 (m, 1H), 2.11-2.05 (m, 2H), 1.80-1.69 (m, 1H), 1.58 (s, 6H), 1.47-1.40 (m, 2H), 1.01-0.91 (m, 2H), 0.64-0.55 (m, 2H) | 418 |
| 45 | 1-(3-Fluoro-azetidin-1-yl)-8,8-dimethyl-3-(3-trifluoromethyl-1H-pyrrolo[2,3-b]pyridin-5-yl-5,6-dihydro-8H-7-oxa-2,4,4b,9-tetraaza-fluorene | ¹H NMR (400 MHz, DMSO-d6) δ: 12.65 (s, 1H), 9.43 (d, J = 2.0 Hz, 1H), 8.91 (d, J = 1.9 Hz, 1H), 8.21 (s, 1H), 5.75-5.44 (m, 1H), 4.87-4.72 (m, 2H), 4.54-4.40 (m, 2H), 4.26-4.18 (m, 2H), 4.17-4.09 (m, 2H), 1.60 (s, 6H) | 462 |
| 46 | 5-[1-(2-Aza-bicyclo[2.1.1]hex-2-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 6.97 (s, 2H), 4.16-4.06 (m, 4H), 3.90-3.55 (m, 2H), 3.03-2.97 (m, 1H), 2.11-2.06 (m, 2H), 1.59 (s, 6H), 1.47-1.41 (m, 2H) | 379 |

| Ex | Structure | ¹H NMR | MS (m/z) |
|---|---|---|---|
| 47 | 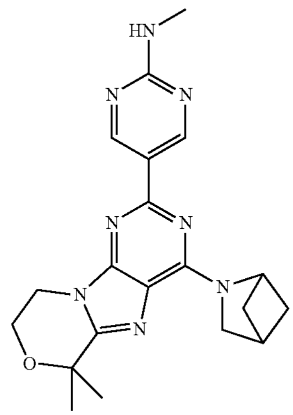 [SMILES: CNc1ncc(-c2nc(N3CC4CC3C4)c3nc4n(c3n2)CCOC4(C)C)cn1] | 1H NMR (400 MHz, DMSO-d6) δ 9.14 (s, 2H), 7.43 (m, 1H), 4.12 (m, 4H), 3.77 (m, 2H), 3.00 (m, 1H), 2.88 (d, J = 4.8 Hz, 3H), 2.52 (m, 1H), 2.08 (m, 2H), 1.59 (s, 6H), 1.44 (m, 2H); MS (m/z) = 393.3 | |
| 48 | 5-(4-(2-azabicyclo[2.1.1]hexan-2-yl)-6,6-dimethyl-8,9-dihydro-6H-[1,4]oxazino[4,3-e]purin-2-yl)-3-methylpyridin-2-amine | ¹H NMR (400 MHz, DMSO-d6) δ 8.83 (d, J = 1.9 Hz, 1H), 8.15 (s, 1H), 6.02 (s, 2H), 4.11 (s, 4H), 3.78 (s, 2H), 3.04-2.96 (m, 1H), 2.12 (s, 3H), 2.07 (s, 2H), 1.58 (s, 6H), 1.43 (d, J = 3.3 Hz, 2H). | 392 |
| 49 | 5-[8,8-Dimethyl-1-(2-oxa-6-aza-spiro[3.4]oct-6-yl)-5,6-dihydro-8H-7-oxa-2,4,4b,9-tetraaza-fluoren-3-yl]-3-trifluoromethyl-pyridin-2-ylamine | ¹H NMR (400 MHz, DMSO-d6) δ 9.17 (s, 1H), 8.58 (2, 1H), 6.81 (s, 2H), 4.64 (d, J = 6.2 Hz, 2H), 4.56 (d, J = 6.0 Hz, 2H), 4.17-4.13 (m, 2H), 4.13-4.08 (m, 2H), 2.28 (s, 2H), 1.59 (s, 6H). | 476 |

| Ex | Structure | ¹H NMR | MS (m/z) |
|---|---|---|---|
| 50 | 5-[8,8-Dimethyl-1-(2-oxa-6-aza-spiro[3.3]hept-6-yl)-5,6-dihydro-8H-7-oxa-2,4,4b,9-tetraaza-fluoren-3-yl]-pyrimidin-2-ylamine | ¹H NMR (400 MHz, DMSO-d6) δ 9.07 (s, 2H), 7.00 (s, 2H), 4.77 (s, 4H), 4.55 (s, 4H), 4.23-3.95 (m, 4H), 1.57 (s, 6H). | 395 |
| 51 | 5-[8,8-Dimethyl-1-(5-oxa-2-aza-spiro[3.4]oct-2-yl)-5,6-dihydro-8H-7-oxa-2,4,4b,9-tetraaza-fluoren-3-yl]-pyrimidin-2-ylamine | 1H NMR (400 MHz, DMSO-d6) δ 9.01 (s, 2H), 6.99 (s, 2H), 4.43 (d, J = 9.8 Hz, 2H), 4.31 (d, J = 9.9 Hz, 2H), 4.17-4.06 (m, 4H), 3.81 (t, J = 6.8 Hz, 2H), 2.15 (t, J = 8.0, 6.5 Hz, 2H), 1.96-1.86 (m, 2H), 1.57 (s, 6H) | 409 |
| 52 | 5-[1-(2-Aza-spiro[3.3]hept-2-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ 9.06 (s, 2H), 6.99 (s, 2H), 4.46-4.26 (m, 4H), 4.15-4.05 (m, 4H), 2.23 (t, J = 7.6 Hz, 4H), 1.83 (p, J = 7.6 Hz, 2H), 1.57 (s, 6H). | 393 |

-continued

| Ex | Structure | ¹H NMR | MS (m/z) |
|---|---|---|---|
| 53 | 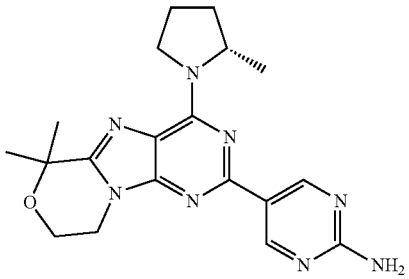<br>5-[8,8-Dimethyl-1-((S)-2-methyl-pyrrolidin-1-yl)-5,6-dihydro-8H-7-oxa-2,4,4b,9-tetraaza-fluoren-3-yl]-pyrimidin-2-ylamine | ¹H NMR (400 MHz, DMSO-d6) δ 9.08 (s, 2H), 6.96 (s, 2H), 4.16-4.08 (m, 4H), 2.12-2.01 (m, 2H), 2.01-1.91 (m, 1H), 1.80-1.67 (m, 1H), 1.58 (s, J = 3.6 Hz, 6H), 1.29 (d, J = 6.1 Hz, 3H). | 381 |
| 54 | 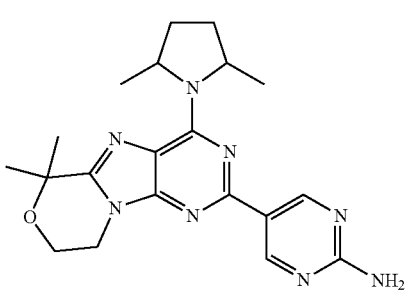 [SMILES: CC1CCC(C)N1c1nc(-c2cnc(N)nc2)nc2c1nc1n2CCOC1(C)C]<br>5-[1-(2,5-Dimethyl-pyrrolidin-1-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ 9.08 (s, 2H), 6.96 (s, 2H), 5.12-4.96 (m, 1H), 4.74-4.56 (m, 1H), 4.18-4.04 (m, 4H), 2.36-2.15 (m, 3H), 1.78-1.68 (m, 1H), 1.68-1.60 (m, 1H), 1.61-1.54 (d, J = 6.6 Hz, 6H), 1.31-1.21 (m, 3H), 1.21-1.10 (m, 3H) | 395 |
| 55 | 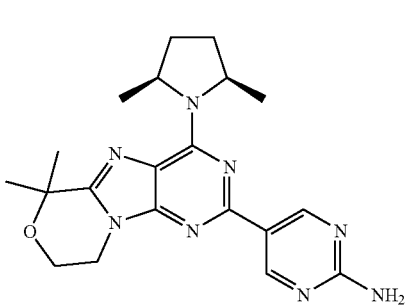 [SMILES: C[C@@H]1CC[C@H](C)N1c1nc(-c2cnc(N)nc2)nc2c1nc1n2CCOC1(C)C]<br>5-(4-((2R,5S)-2,5-dimethylpyrrolidin-1-yl)-6,6-dimethyl-8,9-dihydro-6H-[1,4]oxazino[4,3-e]purin-2-yl)pyrimidin-2-amine | ¹H NMR (400 MHz, DMSO-d6) δ 9.07 (s, 1H), 6.96 (s, 1H), 4.11 (s, 4H), 2.19-2.03 (m, 2H), .86-1.72 (m, 2H), 1.58 (s, 6H), 1.43 (s, 3H), 1.42 (s, 3H), 1.30-1.11 (m, 2H). | 395 |

| Ex | Structure | ¹H NMR | MS (m/z) |
|---|---|---|---|
| 56 | 5-(4-(7-azabicyclo[2.2.1]heptan-7-yl)-6,6-dimethyl-8,9-dihydro-6H-[1,4]oxazino[4,3-e]purin-2-yl)pyrimidin-2-amine | ¹H NMR (400 MHz, DMSO-d6) δ 9.10 (s, 2H), 7.00 (s, 2H), 4.18-4.08 (m, 4H), 1.78-1.67 (m, 4H), 1.60 (s, 6H), 1.54 (d, J = 7.7 Hz, 4H). | 393 |
| 57 | 5-(4-(2-azabicyclo[2.1.1]hexan-2-yl)-6,6-dimethyl-8,9-dihydro-6H-[1,4]oxazino[4,3-e]purin-2-yl)-3-ethoxypyridin-2-amine | 1H NMR (400 MHz, DMSO-d6) δ 8.60 (s, 1H), 7.89 (s, 1H), 6.03 (s, 2H), 4.19-4.00 (m, 5H), 3.88 (s, 3H), 3.85-3.72 (m, 2H), 3.05-2.95 (m, 1H), 2.15-2.03 (m, 2H), 1.59 (s, 6H), 1.56 (s, 1H), 1.48-1.40 (m, 2H). | 408 |
| 58 | 2-(2-aminopyrimidin-5-yl)-N-cyclobutyl-N,6,6-trimethyl-8,9-dihydro-6H-[1,4]oxazino[4,3-e]purin-4-amine | 1H NMR (400 MHz, DMSO-d6) δ 9.09 (s, 2H), 7.61-7.44 (m, 1H), 6.98 (s, 2H), 5.71 (s, 1H), 4.18-4.06 (m, 4H), 3.48 (s, 3H), 2.39-2.26 (m, 2H), 2.25-2.14 (m, 2H), 1.78-1.68 (m, 2H), 1.59 (s, 6H). | 381 |

-continued

| Ex | Structure | ¹H NMR | MS (m/z) |
|---|---|---|---|
| 59 | 2-(2-aminopyrimidin-5-yl)-N-cyclopropyl-6,6-dimethyl-8,9-dihydro-6H-[1,4]oxazino[4,3-e]purin-4-amine | 1H NMR (400 MHz, DMSO-d6) δ 9.12 (s, 2H), 7.80 (s, 2H), 6.96 (s, 2H), 4.19-4.07 (m, 4H), 3.23-3.09 (m, 1H), 1.58 (s, 6H), 0.81-0.70 (m, 2H), 0.70-0.61 (m, 2H). | 353 |
| 60 | 2-(2-aminopyrimidin-5-yl)-N-cyclopropyl-N,6,6-trimethyl-8,9-dihydro-6H-[1,4]oxazino[4,3-e]purin-4-amine | 1H NMR (400 MHz, DMSO-d6) δ 9.11 (s, 2H), 6.97 (s, 2H), 4.18-4.08 (m, 4H), 3.47 (s, 3H), 3.25-3.16 (m, 1H), 1.58 (s, 6H), 0.96-0.88 (m, 2H), 0.77-0.69 (m, 2H). | 367 |
| 61 | 2-(2-aminopyrimidin-5-yl)-N-cyclopropyl-N-ethyl-6,6-dimethyl-8,9-dihydro-6H-[1,4]oxazino[4,3-e]purin-4-amine | ¹H NMR (400 MHz, DMSO-d6) δ 9.11 (s, 2H), 6.97 (s, 2H), 4.16-4.06 (m, 6H), 3.17-3.07 (m, 1H), 1.58 (s, 6H), 1.18 (t, J = 7.0 Hz, 3H), 1.00-0.91 (m, 2H), 0.74-0.66 (m, 3H). | 381 |
| 62 | 2-(2-aminopyrimidin-5-yl)-N-cyclobutyl-N-ethyl-6,6-dimethyl-8,9-dihydro-6H-[1,4]oxazino[4,3-e]purin-4-amine | 1H NMR (400 MHz, DMSO-d6) δ 9.08 (s, 2H), 7.01 (s, 2H), 4.19-3.99 (m, 6H), 2.35-2.18 (m, 4H), 1.79-1.66 (m, 2H), 1.59 (s, 6H), 1.19 (t, J = 6.9 Hz, 3H). | 395 |

| Ex | Structure | ¹H NMR | MS (m/z) |
|---|---|---|---|
| 63 | 2-(2-aminopyrimidin-5-yl)-N-cyclopropyl-N-isopropyl-6,6-dimethyl-8,9-dihydro-6H-[1,4]oxazino[4,3-e]purin-4-amine | 1H NMR (400 MHz, DMSO-d6) δ 9.10 (s, 2H), 7.01 (s, 2H), 5.16-5.01 (m, 1H), 4.18-4.08 (m, 4H), 2.90-2.81 (m, 1H), 1.58 (s, 6H), 141 (d, J = 6.7 Hz, 6H), 1.02-0.91 (m, 2H), 0.73-0.64 (m, 2H). | 395 |
| 64 | 2-(2-aminopyrimidin-5-yl)-N-cyclobutyl-N-isopropyl-6,6-dimethyl-8,9-dihydro-6H-[1,4]oxazino[4,3-e]purin-4-amine | 1H NMR (400 MHz, DMSO-d6) δ 9.09 (s, 2H), 7.03 (s, 2H), 5.26-4.98 (m, 2H), 4.18-4.04 (m, 4H), 3.02-2.83 (m, 2H), 2.20-2.07 (m, 2H), 1.89-1.69 (m, 2H), 1.58 (s, 6H), 1.40 (d, J = 6.7 Hz, 6H). | 409 |

Example 65

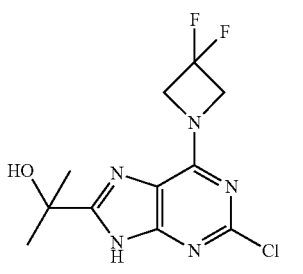 [SMILES: CC(C)(O)c1nc2c(N3CC(F)(F)C3)nc(Cl)nc2[nH]1]

Step 1: 2-(2-chloro-6-(3,3-difluoroazetidin-1-yl)-9H-purin-8-yl)propan-2-ol

To a stirred solution of 2-(2,6-dichloro-9H-purin-8-yl)propan-2-ol (3.5 g, 14.17 mmol) in tetrahydrofuran (50 mL) was added 3, 3 difluoroazetidine hydrochloride (2.91 g, 22.53 mmol) and triethylamine (4.08 mL, 28.34 mmol) at 0° C. After addition was complete the reaction mixture was stirred at RT for 16 h. The reaction mixture was diluted with water (100 mL) and extracted with dichloromethane (2×100 mL). The combined organic layers were dried over sodium sulfate and concentrated to dryness in vacuo affording 2-(2-chloro-6-(3,3-difluoroazetidn-1-yl)-9H-purin-8-yl)propan-2-ol (3.6 g, 81%) used in the next step without any further purification.

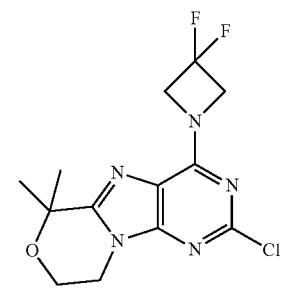 [SMILES: CC1(C)OCCn2c1nc1c(N3CC(F)(F)C3)nc(Cl)nc12]

Step 2: 2-chloro-4-(3,3-difluoroazetidin-1-yl)-6,6-dimethyl-8,9-dihydro-6H-[1,4]oxazino[4,3-e]purine To a stirred solution of 2-(2-chloro-6-(3,3-difluoroazetidin-1-yl)-9H-purin-8-yl)propan-2-ol (3.6 g, 11.8 mmol) in acetonitrile (70 mL) was added cesium carbonate (11.5 g, 35.53 mmol), and 1, 2-dibromoethane (3.1 mL, 35.53 mmol) at RT in a seal tube. After addition was completed the reaction mixture was heated to 80° C. for 16 h and concentrated to dryness in vacuo. The resulting viscous mass was diluted with ethyl acetate (100 mL) and water (50 mL). The separated organic layer was dried over sodium sulfate and concentrated to dryness in vacuo. The resulting residue was purified by column chromatography (silica gel, 100-200 mesh, 10% ethyl acetate in hexane) affording 2-chloro-4-(3,3-difluoroazetidin-1-yl)-6,6-dimethyl-8,9-dihydro-6H-[1,4]oxazino[4,3-e]purine (1.82 g, 46%): $^1$H NMR (300 MHz, Chloroform-d) δ 4.9-4.7 (4H, m), 4.2-4.07 (m, 4H), 1.65 (s, 6H).

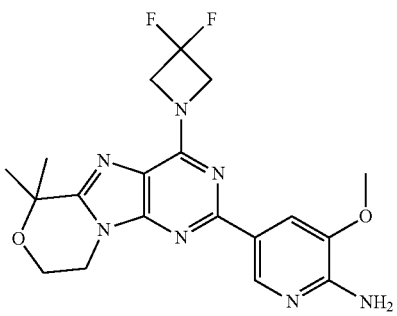 [SMILES: COc1cc(-c2nc(N3CC(F)(F)C3)c3nc4n(c3n2)CCOC4(C)C)cnc1N]

Step 3: 5-(4-(3,3-difluoroazetidin-1-yl)-6,6-dimethyl-8,9-dihydro-6H-[1,4]oxazino[4,3-e]purin-2-yl)-3-methoxypyridin-2-amine 2-chloro-4-(3,3-difluoroazetidin-1-yl)-6,6-dimethyl-8,9-dihydro-6H-[1,4]oxazino[4,3-e]purine (100 mg, 0.303 mmol) was dissolved in a 1:1 mixture of acetonitrile:1M potassium carbonate (4 mL) and transferred to a microwave vial equipped with a stirbar. To the solution was added 3-methoxy-5-(4,4,5,5-tetramethyl-1,3,2-dioxaborolan-2-yl)pyridin-2-amine (113.6 mg, 0.45 mmol), 1,1'-bis(diphenylphosphino)ferrocene-palladium(II)dichloride (11.3 mg, 0.015 mmol) and the mixture was microwaved at 120° C. for 10 min. The reaction mixture was diluted with 10 mL water and extracted with ethyl acetate (3×15 ml). The combined organic layers were dried over magnesium sulfate, filtered and concentrated to dryness in vacuo. The resulting residue was purified by RP-HPLC affording 5-(4-(3,3-difluoroazetidin-1-yl)-6,6-dimethyl-8,9-dihydro-6H-[1,4]oxazino[4,3-e]purin-2-yl)-3-methoxypyridin-2-amine (27 mg, 21%): $^1$H NMR (400 MHz, DMSO-d6) δ 8.60 (s, 1H), 7.86 (s, 1H), 6.17 (s, 2H), 4.88-4.69 (m, 4H), 4.24-4.04 (m, 4H), 3.88 (s, 3H), 1.64-1.53 (s, 6H).

Using a procedure similar to that described in Example 65 the following compounds were prepared.

| Ex | Structure | $^1$H NMR | MS (m/z) |
|---|---|---|---|
| 66 | 1-(3,3-Difluoro-azetidin-1-yl)-8,8-dimethyl-3-(3-methyl-1H-pyrrolo[2,3-b]pyridin-5-yl)-5,6-dihydro-8H-7-oxa-2,4,4b,9-tetraaza-fluorene | $^1$H NMR (400 MHz, DMSO-d6) δ: 11.47 (s, 1H), 9.27 (d, J = 2.0 Hz, 1H), 8.82 (d, J = 2.0 Hz, 1H), 7.28 (s, 1H), 4.86 (t, J = 12.3 Hz, 4H), 4.23 (t, J = 5.0 Hz, 2H), 4.14 (t, J = 5.0 Hz, 2H), 2.33 (s, 3H), 1.60 (s, 6H) | 426 |
| 67 | 1-(3,3-Difluoro-azetidin-1-yl)-3-(3-isopropyl-1H-pyrrolo[2,3-b]pyridin-5-yl)-8,8-dimethyl-5,6-dihydro-8H-7-oxa-2,4,4b,9-tetraaza-fluorene | $^1$H NMR (400 MHz, DMSO-d6) δ: 11.49 (s, 1H), 9.26 (d, J = 2.0 Hz, 1H), 8.89 (s, 1H), 7.25 (d, J = 2.3 Hz, 1H), 4.85 (t, J = 12.3 Hz, 4H), 4.29-4.10 (m, 4H), 3.21 (p, J = 6.9 Hz, 1H), 1.60 (s, 6H), 1.35 (d, J = 6.8 Hz, 6H) | 454 |

-continued

| Ex | Structure | ¹H NMR | MS (m/z) |
|---|---|---|---|
| 68 | 5-[1-(3,3-Difluoro-azetidin-1-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.10 (s, 2H), 7.07 (s, 2H), 4.80 (t, J = 12.3 Hz, 4H), 4.20-4.08 (m, 4H), 1.59 (s, 6H) | 389 |
| 69 | 5-[1-(3,3-Difluoro-azetidin-1-yl)-8,8-dimethyl-5,6-dihydro-8H-7-oxa-2,4,4b,9-tetraaza-fluoren-3-yl]-3-ethoxy-pyridin-2-ylamine | ¹H NMR (400 MHz, DMSO-d6) δ: 8.59 (s, 1H), 7.85 (s, 1H), 6.05 (s, 2H), 4.79 (t, J = 12.4 Hz, 4H), 4.21-4.04 (m, 6H), 1.58 (s, 6H), 1.41 (t, J = 6.9 Hz, 3H) | 432 |
| 70 | 3-Cyclopropylmethoxy-5-[1-(3,3-difluoro-azetidin-1-yl)-8,8-dimethyl-5,6-dihydro-8H-7-oxa-2,4,4b,9-tetraaza-fluoren-3-yl]-pyridin-2-ylamine | ¹H NMR (400 MHz, DMSO-d6) δ: 8.60 (s, 1H), 8.14 (s, 1H), 6.02 (s, 2H), 4.79 (t, J = 12.4 Hz, 4H), 4.20-4.07 (m, 4H), 3.93 (d, J = 6.8 Hz, 2H), 1.58 (s, 6H), 1.35-1.22 (m, 1H), 0.65-0.55 (m, 2H), 0.45-0.36 (m, 2H) | 458 |

| Ex | Structure | ¹H NMR | MS (m/z) |
|---|---|---|---|
| 71 | 5-[1-(3,3-Difluoro-azetidin-1-yl)-8,8-dimethyl-5,6-dihydro-8H-7-oxa-2,4,4b,9-tetraaza-fluoren-3-yl]-3-isopropoxy-pyridin-2-ylamine | ¹H NMR (400 MHz, DMSO-d6) δ: 8.57 (s, 1H), 7.90 (s, 1H), 6.14 (s, 2H), 4.79 (t, J = 12.3 Hz, 4H), 4.70-4.50 (m, 1H), 4.21-4.08 (m, 4H), 1.58 (s, 6H), 1.34 (d, J = 6.0 Hz, 6H) | 446 |
| 72 | 3-sec-Butoxy-5-[1-(3,3-difluoro-azetidin-1-yl)-8,8-dimethyl-5,6-dihydro-8H-7-oxa-2,4,4b,9-tetraaza-fluoren-3-yl]-pyridin-2-ylamine | ¹H NMR (400 MHz, DMSO-d6) δ: 8.57 (s, 1H), 7.88 (s, 1H), 6.10 (s, 2H), 4.79 (t, J = 12.4 Hz, 4H), 4.50-4.40 (m, 1H), 4.21-4.08 (m, 4H), 1.81-1.56 (m, 8H), 1.30 (d, J = 6.0 Hz, 3H), 0.98 (t, J = 7.4 Hz, 3H) | 460 |

Example 73

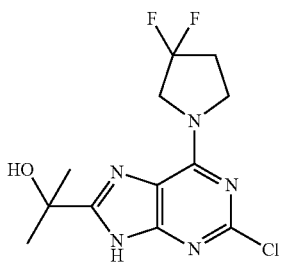 [SMILES: CC(C)(O)c1nc2c(N3CCC(F)(F)C3)nc(Cl)nc2[nH]1]

Step 1: 2-(2-chloro-6-(3,3-difluoropyrrolidin-1-yl)-9H-purin-8-yl)propan-2-ol

To a stirred solution of 2-(2,6-dichloro-9H-purin-8-yl)propan-2-ol (3.5 g, 14.17 mmol) in tetrahydrofuran (50 mL) was added 3,3-difluoropyrrolidine hydrochloride (3.23 g, 22.53 mmol) and triethylamine (4.08 mL, 28.34 mmol) at 0° C. After addition was complete the reaction mixture was stirred at RT for 16 h. The reaction mixture was diluted with water (50 mL) and extracted with dichloromethane (2×50 mL). The combined organic layers were dried over sodium sulfate and concentrated to dryness in vacuo affording 2-(2-chloro-6-(3,3-difluoropyrrolidin-1-yl)-9H-purin-8-yl)propan-2-ol (4.1 g, 91%) used in the next step without any further purification.

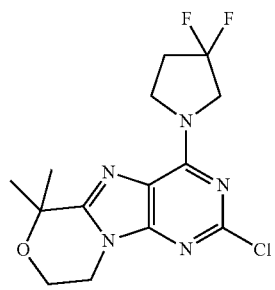 [SMILES: CC1(C)OCCn2c1nc1c(N3CCC(F)(F)C3)nc(Cl)nc12]

Step 2: 2-chloro-4-(3,3-difluoropyrrolidin-1-yl)-6,6-dimethyl-8,9-dihydro-6H-[1,4]oxazino[4,3-e]purine To a stirred solution of 2-(2-chloro-6-(3,3-difluoropyrrolidin-1-yl)-9H-purin-8-yl)propan-2-ol (4.1 g, 12.90 mmol) in acetonitrile (70 mL) was added cesium carbonate (12.6 g, 38.7 mmol), and 1,2-dibromoethane (3.4 mL, 38.7 mmol) at RT in a seal tube. After addition was completed the reaction mixture was heated to 80° C. for 16 h and concentrated to dryness in vacuo. The resulting viscous mass was diluted with ethyl acetate (100 mL) and water (50 mL). The separated organic layer was dried over sodium sulfate and concentrated to dryness in vacuo. The resulting residue was purified by column chromatography (silica gel, 100-200 mesh, 10% ethyl acetate in hexane) affording 2-chloro-4-(3,3-difluoropyrrolidin-1-yl)-6,6-dimethyl-8,9-dihydro-6H-[1,4]oxazino[4,3-e]purine (2.2 g, 50%): $^1$H NMR (300 MHz, DMSO-d6) δ 4.6-3.8 (m, 8H), 2.7-2.6 (m, 2H), 1.58 (s, 6H).

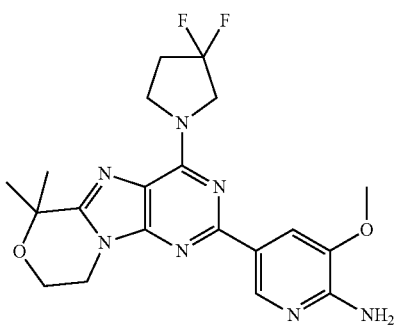

Step 3: 5-(4-(3,3-difluoropyrrolidin-1-yl)-6,6-dimethyl-8,9-dihydro-6H-[1,4]oxazino[4,3-e]purin-2-yl)-3-methoxypyridin-2-amine 2-chloro-4-(3,3-difluoropyrrolidin-1-yl)-6,6-dimethyl-8,9-dihydro-6H-[1,4]oxazino[4,3-e]purine (100 mg, 0.291 mmol) was dissolved in a 1:1 mixture of acetonitrile:1M potassium carbonate (4 mL) and transferred to a microwave vial equipped with a stirbar. To the solution was added 3-methoxy-5-(4,4,5,5-tetramethyl-1,3,2-dioxaborolan-2-yl)pyridin-2-amine (109.1 mg, 0.437 mmol), 1,1'-bis(diphenylphosphino)ferrocene-palladium(II)dichloride (11.3 mg, 0.015 mmol) and the mixture was microwaved at 120° C. for 10 min. The reaction mixture was diluted with 10 mL water and extracted with ethyl acetate (3×15 ml). The combined organic extracts were dried over magnesium sulfate, filtered and concentrated to dryness in vacuo. This resulting residue was purified by RP-HPLC affording 5-(4-(3,3-difluoropyrrolidin-1-yl)-6,6-dimethyl-8,9-dihydro-6H-[1,4]oxazino[4,3-e]purin-2-yl)-3-methoxypyridin-2-amine (9 mg, 7%): $^1$H NMR (400 MHz, DMSO-d6) δ 8.61 (s, 1H), 7.88 (s, 1H), 6.15 (s, 2H), 4.39-4.10 (m, 8H), 3.88 (s, 3H), 2.69-2.56 (m, 2H), 1.59 (s, 6H).

Using a procedure similar to that described in Example 73 the following compounds were prepared.

| Ex | Structure | $^1$H NMR | MS (m/z) |
|---|---|---|---|
| 74 | 1-(3,3-Difluoro-pyrrolidin-1-yl)-8,8-dimethyl-3-(3-methyl-1H-pyrrolo[2,3-b]pyridin-5-yl)-5,6-dihydro-8H-7-oxa-2,4,4b,9-tetraazafluorene | $^1$H NMR (400 MHz, DMSO-d6) δ: 11.45 (s, 1H), 9.29 (d, J = 2.0 Hz, 1H), 8.83 (d, J = 2.0 Hz, 1H), 7.27 (s, 1H), 4.39 (s, 3H), 4.23 (t, J = 5.2 Hz, 2H), 4.14 (t, J = 4.9 Hz, 2H), 2.66-2.58 (m, 1H), 2.33 (s, 3H), 1.61 (s, 6H) | 440 |
| 75 | 1-(3,3-Difluoro-pyrrolidin-1-yl)-3-(3-isopropyl-1H-pyrrolo[2,3-b]pyridin-5-yl)-8,8-dimethyl-5,6-dihydro-8H-7-oxa-2,4,4b,9-tetraazafluorene | $^1$H NMR (400 MHz, DMSO-d6) δ: 11.48 (s, 1H), 9.28 9.26 (d, J = 2.0 Hz, 1H), 8.90 (s, 1H), 7.25 (d, J = 2.3 Hz, 1H), 4.39 (s, 2H), 4.29-4.07 (m, 6H), 3.22 (p, J = 6.9 Hz, 1H), 2.61 (dd, J = 14.6, 7.3 Hz, 2H), 1.61 (s, 6H), 1.35 (d, J = 6.7 Hz, 6H) | 468 |

-continued

| Ex | Structure | ¹H NMR | MS (m/z) |
|---|---|---|---|
| 76 | 5-[1-(3,3-Difluoro-pyrrolidin-1-yl)-8,8-dimethyl-5,6-dihydro-8H-7-oxa-2,4,4b,9-tetraaza-fluoren-3-yl]-pyrimidin-2-ylamine | ¹H NMR (400 MHz, DMSO-d6) δ: 9.12 (s, 2H), 7.02 (s, 2H), 4.50-4.08 (m, 8H), 2.68-2.56 (m, 2H), 1.59 (s, 6H) | 403 |
| 77 | 3-Cyclopropylmethoxy-5-[1-(3,3-difluoro-pyrrolidin-1-yl)-8,8-dimethyl-5,6-dihydro-8H-7-oxa-2,4,4b,9-tetraaza-fluoren-3-yl]-pyridin-2-ylamine | 1H NMR (400 MHz, DMSO-d6) δ: 8.60 (s, 1H), 7.87 (s, 1H), 6.03 (s, 2H), 4.33 (s, 2H), 4.23-4.03 (m, 8H), 3.95 (d, J = 6.8 Hz, 2H), 1.59 (s, 6H), 1.36-1.22 (m, 1H), 0.68-0.55 (m, 2H), 0.47-0.35 (m, 2H) | 472 |
| 78 | 5-[1-(3,3-Difluoro-pyrrolidin-1-yl)-8,8-dimethyl-5,6-dihydro-8H-7-oxa-2,4,4b,9-tetraaza-fluoren-3-yl]-3-ethoxy-pyridin-2-ylamine | ¹H NMR (400 MHz, DMSO-d6) δ: 8.61 (s, 1H), 7.87 (s, 1H), 6.04 (s, 2H), 4.44-4.27 (m, 2H), 4.21-4.03 (m, 8H), 2.69-2.54 (m, 2H), 1.60 (s, 6H), 1.42 (t, J = 6.9 Hz, 3H) | 446 |
| 79 | 5-[1-(3,3-Difluoro-pyrrolidin-1-yl)-8,8-dimethyl-5,6-dihydro-8H-7-oxa-2,4,4b,9-tetraaza-fluoren-3-yl]-3-isopropoxy-pyridin-2-ylamine | ¹H NMR (400 MHz, DMSO-d6) δ: 8.59 (s, 1H), 7.89 (s, 1H), 5.97 (s, 2H), 4.70-4.58 (m, 1H), 4.33 (s, 2H), 4.21-4.06 (m, 8H), 1.59 (s, 6H), 1.34 (d, J = 6.0 Hz, 6H) | 460 |

| Ex | Structure | ¹H NMR | MS (m/z) |
|---|---|---|---|
| 80 | 3-sec-Butoxy-5-[1-(3,3-difluoro-pyrrolidin-1-yl)-8,8-dimethyl-5,6-dihydro-8H-7-oxa-2,4,4b,9-tetraaza-fluoren-3-yl]-pyridin-2-ylamine | ¹H NMR (400 MHz, DMSO-d6) δ: 8.59 (s, 1H), 7.88 (s, 1H), 5.98 (s, 2H), 4.55-4.26 (m, 2H), 4.25-4.03 (m, 7H), 2.71-2.54 (m, 2H), 1.84-1.53 (m, 8H), 1.31 (d, J = 6.0 Hz, 3H), 0.98 (t, J = 7.4 Hz, 3H) | 474 |
| 81 | 3-Chloro-5-[1-(3,3-difluoro-pyrrolidin-1-yl)-8,8-dimethyl-5,6-dihydro-8H-7-oxa-2,4,4b,9-tetraaza-fluoren-3-yl]-pyridin-2-ylamine | ¹H NMR (400 MHz, DMSO-d6) δ: 8.92 (s, 1H), 8.39 (s, 1H), 6.67 (s, 2H), 4.36-4.31 (m, 2H), 4.20-4.08 (m, 6H), 2.66-2.52 (m, 2H), 1.59 (s, 6H) | 436 |
| 82 | 5-[1-(3,3-Difluoro-pyrrolidin-1-yl)-8,8-dimethyl-5,6-dihydro-8H-7-oxa-2,4,4b,9-tetraaza-fluoren-3-yl]-3-fluoro-pyridin-2-ylamine | ¹H NMR (400 MHz, DMSO-d6) δ: 8.80 (s, 1H), 8.12 (dd, J = 12.6, 1.8 Hz, 1H), 6.59 (s, 2H), 4.35-4.30 (m, 2H), 4.21-4.08 (m, 6H), 2.67-2.51 (m, 2H), 1.59 (s, 6H) | 420 |
| 83 | 1-(3,3-Difluoro-pyrrolidin-1-yl)-8,8-dimethyl-3-pyrazolo[1,5-a]pyrimidin-6-yl-5,6-dihydro-8H-7-oxa-2,4,4b,9-tetraaza-fluorene | ¹H NMR (400 MHz, DMSO-d6) δ: 9.73 (s, 1H), 9.46 (s, 1H), 8.33 (d, J = 2.3 Hz, 1H), 6.81 (d, J = 2.3 Hz, 1H), 4.40 (s, 3H), 4.32-4.11 (m, 5H), 2.70-2.54 (m, 2H), 1.61 (s, 6H) | 427 |

Example 84

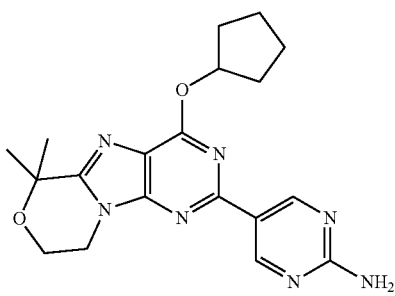 [SMILES: CC1(C)OCCn2c1nc1c(OC3CCCC3)nc(-c3cnc(N)nc3)nc12]

5-(4-(cyclopentyloxy)-6,6-dimethyl-8,9-dihydro-6H-
[1,4]oxazino[4,3-e]purin-2-yl)pyrimidin-2-amine To a solution of cyclopentanol (36 uL, 0.40 mmol) in anhydrous tetrahydrofuran was added sodium hydride (17.5 mg, 0.73 mmol) and the mixture was allowed to shake for 2 to 5 min. The mixture was transferred to a microwave vial equipped with stirbar and 2,4-dichloro-6,6-dimethyl-8,9-dihydro-6H-[1,4]oxazino[4,3-e]purine (100 mg, 0.36 mmol) was added. The reaction mixture was microwaved with stirring at 120° C. for 15 min. The reaction mixture was diluted with water and extracted with ethyl acetate (3×30 mL). The combined organic layers were washed with brine, dried over sodium sulfate and concentrated to dryness in vacuo. The resulting crude was dissolved in a 1:1 mixture of acetonitrile:1M potassium carbonate (4 mL) and transferred to a microwave vial equipped with stirbar. To the solution was added 5-(4,4,5,5-tetramethyl-1,3,2-dioxaborolan-2-yl)pyrimidin-2-amine (121.5 mg, 0.55 mmol), 1,1'-bis(diphenylphosphino)ferrocene-palladium(II)dichloride (13.40 mg, 0.018 mmol) and the mixture was microwaved at 120° C. for 10 min. The reaction mixture was diluted with water and extracted with ethyl acetate (3×15 ml). The combined organic layers were dried with magnesium sulfate, filtered and concentrated to dryness in vacuo. The resulting residue was purified by RP-HPLC affording 5-(4-(cyclopentyloxy)-6,6-dimethyl-8,9-dihydro-6H-[1,4]oxazino[4,3-e]purin-2-yl)pyrimidin-2-amine (40 mg, 29%): $^1$H NMR (400 MHz, DMSO-d6) δ: 9.13 (s, 2H), 7.11 (s, 2H), 5.86-5.71 (m, 1H), 4.23-4.09 (m, 4H), 2.18-2.05 (m, 2H), 1.91-1.62 (m, 6H), 1.60 (s, 6H)

Using a procedure similar to that described in Example 84 the following compounds were prepared.

| Ex | Structure | $^1$H NMR | MS (m/z) |
|---|---|---|---|
| 85 | 5-(1-Isopropoxy-8,8-dimethyl-5,6-dihydro-8H-7-oxa-2,4,4b,9-tetraaza-fluoren-3-yl)-pyrimidin-2-ylamine | $^1$H NMR (400 MHz, DMSO-d6) δ: 9.12 (s, 2H), 7.12 (s, 2H), 5.74-5.66 (m, 1H), 4.23-4.09 (m, 4H), 1.60 (s, 6H), 1.43 (d, J = 6.2 Hz, 6H) | 356 |
| 86 | 5-(1-Cyclopropylmethoxy-8,8-dimethyl-5,6-dihydro-8H-7-oxa-2,4,4b,9-tetraaza-fluoren-3-yl)-pyrimidin-2-ylamine | $^1$H NMR (400 MHz, DMSO-d6) δ: 9.12 (s, 2H), 7.11 (s, 2H), 4.46 (d, J = 7.3 Hz, 2H), 4.24-4.10 (m, 4H), 1.61 (s, 7H), 0.67-0.57 (m, 2H), 0.48-0.39 (m, 2H) | 368 |

-continued

| Ex | Structure | ¹H NMR | MS (m/z) |
|---|---|---|---|
| 87 | 1-Methoxy-8,8-dimethyl-3-(3-trifluoromethyl-1H-pyrrolo[2,3-b]pyridin-5-yl)-5,6-dihydro-8H-7-oxa-2,4,4b,9-tetraaza-fluorene | | 419 |
| 88 | 5-(1-Cyclobutoxy-8,8-dimethyl-5,6-dihydro-8H-7-oxa-2,4,4b,9-tetraaza-fluoren-3-yl)-pyrimidin-2-ylamine | ¹H NMR (400 MHz, DMSO-d6) δ 9.12 (s, 2H), 7.12 (s, 2H), 5.56-5.46 (m, 1H), 4.23-4.16 (m, 2H), 4.16-4.10 (m, 2H), 2.60-2.51 (m, 2H), 2.31-2.11 (m, 2H), 1.97-1.82 (m, 1H), 1.81-1.67 (m, 1H), 1.60 (s, 6H). | 368 |
| 89 | 5-[1-(Bicyclo[3.1.0]hex-3-yloxy)-8,8-dimethyl-5,6-dihydro-8H-7-oxa-2,4,4b,9-tetraaza-fluoren-3-yl]-pyrimidin-2-ylamine | 1H NMR (400 MHz, DMSO-d6) δ 9.11 (s, 2H), 7.11 (s, 2H), 5.88 (t, J = 6.9 Hz, 1H), 4.23-4.16 (m, 2H), 4.16-4.06 (m, 2H), 2.45-2.33 (m, 2H), 1.60 (s, 6H), 1.43-1.32 (m, 2H), 0.67-0.40 (m, 2H). | 394 |

Example 90

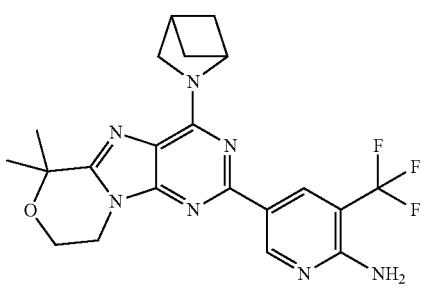 [SMILES: CC1(C)OCCn2c1nc1c(N3CC4CC3C4)nc(-c3cnc(N)c(C(F)(F)F)c3)nc12]

5-(4-(2-azabicyclo[2.1.1]hexan-2-yl)-6,6-dimethyl-8,9-dihydro-6H-[1,4]oxazino[4,3-e]purin-2-yl)-3-(trifluoromethyl)pyridin-2-amine To a microwave vial was added 4-(3-azabicyclo[2.1.1]hexan-3-yl)-2-chloro-6,6-dimethyl-8,9-dihydropurino[8,9-c][1,4]oxazine (38 mg, 0.12 mmol), 5-(4,4,5,5-tetramethyl-1,3,2-dioxaborolan-2-yl)-3-(trifluoromethyl)pyridin-2-amine (47.9 mg, 0.166 mmol), bis(di-tert-butyl(4-dimethylaminophenyl)phosphine)dichloropalladium(II) (8.4 mg, 0.012 mmol), potassium acetate (16.5 mg, 0.17 mmol), and sodium carbonate (17.7 mg, 0.166 mmol). Acetonitrile (2.5 mL) and degassed water (0.5 mL) were added and nitrogen was bubbled through the solution for 3 min. The vial was capped and submitted to microwave heating at 140° C. for 40 min. The reaction mixture was diluted with dichloromethane and filtered through celite, eluting with dichloromethane and the filtrate was concentrated to dryness in vacuo. The resulting residue was purified by column chromatography (silica gel, 100-200 mesh, 0-100% ethyl acetate in heptane). The residue was further purified by RP-HPLC affording 5-(4-(2-azabicyclo[2.1.1]hexan-2-yl)-6,6-dimethyl-8,9-dihydro-6H-[1,4]oxazino[4,3-e]purin-2-yl)-3-(trifluoromethyl)pyridin-2-amine as a white solid (14.4 mg, 27%): $^1$H NMR (400 MHz, DMSO-d6) δ 9.22-9.11 (m, 1H), 8.59 (s, 1H), 6.79 (s, 2H), 4.22-4.06 (m, 4H), 3.78 (s, 2H), 3.09-2.96 (m, 1H), 2.09 (s, 2H), 1.59 (s, 6H), 1.45 (d, J=3.4 Hz, 2H).

Example 91

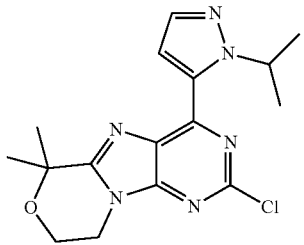 [SMILES: CC(C)n1nccc1-c1nc(Cl)nc2c1nc1n2CCOC1(C)C]

Step 1: 2-chloro-4-(2-isopropylpyrazol-3-yl)-6,6-dimethyl-8,9-dihydropurino[8,9-c][1,4]oxazine To a microwave vial was added 2,4-dichloro-6,6-dimethyl-8,9-dihydropurino[8,9-c][1,4]oxazine (200 mg, 0.73 mmol), [1,1'-bis(diphenylphosphino)ferrocene]palladium (II) dichloride dichloromethane adduct (48.8 mg, 0.0586 mmol), sodium carbonate (109 mg, 1.03 mmol) and potassium acetate (102 mg, 1.03 mmol). Acetonitrile (2.5 mL) and water (0.5 mL) were added followed by 5-(5,5-dimethyl-1,3,2-dioxaborinan-2-yl)-1-isopropyl-pyrazole (163 mg, 0.733 mmol) and nitrogen was bubbled through the reaction mixture for 2 min. The vial was capped and heated to 100° C. under microwave irradiation for 20 min. The reaction mixture was diluted with dichloromethane, filtered through celite, eluting with dichloromethane and the filtrate was concentrated in vacuo. The resulting residue was purified by column chromatography (silica gel, 100-200 mesh, 0 to 100% ethyl acetate in heptane) affording 2-chloro-4-(2-isopropylpyrazol-3-yl)-6,6-dimethyl-8,9-dihydropurino[8,9-c][1,4]oxazine (133 mg, 52%) used as is in the next step: LC-MS (Method A): m/z=347.2 (M+H)+, 1.13 min.

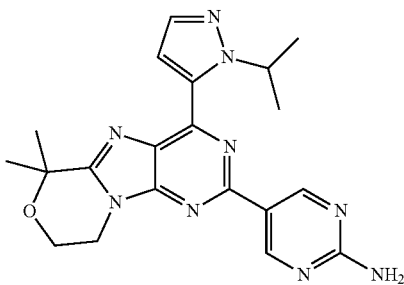 [SMILES: CC(C)n1nccc1-c1nc(-c2cnc(N)nc2)nc2c1nc1n2CCOC1(C)C]

Step 2: 5-(4-(1-isopropyl-1H-pyrazol-5-yl)-6,6-dimethyl-8,9-dihydro-6H-[1,4]oxazino[4,3-e]purin-2-yl)pyrimidin-2-amine To a microwave vial was added 2-chloro-4-(2-isopropylpyrazol-3-yl)-6,6-dimethyl-8,9-dihydropurino[8,9-c][1,4]oxazine (50 mg, 0.14 mmol), 5-(4,4,5,5-tetramethyl-1,3,2-dioxaborolan-2-yl)-3-(trifluoromethyl)pyridin-2-amine (44.6 mg, 0.202 mmol), bis(di-tert-butyl(4-dimethylaminophenyl)phosphine)dichloropalladium(II) (8.2 mg, 0.012 mmol), potassium acetate (20.0 mg, 0.202 mmol) and sodium carbonate (21.4 mg, 0.202 mmol). Acetonitrile (2.5 mL) and degassed water (0.5 mL) were added and nitrogen was bubbled through the solution for 3 min. The vial was capped and submitted to microwave heating at 140° C. for 40 min. The reaction mixture was diluted with dichloromethane and filtered through celite, eluting with dichloromethane and the filtrate was concentrated to dryness in vacuo. The residue was further purified by RP-HPLC affording 5-(4-(1-isopropyl-1H-pyrazol-5-yl)-6,6-dimethyl-8,9-dihydro-6H-[1,4]oxazino[4,3-e]purin-2-yl)pyrimidin-2-amine as a white solid (39.8 mg, 68%): $^1$H NMR (400 MHz, DMSO-d6) δ 9.17 (s, 2H), 7.69 (d, J=1.8 Hz, 1H), 7.50 (d, J=1.8 Hz, 1H), 7.16 (s, 2H), 5.99-5.89 (m, 1H), 4.31-4.15 (m, 4H), 1.66 (s, 6H), 1.54 (d, J=6.6 Hz, 6H).

Example 92

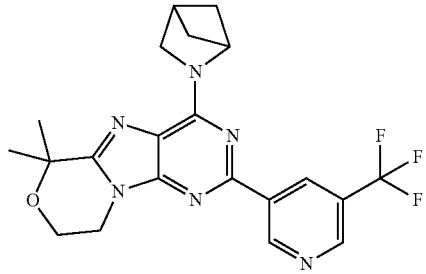 [SMILES: CC1(C)OCCn2c1nc1c(N3CC4CC3C4)nc(-c3cncc(C(F)(F)F)c3)nc12]

4-(2-azabicyclo[2.1.1]hexan-2-yl)-6,6-dimethyl-2-(5-(trifluoromethyl)pyridin-3-yl)-8,9-dihydro-6H-[1,4]oxazino[4,3-e]purine To a microwave vial was added 4-(3-azabicyclo[2.1.1]hexan-3-yl)-2-chloro-6,6-dimethyl-8,9-dihydropurino[8,9-c][1,4]oxazine (30 mg, 0.094 mmol), 5-(4,4,5,5-tetramethyl-1,3,2-dioxaborolan-2-yl)-3-(trifluoromethyl)pyridin-2-amine (25 mg, 0.13 mmol), bis(di-tert-butyl(4-dimethylaminophenyl)phosphine)dichloropalladium(II) (5.3 mg, 0.0075 mmol), potassium acetate (13 mg, 0.13 mmol), and sodium carbonate (14 mg, 0.13 mmol). Acetonitrile (2.5 mL) and degassed water (0.5 mL) were added and nitrogen was bubbled through the solution for 3 min. The vial was capped and submitted to microwave heating at 140° C. for 40 min. The reaction mixture was diluted with dichloromethane and filtered through celite, eluting with dichloromethane and the filtrate was concentrated to dryness in vacuo. The residue was further purified by RP-HPLC affording 4-(2-azabicyclo[2.1.1]hexan-2-yl)-6,6-dimethyl-2-(5-(trifluoromethyl)pyridin-3-yl)-8,9-dihydro-6H-[1,4]oxazino[4,3-e]purine as a white solid (34 mg, 84%): $^1$H NMR (400 MHz, DMSO-d6) δ 9.80 (s, 1H), 9.05 (s, 1H), 8.90 (s, 1H), 5.88 (s, 1H), 4.23-4.09 (m, 4H), 3.81 (s, 2H), 3.02 (s, 1H), 2.13 (s, 2H), 1.61 (s, 6H), 1.48 (s, 2H). δ 9.22-9.11 (m, 1H), 8.59 (s, 1H), 6.79 (s, 2H), 4.22-4.06 (m, 4H), 3.78 (s, 2H), 3.09-2.96 (m, 1H), 2.09 (s, 2H), 1.59 (s, 6H), 1.45 (d, J=3.4 Hz, 2H).

Examples 93 and 94

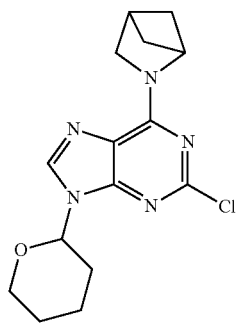 [SMILES: Clc1nc(N2CC3CC2C3)c2ncn(C3CCCCO3)c2n1]

Step 1: 6-(3-azabicyclo[2.1.1]hexan-3-yl)-2-chloro-9-tetrahydropyran-2-yl-purine To a solution of 2,6-dichloro-9-tetrahydropyran-2-yl-purine (1.50 g, 5.49 mmol) in N,N-dimethylformaldehyde (10 mL) was added 3-azabicyclo[2.1.1]hexane hydrochloride (722 mg, 6.04 mmol) followed by N,N'-diisopropylethylamine (2.4 mL, 13.7 mmol). The reaction mixture was stirred at RT for 2 h. The reaction mixture was then poured into water and extracted with ethyl acetate (3×75 mL). The combined organic layers were dried over sodium sulfate, filtered and concentrated in vacuo. The resulting residue was purified by column chromatography (silica gel, 100-200 mesh, 0 to 100% ethyl acetate in heptane) affording 6-(3-azabicyclo[2.1.1]hexan-3-yl)-2-chloro-9-tetrahydropyran-2-yl-purine as a white foam (1.15 g, 66%). LC-MS (Method A): m/z=320.2 (M+H)+, 1.02 min.

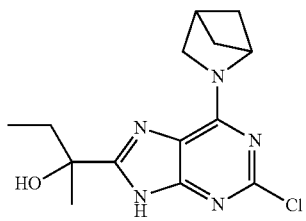 [SMILES: CCC(C)(O)c1nc2c(N3CC4CC3C4)nc(Cl)nc2[nH]1]

Step 2: 2-[6-(3-azabicyclo[2.1.1]hexan-3-yl)-2-chloro-9H-purin-8-yl]butan-2-ol

To a solution of 6-(3-azabicyclo[2.1.1]hexan-3-yl)-2-chloro-9-tetrahydropyran-2-yl-purine (266 mg, 0.832 mmol) in tetrahydrofuran (5.0 mL) cooled to −78° C. was added n-butyllithium (2.5 mol/L) in hexane (0.67 mL, 1.7 mmol). The reaction mixture was stirred for 30 min at −78° C. then methyl ethyl ketone (0.15 mL, 1.7 mmol) was added dropwise and the reaction mixture was stirred at −78° C. for an additional 2 h. The reaction mixture was quenched by the addition of water and extracted with ethyl acetate (3×75 mL). The combined organic layers were dried over sodium sulfate, filtered and concentrated in vacuo. The residue was taken up in methanol (10 mL) and p-toluene sulfonic acid (75 mg, 0.42 mmol) was added. The mixture was heated to 50° C. for 30 min. The reaction mixture was concentrated to dryness in vacuo and the resulting residue was purified by column chromatography with (silica gel, 100-200 mesh, 0 to 100% ethyl acetate in heptane) affording 2-[6-(3-azabicyclo[2.1.1]hexan-3-yl)-2-chloro-9H-purin-8-yl]butan-2-ol the as an orange solid (204 mg, 80%) used as is in the next step: LC-MS (Method A): m/z=308.2 (M+H)+, 0.88 min.

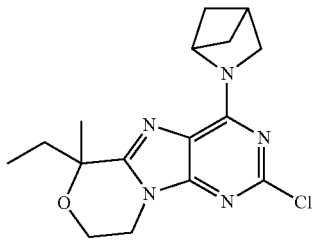 [SMILES: CCC1(C)OCCn2c1nc1c(N3CC4CC3C4)nc(Cl)nc12]

Step 3: 4-(3-azabicyclo[2.1.1]hexan-3-yl)-2-chloro-6-ethyl-6-methyl-8,9-dihydropurino[8,9-c][1,4]oxazine To a vial was added 2-[6-(3-azabicyclo[2.1.1]hexan-3-yl)-2-chloro-9H-purin-8-yl]butan-2-ol (50 mg, 0.16 mmol) and cesium carbonate (159 mg, 0.487 mmol). N,N-dimethylformamide (1.0 mL) was added followed by 1,2-dibromoethane (0.028 mL, 0.33). The vial was capped and heated to 90° C. for 1 h. The reaction mixture was diluted with dichloromethane and water, the layers were separated and the aqueous layer was extracted with dichloromethane (2×50 mL). The combined organic layers were dried over sodium sulfate, filtered and concentrated to dryness in vacuo. The resulting residue was purified by column chromatography (silica gel, 100-200 mesh, 0 to 100% ethyl acetate in heptane) affording 4-(3-azabicyclo[2.1.1]hexan-3-yl)-2-chloro-6-ethyl-6-methyl-8,9-dihydropurino[8,9-c][1,4]oxazine as a white solid (33 mg, 61%) used as is in the next step: LC-MS (Method A): m/z=334.2 (M+H)+, 1.15 min.

93

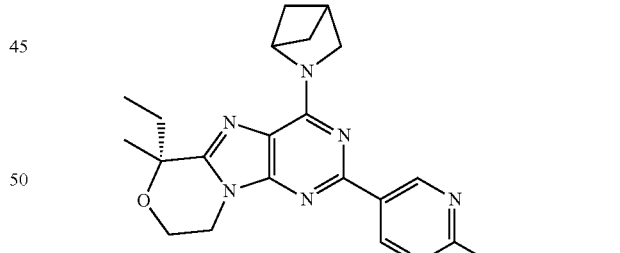

94

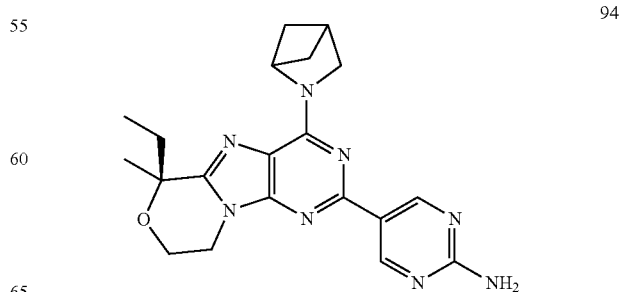

Step 4: (S)-5-(4-(2-azabicyclo[2.1.1]hexan-2-yl)-6-ethyl-6-methyl-8,9-dihydro-6H-[1,4]oxazino[4,3-e]purin-2-yl)pyrimidin-2-amine and (R)-5-(4-(2-azabicyclo[2.1.1]hexan-2-yl)-6-ethyl-6-methyl-8,9-dihydro-6H-[1,4]oxazino[4,3-e]purin-2-yl)pyrimidin-2-amine To a microwave vial was added 4-(3-azabicyclo[2.1.1]hexan-3-yl)-2-chloro-6-ethyl-6-methyl-8,9-dihydropurino[8,9-c][1,4]oxazine (33.2 mg, 0.0995 mmol), 5-(4,4,5,5-tetramethyl-1,3,2-dioxaborolan-2-yl)pyrimidin-2-amine (30.8 mg, 0.139 mmol), bis(di-tert-butyl(4-dimethylaminophenyl)phosphine)dichloropalladium(II) (5.6 mg, 0.0080 mmol), sodium carbonate (14.8 mg, 0.139 mmol) and potassium acetate (13.8 mg, 0.139 mmol). Acetonitrile (2.5 mL) and water (0.5 mL) were added and nitrogen was bubbled through the reaction mixture for 2 min. The vial was capped and heated to 140° C. under microwave irradiation for 40 min then the reaction mixture was diluted with dichloromethane, filtered through celite, eluting with dichloromethane and the filtrate was concentrated to dryness in vacuo. The resulting residue was purified by chiral SFC (Berger MG II, 21.1 mm×150 mm, 5 μm, 70 mL/min, 15% ethanol in 0.1% ammonium hydroxide) affording arbitrarily assigned enantiomers (S)-5-(4-(2-azabicyclo[2.1.1]hexan-2-yl)-6-ethyl-6-methyl-8,9-dihydro-6H-[1,4]oxazino[4,3-e]purin-2-yl)pyrimidin-2-amine and (R)-5-(4-(2-azabicyclo[2.1.1]hexan-2-yl)-6-ethyl-6-methyl-8,9-dihydro-6H-[1,4]oxazino[4,3-e]purin-2-yl)pyrimidin-2-amine as white solids (10.0 mg, 26%; 11.0 mg, 28%): $^1$H NMR (400 MHz, DMSO-d6) δ 9.10 (s, 2H), 6.97 (s, 2H), 4.22-4.02 (m, 4H), 3.77 (s, 2H), 3.04-2.97 (m, 1H), 2.08 (s, 2H), 2.06-1.79 (m, 3H), 1.53 (s, 3H), 1.47-1.40 (m, 2H), 0.83 (t, J=7.3 Hz, 3H), retention time=0.38; $^1$H NMR (400 MHz, DMSO-d6) δ 9.10 (s, 2H), 6.97 (s, 2H), 4.25-4.01 (m, 4H), 3.77 (s, 2H), 3.05-2.96 (m, 1H), 2.08 (s, 2H), 2.06-1.79 (m, 3H), 1.53 (s, 3H), 1.50-1.39 (m, 2H), 0.83 (t, J=7.3 Hz, 3H), retention time=0.36.

Example 95

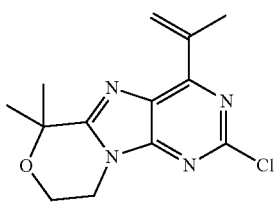 [SMILES: C=C(C)c1nc(Cl)nc2c1nc1n2CCOC1(C)C]

Step 1: 2-chloro-4-isopropenyl-6,6-dimethyl-8,9-dihydropurino[8,9-c][1,4]oxazine To a microwave vial was added 2,4-dichloro-6,6-dimethyl-8,9-dihydropurino[8,9-c][1,4]oxazine (400 mg, 1.46 mmol), bis(di-tert-butyl(4-dimethylaminophenyl)phosphine)dichloropalladium(II) (87 mg, 0.12 mmol), sodium carbonate (217 mg, 2.05 mmol) and potassium acetate (207 mg, 2.05 mmol). Acetonitrile (10 mL), water (2.0 mL) and isopropenylboronic acid pinacol ester (0.32 mL, 1.6 mmol) were added and nitrogen was bubbled through the reaction mixture for 2 min. The vial was then capped and heated to 140° C. under microwave irradiation for 20 min and the reaction mixture was diluted with dichloromethane, filtered through celite, eluting with dichloromethane and the filtrate was concentrated to dryness in vacuo. The resulting residue was purified by column chromatography (silica gel, 100-200 mesh, 0 to 100% ethyl acetate in heptane) to afford the desired compound as a beige solid (143 mg, 35%) used as is in the next step: LC-MS (Method A): m/z=279.1 (M+H)+, 1.10 min.

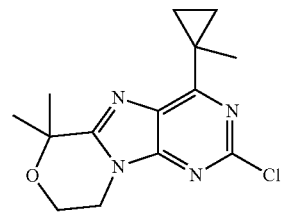 [SMILES: CC1(c2nc(Cl)nc3c2nc2n3CCOC2(C)C)CC1]

Step 2: 2-chloro-6,6-dimethyl-4-(1-methylcyclopropyl)-8,9-dihydropurino[8,9-c][1,4]oxazine To a solution of trimethylsulfoxonium iodide (66.7 mg, 0.296 mmol) in dimethyl sulfoxide (2.0 mL) was added sodium hydride (14.0 mg, 0.350 mmol, 60 wt % dispersion in mineral oil). The reaction mixture was stirred at room temp for 15 min. 2-chloro-4-isopropenyl-6,6-dimethyl-8,9-dihydropurino[8,9-c][1,4]oxazine (75 mg, 0.27 mmol) was then added and the reaction was stirred for 2 h at RT. The reaction was quenched by the addition of water and extracted with ethyl acetate (3×50 mL). The combined organic extracts were washed with brine, dried over sodium, sulfate and concentrated to dryness in vacuo. The resulting residue was purified by column chromatography with (silica gel, 100-200 mesh, 0 to 50% ethyl acetate in heptane) affording 2-chloro-6,6-dimethyl-4-(1-methylcyclopropyl)-8,9-dihydropurino[8,9-c][1,4]oxazine as a white solid (25.2 mg, 32%) used as is in the next step: LC-MS (Method A): m/z=293.2 (M+H)+, 1.18 min.

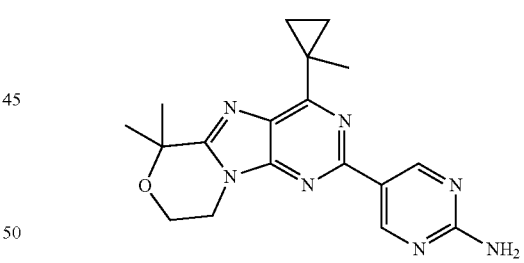

Step 3: 5-(6,6-dimethyl-4-(1-methylcyclopropyl)-8,9-dihydro-6H-[1,4]oxazino[4,3-e]purin-2-yl)pyrimidin-2-amine To a microwave vial was added 2-chloro-6,6-dimethyl-4-(1-methylcyclopropyl)-8,9-dihydropurino[8,9-c][1,4]oxazine (25.2 mg, 0.0861 mmol), 5-(4,4,5,5-tetramethyl-1,3,2-dioxaborolan-2-yl)pyrimidin-2-amine (26.6 mg, 0.120 mmol), bis(di-tert-butyl(4-dimethylaminophenyl)phosphine)dichloropalladium(II) (4.9 mg, 0.0069 mmol), sodium carbonate (12.8 mg, 0.120 mmol) and potassium acetate (11.9 mg, 0.120 mmol). Acetonitrile (2.5 mL) and water (0.5 mL) were added and nitrogen was bubbled through the reaction mixture for 2 min. The vial was capped and heated to 140° C. under microwave irradiation for 30 min and the reaction mixture was diluted with dichloromethane, filtered through celite, eluting with dichloromethane and the filtrate was concentrated to dryness in vacuo. The residue was purified by RP-HPLC affording 5-(6,6-dimethyl-4-(1-methylcyclopropyl)-8,9-dihydro-6H-[1,4]oxazino[4,3-e]purin-2-yl)pyrimidin-2-amine as a white solid (18.9 mg, 63%): $^1$H NMR (400 MHz, DMSO-d6) δ 9.14 (s, 2H), 7.07 (s, 2H), 4.23-4.10 (m, 4H), 1.78-1.73 (m, 5H), 1.61 (s, 6H), 1.02-0.97 (m, 2H).

Examples 96 and 97

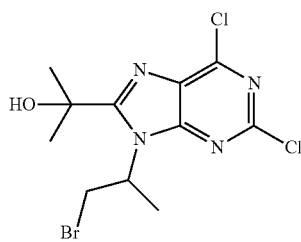 [SMILES: CC(CBr)n1c(C(C)(C)O)nc2c(Cl)nc(Cl)nc21]

Step 1: 2-[9-(2-bromo-1-methyl-ethyl)-2,6-dichloro-purin-8-yl]propan-2-ol

To a solution of 2-(2,6-dichloro-9H-purin-8-yl)propan-2-ol (500 mg, 2.02 mmol), 1-bromo-2-propanol (0.25 mL, 2.2 mmol) and PS-triphenylphosphine (1.91 mmol/g loading) (1170 mg, 2.23 mmol) in tetrahydrofuran (20 mL) was added diisopropyl azodicarboxylate (473.81 mg, 0.4614 mL, 2.23 mmol). A reflux condenser was added and the solution was heated to 70° C. overnight. An additional 1.1 eq. of PS-triphenylphosphine (1.91 mmol/g loading) (1170 mg, 2.23 mmol), diisopropyl azodicarboxylate (473.81 mg, 0.4614 mL, 2.2260 mmol) and 1-bromo-2-propanol (0.25 mL, 2.2 mmol) were added and stirring continued at 70° C. for an additional 3 h. The reaction mixture was diluted with dichloromethane, filtered through celite, eluting with dichloromethane and the filtrate was concentrated to dryness in vacuo. The resulting residue was purified by column chromatography with (silica gel, 100-200 mesh, 0 to 100% ethyl acetate in heptane) affording 2-[9-(2-bromo-1-methyl-ethyl)-2,6-dichloro-purin-8-yl]propan-2-ol as a yellow solid (382 mg, 51%) used as is in the next step; LC-MS (Method A): m/z=369.1 (M+H)+, 1.09 min.

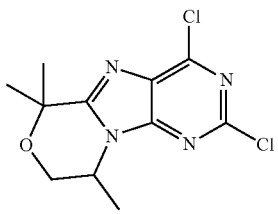 [SMILES: CC1COC(C)(C)c2nc3c(Cl)nc(Cl)nc3n21]

Step 2: 2,4-dichloro-6,6,9-trimethyl-8,9-dihydro-purino[8,9-c][1,4]oxazine

To a solution of 2-[9-(2-bromo-1-methyl-ethyl)-2,6-dichloro-purin-8-yl]propan-2-ol (100 mg, 0.27 mmol) in tetrahydrofuran (2.0 mL) cooled to 0° C. was added sodium hydride (60 wt % dispersion in mineral oil) (12 mg, 0.30 mmol) in one portion. The reaction mixture was stirred at 0° C. and allowed to warm to room temp slowly overnight. The reaction mixture was diluted with saturated aqueous ammonium chloride and ethyl acetate, the layers were separated and the aqueous layer was extracted with ethyl acetate (2×75 mL). The combined organic layers were dried over sodium sulfate, filtered and concentrated to dryness in vacuo. The resulting residue was purified by column chromatography (silica gel, 100-200 mesh, 0 to 100% ethyl acetate in heptane) affording 2,4-dichloro-6,6,9-trimethyl-8,9-dihydropurino[8,9-c][1,4]oxazine as a white solid (60.6 mg, 78%) used as is in the next step; LC-MS (Method A): m/z=287.1 (M+H)+, 0.94 min.

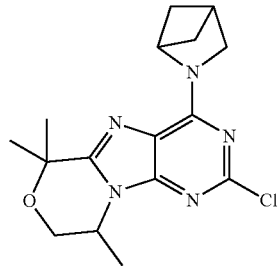 [SMILES: CC1COC(C)(C)c2nc3c(N4CC5CC4C5)nc(Cl)nc3n21]

Step 3: 4-(3-azabicyclo[2.1.1]hexan-3-yl)-2-chloro-6,6,9-trimethyl-8,9-dihydropurino[8,9-c][1,4]oxazine To a solution of 2,4-dichloro-6,6,9-trimethyl-8,9-dihydropurino[8,9-c][1,4]oxazine (60.6 mg, 0.211 mmol) and 2-azabicyclo[2.1.1]hexane hydrochloride (28.6 mg, 0.232 mmol) in N,N-dimethylformamide (2.0 mL) was added N,N-diisopropylethylamine (0.093 mL, 0.528 mmol). The solution was stirred at 60° C. overnight. The reaction mixture was poured into water and extracted with dichloromethane (3×50 mL). The organic layer was dried over sodium sulfate, filtered and concentrated to dryness in vacuo to give a brown solid that was used as crude in the following reaction (65.1 mg, 92%): LC-MS (Method A): m/z=334.1 (M+H)+, 1.16 min.

96

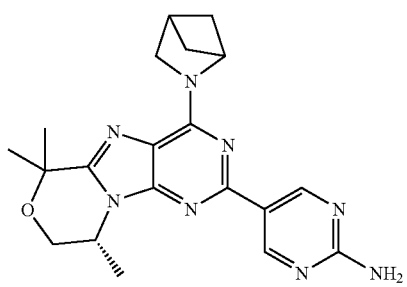

203

-continued

97

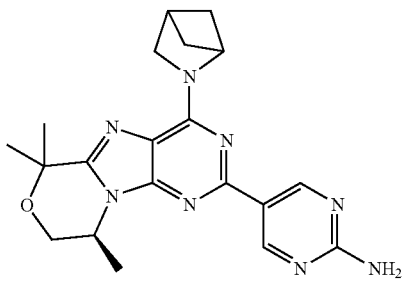

Step 4: (S)-5-(4-(2-azabicyclo[2.1.1]hexan-2-yl)-6,6,9-trimethyl-8,9-dihydro-6H-[1,4]oxazino[4,3-e]purin-2-yl)pyrimidin-2-amine and (R)-5-(4-(2-azabicyclo[2.1.1]hexan-2-yl)-6,6,9-trimethyl-8,9-dihydro-6H-[1,4]oxazino[4,3-e]purin-2-yl)pyrimidin-2-amine To a microwave vial was added 4-(3-azabicyclo[2.1.1]hexan-3-yl)-2-chloro-6,6,9-trimethyl-8,9-dihydropurino[8,9-c][1,4]oxazine (65.1 mg, 0.195 mmol), 5-(4,4,5,5-tetramethyl-1,3,2-dioxaborolan-2-yl)pyrimidin-2-amine (60.4 mg, 0.273 mmol), bis(di-tert-butyl(4-dimethylaminophenyl)phosphine)dichloropalladium(II) (11 mg, 0.016 mmol), sodium carbonate (29 mg, 0.27 mmol) and potassium acetate (27 mg, 0.27 mmol). Acetonitrile (2.5 mL) and water (0.5 mL) were added and nitrogen was bubbled through the reaction mixture for 2 min. The vial was capped and heated to 140° C. under microwave irradiation for 30 min then the reaction mixture was diluted with dichloromethane, filtered through celite, eluting with dichloromethane and the filtrate was concentrated in vacuo. The resulting residue was purified by chiral SFC affording arbitrarily assigned enantiomers (S)-5-(4-(2-azabicyclo[2.1.1]hexan-2-yl)-6,6,9-trimethyl-8,9-dihydro-6H-[1,4]oxazino[4,3-e]purin-2-yl)pyrimidin-2-amine and (R)-5-(4-(2-azabicyclo[2.1.1]hexan-2-yl)-6,6,9-trimethyl-8,9-dihydro-6H-[1,4]oxazino[4,3-e]purin-2-yl)pyrimidin-2-amine as white solids (16.0 mg, 21%; 16.8 mg, 22%): $^1$H NMR (400 MHz, DMSO-d6) δ 9.09 (s, 2H), 6.96 (s, 2H), 5.78 (s, 1H), 4.58-4.49 (m, 1H), 4.16 (dd, J=12.3, 3.6 Hz, 1H), 3.85-3.64 (m, 3H), 3.03-2.96 (m, 1H), 2.13-2.03 (m, 2H), 1.61 (s, 3H), 1.58-1.52 (m, 6H), 1.48-1.39 (m, 2H), retention time=0.526 (Thar 350, 3×250 mm, Sum, 200 mL/min, 15% methanol in 0.1% ammonium hydroxide); $^1$H NMR (400 MHz, DMSO-d6) δ 9.09 (s, 2H), 6.97 (s, 2H), 5.76 (br s, 1H), 4.58-4.49 (m, 1H), 4.16 (dd, J=12.3, 3.6 Hz, 1H), 3.87-3.67 (m, 3H), 3.03-2.96 (m, 1H), 2.14-2.02 (m, 2H), 1.61 (s, 3H), 1.58-1.50 (m, 6H), 1.49-1.38 (m, 2H), retention time=0.760 (Berger MG II, 21.1 mm×150 mm, 5 μm, 70 mL/min, 30% methanol in 0.1% ammonium hydroxide)

Examples 98 and 99

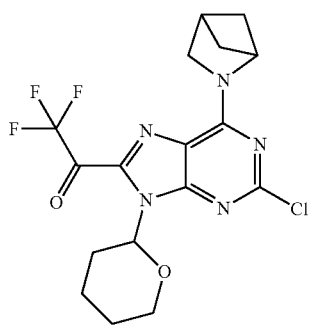 [SMILES: O=C(c1nc2c(N3CC4CC3C4)nc(Cl)nc2n1C1CCCCO1)C(F)(F)F]

204

Step 1: 1-[6-(3-azabicyclo[2.1.1]hexan-3-yl)-2-chloro-9-tetrahydropyran-2-yl-purin-8-yl]-2,2,2-trifluoro-ethanone To a solution of 6-(3-azabicyclo[2.1.1]hexan-3-yl)-2-chloro-9-tetrahydropyran-2-yl-purine (500 mg, 1.56 mmol) and N,N,N',N'-tetramethyl ethylenediamine (0.35 mL, 2.35 mmol) in tetrahydrofuran (12 mL) cooled to −78° C. was added n-butyllithium (2.5 mol/L in hexanes) (0.94 mL, 2.35 mmol) dropwise. The solution was stirred at −78° C. for 45 min then ethyl trifluoroacetate (0.38 mL, 3.13 mmol) was added dropwise. The solution was stirred for an additional 2 h at −78° C. The reaction mixture was quenched by the addition of water and warmed to room temp and extracted with ethyl acetate (3×100 mL). The combined organic layers were dried over sodium sulfate, filtered and concentrated to dryness in vacuo affording crude 1-[6-(3-azabicyclo[2.1.1]hexan-3-yl)-2-chloro-9-tetrahydropyran-2-yl-purin-8-yl]-2,2,2-trifluoro-ethanone used in the next step without any further purification

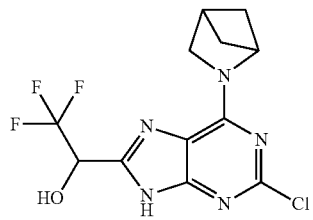 [SMILES: OC(c1nc2c(N3CC4CC3C4)nc(Cl)nc2[nH]1)C(F)(F)F]

Step 2: 1-[6-(3-azabicyclo[2.1.1]hexan-3-yl)-2-chloro-9H-purin-8-yl]-2,2,2-trifluoro-ethanol To a solution of 1-[6-(3-azabicyclo[2.1.1]hexan-3-yl)-2-chloro-9-tetrahydropyran-2-yl-purin-8-yl]-2,2,2-trifluoro-ethanone (177 mg, 0.426 mmol) in methanol (2.0 mL) was added slowly sodium borohydride (33 mg, 0.85 mmol). The reaction mixture was stirred at room temp for 1 h. The reaction mixture was diluted with ethyl acetate and water, the layers were separated and the aqueous layer was extracted with ethyl acetate (2×100 mL). The combined organic layers were dried over sodium sulfate, filtered and concentrated to dryness in vacuo. The crude residue was taken up in methanol (2.0 mL) and p-toluenesulfonic acid (7.5 mg, 0.043 mmol) was added. The reaction mixture was stirred at 50° C. for 1 h. The reaction mixture was concentrated to dryness in vacuo, the residue was diluted with ethyl acetate and water, the layers were separated and the aqueous layer was extracted with ethyl acetate (2×100 mL). The combined organic layers were dried over sodium sulfate, filtered and concentrated to dryness in vacuo to afford 1-[6-(3-azabicyclo[2.1.1]hexan-3-yl)-2-chloro-9H-purin-8-yl]-2,2,2-trifluoro-ethanol as a beige solid which was used as crude in the following step (128.6 mg, 90% over two steps) used in the next step without any further purification: LC-MS (Method A): m/z=334.1 (M+H)+, 0.87 min.

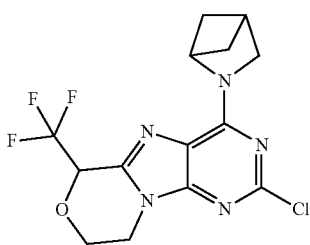 [SMILES: FC(F)(F)C1OCCn2c1nc1c(N3CC4CC3C4)nc(Cl)nc12]

Step 3: 4-(3-azabicyclo[2.1.1]hexan-3-yl)-2-chloro-6-(trifluoromethyl)-8,9-dihydro-6H-purino[8,9-c][1,4]oxazine To a solution of 1-[6-(3-azabicyclo[2.1.1]hexan-3-yl)-2-chloro-9H-purin-8-yl]-2,2,2-trifluoro-ethanol (129 mg, 0.385 mmol) and cesium carbonate (377 mg, 1.16 mmol) in N,N-dimethylformamide (3.0 mL) was added 1,2-dibromoethane (0.067 mL, 0.771 mmol). The reaction mixture was heated to 90° C. overnight. The reaction mixture was diluted with dichloromethane and water, the layers were separated and the aqueous layer was extracted with dichloromethane (2×100 mL). The combined organic layers were dried over sodium sulfate, filtered and concentrated to dryness in vacuo. The resulting residue was purified by column chromatography with (silica gel, 100-200 mesh, 0-100% ethyl acetate in heptane) affording 4-(3-azabicyclo[2.1.1]hexan-3-yl)-2-chloro-6-(trifluoromethyl)-8,9-dihydro-6H-purino[8,9-c][1,4]oxazine as a yellow solid (34 mg, 25%) used as is in the next step.

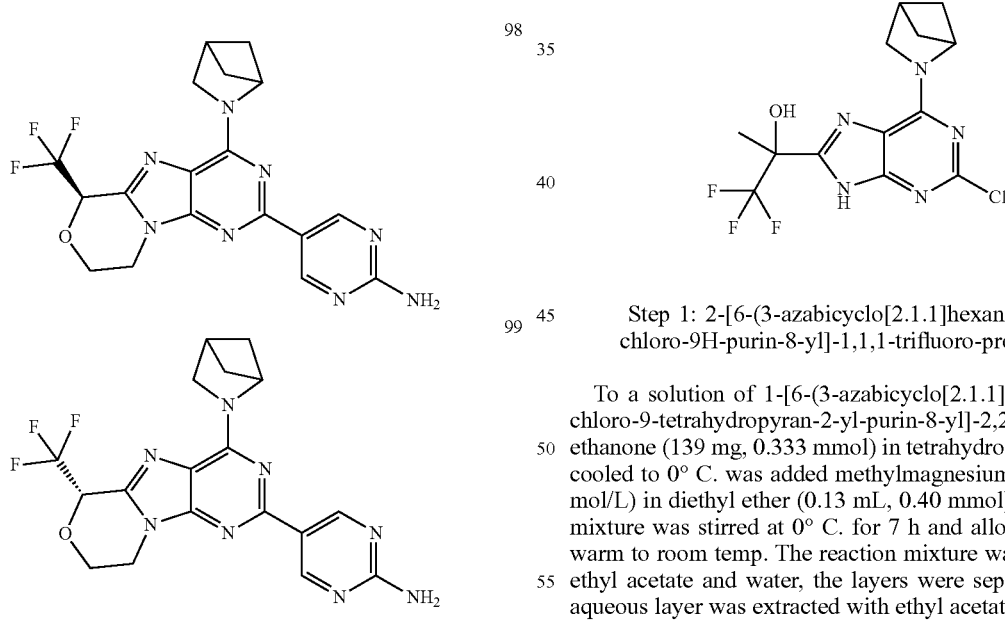

Step 4: (R)-5-(4-(2-azabicyclo[2.1.1]hexan-2-yl)-6-(trifluoromethyl)-8,9-dihydro-6H-[1,4]oxazino[4,3-e]purin-2-yl)pyrimidin-2-amine and (S)-5-(4-(2-azabicyclo[2.1.1]hexan-2-yl)-6-(trifluoromethyl)-8,9-dihydro-6H-[1,4]oxazino[4,3-e]purin-2-yl)pyrimidin-2-amine To a microwave vial was added 4-(3-azabicyclo[2.1.1]hexan-3-yl)-2-chloro-6-(trifluoromethyl)-8,9-dihydro-6H-purino[8,9-c][1,4]oxazine (34.0 mg, 0.0945 mmol), 5-(4,4,5,5-tetramethyl-1,3,2-dioxaborolan-2-yl)pyrimidin-2-amine (29.3 mg, 0.132 mmol), bis(di-tert-butyl(4-dimethylaminophenyl)phosphine)dichloropalladium(II) (5.4 mg, 0.0076 mmol), sodium carbonate (14 mg, 0.13 mmol) and potassium acetate (13 mg, 0.13 mmol). Acetonitrile (2.5 mL) and water (0.5 mL) were added and nitrogen was bubbled through the reaction mixture for 2 min. The vial was capped and heated to 140° C. under microwave irradiation for 30 min then the reaction mixture was diluted with dichloromethane, filtered through celite, eluting with dichloromethane and the filtrate was concentrated to dryness in vacuo. The crude resulting residue was purified by column chromatography (silica gel, 100-200 mesh, 0-10% methanol in dichloromethane) to afford partially purified desired product. The resulting residue was further purified by chiral SFC (Berger MG II, 21.1 mm×150 mm, 5 µm, 70 mL/min, 15% methanol in 0.1% ammonium hydroxide) affording arbitrarily assigned enantiomers (R)-5-(4-(2-azabicyclo[2.1.1]hexan-2-yl)-6-(trifluoromethyl)-8,9-dihydro-6H-[1,4]oxazino[4,3-e]purin-2-yl)pyrimidin-2-amine and (S)-5-(4-(2-azabicyclo[2.1.1]hexan-2-yl)-6-(trifluoromethyl)-8,9-dihydro-6H-[1,4]oxazino[4,3-e]purin-2-yl)pyrimidin-2-amine as white solids (3.6 mg, 9%) retention time=0.709: LC-MS (Method B): m/z=419.2 (M+H)+, 5.00 min; (3.4 mg, 9%) retention time=0.807: LC-MS (Method B): m/z=419.2 (M+H)+, 5.01 min.

Example 100

Step 1: 2-[6-(3-azabicyclo[2.1.1]hexan-3-yl)-2-chloro-9H-purin-8-yl]-1,1,1-trifluoro-propan-2-ol To a solution of 1-[6-(3-azabicyclo[2.1.1]hexan-3-yl)-2-chloro-9-tetrahydropyran-2-yl-purin-8-yl]-2,2,2-trifluoro-ethanone (139 mg, 0.333 mmol) in tetrahydrofuran (5.0 mL) cooled to 0° C. was added methylmagnesium bromide (3.0 mol/L) in diethyl ether (0.13 mL, 0.40 mmol). The reaction mixture was stirred at 0° C. for 7 h and allowed to slowly warm to room temp. The reaction mixture was diluted with ethyl acetate and water, the layers were separated and the aqueous layer was extracted with ethyl acetate (2×100 mL). The combined organic layers were dried over sodium sulfate, filtered and concentrated to dryness in vacuo. The crude residue was taken up in methanol (2.0 mL) and p-toluenesulfonic acid (5.9 mg, 0.033 mmol) was added. The reaction mixture was stirred at 50° C. for 7 h. The reaction mixture was quenched by the addition of saturated aqueous sodium bicarbonate and extracted with ethyl acetate (3×100 mL). The combined organic layers were dried over sodium sulfate, filtered and concentrated to dryness in vacuo. The residue was adsorbed onto silica and purified by column chromatography (silica gel, 100-200 mesh, 0-100% ethyl acetate in heptane to affording 2-[6-(3-azabicyclo[2.1.1]hexan-3-yl)-2-chloro-9H-purin-8-yl]-1,1,1-trifluoro-propan-2-ol as a yellow solid (27 mg, 23%) used as is in the next step: LC-MS (Method A): m/z=348.2 (M+H)+, 0.96 min.

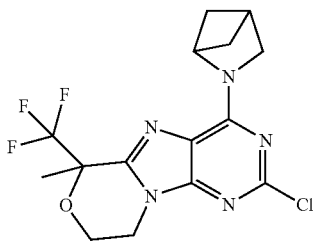 [SMILES: CC1(C(F)(F)F)OCCn2c1nc1c(N3CC4CC3C4)nc(Cl)nc12]

Step 2: 4-(3-azabicyclo[2.1.1]hexan-3-yl)-2-chloro-6-methyl-6-(trifluoromethyl)-8,9-dihydropurino[8,9-c][1,4]oxazine To a solution of 2-[6-(3-azabicyclo[2.1.1]hexan-3-yl)-2-chloro-9H-purin-8-yl]-1,1,1-trifluoro-propan-2-ol (27.0 mg, 0.08 mmol) and cesium carbonate (75.9 mg, 0.233 mmol) in N,N-dimethylformamide (2.0 mL) was added 1,2-dibromoethane (0.014 mL, 0.16 mmol). The reaction mixture was heated to 90° C. for 4 h. Further 1,2-dibromoethane (0.014 mL, 0.16 mmol) was added and stirred at 90° C. for an additional 6 h. The reaction mixture was diluted with dichloromethane and water, the layers were separated and the aqueous layer was extracted with dichloromethane (2×50 mL). The combined organic layers were dried over sodium sulfate, filtered and concentrated to dryness in vacuo. The resulting residue was purified by column chromatography (silica gel, 100-200 mesh, 0-100% ethyl acetate in heptane) affording 4-(3-azabicyclo[2.1.1]hexan-3-yl)-2-chloro-6-methyl-6-(trifluoromethyl)-8,9-dihydropurino[8,9-c][1,4]oxazine as a beige solid (9.7 mg, 33%) used as is in the next step: LC-MS (Method A): m/z=374.2 (M+H)+, 0.97 min.

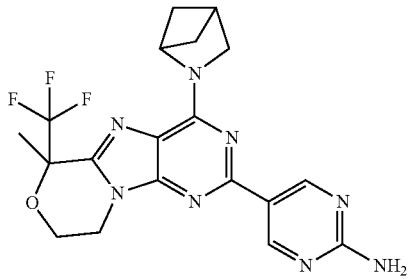 [SMILES: CC1(C(F)(F)F)OCCn2c1nc1c(N3CC4CC3C4)nc(-c3cnc(N)nc3)nc12]

Step 3: 5-(4-(2-azabicyclo[2.1.1]hexan-2-yl)-6-methyl-6-(trifluoromethyl)-8,9-dihydro-6H-[1,4]oxazino[4,3-e]purin-2-yl)pyrimidin-2-amine To a microwave vial was added 4-(3-azabicyclo[2.1.1]hexan-3-yl)-2-chloro-6-methyl-6-(trifluoromethyl)-8,9-dihydropurino[8,9-c][1,4]oxazine (9.7 mg, 0.026 mmol), 5-(4,4,5,5-tetramethyl-1,3,2-dioxaborolan-2-yl)pyrimidin-2-amine (8.0 mg, 0.036 mmol), bis(di-tert-butyl(4-dimethylaminophenyl)phosphine)dichloropalladium(II) (1.5 mg, 0.0021 mmol), sodium carbonate (3.9 mg, 0.036 mmol) and potassium acetate (3.6 mg, 0.036 mmol). Acetonitrile (2.5 mL) and water (0.5 mL) were added and nitrogen was bubbled through the reaction mixture for 2 min. The vial was capped and heated to 140° C. under microwave irradiation for 30 min then the reaction mixture was diluted with dichloromethane, filtered through celite, eluting with dichloromethane and the filtrate was concentrated to dryness in vacuo. The residue was purified by RP-HPLC affording 5-(4-(2-azabicyclo[2.1.1]hexan-2-yl)-6-methyl-6-(trifluoromethyl)-8,9-dihydro-6H-[1,4]oxazino[4,3-e]purin-2-yl)pyrimidin-2-amine as a white solid (5.1 mg, 46%):n $^1$H NMR (400 MHz, DMSO-d6) δ 9.12 (s, 2H), 7.02 (s, 2H), 5.83 (br s, 1H), 4.34-4.16 (m, 4H), 3.75 (br s, 2H), 3.06-2.95 (m, 1H), 2.12 (br s, 2H), 1.78 (s, 3H), 1.54-1.40 (m, 2H).

Examples 101 and 102

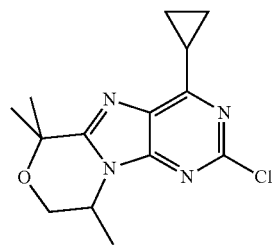 [SMILES: CC1COC(C)(C)c2nc3c(C4CC4)nc(Cl)nc3n21]

Step 1: 2-chloro-4-cyclopropyl-6,6,9-trimethyl-8,9-dihydropurino[8,9-c][1,4]oxazine To a vial was added 2,4-dichloro-6,6,9-trimethyl-8,9-dihydropurino[8,9-c][1,4]oxazine (141 mg, 0.492 mmol), cyclopropylboronic acid (46.5 mg, 0.541 mmol), [1,1'-bis(diphenylphosphino)ferrocene]palladium(II) dichloride dichloromethane adduct (41.0 mg, 0.0492 mmol) and potassium phosphate tribasic (266 mg, 1.23 mmol). Tetrahydrofuran (2.5 mL) was added, the reaction mixture was degassed with nitrogen and heated to 80° C. overnight. The reaction mixture was diluted with dichloromethane, filtered through celite and concentrated to dryness in vacuo. The residue was adsorbed onto silica and purified by column chromatography (silica gel, 0-100% ethyl acetate in heptane) to affording 2-chloro-4-cyclopropyl-6,6,9-trimethyl-8,9-dihydropurino[8,9-c][1,4]oxazine as a beige solid (56.6 mg, 39%). Use as is in the next step: LC-MS (Method A): m/z=293.1 (M+H)+, 1.03 min.

101

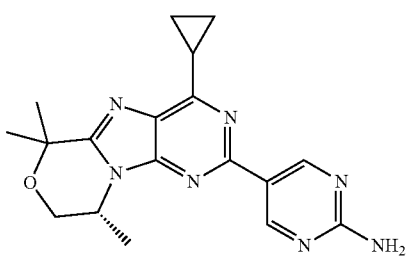

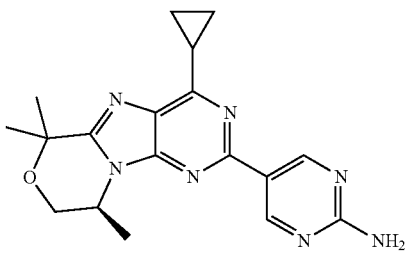

Step 2: (S)-5-(4-cyclopropyl-6,6,9-trimethyl-8,9-dihydro-6H-[1,4]oxazino[4,3-e]purin-2-yl)pyrimidin-2-amine and (R)-5-(4-cyclopropyl-6,6,9-trimethyl-8,9-dihydro-6H-[1,4]oxazino[4,3-e]purin-2-yl)pyrimidin-2-amine To a microwave vial was added 2-chloro-4-cyclopropyl-6,6,9-trimethyl-8,9-dihydropurino[8,9-c][1,4]oxazine (56.6 mg, 0.193 mmol), 5-(4,4,5,5-tetramethyl-1,3,2-dioxaborolan-2-yl)pyrimidin-2-amine (59.8 mg, 0.271 mmol), bis(di-tert-butyl(4-dimethylaminophenyl)phosphine)dichloropalladium(II) (11.0 mg, 0.0155 mmol), sodium carbonate (28.7 mg, 0.271 mmol) and potassium acetate (26.8 mg, 0.271 mmol). Acetonitrile (2.5 mL) and water (0.5 mL) were added and nitrogen was bubbled through the reaction mixture for 2 min. The vial was capped and heated to 140° C. under microwave irradiation for 30 min then the reaction mixture was diluted with dichloromethane, filtered through celite, eluting with dichloromethane and the filtrate was concentrated to dryness in vacuo. The residue was adsorbed onto silica and purified by column chromatography (silica gel, 100-200 mesh, 0 to 10% methanol in dichloromethane to afford the partially purified product. The residue was further purified by chiral SFC (Berger MG II, 21.1 mm×150 mm, 5 μm, 70 mL/min, 40% methanol in 0.1% ammonium hydroxide) affording arbitrarily assigned enantiomers (S)-5-(4-cyclopropyl-6,6,9-trimethyl-8,9-dihydro-6H-[1,4]oxazino[4,3-e]purin-2-yl)pyrimidin-2-amine and (R)-5-(4-cyclopropyl-6,6,9-trimethyl-8,9-dihydro-6H-[1,4]oxazino[4,3-e]purin-2-yl)pyrimidin-2-amine as white solids (12.5 mg, 18%, 14.1 mg, 21%): $^1$H NMR (400 MHz, DMSO-d6) δ 9.10 (s, 2H), 7.07 (s, 2H), 4.67-4.59 (m, 1H), 4.19 (dd, J=12.3, 3.7 Hz, 1H), 3.86 (dd, J=12.4, 3.1 Hz, 1H), 2.69-2.61 (m, 1H), 1.65 (s, 3H), 1.61 (s, 3H), 1.58 (d, J=6.5 Hz, 3H), 1.35-1.30 (m, 2H), 1.22-1.16 (m, 2H), retention time=0.709; $^1$H NMR (400 MHz, DMSO-d6) δ 9.10 (s, 2H), 7.07 (s, 2H), 4.67-4.58 (m, 1H), 4.19 (dd, J=12.3, 3.6 Hz, 1H), 3.86 (dd, J=12.4, 3.1 Hz, 1H), 2.70-2.60 (m, 1H), 1.65 (s, 3H), 1.61 (s, 3H), 1.58 (d, J=6.6 Hz, 3H), 1.37-1.29 (m, 2H), 1.22-1.15 (m, 2H), retention time=0.807.

Example 103

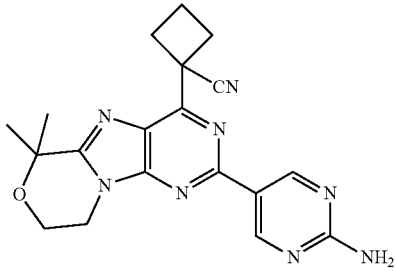 [SMILES: CC1(C)OCCn2c1nc1c(C3(C#N)CCC3)nc(-c3cnc(N)nc3)nc12]

1-(2-(2-aminopyrimidin-5-yl)-6,6-dimethyl-8,9-dihydro-6H-[1,4]oxazino[4,3-e]purin-4-yl)cyclobutanecarbonitrile To a solution of 2,4-dichloro-6,6-dimethyl-8,9-dihydro-6H-[1,4]oxazino[4,3-e]purine (130 mg, 0.476 mmol) in tetrahydrofuran (2.4 mL) under nitrogen and at −78° C. was added cyclobutanecarbonitrile (46 μL, 0.48 mmol) and lithium bis(trimethylsilyl)amide (520 μL, 0.52 mmol, 1.0 M in tetrahydrofuran [untitrated]). After 15 min, the cooling bath was removed to allow warming to RT. After stirring 19 h, the reaction mixture was diluted with saturated aqueous ammonium chlorides and extracted with dichloromethane, dried over magnesium sulfate and concentration to dryness in vacuo.

To the resulting crude in a vial bis(di-tert-butyl(4-dimethylaminophenyl)phosphine)dichloropalladium(II) (35.5 mg, 10 mol %), 2-aminopyrimidine-5-boronic acid pinacol ester (163 mg, 0.714 mmol), sodium carbonate (76 mg, 0.71 mmol), and potassium acetate (70 mg, 0.71 mmol) were added. Under a flow of nitrogen, acetonitrile (2.4 mL) and distilled water (0.5 mL) were added and the vial was sealed. The reaction mixture was stirred at 90° C. for 3 hr. After cooling to RT the mixture was concentrated to dryness in vacuo and the resulting residue was purified by column chromatography (silica gel, 100-200 mesh, 10% methanol in dichloromethane) and then RP-HPLC, affording 1-(2-(2-aminopyrimidin-5-yl)-6,6-dimethyl-8,9-dihydro-6H-[1,4]oxazino[4,3-e]purin-4-yl)cyclobutanecarbonitrile as a white solid (60 mg, 33% over two steps): $^1$H NMR (400 MHz, DMSO-d6) δ 9.19 (s, 2H), 7.19 (br s, 2H), 4.32-4.10 (m, 4H), 3.27-3.17 (m, 2H), 2.93-2.79 (m, 2H), 2.41-2.26 (m, 1H), 2.24-2.10 (m, 1H), 1.65 (s, 6H).

Example 104

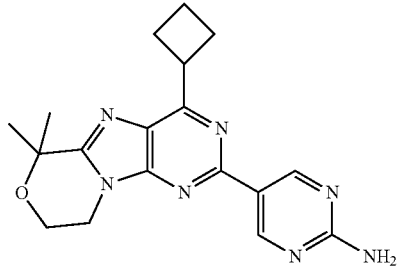 [SMILES: CC1(C)OCCn2c1nc1c(C3CCC3)nc(-c3cnc(N)nc3)nc12]

5-(4-cyclobutyl-6,6-dimethyl-8,9-dihydro-6H-[1,4]oxazino[4,3-e]purin-2-yl)pyrimidin-2-amine In a vial was weighed 2,4-dichloro-6,6-dimethyl-8,9-dihydro-6H-[1,4]oxazino[4,3-e]purine (85.2 mg, 0.312 mmol) and [1,1'-bis(diphenylphosphino)ferrocene]dichloropalladium(II) (12.9 mg, 5 mol %). Under a flow of nitrogen anhydrous tetrahydrofuran (1 mL) and cyclobutylzinc bromide (0.7 mL, 0.343 mmol, 0.5 M in tetrahydrofuran [untitrated]) were added and the vial was sealed. The reaction mixture was stirred at 60° C. for 19 h. After cooling to RT the mixture was diluted with saturated aqueous ammonium chloride and extracted with dichloromethane, dried over magnesium sulfate and concentrated to dryness in vacuo. To the resulting crude in a vial were added bis(di-tert-butyl(4-dimethylaminophenyl)phosphine)dichloropalladium(II)

(26.7 mg, 10 mol %), 2-aminopyrimidine-5-boronic acid pinacol ester (123 mg, 0.537 mmol), sodium carbonate (57 mg, 0.54 mmol), and potassium acetate (53 mg, 0.54 mmol). Under a flow of nitrogen, acetonitrile (1.8 mL) and distilled water (0.4 mL) were added and the vial was sealed. The reaction mixture was stirred at 100° C. for 2 h. After cooling to RT, the mixture was concentrated to dryness in vacuo and the resulting residue was purified by column chromatography (silica gel, 100-200 mesh, 10% methanol in dichloromethane) and then RP-HPLC, affording 5-(4-cyclobutyl-6,6-dimethyl-8,9-dihydro-6H-[1,4]oxazino[4,3-e]purin-2-yl)pyrimidin-2-amine as a white solid (48 mg, 38% over two steps): $^1$H NMR (400 MHz, DMSO-d6) δ 9.22 (s, 2H), 7.14 (br s, 2H), 4.27-4.10 (m, 5H), 2.62-2.55 (m, 2H), 2.42-2.26 (m, 2H), 2.19-1.95 (m, 2H), 1.62 (s, 6H).

Examples 105 and 106

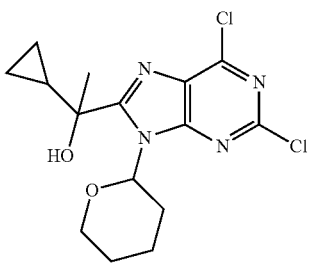 [SMILES: CC(O)(c1nc2c(Cl)nc(Cl)nc2n1C1CCCCO1)C1CC1]

Step 1: 1-cyclopropyl-1-(2,6-dichloro-9-(tetrahydro-2H-pyran-2-yl)-9H-purin-8-yl)ethanol To a solution of 2,6-dichloro-9-(tetrahydro-2H-pyran-2-yl)-9H-purine (3.00 g, 11.0 mmol) cooled to −78° C. in dry tetrahydrofuran (44 mL) was added over 15 min lithium diisopropylamide (11 mL, 22 mmol, 2 M in tetrahydrofuran [untitrated]). After addition was completed, the resulting solution was stirred at −78° C. for 30 min, cyclopropyl methyl ketone (3.3 mL, 33 mmol) was added and the reaction mixture was stirred at −78° C. for another 1.5 h. The reaction mixture was quenched with saturated ammonium chloride and allowed to warm to room temperature. The aqueous layer was extracted with ethyl acetate and the organics were dried over magnesium sulfate and concentrated to dryness in vacuo. The resulting residue was purified by column chromatography (silica gel, 100-200 mesh, 40% ethyl acetate in heptanes). The residue was redissolved in dichloromethane and heptanes were added. The slurry was concentrated partially and the precipitate was collected and washed with heptanes to afford racemic 1-cyclopropyl-1-(2,6-dichloro-9-(tetrahydro-2H-pyran-2-yl)-9H-purin-8-yl)ethanol as a white solid (2.24 g, 57%): $^1$H NMR (400 MHz, DMSO-d6) δ 6.49-6.40 (m, 1H), 6.00-5.87 (m, 1H), 4.13-4.05 (m, 1H), 3.66-3.53 (m, 1H), 2.94-2.72 (m, 1H), 2.08-1.94 (m, 1H), 1.88-1.78 (m, 1H), 1.69-1.52 (m, 6H), 1.47-1.23 (m, 1H), 0.67-0.57 (m, 1H), 0.53-0.38 (m, 3H).

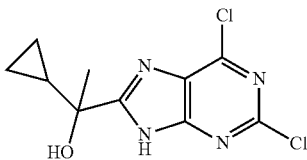 [SMILES: CC(O)(c1nc2c(Cl)nc(Cl)nc2[nH]1)C1CC1]

Step 2: 1-cyclopropyl-1-(2,6-dichloro-9H-purin-8-yl)ethanol

To a suspension of racemic 1-cyclopropyl-1-(2,6-dichloro-9-(tetrahydro-2H-pyran-2-yl)-9H-purin-8-yl)ethanol (1.30 g, 3.64 mmol) in methanol (7.3 mL) was added p-toluenesulfonic acid (7 mg, 1 mol %) and the mixture was stirred vigorously for 19 h. After filtration, the precipitate was washed with heptanes and collected. Additional compound was afforded by concentrating the mother liquor to dryness, re-dissolving in a minimal amount of dichloromethane, adding heptanes, concentrating in vacuo partially, and filtering the precipitate and washing with heptanes. The combined solids afforded racemic 1-cyclopropyl-1-(2,6-dichloro-9H-purin-8-yl)ethanol as a white solid (965 mg, 97%): $^1$H NMR (400 MHz, DMSO-d6) δ 13.68 (br s, 1H), 5.65 (br s, 1H), 1.62 (s, 3H), 1.34-1.20 (m, 1H), 0.61-0.53 (m, 1H), 0.53-0.32 (m, 2H), 0.32-0.17 (m, 1H).

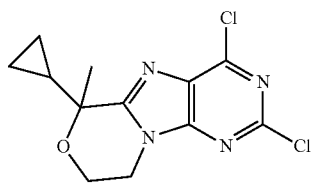 [SMILES: CC1(C2CC2)OCCn2c1nc1c(Cl)nc(Cl)nc12]

Step 3: 2,4-dichloro-6-cyclopropyl-6-methyl-8,9-dihydro-6H-[1,4]oxazino[4,3-e]purine To a solution of racemic 1-cyclopropyl-1-(2,6-dichloro-9H-purin-8-yl)ethanol (503 mg, 1.84 mmol) in N,N-dimethylformamide (5.5 mL) was added cesium carbonate (1.80 g, 5.53 mmol), and 1,2-dibromoethane (0.48 mL, 5.6 mmol). The vial was sealed and the reaction mixture was stirred at 80° C. for 16 h. After cooling to RT the mixture was filtered, washing with dichloromethane and the filtrate was concentrated to dryness in vacuo. The resulting residue was purified by column chromatography (silica gel, 100-200 mesh, 30% ethyl acetate in hexane) affording racemic 2,4-dichloro-6-cyclopropyl-6-methyl-8,9-dihydro-6H-[1,4]oxazino[4,3-e]purine as a white solid (166 mg, 30%): $^1$H NMR (400 MHz, Chloroform-d) δ 4.45-4.36 (m, 1H), 4.29-4.16 (m, 2H), 4.16-4.05 (m, 1H), 1.75 (s, 3H), 1.55-1.45 (m, 1H), 0.71-0.56 (m, 2H), 0.51-0.40 (m, 1H), 0.28-0.18 (m, 1H).

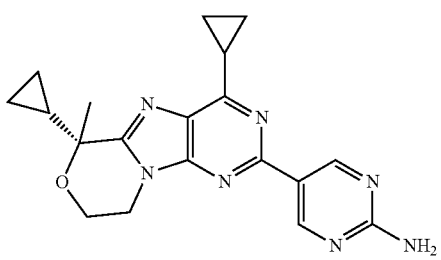

105

-continued

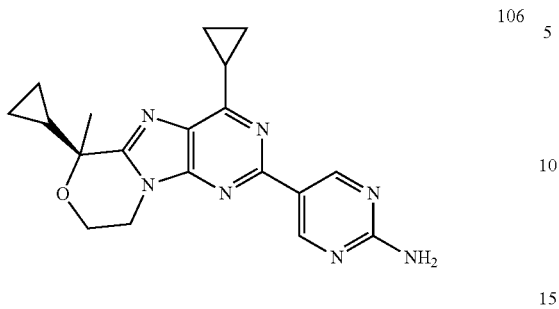

106

Step 4: (R)-5-(4,6-dicyclopropyl-6-methyl-8,9-dihydro-6H-[1,4]oxazino[4,3-e]purin-2-yl)pyrimidin-2-amine and (S)-5-(4,6-dicyclopropyl-6-methyl-8,9-dihydro-6H-[1,4]oxazino[4,3-e]purin-2-yl)pyrimidin-2-amine To a vial was weighed racemic 2,4-dichloro-6-cyclopropyl-6-methyl-8,9-dihydro-6H-[1,4]oxazino[4,3-e]purine (166 mg, 0.553 mmol), palladium(II) acetate (6.2 mg, 5 mol %), n-butyldi-1-adamantylphosphine (20.9 mg, 10 mol %), potassium cyclopropyltrifluoroborate (87.7 mg, 0.581 mmol), and cesium carbonate (541 mg, 1.66 mmol). Under a flow of nitrogen, degassed toluene (2.8 mL) and distilled water (0.3 mL) were added and the vial was sealed. The reaction mixture was stirred at 110° C. for 18 h. After cooling to room temperature, the mixture was filtered through celite, washed with dichloromethane and concentrated to dryness in vacuo, To the resulting crude in a vial, were added bis(di-tert-butyl(4-dimethylaminophenyl)phosphine)dichloropalladium(II) (41 mg, 10 mol %), 2-aminopyrimidine-5-boronic acid pinacol ester (189 mg, 0.830 mmol), sodium carbonate (118 mg, 1.11 mmol), and potassium acetate (109 mg, 1.11 mmol). Under a flow of nitrogen, acetonitrile (2.8 mL) and distilled water (0.6 mL) were added and the vial was sealed. The reaction mixture was stirred at 105° C. for 2.5 h. After cooling to RT the mixture was concentrated to dryness in vacuo and the resulting residue was purified by column chromatography (silica gel, 100-200 mesh, 10% methanol in dichloromethane) and thereafter by chiral SFC (Berger Cel-1, 21.2 mm×150 mm, 5 μm, 70 mL/min, 35% methanol in 0.1% ammonium hydroxide) affording arbitrarily assigned enantiomers (R) 5-(4,6-dicyclopropyl-6-methyl-8,9-dihydro-6H-[1,4]oxazino[4,3-e]purin-2-yl)pyrimidin-2-amine and (S) 5-(4,6-dicyclopropyl-6-methyl-8,9-dihydro-6H-[1,4]oxazino[4,3-e]purin-2-yl)pyrimidin-2-amine as a white solids (23.3 mg ($t_r$=0.716 min) and 20.8 mg ($t_r$=0.629 min), 22% total over 2 steps): $^1$H NMR (400 MHz, DMSO-d6) δ 9.10 (s, 2H), 7.07 (br s, 2H), 4.37-4.05 (m, 4H), 2.73-2.61 (m, 1H), 1.63 (s, 3H), 1.48-1.28 (m, 3H), 1.23-1.18 (m, 2H), 0.67-0.47 (m, 2H), 0.42-0.29 (m, 1H), 0.25-0.13 (m, 1H).

Examples 107 and 108

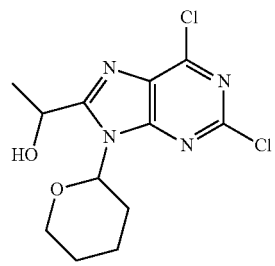 [SMILES: CC(O)c1nc2c(Cl)nc(Cl)nc2n1C1CCCCO1]

Step 1: 1-(2,6-dichloro-9-(tetrahydro-2H-pyran-2-yl)-9H-purin-8-yl)ethanol

To a solution of 2,6-dichloro-9-(tetrahydro-2H-pyran-2-yl)-9H-purine (5.00 g, 18.3 mmol) cooled to −78° C. in dry tetrahydrofuran (73 mL) was added dropwise over 10 min n-butyl lithium (11.0 mL, 27.5 mmol, 2.5 M in hexanes [untitrated]). After addition was completed, the resulting solution was stirred at −78° C. for 35 min, acetaldehyde (3.2 mL, 55 mmol) was added and the reaction mixture was stirred at −78° C. for another 2 h. The reaction mixture was quenched with aqueous saturated ammonium chloride and allowed to warm to room temperature. The aqueous layer was extracted with ethyl acetate and the organics were dried over magnesium sulfate and concentrated to dryness in vacuo. The resulting residue was purified twice by column chromatography (silica gel, 100-200 mesh, 50% ethyl acetate in heptanes) to afford racemic 1-(2,6-dichloro-9-(tetrahydro-2H-pyran-2-yl)-9H-purin-8-yl)ethanol as a yellow solid (2.34 g, 40%): $^1$H NMR (400 MHz, Chloroform-d) δ 5.97-5.86 (m, 1H), 5.39-5.21 (m, 1H), 4.33-4.18 (m, 1H), 3.86-3.69 (m, 1H), 2.51-2.28 (m, 1H), 2.15-1.92 (m, 2H), 1.84-1.67 (m, 6H).

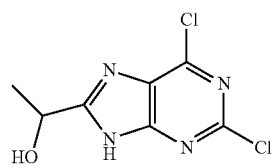

Step 2: 1-(2,6-dichloro-9H-purin-8-yl)ethanol

To a suspension of racemic 1-(2,6-dichloro-9-(tetrahydro-2H-pyran-2-yl)-9H-purin-8-yl)ethanol (1.52 g, 4.81 mmol) in methanol (9.6 mL) was added p-toluenesulfonic acid (9 mg, 1 mol %) and the mixture was stirred vigorously for 3 h. The reaction mixture was concentrated to dryness and dissolved in a minimal amount of dichloromethane. Heptanes were added and the solution was concentrated partially in vacuo and the precipitate was filtered and washed with heptanes affording racemic 1-(2,6-dichloro-9H-purin-8-yl)ethanol as a yellow solid (1.08 g, 96%): $^1$H NMR (400 MHz, DMSO-d6) δ 13.82 (br s, 1H), 6.01 (br s, 1H), 4.98 (q, J=6.5 Hz, 1H), 1.52 (d, J=6.5 Hz, 3H).

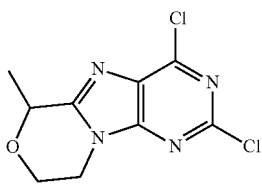 [SMILES: CC1OCCn2c1nc1c(Cl)nc(Cl)nc12]

Step 3: 2,4-dichloro-6-methyl-8,9-dihydro-6H-[1,4]oxazino[4,3-e]purine

To a solution of racemic 1-(2,6-dichloro-9H-purin-8-yl)ethanol (767 mg, 3.30 mmol) in N,N-dimethylformaldehyde (9.9 mL) was added cesium carbonate (3.23 g, 9.9 mmol), and 1,2-dibromoethane (0.86 mL, 9.9 mmol). The vial was sealed and the reaction mixture stirred at 80° C. for 3 h. After cooling to room temperature, the mixture was filtered, rinsed with dichloromethane and the filtrate was concentrated to dryness in vacuo. The resulting residue was purified by column chromatography (silica gel, 100-200 mesh, 40% ethyl acetate in hexane) affording racemic 2,4-dichloro-6-methyl-8,9-dihydro-6H-[1,4]oxazino[4,3-e]purine as a white solid (223 mg, 26%): $^1$H NMR (400 MHz, Chloroform-d) δ 5.01 (q, J=6.7 Hz, 1H), 4.46-4.38 (m, 1H), 4.36-4.21 (m, 2H), 4.07-3.98 (m, 1H), 1.79 (d, J=6.7 Hz, 3H).

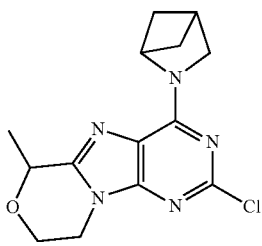 [SMILES: CC1OCCn2c1nc1c(N3CC4CC3C4)nc(Cl)nc12]

Step 4: 4-(2-azabicyclo[2.1.1]hexan-2-yl)-2-chloro-6-methyl-8,9-dihydro-6H-[1,4]oxazino[4,3-e]purine To a solution of racemic 2,4-dichloro-6-methyl-8,9-dihydro-6H-[1,4]oxazino[4,3-e]purine (223 mg, 0.860 mmol) and 2-azabicyclo[2.1.1]hexane hydrochloride (149 mg, 1.20 mmol) in N,N-dimethylformaldehyde (3.4 mL) was added N,N-diisopropylethylamine (0.38 mL, 2.2 mmol) and the mixture was stirred at 50° C. for 19 h. The mixture was then diluted with dichloromethane and washed with aqueous saturated sodium bicarbonate. The organics were dried over magnesium sulfate and concentrated in vacuo. The resulting residue was purified by column chromatography (silica gel, 100-200 mesh, 40% ethyl acetate in hexane) affording racemic 4-(2-azabicyclo[2.1.1]hexan-2-yl)-2-chloro-6-methyl-8,9-dihydro-6H-[1,4]oxazino[4,3-e]purine as a yellow solid (199 mg, 76%): $^1$H NMR (400 MHz, Chloroform-d) δ 5.60-5.40 (m, 1H), 5.18-4.79 (m, 1H), 4.67-3.80 (m, 5H), 3.76-3.62 (m, 1H), 3.06-2.95 (m, 1H), 2.19-1.95 (m, 2H), 1.69 (d, J=6.7 Hz, 3H), 1.54-1.44 (m, 2H).

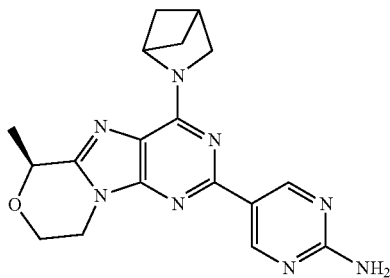

107

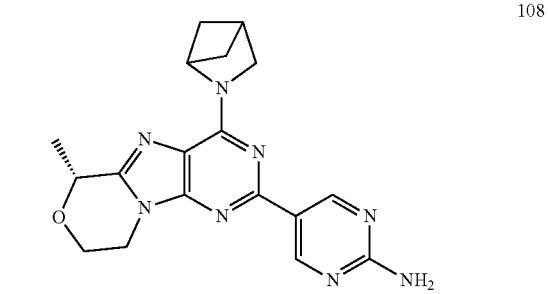

108

Step 5: (S)-5-(4-(2-azabicyclo[2.1.1]hexan-2-yl)-6-methyl-8,9-dihydro-6H-[1,4]oxazino[4,3-e]purin-2-yl)pyrimidin-2-amine and (R)-5-(4-(2-azabicyclo[2.1.1]hexan-2-yl)-6-methyl-8,9-dihydro-6H-[1,4]oxazino[4,3-e]purin-2-yl)pyrimidin-2-amine To a vial was weighed racemic 4-(2-azabicyclo[2.1.1]hexan-2-yl)-2-chloro-6-methyl-8,9-dihydro-6H-[1,4]oxazino[4,3-e]purine (198 mg, 0.648 mmol), bis(di-tert-butyl(4-dimethylaminophenyl)phosphine)dichloropalladium(II) (48.3 mg, 10 mol %), 2-aminopyrimidine-5-boronic acid pinacol ester (221 mg, 0.971 mmol), sodium carbonate (103 mg, 0.971 mmol), and potassium acetate (95.3 mg, 0.971 mmol). Under a flow of nitrogen, acetonitrile (3.2 mL) and distilled water (0.7 mL) were added and the vial was sealed. The reaction mixture was stirred at 100° C. for 48 h. After cooling to RT, the mixture was concentrated to dryness in vacuo and the resulting residue was purified by column chromatography (silica gel, 100-200 mesh, 10% methanol in dichloromethane) and subsequent chiral SFC (Berger Cel-1, 21.2 mm×150 mm, 5 μm, 70 mL/min, 35% methanol in 0.1% ammonium hydroxide) affording arbitrarily assigned enantiomers (S)-5-(4-(2-azabicyclo[2.1.1]hexan-2-yl)-6-methyl-8,9-dihydro-6H-[1,4]oxazino[4,3-e]purin-2-yl)pyrimidin-2-amine and (R)-5-(4-(2-azabicyclo[2.1.1]hexan-2-yl)-6-methyl-8,9-dihydro-6H-[1,4]oxazino[4,3-e]purin-2-yl)pyrimidin-2-amine as white solids (12.7 mg (t$_r$=0.579 min) and 15.2 mg (t$_r$=0.445 min), 12% total); $^1$H NMR (400 MHz, DMSO) δ 9.10 (s, 2H), 6.97 (br s, 2H), 6.11-5.47 (m, 1H), 4.95 (q, J=6.6 Hz, 1H), 4.35-4.15 (m, 2H), 4.14-3.93 (m, 2H), 3.90-3.60 (m, 2H), 3.04-2.95 (m, 1H), 2.08 (s, 2H), 1.58 (d, J=6.6 Hz, 3H), 1.49-1.38 (m, 2H).

Example 109

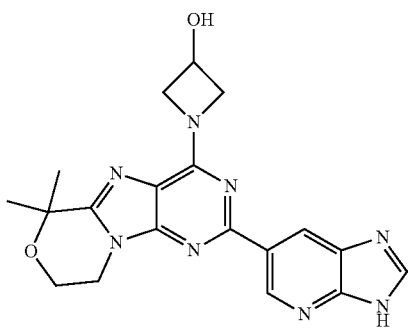 [SMILES: CC1(C)OCCn2c1nc1c(N3CC(O)C3)nc(-c3cnc4[nH]cnc4c3)nc12]

1-(2-chloro-6,6-dimethyl-8,9-dihydro-6H-[1,4]oxazino[4,3-e]purin-4-yl)azetidin-3-ol To a solution of 2,4-dichloro-6,6-dimethyl-8,9-dihydro-6H-[1,4]oxazino[4,3-e]purine (80.0 mg, 0.293 mmol) in N,N-dimethylformaldehyde (1 mL) was added azetidin-3-ol hydrochloride (32 mg, 0.293 mmol) and N,N-diisopropylethylamine (0.153 mL, 0.879 mmol). The reaction mixture was shaken at 70° C. for 16 h and concentrated to dryness in vacuo. The crude was redissolved in a 1:1 mixture of acetonitrile:1M potassium carbonate (2.2 mL) and transferred to a microwave vial equipped with a stirbar. To the solution was added 6-(4,4,5,5-tetramethyl-1,3,2-dioxaborolan-2-yl)-3-((2-(trimethylsilyl)ethoxy)methyl)-3H-imidazo[4,5-b]pyridine (110 mg, 0.293 mmol), 1,1'-bis(diphenylphosphino)ferrocene-palladium(II)dichloride (23.9 mg, 0.0293 mmol) and the mixture was microwaved at 120° C. for 5 min. The aqueous layer was extracted with ethyl acetate (2×1 ml). The combined organic layers were concentrated to dryness in vacuo. The resulting residue was purified by column chromatography (silica gel, 100-200 mesh, 0 to 100% ethyl acetate in heptane) affording 1-(6,6-dimethyl-2-(3-((2-(trimethylsilyl)ethoxy)methyl)-3H-imidazo[4,5-b]pyridin-6-yl)-8,9-dihydro-6H-[1,4]oxazino[4,3-e]purin-4-yl)azetidin-3-ol. A solution of 4.0 M hydrogen chloride in dioxane (3.52 mmol, 0.879 mL) was added, and the resulting mixture was stirred at RT for 2 h. The reaction mixture was concentrated in vacuo and purified by RP-HPLC affording 1-(2-(3H-imidazo[4,5-b]pyridin-6-yl)-6,6-dimethyl-8,9-dihydro-6H-[1,4]oxazino[4,3-e]purin-4-yl)azetidin-3-ol (25.7 mg, 22%): $^1$H NMR (400 MHz, DMSO-d6) δ 9.41 (s, 1H), 8.84 (s, 1H), 8.50 (s, 1H), 5.89-5.68 (m, 1H), 4.76-4.60 (m, 3H), 4.23-4.04 (m, 6H), 1.60 (s, 6H).

Example 110

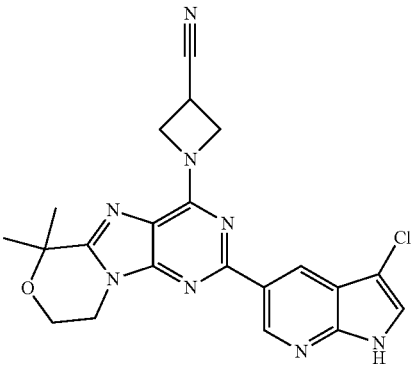 [SMILES: CC1(C)OCCn2c1nc1c(N3CC(C#N)C3)nc(-c3cnc4[nH]cc(Cl)c4c3)nc12]

1-(2-(3-chloro-1H-pyrrolo[2,3-b]pyridin-5-yl)-6,6-dimethyl-8,9-dihydro-6H-[1,4]oxazino[4,3-e]purin-4-yl)azetidine-3-carbonitrile To a solution of 2,4-dichloro-6,6-dimethyl-8,9-dihydro-6H-[1,4]oxazino[4,3-e]purine (80.0 mg, 0.293 mmol) in N,N-dimethylformaldehyde (1 mL) was added azetidine-3-carbonitrile hydrochloride (34.7 mg, 0.293 mmol) and N,N-diisopropylethylamine (0.153 mL, 0.879 mmol). The reaction mixture was shaken at 70° C. for 16 h and concentrated to dryness in vacuo. The crude was redissolved in a 1:1 mixture of acetonitrile:1M potassium carbonate (2.2 mL) and transferred to a microwave vial equipped with a stirbar. To the solution was added 3-chloro-5-(4,4,5,5-tetramethyl-1,3,2-dioxaborolan-2-yl)-1H-pyrrolo[2,3-b]pyridine (81.6 mg, 0.293 mmol), 1,1'-bis(diphenylphosphino)ferrocene-palladium(II)dichloride (23.9 mg, 0.0293 mmol) and the mixture was microwaved at 90° C. for 5 min. The aqueous layer was extracted with ethyl acetate (2×1 mL). The combined organic layers were concentrated to dryness in vacuo. The resulting residue was purified by RP-HPLC affording 1-(2-(3-chloro-1H-pyrrolo[2,3-b]pyridin-5-yl)-6,6-dimethyl-8,9-dihydro-6H-[1,4]oxazino[4,3-e]purin-4-yl)azetidine-3-carbonitrile (4.05 mg, 3%): $^1$H NMR (400 MHz, DMSO-d6) δ 12.14 (s, 1H), 9.35 (s, 1H), 8.80 (s, 1H), 7.74 (s, 1H), 4.75 (t, J=9.0 Hz, 2H), 4.58 (dd, J=9.0, 6.0 Hz, 2H), 4.26-4.21 (m, 2H), 4.18-4.12 (m, 2H), 4.11-3.90 (m, 2H), 1.61 (s, 6H).

Example 111

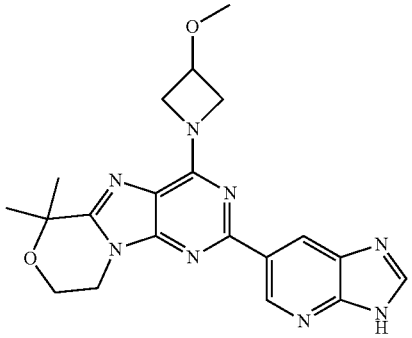 [SMILES: COC1CN(c2nc(-c3cnc4[nH]cnc4c3)nc3c2nc2n3CCOC2(C)C)C1]

2-(3H-imidazo[4,5-b]pyridin-6-yl)-4-(3-methoxyazetidin-1-yl)-6,6-dimethyl-8,9-dihydro-6H-[1,4]oxazino[4,3-e]purine To a solution of 2,4-dichloro-6,6-dimethyl-8,9-dihydro-6H-[1,4]oxazino[4,3-e]purine (80.0 mg, 0.293 mmol) in N,N-dimethylformaldehyde (1 mL) was added 3-methoxyazetidine hydrochloride (36.2 mg, 0.293 mmol) and N,N-diisopropylethylamine (0.153 mL, 0.879 mmol). The reaction mixture was shaken at 70° C. for 16 h and concentrated to dryness in vacuo. The crude was redissolved in a 1:1 mixture of acetonitrile:1M potassium carbonate (2.2 mL) and transferred to a microwave vial equipped with a stirbar. To the solution was added 6-(4,4,5,5-tetramethyl-1,3,2-dioxaborolan-2-yl)-3-((2-(trimethylsilyl)ethoxy)methyl)-3H-imidazo[4,5-b]pyridine (110 mg, 0.293 mmol), 1,1'-bis(diphenylphosphino)ferrocene-palladium(II)dichloride (23.9 mg, 0.0293 mmol) and the mixture was microwaved at 100° C. for 5 min. The aqueous layer was extracted with ethyl acetate (2×1 mL). The combined organic layers were concentrated to dryness in vacuo. The resulting residue was purified by column chromatography (silica gel, 100-200 mesh, 0 to 100% ethyl acetate in heptane) affording 4-(3-methoxyazetidin-1-yl)-6,6-dimethyl-2-(3-((2-(trimethylsilyl)ethoxy)methyl)-3H-imidazo[4,5-b]pyridin-6-yl)-8,9-dihydro-6H-[1,4]oxazino[4,3-e]purine. A solution of 4.0 M hydrogen chloride in dioxane (3.52 mmol, 0.879 mL) was added, and the resulting mixture was stirred at RT for 2 h. The reaction mixture was concentrated in vacuo and the resulting residue was purified by RP-HPLC affording 2-(3H-imidazo[4,5-b]pyridin-6-yl)-4-(3-methoxyazetidin-1-yl)-6,6-dimethyl-8,9-dihydro-6H-[1,4]oxazino[4,3-e]purine (6.86 mg, 6%): $^1$H NMR (400 MHz, DMSO-d6) δ 9.42 (s, 1H), 8.86 (s, 1H), 8.59 (s, 1H), 4.70-4.59 (m, 2H), 4.49-4.41 (m, 1H), 6.3, 3.9 Hz, 5H), 4.28-4.17 (m, 4H), 4.17-4.10 (m, 2H), 3.31 (s, 3H), 1.60 (s, 6H).

Example 112

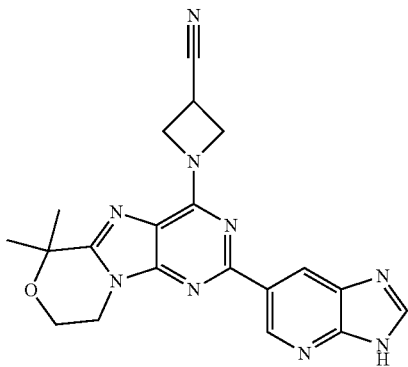 [SMILES: CC1(C)OCCn2c1nc1c(N3CC(C#N)C3)nc(-c3cnc4[nH]cnc4c3)nc12]

1-(2-(3H-imidazo[4,5-b]pyridin-6-yl)-6,6-dimethyl-8,9-dihydro-6H-[1,4]oxazino[4,3-e]purin-4-yl)azetidine-3-carbonitrile To a solution of 2,4-dichloro-6,6-dimethyl-8,9-dihydro-6H-[1,4]oxazino[4,3-e]purine (80.0 mg, 0.293 mmol) in N,N-dimethylformaldehyde (1 mL) was added 3-methoxyazetidine hydrochloride (36.2 mg, 0.293 mmol) and N,N-diisopropylethylamine (0.153 mL, 0.879 mmol). The reaction mixture was shaken at 70° C. for 16 h and concentrated to dryness in vacuo. The crude was redissolved in a 1:1 mixture of acetonitrile:1M potassium carbonate (2.2 mL) and transferred to a microwave vial equipped with a stirbar. To the solution was added 6-(4,4,5,5-tetramethyl-1,3,2-dioxaborolan-2-yl)-3-((2-(trimethylsilyl)ethoxy)methyl)-3H-imidazo[4,5-b]pyridine (110 mg, 0.293 mmol), 1,1'-bis(diphenylphosphino)ferrocene-palladium(II)dichloride (23.9 mg, 0.0293 mmol) and the mixture was microwaved at 100° C. for 5 min. The aqueous layer was extracted with ethyl acetate (2×1 mL). The combined organic layers were concentrated to dryness in vacuo. The resulting residue was purified by column chromatography (silica gel, 100-200 mesh, 0 to 100% ethyl acetate in heptane) affording 1-(6,6-dimethyl-2-(3-((2-(trimethylsilyl)ethoxy)methyl)-3H-imidazo[4,5-b]pyridin-6-yl)-8,9-dihydro-6H-[1,4]oxazino[4,3-e]purin-4-yl)azetidine-3-carbonitrile. A solution of 4.0 M hydrogen chloride in dioxane (3.52 mmol, 0.879 mL) was added, and the resulting mixture was stirred at RT for 2 h. The reaction mixture was concentrated to dryness in vacuo and purified by RP-HPLC affording 1-(2-(3H-imidazo[4,5-b]pyridin-6-yl)-6,6-dimethyl-8,9-dihydro-6H-[1,4]oxazino[4,3-e]purin-4-yl)azetidine-3-carbonitrile (47.6 mg, 41%): $^1$H NMR (400 MHz, DMSO-d6) δ 9.41 (s, 1H), 8.86 (s, 1H), 8.50 (s, 1H), 4.74 (t, J=9.0 Hz, 2H), 4.57 (dd, J=9.0, 5.9 Hz, 2H), 4.26-4.18 (m, 2H), 4.18-4.11 (m, 2H), 4.09-3.99 (m, 1H), 1.60 (s, 6H).

Example 113

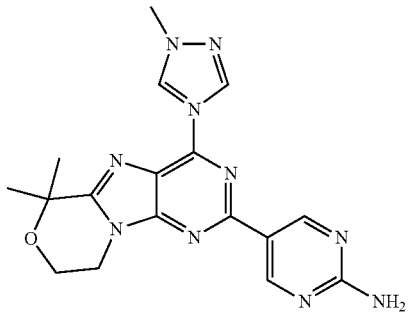

5-(6,6-dimethyl-4-(1-methyl-1H-pyrazol-4-yl)-8,9-dihydro-6H-[1,4]oxazino[4,3-e]purin-2-yl)pyrimidin-2-amine 2,4-dichloro-6,6-dimethyl-8,9-dihydro-6H-[1,4]oxazino[4,3-e]purine (120 mg, 0.439 mmol) was dissolved in a 1:1 mixture of acetonitrile:1M potassium carbonate (2.2 mL) and transferred to a microwave vial equipped with a stirbar. To the solution was added 5-(4,4,5,5-tetramethyl-1,3,2-dioxaborolan-2-yl)pyrimidin-2-amine (35.4 mg, 0.439 mmol), 1,1'-bis(diphenylphosphino)ferrocene-palladium(II)dichloride (36.6 mg, 0.0439 mmol) and the mixture was microwaved at 100° C. for 5 min. The aqueous layer was extracted with ethyl acetate (2×1 ml) and the combined organic layers were concentrated to dryness in vacuo. The resulting residue was purified by column chromatography (silica gel, 100-200 mesh, 0 to 100% ethyl acetate in heptane) affording 2-chloro-6,6-dimethyl-4-(1-methyl-1H-pyrazol-4-yl)-8,9-dihydro-6H-[1,4]oxazino[4,3-e]purine (51.0 mg, 36%). The material was redissolved in a 1:1 mixture of acetonitrile:1M potassium carbonate (1.4 mL) and transferred to a microwave vial equipped with a stirbar. To the solution was added 5-(4,4,5,5-tetramethyl-1,3,2-dioxaborolan-2-yl)pyrimidin-2-amine (35.4 mg, 0.160 mmol), 1,1'-bis(diphenylphosphino)ferrocene-palladium(II)dichloride (13.1 mg, 0.0160 mmol) and the mixture was microwaved at 110° C. for 5 min. The aqueous layer was extracted with ethyl acetate (3×1 mL). The combined organic layers were concentrated to dryness in vacuo and the resulting residue was purified by RP-HPLC affording 5-(6,6-dimethyl-4-(1-methyl-1H-pyrazol-4-yl)-8,9-dihydro-6H-[1,4]oxazino[4,3-e]purin-2-yl)pyrimidin-2-amine (13.9 mg, 23%): 1H NMR (400 MHz, DMSO-d6) δ 9.27 (s, 2H), 8.79 (s, 1H), 8.51 (s, 1H), 7.08 (s, 2H), 4.28-4.21 (m, 2H), 4.21-4.12 (m, 2H), 3.99 (s, 3H), 1.68 (s, 6H).

Example 114

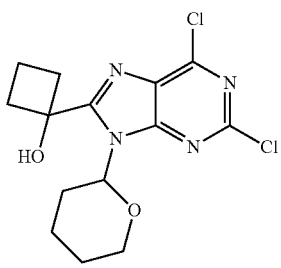 [SMILES: OC1(c2nc3c(Cl)nc(Cl)nc3n2C2CCCCO2)CCC1]

Step 1: 1-(2,6-dichloro-9-(tetrahydro-2H-pyran-2-yl)-9H-purin-8-yl)cyclobutanol To a solution of 2,6-dichloro-9-(tetrahydro-2H-pyran-2-yl)-9H-purine (3.00 g, 11.0 mmol) cooled to −78° C. in dry tetrahydrofuran (52 mL) was added drop wise a 2M solution of lithium diisopropylamide in a mixture of tetrahydrofuran/heptane/ethylbenzene (11 mL, 22 mmol). After addition was completed, the resulting solution was stirred at −78° C. for 30 min, cyclobutanone (2.46 mL, 33 mmol) was added and the reaction mixture was stirred at −78° C. for another 30 min. The reaction mixture was quenched with saturated ammonium chloride/ice solution and the aqueous layer extracted with diethyl ether (3×50 mL). The combined organic layers were concentrated to dryness in vacuo. The resulting residue was suspended in 10 mL dichloromethane, and solid was collected by filtration and dried affording 1-(2,6-dichloro-9-(tetrahydro-2H-pyran-2-yl)-9H-purin-8-yl)cyclobutanol (2.29 g, 61%), which was used as is for next step.

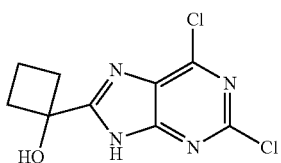 [SMILES: OC1(c2nc3c(Cl)nc(Cl)nc3[nH]2)CCC1]

Step 2: 1-(2,6-dichloro-9H-purin-8-yl)cyclobutanol

To a stirred solution of 1-(2,6-dichloro-9-(tetrahydro-2H-pyran-2-yl)-9H-purin-8-yl)cyclobutanol (2.29 g, 6.67 mmol) in methanol (27 mL) was added p-toluenesulfonic acid monohydrate (5.75 mg, 0.0334 mmol) and the resulting mixture was stirred at RT for 2 h. The reaction mixture was concentrated in vacuo leaving behind a viscous mass which was diluted with dichloromethane (5 mL). The resulting precipitate was filtered and washed with dichloromethane and dried. The resulting solid was purified by column chromatography (silica gel, 100-200 mesh, 0 to 100% ethyl acetate in heptane) affording 1-(2,6-dichloro-9H-purin-8-yl)cyclobutanol (1.57 g, 6.06 mmol): ¹H NMR (400 MHz, DMSO-d6) δ 13.94 (s, 1H), 6.48 (s, 1H), 2.69-2.58 (m, 2H), 2.43-2.29 (m, 2H), 1.98-1.76 (m, 2H).

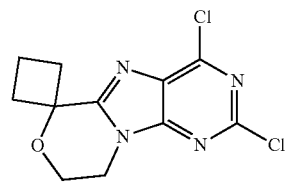 [SMILES: Clc1nc(Cl)c2nc3n(c2n1)CCOC31CCC1]

Step 3: 2,4-dichloro-8,9-dihydrospiro[[1,4]oxazino[4,3-e]purine-6,1'-cyclobutane]

To a solution of 1-(2,6-dichloro-9H-purin-8-yl)cyclobutanol (500 mg, 1.93 mmol) in acetonitrile (5.6 mL) was added cesium carbonate (1.57 g, 4.82 mmol), and 1, 2-dibromoethane (0.334 mL, 3.86 mmol) in a capped vial. The reaction mixture was heated to 80° C. for 16 h and subsequently concentrated to dryness in vacuo. The resulting viscous mass was diluted with water and extracted with ethyl acetate (2×10 mL). The combined organic layers were concentrated to dryness in vacuo. The resulting residue was purified by column chromatography (silica gel, 100-200 mesh, 0 to 15% ethyl acetate in heptane) affording 2,4-dichloro-8,9-dihydrospiro[[1,4]oxazino[4,3-e]purine-6,1'-cyclobutane] (345 mg, 63%): ¹H NMR (400 MHz, DMSO-d6) δ 4.25-4.15 (m, 2H), 4.13-4.05 (m, 2H), 2.71-2.60 (m, 2H), 2.45-2.34 (m, 2H), 2.20-2.00 (m, 2H).

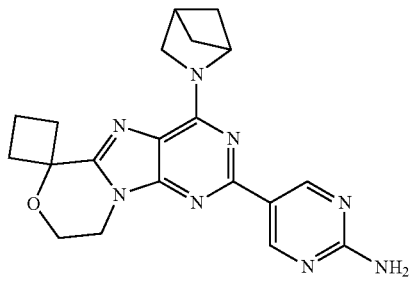 [SMILES: Nc1ncc(-c2nc(N3CC4CC3C4)c3nc4n(c3n2)CCOC42CCC2)cn1]

Step 4: 5-(4-(2-azabicyclo[2.1.1]hexan-2-yl)-8,9-dihydrospiro[[1,4]oxazino[4,3-e]purine-6,1'-cyclobutan]-2-yl)pyrimidin-2-amine To a solution of 2,4-dichloro-8,9-dihydrospiro[[1,4]oxazino[4,3-e]purine-6,1'-cyclobutane] (80.0 mg, 0.281 mmol) in N,N-dimethylformaldehyde (1.1 mL) was added 3-azabicyclo[2.2.1]hexane hydrochloride (40.3 mg, 0.337 mmol) and N,N-diisopropylethylamine (0.148 mL, 0.842 mmol). The reaction mixture was shaken at 70° C. for 16 h and concentrated to dryness in vacuo.

The crude was redissolved in a 1:1 mixture of acetonitrile: 1M potassium carbonate (2.6 mL) and transferred to a microwave vial equipped with a stirbar. To the solution was added 5-(4,4,5,5-tetramethyl-1,3,2-dioxaborolan-2-yl)pyrimidin-2-amine (62 mg, 0.281 mmol), 1,1'-bis(diphenylphosphino)ferrocene-palladium(II)dichloride (11.7 mg, 0.0140 mmol) and the mixture was microwaved at 110° C. for 5 min. The aqueous layer was extracted with ethyl acetate (1x 2 mL). The combined organic layers were concentrated to dryness in vacuo and the resulting residue was purified by RP-HPLC affording 5-(4-(2-azabicyclo[2.1.1]hexan-2-yl)-8,9-dihydrospiro[[1,4]oxazino[4,3-e]purine-6,1'-cyclobutan]-2-yl)pyrimidin-2-amine (38.8 mg, 35%): ¹H NMR (400 MHz, DMSO-d6) δ 9.10 (s, 2H), 6.97 (s, 2H), 4.16-4.09 (m, 2H), 4.08-4.00 (m, 2H), 3.05-2.98 (m, 1H), 2.65-2.54 (m, 2H), 2.42-2.26 (m, 3H), 2.18-1.93 (m, 5H), 1.51-1.40 (m, 2H).

Example 115

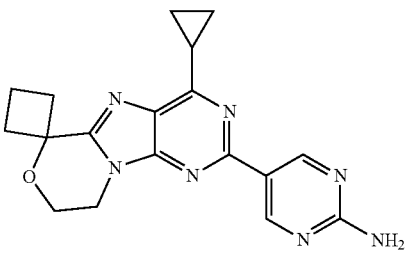 [SMILES: Nc1ncc(-c2nc(C3CC3)c3nc4n(c3n2)CCOC42CCC2)cn1]

5-(4-cyclopropyl-8,9-dihydrospiro[[1,4]oxazino[4,3-e]purine-6,1'-cyclobutan]-2-yl)pyrimidin-2-amine 2,4-dichloro-8,9-dihydrospiro[[1,4]oxazino[4,3-e]purine-6,1'-cyclobutane] (100 mg, 0.351 mmol) was dissolved in a 1:1 mixture of acetonitrile:1M potassium carbonate (2.8 mL) and transferred to a microwave vial equipped with a stirbar. To the solution was added cyclopropylboronic acid (30.1 mg, 0.351 mmol), 1,1'-bis(diphenylphosphino)ferrocene-palladium(II)dichloride (14.3 mg, 0.0175 mmol) and the mixture was microwaved at 120° C. for 5 min. The aqueous layer was extracted with ethyl acetate (2×1 mL). The combined organic layers were concentrated to dryness in vacuo. The resulting residue was purified by column chromatography (silica gel, 100-200 mesh, 0 to 100% ethyl acetate in heptane) affording 2-chloro-4-cyclopropyl-8,9-dihydrospiro[[1,4]oxazino[4,3-e]purine-6,1'-cyclobutane]. The material was redissolved in a 1:1 mixture of acetonitrile: 1M potassium carbonate (3.2 mL) and transferred to a microwave vial equipped with a stirbar. To the solution was added 5-(4,4,5,5-tetramethyl-1,3,2-dioxaborolan-2-yl)pyrimidin-2-amine (77.6 mg, 0.351 mmol), 1,1'-bis(diphenylphosphino)ferrocene-palladium(II)dichloride (14.3 mg, 0.0175 mmol) and the mixture was microwaved at 110° C. for 5 min. The aqueous layer was extracted with ethyl acetate (2×1 mL). The combined organic layers were concentrated to dryness in vacuo and the resulting residue was purified by RP-HPLC affording 5-(4-cyclopropyl-8,9-dihydrospiro[[1,4]oxazino[4,3-e]purine-6,1'-cyclobutan]-2-yl)pyrimidin-2-amine (38 mg, 31%): $^1$H NMR (400 MHz, DMSO-d6) δ 9.10 (s, 2H), 7.07 (s, 2H), 4.27-4.16 (m, 2H), 4.14-4.05 (m, 2H), 2.75-2.60 (m, 3H), 2.47-2.31 (m, 2H), 2.23-2.10 (m, 1H), 2.10-1.98 (m, 1H), 1.39-1.32 (m, 2H), 1.26-1.17 (m, 2H).

Example 116

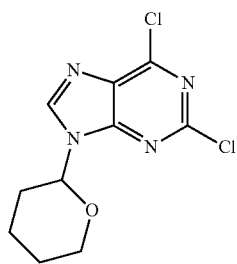 [SMILES: Clc1nc(Cl)c2ncn(C3CCCCO3)c2n1]

Step 1: 4,6-dichloro-1-(tetrahydro-2H-pyran-2-yl)-1H-imidazo[4,5-c]pyridine

To a stirred solution of 4,6-dichloro-1H-imidazo[4,5-c]pyridine (1.32 g, 4.85 mmol) in dichloromethane (20 mL), was added p-toluenesulfonic acid (27.3 mg, 0.160 mmol) and 3,4-dihydro-2H-pyran (1.12 g, 13.3 mmol). The reaction mixture was stirred at RT for 3 h and concentrated to dryness in vacuo. The resulting residue was purified by column chromatography (silica gel, 100-200 mesh, 0 to 100% ethyl acetate in heptane) affording 4,6-dichloro-1-(tetrahydro-2H-pyran-2-yl)-1H-imidazo[4,5-c]pyridine (1.32 g, 91%): $^1$H NMR (400 MHz, DMSO-d6) δ 8.73 (s, 1H), 7.98 (s, 1H), 5.78-5.71 (m, 2H), 4.06-3.94 (m, 1H), 3.81-3.70 (m, 1H), 2.23-2.10 (m, 2H), 2.08-1.92 (m, 2H), 1.76-1.54 (m, 3H), 4.06-3.95 (m, 2H), 4.06-3.94 (m, 1H), 8.77-8.70 (m, 2H), 7.98 (s, 1H), 5.75 (dd, J=10.2, 2.5 Hz, 1H).

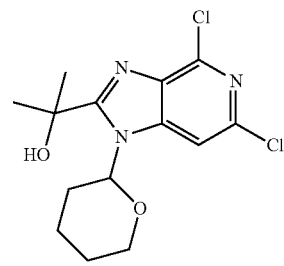 [SMILES: CC(C)(O)c1nc2c(Cl)nc(Cl)cc2n1C1CCCCO1]

Step 2: 2-(4,6-dichloro-1-(tetrahydro-2H-pyran-2-yl)-1H-imidazo[4,5-c]pyridin-2-yl) propan-2-ol To a solution of 4,6-dichloro-1-(tetrahydro-2H-pyran-2-yl)-1H-imidazo[4,5-c]pyridine (1.32 g, 4.85 mmol) cooled to −78° C. in dry tetrahydrofuran (23 mL) was added drop wise a 2M solution of lithium diisopropylamide in tetrahydrofuran/heptane/ethylbenzene (4.85 mL, 9.7 mmol). After addition was completed, the resulting solution was stirred at −78° C. for 30 min, acetone (1.1 mL, 14.6 mmol) was added and the reaction mixture was stirred at −78° C. for another 30 min. The reaction mixture was quenched with saturated ammonium chloride/ice solution and the aqueous layer extracted with diethyl ether (3×20 mL). The combined organic layers were concentrated to dryness in vacuo. The resulting residue was diluted with dichloromethane (10 mL) and the resulting precipitate was filtered, washed with dichloromethane and dried. The resulting solid was purified by column chromatography (silica gel, 100-200 mesh, 0 to 100% ethyl acetate in hexane) affording 2-(2,6-dichloro-9-(tetrahydro-2H-pyran-2-yl)-9H-purin-8-yl)propan-2-ol (1.29 g, 80%): $^1$H NMR (400 MHz, DMSO-d6) δ 7.81 (s, 1H), 6.36 (d, J=11.0, 2.4 Hz, 1H), 6.04 (s, 1H), 4.16 (d, J=11.4, 4.2 Hz, 1H), 3.72-3.58 (m, 1H), 2.19-2.04 (m, 1H), 2.01-1.87 (m, 3H), 1.87-1.74 (m, 1H), 1.74-1.48 (m, 8H).

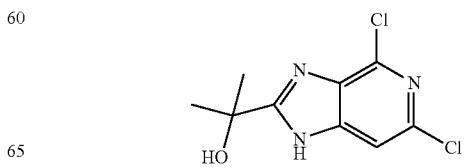

Step 3: 2-(4,6-dichloro-1H-imidazo[4,5-c]pyridin-2-yl)propan-2-ol

To a stirred solution of 2-(4,6-dichloro-1-(tetrahydro-2H-pyran-2-yl)-1H-imidazo[4,5-c]pyridin-2-yl)propan-2-ol (1.29 g, 3.91 mmol) in methanol (16 mL) was added p-toluenesulfonic acid monohydrate (1.68 mg, 0.00977 mmol) and the resulting mixture was stirred at 35° C. for 16 h. The reaction mixture was concentrated to dryness in vacuo leaving behind a viscous mass which was diluted with dichloromethane (5 mL). The resulting precipitate was filtered and washed with dichloromethane, affording 2-(4,6-dichloro-1H-imidazo[4,5-c]pyridin-2-yl)propan-2-ol (946 mg, 98%): $^1$H NMR (400 MHz, DMSO-d6) δ 13.16 (s, 1H), 7.48 (s, 1H), 1.57 (s, 6H).

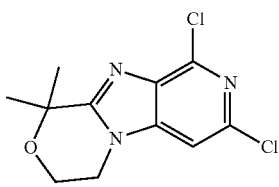 [SMILES: CC1(C)OCCn2c1nc1c(Cl)nc(Cl)cc12]

Step 4: 7,9-dichloro-1,1-dimethyl-3,4-dihydro-1H-pyrido[3',4':4,5]imidazo[2,1-c][1,4]oxazine To a solution of 2-(4,6-dichloro-1H-imidazo[4,5-c]pyridin-2-yl)propan-2-ol (860 mg, 3.49 mmol) in dichloromethane (17.5 mL) at 0° C. was added sodium hydride (309 mg, 12.2 mmol), and the suspension was stirred for 15 min. 2-bromoethyldiphenylsulfonium trifluoromethanesulfonate (1.71 g, 4.19 mmol) was added, and the suspension was stirred at 0° C. for 2 h. The reaction mixture was quenched with saturated aqueous ammonium chloride, and the aqueous layer was extracted with ethyl acetate (3×10 mL) and the combined organic layers were concentrated to dryness in vacuo. The resulting residue was purified by column chromatography (silica gel, 100-200 mesh, 0 to 25% ethyl acetate in heptane) affording 7,9-dichloro-1,1-dimethyl-3,4-dihydro-1H-pyrido[3',4':4,5]imidazo[2,1-c][1,4]oxazine (228 mg, 24%): $^1$H NMR (400 MHz, DMSO-d6) δ 7.88 (s, 1H), 4.24-4.20 (m, 2H), 4.17-4.12 (m, 2H), 1.62 (s, 6H).

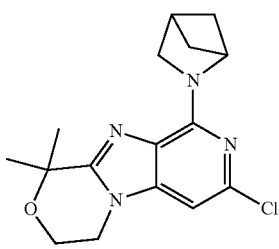 [SMILES: CC1(C)OCCn2c1nc1c(N3CC4CC3C4)nc(Cl)cc12]

Step 5: 9-(2-azabicyclo[2.1.1]hexan-2-yl)-7-chloro-1,1-dimethyl-3,4-dihydro-1H-pyrido[3',4':4,5]imidazo[2,1-c][1,4]oxazine To a stirred solution of 7,9-dichloro-1,1-dimethyl-3,4-dihydro-1H-pyrido[3',4':4,5]imidazo[2,1-c][1,4]oxazine (140 mg, 0.514 mmol) in isopropanol (2 mL) was added 3-azabicyclo[2.2.1]hexane hydrochloride (73.8 mg, 0.618 mmol) and diisopropylamine (0.272 mL, 1.54 mmol). After addition was complete the reaction mixture was stirred at 150° C. in a sealed tube for 12 h. The reaction mixture was allowed to cool to RT and concentrated to dryness in vacuo. The resulting residue was purified by column chromatography (silica gel, 100-200 mesh, 0 to 100% ethyl acetate in heptane) affording 9-(2-azabicyclo[2.1.1]hexan-2-yl)-7-chloro-1,1-dimethyl-3,4-dihydro-1H-pyrido[3',4':4,5]imidazo[2,1-c][1,4]oxazine (134 mg, 82%) use as is in the next step

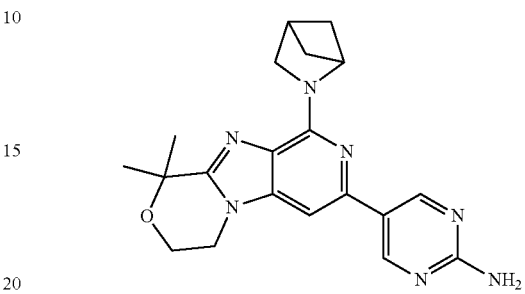

Step 6: 5-(9-(2-azabicyclo[2.1.1]hexan-2-yl)-1,1-dimethyl-3,4-dihydro-1H-pyrido[3',4':4,5]imidazo[2,1-c][1,4]oxazin-7-yl)pyrimidin-2-amine 9-(2-azabicyclo[2.1.1]hexan-2-yl)-7-chloro-1,1-dimethyl-3,4-dihydro-1H pyrido[3',4':4,5]imidazo-[2,1-c][1,4]oxazine (62.0 mg 0.194 mmol) was dissolved in a 1:1 mixture of acetonitrile:1M potassium carbonate (2 mL) and transferred to a microwave vial equipped with a stirbar. To the solution was added 5-(4,4,5,5-tetramethyl-1,3,2-dioxaborolan-2-yl)pyrimidin-2-amine (42.9 mg, 0.194 mmol), 1,1'-bis(diphenylphosphino)ferrocene-palladium(II)dichloride (8.08 mg, 0.00969 mmol) and the mixture was microwaved at 120° C. for 5 min. The aqueous layer was extracted with ethyl acetate (2×1 mL). The combined organic layers were concentrated to dryness in vacuo and purified by RP-HPLC affording 5-(9-(2-azabicyclo[2.1.1]hexan-2-yl)-1,1-dimethyl-3,4-dihydro-1H-pyrido[3',4':4,5]imidazo[2,1-c][1,4]oxazin-7-yl)pyrimidin-2-amine (28.2 mg, 38%): $^1$HNMR (400 MHz, DMSO-d6) δ 8.90 (s, 1H), 7.80 (s, 1H), 6.79 (s, 2H), 4.24-4.13 (m, 4H), 2.76-2.65 (m, 1H), 1.63 (s, 6H), 1.23-1.16 (m, 2H), 1.09-1.01 (m, 2H).

Example 117

Using a procedure similar to that described in Example 116, the following compound was prepared.

| Ex | Structure | $^1$H NMR | MS (m/z) |
|---|---|---|---|
| 117 | 2-(2-aminopyrimidin-5-yl)-N-cyclopropyl-N-ethyl-6,6-dimethyl-8,9-dihydro-6H-[1,4]oxazino[4,3-e]purin-4-amine | 1H NMR (400 MHz, DMSO-d6) δ 8.58 (d, J = 1.8 Hz, 1H), 8.02 (d, J = 1.7 Hz, 1H), 7.32 (s, 1H), 7.20 (m, 1H), 6.21 (s, 2H), 5.69-5.59 (m, 1H), 4.19-4.09 (m, 4H), 3.75 (s, 2H), 2.98-2.93 (m, 1H), 2.02-1.94 (m, 2H), 1.59 (s, 6H), 1.39-1.35 (m, 2H). | 381 |

Example 118

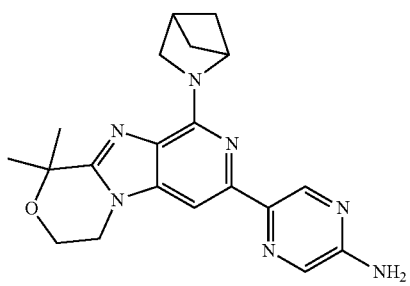 [SMILES: CC1(C)OCCn2c1nc1c(N3CC4CC3C4)nc(-c3cnc(N)cn3)cc12]

5-(9-(2-azabicyclo[2.1.1]hexan-2-yl)-1,1-dimethyl-3,4-dihydro-1H-pyrido[3',4':4,5]imidazo[2,1-c][1,4]oxazin-7-yl)pyrazin-2-amine 9-(2-azabicyclo[2.1.1]hexan-2-yl)-7-chloro-1,1-dimethyl-3,4-dihydro-1H-pyrido[3',4':4,5]imidazo[2,1-c][1,4]oxazine (62.0 mg 0.194 mmol) was dissolved in a 1:1 mixture of acetonitrile:1M potassium carbonate (2 mL) and transferred to a microwave vial equipped with a stirbar. To the solution was added 5-(4,4,5,5-tetramethyl-1,3,2-dioxaborolan-2-yl)pyrazin-2-amine (42.9 mg, 0.194 mmol), 1,1'-bis(diphenylphosphino)ferrocene-palladium(II)dichloride (8.08 mg, 0.00969 mmol) and the mixture was microwaved at 120° C. for 5 min. The aqueous layer was extracted with ethyl acetate (2×1 mL). The combined organic layers were concentrated to dryness in vacuo and purified by RP-HPLC affording 5-(9-(2-azabicyclo[2.1.1]hexan-2-yl)-1,1-dimethyl-3,4-dihydro-1H-pyrido[3',4':4,5]imidazo[2,1-c][1,4]oxazin-7-yl)pyrazin-2-amine (18.3 mg, 25%): $^1$H NMR (400 MHz, DMSO-d6) δ 8.84 (d, J=2.0 Hz, 1H), 7.91 (s, 1H), 7.49 (s, 1H), 6.50 (s, 2H), 5.65 (d, J=6.8 Hz, 3H), 4.18-4.09 (m, 4H), 3.77 (s, 2H), 2.97-2.92 (m, 2H), 2.02-1.96 (m, 2H), 1.60 (s, 6H), 1.40-1.36 (m, 2H).

Example 119

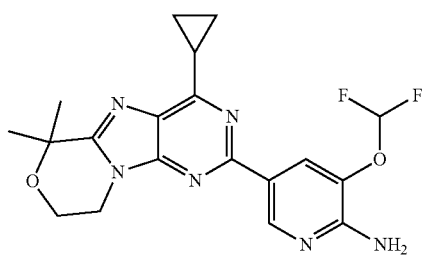 [SMILES: CC1(C)OCCn2c1nc1c(C3CC3)nc(-c3cnc(N)c(OC(F)F)c3)nc12]

5-(4-cyclopropyl-6,6-dimethyl-8,9-dihydro-6H-[1,4]oxazino[4,3-e]purin-2-yl)-3-(difluoromethoxy)pyridin-2-amine 2-chloro-4-cyclopropyl-6,6-dimethyl-8,9-dihydro-6H-[1,4]oxazino[4,3-e]purine (50.0 mg, 0.179 mmol) was dissolved in a 1:1 mixture of acetonitrile:1M potassium carbonate (1.6 mL) and transferred to a microwave vial equipped with a stirbar. To the solution was added 3-(difluoromethoxy)-5-(4,4,5,5-tetramethyl-1,3,2-dioxaborolan-2-yl)pyridin-2-amine (51.3 mg, 0.179 mmol), 1,1'-bis(diphenylphosphino)ferrocene-palladium(II)dichloride (7.48 mg, 0.00897 mmol) and the mixture was microwaved at 110° C. for 5 min. The aqueous layer was extracted with ethyl acetate (3×1 mL) and the combined organic layers were concentrated to dryness in vacuo. The resulting residue was purified by RP-HPLC affording 5-(4-cyclopropyl-6,6-dimethyl-8,9-dihydro-6H-[1,4]oxazino[4,3-e]purin-2-yl)-3-(difluoromethoxy)pyridin-2-amine (19.7 mg, 27%): $^1$H NMR (400 MHz, DMSO-d6) δ 8.85 (s, 1H), 8.15 (s, 1H), 7.39-6.99 (m, 2H), 6.53 (s, 2H), 4.26-4.19 (m, 2H), 4.19-4.12 (m, 2H), 2.71-2.60 (m, 1H), 1.63 (s, 6H), 1.37-1.28 (m, 2H), 1.23-1.15 (m, 2H).

Examples 120-122

Using a procedure similar to that described in Example 119, the following compounds were prepared.

| Ex | Structure | $^1$H NMR | MS (m/z) |
|---|---|---|---|
| 120 | 5-(9-cyclopropyl-1,1-dimethyl-3,4-dihydro-1H-pyrido-[3',4':4,5]imidazo[2,1-c]-[1,4]oxazin-7-yl)pyrimidin-2-amine | $^1$H NMR (400 MHz, DMSO-d6) δ 8.90 (s, 2H), 7.80 (s, 1H), 6.79 (s, 2H), 4.25-4.13 (m, 4H), 2.78-2.68 (m, 1H), 1.63 (s, 6H), 1.23-1.16 (m, 2H), 1.09-1.02 (m, 2H), 5.83-5.66 (m, 2H). | 337 |
| 121 | 1-Cyclopropyl-8,8-dimethyl-3-(3-methyl-1H-pyrrolo[2,3-b]-pyridin-5-yl)-5,6-dihydro-8H-7-oxa-2,4,4b,9-tetraaza-fluorene | $^1$H NMR (400 MHz, DMSO-d6) δ: 11.45 (s, 1H), 9.26 (d, J = 2.0 Hz, 1H), 8.81 (d, J = 2.0 Hz, 1H), 7.28 (s, 1H), 4.32-4.24 (m, 2H), 4.21-4.13 (m, 2H), 2.75-2.66 (m, 1H), 2.33 (s, 3H), 1.65 (s, 6H), 1.45-1.36 (m, 2H), 1.28-1.18 (m, 2H) | 375 |

| Ex | Structure | ¹H NMR | MS (m/z) |
|---|---|---|---|
| 122 | 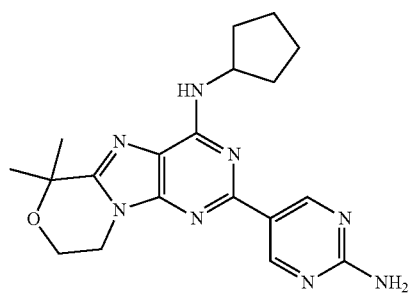<br>5-(4-cyclopropyl-6,6-dimethyl-8,9-dihydro-6H-[1,4]oxazino[4,3-e]purin-2-yl)pyrimidin-2-amine | ¹H NMR (400 MHz, DMSO-d6) δ 9.10 (s, 2H), 7.07 (s, 2H), 4.21 (t, J = 5.0 Hz, 2H), 4.15 (t, J = 4.9 Hz, 2H), 2.69-2.61 (m, 1H), 1.63 (s, 6H), 1.36-1.30 (m, 2H), 1.19 (dt, J = 11.7, 3.4 Hz, 2H). | 338 |

Example 123

2-(2-aminopyrimidin-5-yl)-N-cyclopentyl-6,6-dimethyl-8,9-dihydro-6H-[1,4]oxazino[4,3-e]purin-4-amine To a solution of 2,4-dichloro-6,6-dimethyl-8,9-dihydro-6H-[1,4]oxazino[4,3-e]purine (40 mg, 0.146 mmol) in N,N-dimethylformaldehyde (0.586 mL) was added aminocyclopentane (13.1 mg, 0.153 mmol) and N,N-diisopropylethylamine (0.0773 mL, 0.438 mmol). The reaction mixture was shaken at 70° C. for 16 h and concentrated to dryness in vacuo. The resulting crude was redissolved in a 1:1 mixture of acetonitrile:1M potassium carbonate (1.3 mL) and transferred to a microwave vial equipped with a stirbar. To the solution was added 5-(4,4,5,5-tetramethyl-1,3,2-dioxaborolan-2-yl)pyrimidin-2-amine (32.3 mg, 0.146 mmol), 1,1'-bis(diphenylphosphino)ferrocene-palladium(II)dichloride (6.1 mg, 0.0146 mmol) and the mixture was microwaved at 110° C. for 5 min. The aqueous layer was extracted with ethyl acetate (1x 2 ml) and the combined organic layers were concentrated to dryness in vacuo. The resulting residue was purified by RP-HPLC affording 2-(2-aminopyrimidin-5-yl)-N-cyclopentyl-6,6-dimethyl-8,9-dihydro-6H-[1,4]oxazino[4,3-e]purin-4-amine (43.3 mg, 78%): ¹H NMR (400 MHz, DMSO-d6) δ 9.08 (s, 2H), 7.54 (s, 1H), 6.95 (s, 2H), 1.60-1.58 (m, 7H), 4.63 (s, 1H), 4.17-4.07 (m, 4H), 2.06-1.92 (m, 2H), 1.79-1.52 (m, 7H), 1.59 (s, 6H), 4.70-4.55 (m, 1H).

Example 124

Using a procedure similar to that described in Example 123, the following compound was prepared.

| Ex | Structure | ¹H NMR | MS (m/z) |
|---|---|---|---|
| 124 | 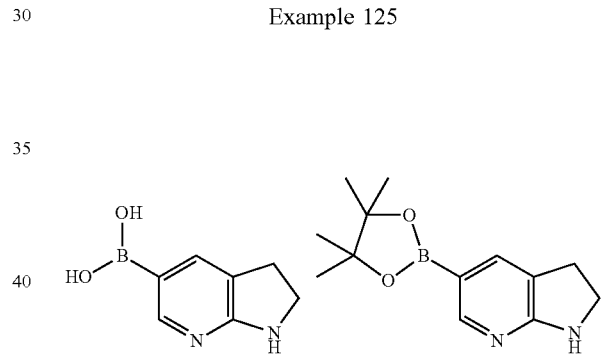<br>2-(2-aminopyrimidin-5-yl)-N-cyclobutyl-6,6-dimethyl-8,9-dihydro-6H-[1,4]oxazino-[4,3-e]purin-4-amine | 1H NMR (400 MHz, DMSO-d6) δ 9.09 (s, 1H), 7.90 (s, 1H), 6.96 (s, 2H), 4.81 (s, 1H), 4.16-4.07 (m, 4H), 2.34-2.25 (m, 2H), 2.24-2.11 (m, 2H), 1.77-1.66 (m, 2H), 1.60 (s, 6H). | 367 |

Example 125

Step 1: (2,3-dihydro-1H-pyrrolo[2,3-b]pyridin-5-yl)boronic acid and 5-(4,4,5,5-tetramethyl-1,3,2-dioxaborolan-2-yl)-2,3-dihydro-1H-pyrrolo[2,3-b]pyridine To a stirred solution of 5-bromo-2,3-dihydro-1H-pyrrolo[2,3-b]pyridine (100 mg, 0.50 mmol) and 1,2-dimethoxyethane (4 mL) in a microwave vial equipped with a stirbar was added bis(pinacolato diborane) (175 mg, 0.65 mmol), potassium acetate (148 mg, 1.5 mmol) and 1,1'-bis(diphenylphosphino)ferrocene-palladium(II)dichloride (20.9 mg, 0.025 mmol). The mixture was purged with nitrogen gas for 5 min and the reaction mixture was stirred at 90° C. for 5.5 h. The reaction mixture was filtered through a celite bed and washed with dichloromethane (10 mL). The filtrate was concentrated to dryness in vacuo affording a crude mixture of (2,3-dihydro-1H-pyrrolo[2,3-b]pyridin-5-yl)boronic acid and 5-(4,4,5,5-tetramethyl-1,3,2-dioxaborolan-2-yl)-2,3-dihydro-1H-pyrrolo[2,3-b]pyridine used for the next step without any further purification.

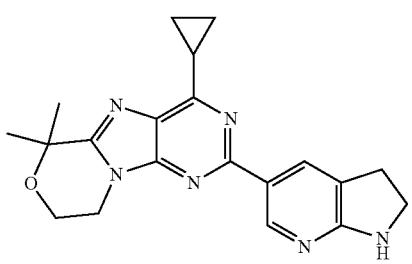 [SMILES: CC1(C)OCCn2c1nc1c(C3CC3)nc(-c3cnc4c(c3)CCN4)nc12]

Step 2: 4-cyclopropyl-2-(2,3-dihydro-1H-pyrrolo[2,3-b]pyridin-5-yl)-6,6-dimethyl-8,9-dihydro-6H-[1,4]oxazino[4,3-e]purine 2-chloro-4-cyclopropyl-6,6-dimethyl-8,9-dihydro-6H-[1,4]oxazino[4,3-e]purine (50 mg, 0.18 mmol) and a crude mixture of (2,3-dihydro-1H-pyrrolo[2,3-b]pyridin-5-yl)boronic acid and 5-(4,4,5,5-tetramethyl-1,3,2-dioxaborolan-2-yl)-2,3-dihydro-1H-pyrrolo[2,3-b]pyridine (120 mg) was dissolved in acetonitrile (2.5 mL) and degassed water (0.5 mL) in a microwave vial equipped with a stirbar. To the solution was added bis(di-tert-butyl(4-dimethylaminophenyl)phosphine) dichloropalladium(II) (12.7 mg, 0.018 mmol), potassium acetate (25 mg, 0.25 mmol) and sodium carbonate (27 mg, 0.25 mmol) and the mixture was microwaved at 140° C. for 40 min. The reaction mixture was filtered through a celite bed and washed with dichloromethane (10 mL). The filtrate was concentrated to dryness in vacuo. The resulting residue was purified by RP-HPLC affording 4-cyclopropyl-2-(2,3-dihydro-1H-pyrrolo[2,3-b]pyridin-5-yl)-6,6-dimethyl-8,9-dihydro-6H-[1,4]oxazino[4,3-e]purine (30.6 mg, 47%, two steps): $^1$H NMR (400 MHz, DMSO-d6) δ 8.77 (d, J=2.0 Hz, 1H), 8.13 (d, J=1.2 Hz, 1H), 6.82 (s, 1H), 4.21-4.08 (m, 4H), 3.55 (t, J=8.4 Hz, 2H), 3.06 (t, J=8.4 Hz, 2H), 2.67-2.58 (m, 1H), 1.63 (s, 6H), 1.33-1.26 (m, 2H), 1.19-1.11 (m, 2H).

Example 126

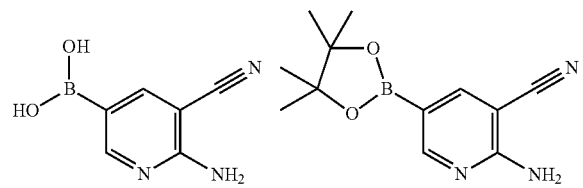

Step 1: (6-amino-5-cyanopyridin-3-yl)boronic acid and 2-amino-5-(4,4,5,5-tetramethyl-1,3,2-dioxaborolan-2-yl)nicotinonitrile To a stirred solution of 2-amino-5-bromonicotinonitrile (100 mg, 0.51 mmol) and 1,2-dimethoxyethane (4 mL) in a microwave vial equipped with a stirbar was added bis(pinacolato diborane) (175 mg, 0.66 mmol), potassium acetate (149 mg, 1.52 mmol) and 1,1'-bis(diphenylphosphino)ferrocene-palladium(II)dichloride (21 mg, 0.025 mmol). The mixture was purged with nitrogen gas for 5 min and the reaction mixture was stirred at 90° C. for 3 h. The reaction mixture was filtered through a celite bed and washed with dichloromethane (10 mL). The filtrate was concentrated to dryness in vacuo affording a crude mixture of (6-amino-5-cyanopyridin-3-yl)boronic acid and 2-amino-5-(4,4,5,5-tetramethyl-1,3,2-dioxaborolan-2-yl)nicotinonitrile used for the next step without any further purification.

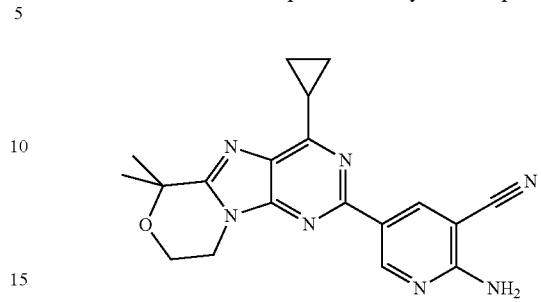

Step 2: 2-amino-5-(4-cyclopropyl-6,6-dimethyl-8,9-dihydro-6H-[1,4]oxazino[4,3-e]purin-2-yl)nicotinonitrile 2-chloro-4-cyclopropyl-6,6-dimethyl-8,9-dihydro-6H-[1,4]oxazino[4,3-e]purine (50 mg, 0.18 mmol) and a crude mixture of (6-amino-5-cyanopyridin-3-yl)boronic acid and 2-amino-5-(4,4,5,5-tetramethyl-1,3,2-dioxaborolan-2-yl)nicotinonitrile (120 mg) was dissolved in acetonitrile (2.5 mL) and degassed water (0.5 mL) in a microwave vial equipped with a stirbar. To the solution was added bis(di-tert-butyl(4-dimethylaminophenyl)phosphine)dichloropalladium(II) (12.7 mg, 0.018 mmol), potassium acetate (25 mg, 0.25 mmol) and sodium carbonate (27 mg, 0.25 mmol) and the mixture was microwaved at 140° C. for 40 min. The reaction mixture was filtered through a celite bed and washed with dichloromethane (10 mL). The filtrate was concentrated to dryness in vacuo. The resulting residue was purified by RP-HPLC affording 2-amino-5-(4-cyclopropyl-6,6-dimethyl-8,9-dihydro-6H-[1,4]oxazino[4,3-e]purin-2-yl)nicotinonitrile (4.1 mg, 6%, two steps): LCMS $R_T$=5.07 min, m/z=362.2 [M+H]$^+$.

Example 127

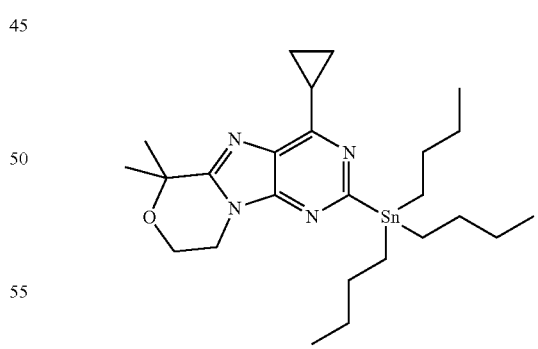

Step 1: 4-cyclopropyl-6,6-dimethyl-2-(tributylstannyl)-8,9-dihydro-6H-[1,4]oxazino[4,3-e]purine 2-chloro-4-cyclopropyl-6,6-dimethyl-8,9-dihydro-6H-[1,4]oxazino[4,3-e]purine (80 mg, 0.287 mmol) and bis(tributyltin) (0.25 mL, 0.502 mmol) were dissolved in 1,4-dioxane (2 mL) in a microwave vial equipped with a stir bar and the mixture was purged with nitrogen gas for 15 min. bis(ditert-butyl(4-dimethylaminophenyl)phosphine)dichloropalladium(II) (34.2 mg, 0.046 mmol) was then added and the reaction mixture was microwaved at 150° C. for 30 min. The reaction mixture was filtered and washed with ethyl acetate (10 mL). The filtrate was concentrated to dryness in vacuo, dissolved in ethyl acetate and washed with brine (10 mL). The organic layer was separated, dried over sodium sulfate, filtered and concentrated in vacuo. The resulting residue was absorbed onto celite and purified by column chromatography (silica gel, 100-200 mesh, 0 to 15% ethyl acetate in heptane) to afford 4-cyclopropyl-6,6-dimethyl-2-(tributylstannyl)-8,9-dihydro-6H-[1,4]oxazino[4,3-e]purine (115 mg, 75%) as a clear oil: $^1$H NMR (400 MHz, DMSO-d6) δ 4.26-4.20 (m, 2H), 4.17-4.14 (m, 2H), 2.73-2.67 (m, 1H), 1.73 (s, 6H), 1.65-1.56 (m, 8H), 1.39-1.28 (m, 8H), 1.14-1.08 (m, 6H), 0.94-0.86 (m, 9H).

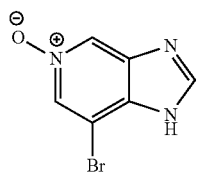 [SMILES: [O-][n+]1cc(Br)c2[nH]cnc2c1]

Step 2: 7-bromo-1H-imidazo[4,5-c]pyridine 5-oxide

To a stirred solution of 7-bromo-1H-imidazo[4,5-c]pyridine (1.0 g, 5.05 mol) and chloroform (20 mL) was added m-chloroperoxybenzoic acid (2.83 g, 12.6 mmol) and the reaction mixture stirred for 30 min at RT. The reaction mixture was filtered, washed with chloroform (10 mL), and the white solid was dried under high vacuum. The solid resulting solid was dissolved in a dichloromethane and methanol mixture, absorbed onto celite and purified by column chromatography (silica gel, 100-200 mesh, 0 to 20% methanol in dichloromethane with 3% triethylamine) affording 7-bromo-1H-imidazo[4,5-c]pyridine 5-oxide as a white solid (580 mg, 54%) used as is in the next step.

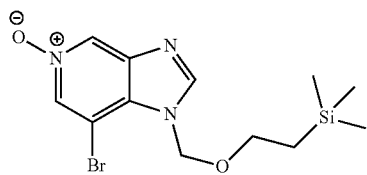 [SMILES: C[Si](C)(C)CCOCn1cnc2c[n+]([O-])cc(Br)c21]

Step 3: 7-bromo-1-((2-(trimethylsilyl)ethoxy)methyl)-1H-imidazo[4,5-c]pyridine 5-oxide To a stirred solution of 7-bromo-1H-imidazo[4,5-c]pyridine 5-oxide (425 mg, 1.99 mmol) and N,N-dimethylformaldehyde (5.5 mL) at 0° C. was added N,N-diisopropylethylamine (1.05 mL, 5.96 mmol), tetrabutylammonium iodide (74 mg, 0.199 mmol) and 2-(trimethylsilyl)ethoxymethyl chloride (0.78 mL, 3.97 mmol) and the reaction mixture stirred for 30 min at RT. The reaction mixture was washed with water (10 mL) and extracted with dichloromethane (2×10 mL). The combined organic layers were dried over sodium sulfate and concentrated to dryness in vacuo. The resulting residue was purified by column chromatography (silica gel, 100-200 mesh, 0 to 10% methanol in dichloromethane) affording an approximate 3:2 mixture of 7-bromo-1-((2-(trimethylsilyl)ethoxy)methyl)-1H-imidazo[4,5-c]pyridine 5-oxide and 7-bromo-3-((2-(trimethylsilyl)ethoxy)methyl)-3H-imidazo[4,5-c]pyridine 5-oxide N-(2-(trimethylsilyl)ethoxy)methane regioisomers as an orange foam (580 mg, 54%): $^1$H NMR (400 MHz, DMSO-d6; reported as an approximate 3:2 mixture of N-(2-(trimethylsilyl)ethoxy)methane isomers) δ 8.73 (d, J=1.5 Hz, 0.6H), 8.60 (d, J=1.6 Hz, 1H), 8.38 (d, J=1.5 Hz, 1H), 8.36 (d, J=1.5 Hz, 0.6H), 8.10 (s, 1H), 8.09 (s, 0.6H), 5.76 (s, 1.3H), 5.48 (s, 2H), 3.63-3.59 (m, 1.4H), 3.56-3.50 (m, 2H), 0.97-0.91 (m, 3H), −0.01 (s, 9H), −0.02 (s, 6H).

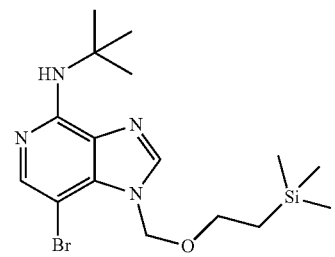 [SMILES: CC(C)(C)Nc1ncc(Br)c2c1ncn2COCC[Si](C)(C)C]

Step 4: 7-bromo-N-(tert-butyl)-1-((2-(trimethylsilyl)ethoxy)methyl)-1H-imidazo[4,5-c]pyridin-4-amine To a stirred solution of 7-bromo-1-((2-(trimethylsilyl)ethoxy)methyl)-1H-imidazo[4,5-c]pyridine 5-oxide (102 mg, 0.296 mmol) and 1,2-dichloroethane (1.5 mL) was added N,N-diisopropylethylamine (0.195 mL, 1.11 mmol), t-butylamine (0.039 mL, 0.37 mmol) and bromotripyrrolidinophosphonium hexafluorophosphate (180 mg, 0.385 mmol) and the reaction mixture stirred for 22 h at RT. The reaction mixture was washed with saturated sodium bicarbonate solution (10 mL) and extracted with dichloromethane (2×10 mL). The combined organic layers were dried over sodium sulfate, filtered and concentrated to dryness in vacuo. The resulting residue was purified by column chromatography (silica gel, 100-200 mesh, 0 to 50% ethyl acetate in heptane) affording an approximate 3:2 mixture of 7-bromo-N-(tert-butyl)-1-((2-(trimethylsilyl)ethoxy)methyl)-1H-imidazo[4,5-c]pyridin-4-amine and 7-bromo-N-(tert-butyl)-3-((2-(trimethylsilyl)ethoxy)methyl)-3H-imidazo[4,5-c]pyridin-4-amine N-SEM regioisomers (47 mg, 40%): $^1$H NMR (400 MHz, DMSO-d6; reported as an approximate 3:2 mixture of N-SEM isomers) δ 8.00 (s, 0.7H), 7.95 (s, 1H), 7.81 (s, 0.7H), 7.77 (s, 1H), 6.02 (br s, 0.8H), 5.77 (s, 2H), 5.54 (s, 1.6H), 5.43 (br s, 1H), 3.63-3.57 (m, 3.7H), 1.02-0.89 (m, 3.8H), 0.00 (s, 6H), −0.02 (s, 9H).

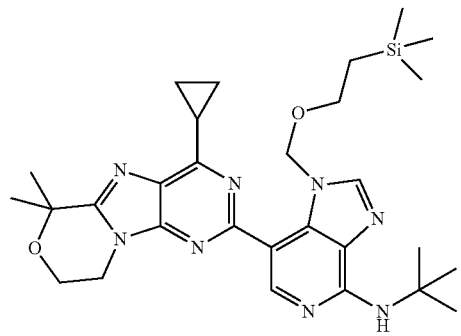 [SMILES: CC(C)(C)Nc1ncc(-c2nc(C3CC3)c3nc4n(c3n2)CCOC4(C)C)c2c1ncn2COCC[Si](C)(C)C]

Step 5: N-(tert-butyl)-7-(4-cyclopropyl-6,6-dimethyl-8,9-dihydro-6H-[1,4]oxazino[4,3-e]purin-2-yl)-1-((2-(trimethylsilyl)ethoxy)methyl)-1H-imidazo[4,5-c]pyridin-4-amine 4-cyclopropyl-6,6-dimethyl-2-(tributylstannyl)-8,9-dihydro-6H-[1,4]oxazino[4,3-e]purine (64.5 mg, 0.12 mmol) and 7-bromo-N-(tert-butyl)-1-((2-(trimethylsilyl)ethoxy)methyl)-1H-imidazo[4,5-c]pyridin-4-amine (46 mg, 0.115 mmol) were dissolved in 1,4-dioxane (2.5 mL) in a microwave vial equipped with a stir bar and the mixture was purged with nitrogen gas for 10 min. Copper(I) thiophene-2-carboxylate (22 mg, 0.115 mmol) and tetrakis(triphenylphosphine)palladium(0) (13.3 mg, 0.012 mmol) were then added and the reaction mixture was microwaved at 140° C. for 35 min. The reaction mixture was filtered through a celite bed and washed with dichloromethane (10 mL). The filtrate was concentrated to dryness in vacuo, dissolved in ethyl acetate and washed with brine (10 mL). The organic layer was separated, dried over sodium sulfate and concentrated to afford crude N-(tert-butyl)-7-(4-cyclopropyl-6,6-dimethyl-8,9-dihydro-6H-[1,4]oxazino[4,3-e]purin-2-yl)-1-((2-(trimethylsilyl)ethoxy)methyl)-1H-imidazo[4,5-c]pyridin-4-amine used for the next step without any further purification.

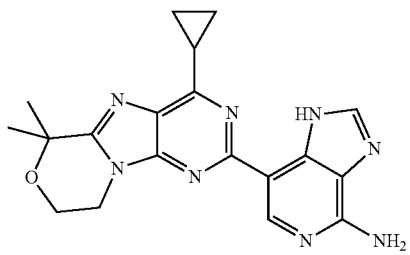 [SMILES: CC1(C)OCCn2c1nc1c(C3CC3)nc(-c3cnc(N)c4nc[nH]c34)nc12]

Step 6: 7-(4-cyclopropyl-6,6-dimethyl-8,9-dihydro-6H-[1,4]oxazino[4,3-e]purin-2-yl)-1H-imidazo[4,5-c]pyridin-4-amine N-(tert-butyl)-7-(4-cyclopropyl-6,6-dimethyl-8,9-dihydro-6H-[1,4]oxazino[4,3-e]purin-2-yl)-1-((2-(trimethylsilyl)ethoxy)methyl)-1H-imidazo[4,5-c]pyridin-4-amine (64.7 mg, 0.115 mmol) was dissolved in dichloromethane (1 mL) and trifluoroacetic acid (1 mL) in a microwave vial equipped with a stir bar and the reaction mixture was microwaved at 120° C. for 20 min. The reaction mixture was washed with saturated sodium bicarbonate solution (10 mL) and extracted with dichloromethane (2×10 mL). The combined organic layers were dried over sodium sulfate, filtered and concentrated to dryness in vacuo. The resulting residue was purified by RP-HPLC affording 7-(4-cyclopropyl-6,6-dimethyl-8,9-dihydro-6H-[1,4]oxazino[4,3-e]purin-2-yl)-1H-imidazo[4,5-c]pyridin-4-amine (4.1 mg, 10%, two steps): LCMS $R_T$=4.06 min, m/z=377.2 [M+H]$^+$.

Example 128

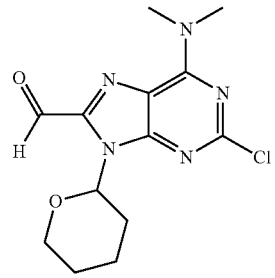 [SMILES: CN(C)c1nc(Cl)nc2c1nc(C=O)n2C1CCCCO1]

Step 1: 2-chloro-6-(dimethylamino)-9-(tetrahydro-2H-pyran-2-yl)-9H-purine-8-carbaldehyde To a solution of compound 2,6-dichloro-9-(tetrahydro-2H-pyran-2-yl)-9H-purine (10 g, 36.6 mmol) cooled to −78° C. in tetrahydrofuran (100 mL) was added dropwise a 2M solution of lithium diisopropylamide in tetrahydrofuran (36.6 mL, 73.2 mmol). After addition was completed, the resulting solution was stirred at −78° C. for 45 min. A solution of N,N-dimethylformaldehyde (8.03 g, 109.8 mmol) in tetrahydrofuran (20 mL) was added dropwise and the reaction mixture was stirred at −78° C. for another 30 min. The reaction mixture was quenched with saturated ammonium chloride (100 mL) and the aqueous layer extracted with ethyl acetate (2×100 mL). The combined organic layers were dried over sodium sulfate and concentrated to dryness in vacuo. The resulting residue was purified by column chromatography (silica gel, 100-200 mesh, 20% ethyl acetate in hexane) affording crude 2-chloro-6-(dimethylamino)-9-(tetrahydro-2H-pyran-2-yl)-9H-purine-8-carbaldehyde (6 g, 54%) used as is in the next step: LCMS (ESI, 10-80AB/2.0 min): $R_T$=1.082 min, m/z 310.1 [M+H$^+$].

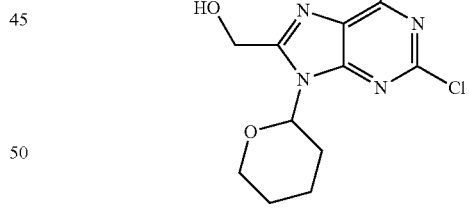

Step 2: (2-chloro-6-(dimethylamino)-9-(tetrahydro-2H-pyran-2-yl)-9H-purin-8-yl)methanol To a solution of compound 2-chloro-6-(dimethylamino)-9-(tetrahydro-2H-pyran-2-yl)-9H-purine-8-carbaldehyde (6 g, 19.37 mmol) in methanol (50 mL) was added sodium borohydride (733 mg, 19.37 mmol). The reaction mixture was stirred at this temperature for 30 min. The reaction mixture was diluted with water (100 mL) and extracted with ethyl acetate (2×100 mL). The combined organic layers were dried over sodium sulfate and concentrated to dryness in vacuo. The resulting residue was purified by column chromatography (silica gel, 100-200 mesh, 30% ethyl acetate in hexane) affording (2-chloro-6-(dimethylamino)-9-(tetrahydro-2H-pyran-2-yl)-9H-purin-8-yl)methanol (3 g, 49%): LCMS (ESI, 10-80AB/2.0 min): R$_T$=0.937 min, m/z 228.0 [M-THP+H$^+$].

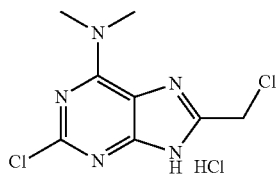

Step 3: 2-chloro-8-(chloromethyl)-N,N-dimethyl-9H-purin-6-amine hydrochloride To a stirred solution of compound (2-chloro-6-(dimethylamino)-9-(tetrahydro-2H-pyran-2-yl)-9H-purin-8-yl)methanol (311 mg, 0.9975 mmol) in dichloromethane (10 mL) was added sulfuryl dichloride (1 mL). The reaction mixture was stirred at room temperature for 30 min and subsequently concentrated to dryness in vacuo affording 2-chloro-8-(chloromethyl)-N,N-dimethyl-9H-purin-6-amine hydrochloride (251 mg, quantitive) as a yellow solid and used for the next step without any further purification: LCMS (ESI, 10-80AB/2.0 min): R$_T$=0.904 min, m/z 245.9 [M+H$^+$], 247.9 [M+3].

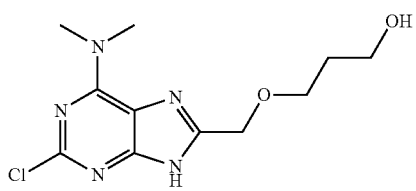 [SMILES: CN(C)c1nc(Cl)nc2[nH]c(COCCCO)nc12]

Step 4: 3-((2-chloro-6-(dimethylamino)-9H-purin-8-yl)methoxy)propan-1-ol

To a mixture of 2-chloro-8-(chloromethyl)-N,N-dimethyl-9H-purin-6-amine hydrochloride (245 mg, 0.867 mmol) in 1,3-propanediol (3 mL) was stirred at 100° C. for 16 h. The reaction mixture was concentrated to dryness in vacuo and purified by RP-HPLC to afford compound 3-((2-chloro-6-(dimethylamino)-9H-purin-8-yl)methoxy)propan-1-ol (138 mg, 56%) as a white solid: LCMS (ESI, 5-95AB/1.5 min): R$_T$=0.799 min, m/z 286.1 [M+H$^+$], 288.1 [M+3].

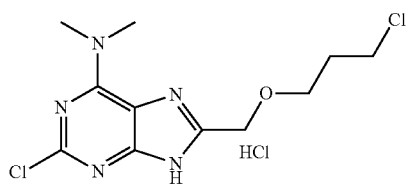 [SMILES: CN(C)c1nc(Cl)nc2[nH]c(COCCCCl)nc12 ; Cl]

Step 5: 2-chloro-8-((3-chloropropoxy)methyl)-N,N-dimethyl-9H-purin-6-amine

To a stirred solution of compound 3-((2-chloro-6-(dimethylamino)-9H-purin-8-yl)methoxy)propan-1-ol (285 mg, 0.997 mmol) in dichloromethane (10 mL) was added sulfuryl dichloride (1 mL). The reaction mixture was stirred at room temperature for 5 min and subsequently concentrated to dryness in vacuo affording 2-chloro-8-((3-chloropropoxy)methyl)-N,N-dimethyl-9H-purin-6-amine (342 mg, quantitive) as a yellow solid and used for the next step without any further purification: LCMS (ESI, 5-95AB/1.5 min): R$_T$=0.856 min, m/z 303.8 [M+H$^+$].

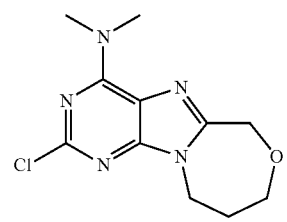 [SMILES: CN(C)c1nc(Cl)nc2c1nc1n2CCCOC1]

Step 6: 2-chloro-N,N-dimethyl-6,8,9,10-tetrahydro-[1,4]oxazepino-[4,3-e]purin-4-amine To a stirred solution of compound 2-chloro-8-((3-chloropropoxy)methyl)-N,N-dimethyl-9H-purin-6-amine (339 mg, 0.995 mmol) in N,N-dimethylformaldehyde (5 mL) was added potassium carbonate (412 mg, 2.99 mmol). The reaction mixture was heated at 100° C. for 30 min and concentrated to dryness in vacuo. The resulting mixture was diluted with ethyl acetate (80 mL) and water (30 mL). The separated organic layer was dried over sodium sulfate and concentrated to dryness in vacuo. The residue was purified by RP-HPLC affording 2-chloro-N,N-dimethyl-6,8,9,10-tetrahydro-[1,4]oxazepino[4,3-e]purin-4-amine (70 mg, 26%): LCMS (ESI, 10-80AB/2.0 min): R$_T$=0.945 min, m/z 268.1 [M+H$^+$], 270.1 [M+3].

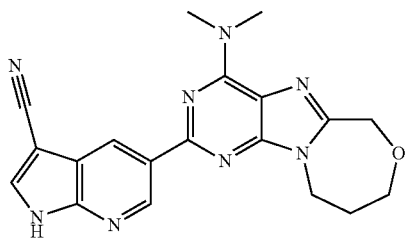 [SMILES: CN(C)c1nc(-c2cnc3[nH]cc(C#N)c3c2)nc2c1nc1n2CCCOC1]

Step 7: 5-(4-(dimethylamino)-6,8,9,10-tetrahydro-[1,4]oxazepino[4,3-e]purin-2-yl)-1H-pyrrolo[2,3-b]pyridine-3-carbonitrile 2-chloro-N,N-dimethyl-6,8,9,10-tetrahydro-[1,4]oxazepino[4,3-e]purin-4-amine (30 mg, 0.112 mmol) was dissolved in a mixed solvent of 1,4-dioxane/water (3:1, 2.0 mL) and transferred to a microwave vial equipped with a stirbar. To this solution was added 5-(4,4,5,5-tetramethyl-1,3,2-dioxaborolan-2-yl)-1H-pyrrolo[2,3-b]pyridine-3-carbonitrile (30 mg, 0.112 mmol), potassium carbonate (46 mg, 0.336 mmol), 1,1'-bis(diphenylphosphino)ferrocene-palladium(II)dichloride (10 mg, 0.0141 mmol) and the mixture was microwaved at 110° C. for 30 min. The reaction mixture was diluted with water (10 mL) and extracted with ethyl acetate (3×20 mL). The combined organic extracts were dried over magnesium sulfate, filtered and concentrated to dryness in vacuo. This resulting residue was purified by RP-HPLC affording 5-(4-(dimethylamino)-6,8,9,10-tetrahydro-[1,4]oxazepino[4,3-e]purin-2-yl)-1H-pyrrolo[2,3-b]pyridine-3-carbonitrile (8 mg, 19%): $^1$H NMR (400 MHz, DMSO-d6) δ 9.43 (d, J=2.0 Hz, 1H), 8.91 (d, J=2.0 Hz, 1H), 8.46 (s, 1H), 4.78 (s, 2H), 4.48-4.46 (m, 2H), 4.04 (t, J=4.4 Hz, 2H), 3.51 (s, 6H), 2.05-1.90 (m, 2H). LCMS (ESI, 5-95AB/1.5 min): $R_T$=0.789 min, m/z 374.9 [M+H$^+$]

Example 129

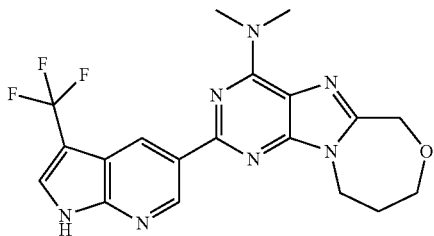 [SMILES: CN(C)c1nc(-c2cnc3[nH]cc(C(F)(F)F)c3c2)nc2c1nc1n2CCCOC1]

N,N-dimethyl-2-(3-(trifluoromethyl)-1H-pyrrolo[2,3-b]pyridin-5-yl)-6,8,9,10-tetrahydro-[1,4]oxazepino[4,3-e]purin-4-amine 2-chloro-N,N-dimethyl-6,8,9,10-tetrahydro-[1,4]oxazepino[4,3-e]purin-4-amine (30 mg, 0.112 mmol) was dissolved in a mixed solvent of 1,4-dioxane/water (3:1, 3.0 mL) and transferred to a microwave vial equipped with a stirbar. To the solution was added 5-(4,4,5,5-tetramethyl-1,3,2-dioxaborolan-2-yl)-3-(trifluoromethyl)-1H-pyrrolo[2,3-b]pyridine (35 mg, 0.112 mmol), potassium phosphate (71 mg, 0.336 mmol), 1,1'-bis(diphenylphosphino)ferrocene-palladium(II)dichloride (5 mg, 0.0071 mmol) and the mixture was microwaved at 110° C. for 30 min. The reaction mixture was diluted with 10 mL of water and extracted with ethyl acetate (3×20 mL). The combined organic extracts were dried over magnesium sulfate, filtered and concentrated to dryness in vacuo. This resulting residue was purified by RP-HPLC affording N,N-dimethyl-2-(3-(trifluoromethyl)-1H-pyrrolo[2,3-b]pyridin-5-yl)-6,8,9, 10-tetrahydro-[1,4]oxazepino[4,3-e]purin-4-amine (5.6 mg, 12%): $^1$H NMR (400 MHz, Methanol-d4) δ 9.40 (d, J=2.0 Hz, 1H), 9.15 (s, 1H), 8.11 (d, J=1.2 Hz, 1H), 5.03 (s, 2H), 4.74-4.72 (m, 2H), 4.23 (t, J=5.2 Hz, 2H), 3.69 (s, 6H), 2.23-2.20 (m, 2H). LCMS (ESI, 10-80AB/2.0 min): $R_T$=1.363 min, m/z 418.1 [M+H$^+$]

Example 131

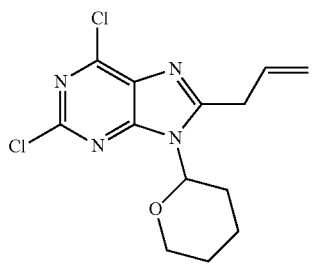 [SMILES: C=CCc1nc2c(Cl)nc(Cl)nc2n1C1CCCCO1]

Step 1: 8-allyl-2,6-dichloro-9-(tetrahydro-2H-pyran-2-yl)-9H-purine

To a solution of 2,6-dichloro-9-(tetrahydro-2H-pyran-2-yl)-9H-purine (15 g, 54.92 mmol) in tetrahydrofuran (250 mL) was added 1,2-dichloroethane (50 mL), [1,3-Bis(diphenylphosphino)propane]nickel(II) chloride (7.44 g, 13.73 mmol) and 1M solution of allylmagnesium bromide in diethyl ether (274.6 mL, 274.6 mmol). The mixture was stirred at 25° C. for 2 h. 2,3-dichloro-5,6-dicyano-1,4-benzoquinone (24.93 g, 109.84 mmol) was added and the resulting mixture was stirred at 25° C. for another 30 min. The reaction was quenched with saturated ammonium chloride solution (50 mL). The organic layer was separated and the aqueous phase was extracted with ethyl acetate (3×100 mL). The combined organic layers were dried over magnesium sulfate and concentrated to dryness in vacuo. The resulting residue was purified by column chromatography (silica gel, 100-200 mesh, 30% ethyl acetate in hexane) affording 8-allyl-2,6-dichloro-9-(tetrahydro-2H-pyran-2-yl)-9H-purine (7.5 g, 44%): $^1$H NMR (400 MHz, Chloroform-d) δ 6.17-6.07 (m, 1H), 5.74-5.70 (m, 1H), 5.30-5.22 (m, 2H), 4.21-4.17 (m, 1H), 3.91-3.89 (m, 2H), 3.79-3.68 (m, 1H), 2.53-2.47 (m, 1H), 2.12-2.09 (m, 1H), 1.92-1.63 (m, 4H).

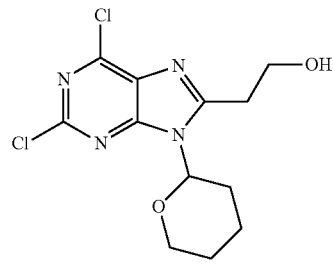 [SMILES: OCCc1nc2c(Cl)nc(Cl)nc2n1C1CCCCO1]

Step 2: 2-(2,6-dichloro-9-(tetrahydro-2H-pyran-2-yl)-9H-purin-8-yl)ethanol

A solution of 8-allyl-2,6-dichloro-9-(tetrahydro-2H-pyran-2-yl)-9H-purine (4 g, 12.77 mmol) in dry dichloromethane (20 mL) was cooled to −78° C. Ozone was bubbled through the solution with stirring for 15 min. The excess ozone was removed by bubbling nitrogen through the solution for 5 min. Sodium borohydride (966 mg, 25.54 mmol) was added to and the mixture was stirred at 25° C. for 2 h. The reaction was quenched with saturated ammonium solution (20 mL) and extracted with ethyl acetate (3×60 mL). The organic layers were dried over magnesium sulfate and concentrated to dryness in vacuo. The resulting residue was purified by RP-HPLC to afford 2-(2,6-dichloro-9-(tetrahydro-2H-pyran-2-yl)-9H-purin-8-yl)ethanol (1.5 g, 37%): LCMS (ESI, 0-60AB/2 min): $R_T$=1.178 min, m/z 232.9 [M-THP+H$^+$].

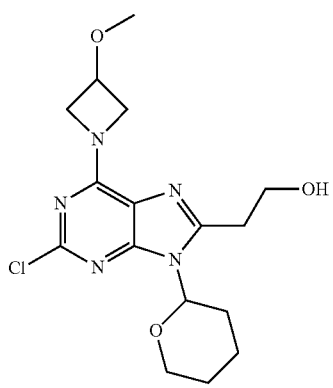 [SMILES: COC1CN(c2nc(Cl)nc3c2nc(CCO)n3C2CCCCO2)C1]

Step 3: 2-(2-chloro-6-(3-methoxyazetidin-1-yl)-9-(tetrahydro-2H-pyran-2-yl)-9H-purin-8-yl)ethanol To a solution of 2-(2,6-dichloro-9-(tetrahydro-2H-pyran-2-yl)-9H-purin-8-yl)ethanol (121 mg, 0.382 mmol) in acetonitrile (5 mL) was added 3-methoxy-azetidine hydrochloride (71 mg, 0.573 mmol) and potassium carbonate (158 mg, 1.14 mmol). The mixture was stirred at 25° C. for 16 h. The mixture was filtered and the filtrate was concentrated to dryness in vacuo. The resulting residue was purified by column chromatography (silica gel, 100-200 mesh, 100% ethyl acetate) affording 2-(2-chloro-6-(3-methoxyazetidin-1-yl)-9-(tetrahydro-2H-pyran-2-yl)-9H-purin-8-yl)ethanol (70 mg, 50%): LCMS (ESI, 5-95AB/1.5 min): $R_T$=0.680 min, m/z 368.1 [M+H$^+$].

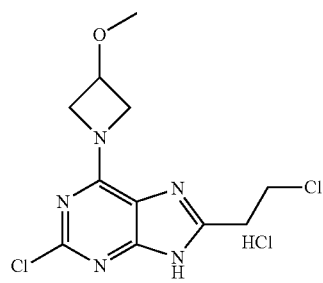 [SMILES: COC1CN(c2nc(Cl)nc3[nH]c(CCCl)nc23)C1 ; Cl]

Step 4: 2-chloro-8-(2-chloroethyl)-6-(3-methoxyazetidin-1-yl)-9H-purine hydrochloride To a solution of 2-(2-chloro-6-(3-methoxyazetidin-1-yl)-9-(tetrahydro-2H-pyran-2-yl)-9H-purin-8-yl)ethanol (50 mg, 0.136 mmol) in dichloromethane (10 mL) was added sulfuryl dichloride (2 mL).

The reaction mixture was stirred under reflux for 30 min. The reaction mixture was concentrated to dryness in vacuo affording the crude 2-chloro-8-(2-chloroethyl)-6-(3-methoxyazetidin-1-yl)-9H-purine hydrochloride (41 mg, quantitive) as a yellow solid and used for the next step without any further purification: LCMS (ESI, 0-60AB/2 min): $R_T$=1.081 min, m/z 302.0 [M+H$^+$].

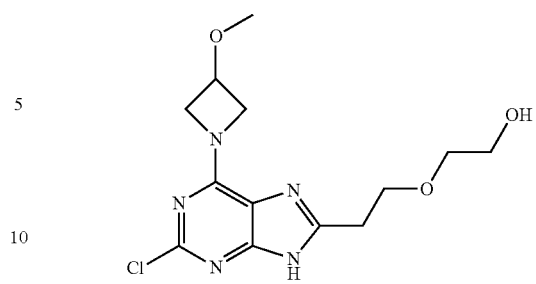

Step 5: 2-(2-(2-chloro-6-(3-methoxyazetidin-1-yl)-9H-purin-8-yl)ethoxy)ethanol

To crude 2-chloro-8-(2-chloroethyl)-6-(3-methoxyazetidin-1-yl)-9H-purine hydrochloride (229 mg, 0.758 mmol) in ethylene glycol (10 mL) was stirred at 100° C. for 16 h. The reaction mixture was concentrated to dryness in vacuo and purified by RP-HPLC to afford 2-(2-(2-chloro-6-(3-methoxyazetidin-1-yl)-9H-purin-8-yl)ethoxy)ethanol (20 mg, 8%): LCMS (ESI, 0-60AB/2 min): $R_T$=0.995 min, m/z 327.9 [M+H$^+$].

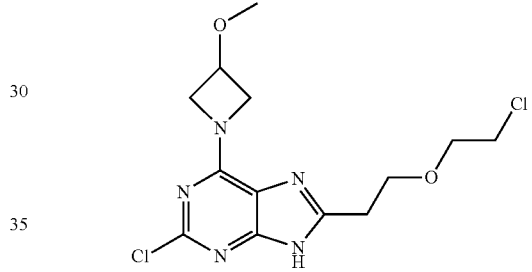

Step 6: 2-chloro-8-(2-(2-chloroethoxy)ethyl)-6-(3-methoxyazetidin-1-yl)-9H-purine To a stirred solution of 2-(2-(2-chloro-6-(3-methoxyazetidin-1-yl)-9H-purin-8-yl)ethoxy)ethanol (20 mg, 0.061 mmol) in dichloromethane (1 mL) was added sulfuryl dichloride (1 mL). The reaction mixture was stirred under reflux for 2 min. The reaction mixture was concentrated to dryness in vacuo affording the crude 2-chloro-8-(2-(2-chloroethoxy)ethyl)-6-(3-methoxyazetidin-1-yl)-9H-purine (21 mg, quantitive) used for the next step without any further purification: LCMS (ESI, 0-60AB/2 min): $R_T$=1.126 min, m/z 346.0 [M+H$^+$].

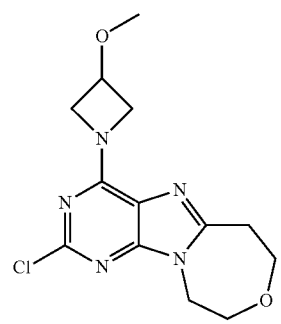 [SMILES: COC1CN(c2nc(Cl)nc3c2nc2n3CCOCC2)C1]

Step 7: 2-chloro-4-(3-methoxyazetidin-1-yl)-6,7,9,10-tetrahydro-[1,4]oxazepino[4,5-e]purine To a stirred solution of 2-chloro-8-(2-(2-chloroethoxy)ethyl)-6-(3-methoxyazetidin-1-yl)-9H-purine (20 mg, 0.058 mmol) in N,N-dimethylformaldehyde (5 mL) was added potassium carbonate (40 mg, 0.29 mmol). The reaction mixture was stirred at 120° C. for 2 h and concentrated to dryness in vacuo. The resulting mixture was filtered and the filtrate was concentrated in vacuo to afford 2-chloro-4-(3-methoxyazetidin-1-yl)-6,7,9,10-tetrahydro-[1,4]oxazepino[4,5-e]purine (10 mg, 56%) used for the next step without any further purification: LCMS (ESI, 0-60AB/2 min): $R_T$=1.007 min, m/z 309.8 [M+H$^+$].

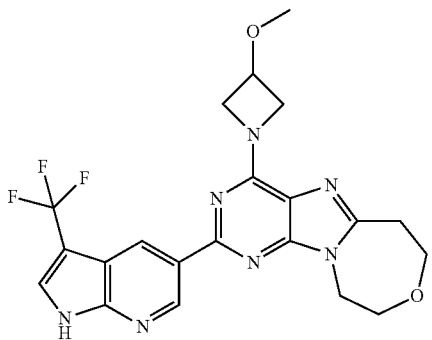 [SMILES: COC1CN(c2nc(-c3cnc4[nH]cc(C(F)(F)F)c4c3)nc3c2nc2n3CCOCC2)C1]

Step 8: 4-(3-methoxyazetidin-1-yl)-2-(3-(trifluoromethyl)-1H-pyrrolo[2,3-b]pyridin-5-yl)-6,7,9,10-tetrahydro-[1,4]oxazepino[4,5-e]purine 2-chloro-4-(3-methoxyazetidin-1-yl)-6,7,9,10-tetrahydro-[1,4]oxazepino[4,5-e]purine (30 mg, 0.097 mmol) was dissolved in a mixed solvent of 1,4-dioxane/water (2:1, 3.0 mL) and transferred to a microwave vial equipped with a stirbar. To the solution was added 5-(4,4,5,5-tetramethyl-1,3,2-dioxaborolan-2-yl)-3-(trifluoromethyl)-1H-pyrrolo[2,3-b]pyridine (32 mg, 0.146 mmol), potassium phosphate (62 mg, 0.29 mmol), 1,1'-bis(diphenylphosphino)ferrocene-palladium(II)dichloride (7 mg, 0.097 mmol) and the mixture was microwaved at 110° C. for 30 min. The reaction mixture was diluted with 10 mL of water and extracted with ethyl acetate (3×15 mL). The combined organic extracts were dried over magnesium sulfate, filtered and concentrated to dryness in vacuo. The residue was purified by RP-HPLC affording 4-(3-methoxyazetidin-1-yl)-2-(3-(trifluoromethyl)-1H-pyrrolo[2,3-b]pyridin-5-yl)-6,7,9,10-tetrahydro-[1,4]oxazepino[4,5-e]purine (5.3 mg, 12%): $^1$H NMR (400 MHz, Methanol-d4) δ 9.34 (d, J=2.0 Hz, 1H), 9.04 (s, 1H), 8.03 (d, J=1.2 Hz, 1H), 4.72-4.70 (m, 2H), 4.58-4.53 (m, 1H), 4.48-4.45 (m, 2H), 4.07-4.01 (m, 4H), 3.51-3.49 (m, 2H), 3.37 (s, 3H), 3.37-3.34 (m, 2H).

Example 132

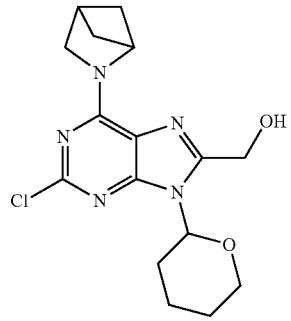 [SMILES: OCc1nc2c(N3CC4CC3C4)nc(Cl)nc2n1C1CCCCO1]

Step 1: (6-(2-azabicyclo[2.1.1]hexan-2-yl)-2-chloro-9-(tetrahydro-2H-pyran-2-yl)-9H-purin-8-yl)methanol To a solution of (2,6-dichloro-9-(tetrahydro-2H-pyran-2-yl)-9H-purin-8-yl)methanol (100 mg, 0.33 mmol) and N,N-diisopropylethylamine (128 mg, 0.99 mmol) in acetonitrile (1 mL) was added 2-azabicyclo[2.1.1]hexane hydrochloride (39 mg, 0.33 mmol). The reaction mixture was stirred at room temperature for 16 h and concentrated to dryness in vacuo. The resulting mixture was diluted with water (50 mL) and extracted with ethyl acetate (2×50 mL). The combined organic layers were dried over sodium sulfate and concentrated to dryness in vacuo. The resulting residue was purified by preparative TLC (50% ethyl acetate in petroleum ether) affording (6-(2-azabicyclo[2.1.1]hexan-2-yl)-2-chloro-9-(tetrahydro-2H-pyran-2-yl)-9H-purin-8-yl)methanol (97 mg, 84%): LCMS (ESI, 5-95AB/1.5 min): $R_T$=0.825 min, m/z 349.8 [M+H$^+$].

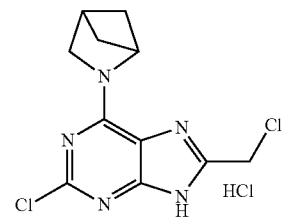 [SMILES: ClCc1nc2c(N3CC4CC3C4)nc(Cl)nc2[nH]1 ; Cl]

Step 2: 2-(2-chloro-8-(chloromethyl)-9H-purin-6-yl)-2-azabicyclo[2.1.1]hexane hydrochloride To a stirred solution of (6-(2-azabicyclo[2.1.1]hexan-2-yl)-2-chloro-9-(tetrahydro-2H-pyran-2-yl)-9H-purin-8-yl)methanol (20 mg, 0.0572 mmol) in dichloromethane (2 mL) was added sulfuryl dichloride (20 mg, 0.172 mmol). The reaction mixture was stirred at 40° C. for 1 h. The reaction mixture was concentrated to dryness in vacuo affording the crude 2-(2-chloro-8-(chloromethyl)-9H-purin-6-yl)-2-azabicyclo[2.1.1]hexane hydrochloride (23 mg, quantitive) as a yellow solid and used for the next step without any further purification: LCMS (ESI, 10-80AB/2.0 min): $R_T$=0.797 min, m/z 283.9 [M+H$^+$].

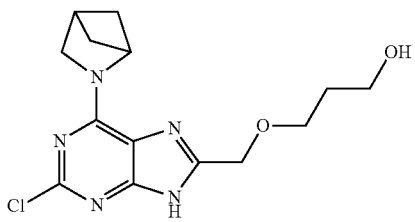 [SMILES: OCCCOCc1nc2c(N3CC4CC3C4)nc(Cl)nc2[nH]1]

Step 3: 3-((6-(2-azabicyclo[2.1.1]hexan-2-yl)-2-chloro-9H-purin-8-yl)methoxy)propan-1-ol The mixture of 2-(2-chloro-8-(chloromethyl)-9H-purin-6-yl)-2-azabicyclo[2.1.1]hexane hydrochloride (350 mg, 1.092 mmol) in 1,3-propanediol (3 mL) was stirred at 100° C. for 2 h. The reaction mixture was concentrated to dryness in vacuo and purified by RP-HPLC to afford 3-((6-(2-azabicyclo[2.1.1]hexan-2-yl)-2-chloro-9H-purin-8-yl)methoxy)propan-1-ol (268 mg, 76%) as a white solid: LCMS (ESI, 5-95AB/1.5 min): $R_T$=0.727 min, m/z 323.9 [M+H$^+$].

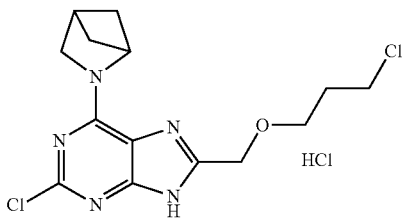 [SMILES: ClCCCOCc1nc2c(N3CC4CC3C4)nc(Cl)nc2[nH]1 ; Cl]

Step 4: 2-(2-chloro-8-((3-chloropropoxy)methyl)-9H-purin-6-yl)-2-azabicyclo[2.1.1]hexane hydrochloride To a stirred solution of 3-((6-(2-azabicyclo[2.1.1]hexan-2-yl)-2-chloro-9H-purin-8-yl)methoxy)propan-1-ol (250 mg, 0.772 mmol) in dichloromethane (5 mL) was added sulfuryl dichloride (246 mg, 2.082 mmol). The reaction mixture was stirred at 40° C. for 1 h and subsequently concentrated to dryness in vacuo affording 2-(2-chloro-8-((3-chloropropoxy)methyl)-9H-purin-6-yl)-2-azabicyclo[2.1.1]hexane hydrochloride (278 mg, quantitive) as a yellow oil and used for the next step without any further purification: LCMS (ESI, 5-95AB/1.5 min): $R_T$=0.776 min, m/z 342.1, 344.1 [M+H$^+$].

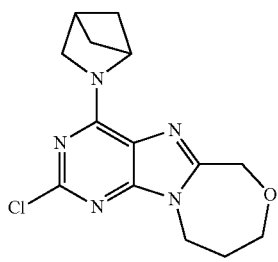 [SMILES: Clc1nc(N2CC3CC2C3)c2nc3n(c2n1)CCCOC3]

Step 5: 4-(2-azabicyclo[2.1.1]hexan-2-yl)-2-chloro-6,8,9,10-tetrahydro-[1,4]oxazepino[4,3-e]purine To a stirred solution of 2-(2-chloro-8-((3-chloropropoxy)methyl)-9H-purin-6-yl)-2-azabicyclo[2.1.1]hexane hydrochloride (250 mg, 0.66 mmol) in N,N-dimethylformaldehyde (5 mL) was added potassium carbonate (273 mg, 1.98 mmol). The reaction mixture was heated to 100° C. for 30 min and concentrated to dryness in vacuo. The resulting mixture was diluted with ethyl acetate (100 mL) and water (50 mL). The separated organic layer was dried over sodium sulfate and concentrated to dryness in vacuo to afford the 4-(2-azabicyclo[2.1.1]hexan-2-yl)-2-chloro-6,8,9,10-tetrahydro-[1,4]oxazepino[4,3-e]purine (151 mg, 74.8%) used for the next step without any further purification: LCMS (ESI, 5-95AB/1.5 min): $R_T$=0.797 min, m/z 305.8 [M+H$^+$].

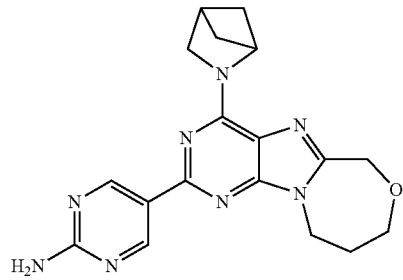

Step 6: 5-(4-(2-azabicyclo[2.1.1]hexan-2-yl)-6,8,9,10-tetrahydro-[1,4]oxazepino[4,3-e]purin-2-yl)pyrimidin-2-amine 4-(2-azabicyclo[2.1.1]hexan-2-yl)-2-chloro-6,8,9,10-tetrahydro-[1,4]oxazepino[4,3-e]purine (50 mg, 0.164 mmol) was dissolved in a mixed solvent of 1,4-dioxane/water (2:1, 3.0 mL) and transferred to a microwave vial equipped with a stirbar. To the solution was added 5-(4,4,5,5-tetramethyl-1,3,2-dioxaborolan-2-yl)pyrimidin-2-amine (36 mg, 0.164 mmol), potassium phosphate (104 mg, 0.492 mmol), 1,1'-bis(diphenylphosphino)ferrocene-palladium(II)dichloride (10 mg, 0.0141 mmol) and the mixture was microwaved at 110° C. for 30 min. The reaction mixture was diluted with water (10 mL) and extracted with ethyl acetate (3×20 mL). The combined organic layers were dried over magnesium sulfate, filtered and concentrated to dryness in vacuo. This resulting residue was purified by RP-HPLC affording 5-(4-(2-azabicyclo[2.1.1]hexan-2-yl)-6,8,9,10-tetrahydro-[1,4]oxazepino[4,3-e]purin-2-yl)pyrimidin-2-amine (7 mg, 12%): $^1$H NMR (400 MHz, DMSO-d6) δ 9.10 (s, 2H), 6.99 (s, 2H), 4.75 (s, 2H), 4.48-4.32 (m, 2H), 4.10-3.98 (m, 2H), 2.98-2.96 (m, 1H), 2.10-2.02 (m, 4H), 1.99-1.83 (m, 2H), 1.52-1.35 (m, 2H), 1.25-1.15 (m, 1H). LCMS (ESI, 10-80AB/2.0 min): $R_T$=1.118 min, m/z 365.2 [M+H$^+$].

Example 133

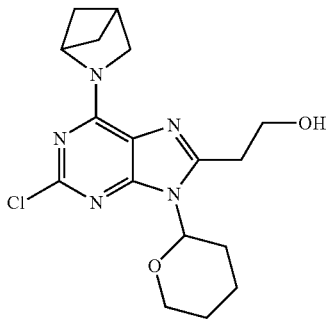 [SMILES: OCCc1nc2c(N3CC4CC3C4)nc(Cl)nc2n1C1CCCCO1]

Step 1: 2-(6-(2-azabicyclo[2.1.1]hexan-2-yl)-2-chloro-9-(tetrahydro-2H-pyran-2-yl)-9H-purin-8-yl)ethanol To a solution of 2-(2,6-dichloro-9-(tetrahydro-2H-pyran-2-yl)-9H-purin-8-yl)ethanol (900 mg, 2.84 mmol) and N,N-diisopropylethylamine (919 mg, 7.13 mmol) in dichloromethane (10 mL) was added 2-azabicyclo[2.1.1]hexane hydrochloride (355 mg, 2.99 mmol). The reaction mixture was stirred at room temperature for 16 h and subsequently concentrated to dryness in vacuo. The resulting mixture was diluted with water (60 mL) and extracted with ethyl acetate (2×50 mL). The combined organic layers were dried over sodium sulfate and concentrated to dryness in vacuo. The resulting residue was purified by column chromatography (silica gel, 100-200 mesh, 100% ethyl acetate) affording 2-(6-(2-azabicyclo[2.1.1]hexan-2-yl)-2-chloro-9-(tetrahydro-2H-pyran-2-yl)-9H-purin-8-yl)ethanol (750 mg, 73%): LCMS (ESI, 0-60AB/2 min): $R_T$=1.309 min, m/z 364.1 [M+H$^+$].

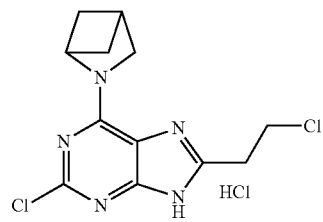 [SMILES: ClCCc1nc2c(N3CC4CC3C4)nc(Cl)nc2[nH]1 ; Cl]

Step 2: 2-(2-chloro-8-(2-chloroethyl)-9H-purin-6-yl)-2-azabicyclo[2.1.1]hexane hydrochloride To a stirred solution of 2-(6-(2-azabicyclo[2.1.1]hexan-2-yl)-2-chloro-9-(tetrahydro-2H-pyran-2-yl)-9H-purin-8-yl)ethanol (750 mg, 2.06 mmol) in dichloromethane (10 mL) was added sulfuryl dichloride (2 mL). The reaction mixture was stirred under reflux for 2 h. The reaction mixture was concentrated to dryness in vacuo affording the crude 2-(2-chloro-8-(2-chloroethyl)-9H-purin-6-yl)-2-azabicyclo[2.1.1]hexane hydrochloride (615 mg, 89%) used for the next step without any further purification: LCMS (ESI, 0-60AB/2 min): $R_T$=1.231 min, m/z 298.0 [M+H$^+$].

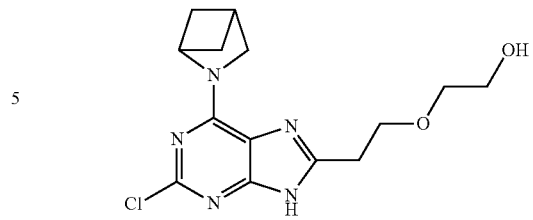

Step 3: 2-(2-(6-(2-azabicyclo[2.1.1]hexan-2-yl)-2-chloro-9H-purin-8-yl)ethoxy)ethanol The mixture of 2-(2-chloro-8-(2-chloroethyl)-9H-purin-6-yl)-2-azabicyclo[2.1.1]hexane hydrochloride (615 mg, 1.84 mmol) in ethylene glycol (10 mL) was stirred at 110° C. for 20 h. The reaction mixture was concentrated to dryness in vacuo. The resulting residue was purified by RP-HPLC to afford 2-(2-(6-(2-azabicyclo[2.1.1]hexan-2-yl)-2-chloro-9H-purin-8-yl)ethoxy)ethanol (100 mg, 17%): LCMS (ESI, 10-80AB/2 min): $R_T$=0.968 min, m/z 323.9 [M+H$^+$].

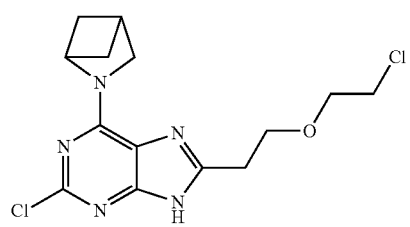 [SMILES: ClCCOCCc1nc2c(N3CC4CC3C4)nc(Cl)nc2[nH]1]

Step 4: 2-(2-chloro-8-(2-(2-chloroethoxy)ethyl)-9H-purin-6-yl)-2-azabicyclo[2.1.1]hexane To a stirred solution of 2-(2-(6-(2-azabicyclo[2.1.1]hexan-2-yl)-2-chloro-9H-purin-8-yl)ethoxy)ethanol (100 mg, 0.309 mmol) in dichloromethane (10 mL) was added sulfuryl dichloride (1 mL). The reaction mixture was stirred under reflux for 2 h and concentrated to dryness in vacuo affording 2-(2-chloro-8-(2-(2-chloroethoxy)ethyl)-9H-purin-6-yl)-2-azabicyclo[2.1.1]hexane (105 mg, quantitive) used for the next step without any further purification: LCMS (ESI, 5-95AB/2 min): $R_T$=0.727 min, m/z 342.0 [M+H$^+$].

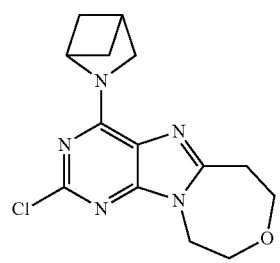 [SMILES: Clc1nc(N2CC3CC2C3)c2nc3n(c2n1)CCOCC3]

Step 5: 4-(2-azabicyclo[2.1.1]hexan-2-yl)-2-chloro-6,7,9,10-tetrahydro-[1,4]oxazepino[4,5-e]purine To a stirred solution of 2-(2-chloro-8-(2-(2-chloroethoxy)ethyl)-9H-purin-6-yl)-2-azabicyclo[2.1.1]hexane (105 mg, 0.309 mmol) in 4-(2-azabicyclo[2.1.1]hexan-2-yl)-2-chloro-6,8,9,10-tetrahydro-[1,4]oxazepino[4,3-e]purine (5 mL) was added potassium carbonate (213 mg, 1.55 mmol). The reaction mixture was heated to 110° C. for 1 h and concentrated to dryness in vacuo. The resulting mixture was diluted with ethyl acetate (60 mL) and water (50 mL). The separated organic layer was dried over sodium sulfate and concentrated to dryness in vacuo to afford the 4-(2-azabicyclo[2.1.1]hexan-2-yl)-2-chloro-6,7,9,10-tetrahydro-[1,4]oxazepino[4,5-e]purine (60 mg, 64%) used for the next step without any further purification: LCMS (ESI, 5-95AB/2 min): $R_T$=0.708 min, m/z 306.0 [M+H$^+$].

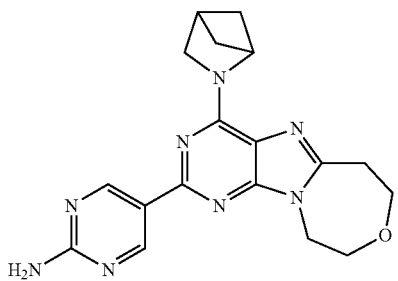 [SMILES: Nc1ncc(-c2nc(N3CC4CC3C4)c3nc4n(c3n2)CCOCC4)cn1]

Step 6: 5-(4-(2-azabicyclo[2.1.1]hexan-2-yl)-6,7,9,10-tetrahydro-[1,4]oxazepino[4,5-e]purin-2-yl)pyrimidin-2-amine 4-(2-azabicyclo[2.1.1]hexan-2-yl)-2-chloro-6,7,9,10-tetrahydro-[1,4]oxazepino[4,5-e]purine (30 mg, 0.0983 mmol) was dissolved in a mixed solvent of 1,4-dioxane/water (2:1, 3.0 mL) and transferred to a microwave vial equipped with a stirbar. To the solution was added 5-(4,4,5,5-tetramethyl-1,3,2-dioxaborolan-2-yl)pyrimidin-2-amine (33 mg, 0.147 mmol), potassium phosphate (63 mg, 0.295 mmol), 1,1'-bis(diphenylphosphino)ferrocene-palladium(II)dichloride (7 mg, 0.098 mmol) and the mixture was microwaved at 110° C. for 30 min. The reaction mixture was diluted with water (10 mL) and extracted with ethyl acetate (3×20 mL). The combined organic extracts were dried over magnesium sulfate, filtered and concentrated to dryness in vacuo. This resulting residue was purified by RP-HPLC affording 5-(4-(2-azabicyclo[2.1.1]hexan-2-yl)-6,7,9,10-tetrahydro-[1,4]oxazepino[4,5-e]purin-2-yl)pyrimidin-2-amine (4.0 mg, 11%): $^1$H NMR (400 MHz, Methanol-d4) δ 9.42 (s, 2H), 5.51-5.48 (m, 1H), 4.67-4.66 (m, 2H), 4.04-4.00 (m, 4H), 3.98-3.90 (m, 2H), 3.60-3.50 (m, 2H), 3.15-3.13 (m, 1H), 2.25-2.24 (m, 2H), 1.60-1.54 (m, 2H).

Example 134

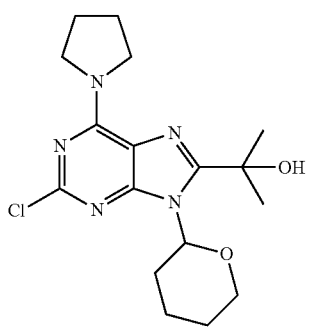 [SMILES: CC(C)(O)c1nc2c(N3CCCC3)nc(Cl)nc2n1C1CCCCO1]

Step 1: 2-(2-chloro-6-(pyrrolidin-1-yl)-9-(tetrahydro-2H-pyran-2-yl)-9H-purin-8-yl)propan-2-ol To a solution of 2-(2,6-dichloro-9-(tetrahydro-2H-pyran-2-yl)-9H-purin-8-yl)propan-2-ol (2.0 g, 5.67 mmol) and N,N-diisopropylethylamine (2.19 g, 17.01 mmol) in acetonitrile (20 mL) was added pyrrolidine (431 mg, 6.06 mmol). The reaction mixture was stirred at room temperature for 16 h and concentrated to dryness in vacuo. The resulting mixture was diluted with water (50 mL) and extracted with ethyl acetate (2×80 mL). The combined organic layers were dried over sodium sulfate and concentrated to dryness in vacuo. The resulting residue was purified by column chromatography (silica gel, 100-200 mesh, 35% ethyl acetate in hexane) affording 2-(2-chloro-6-(pyrrolidin-1-yl)-9-(tetrahydro-2H-pyran-2-yl)-9H-purin-8-yl)propan-2-ol (1.7 g, 82%): LCMS (ESI, 5-95AB/1.5 min): $R_T$=0.847 min, m/z 366.1 [M+H$^+$].

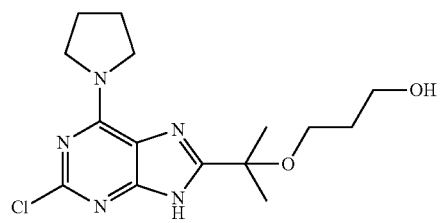 [SMILES: CC(C)(OCCCO)c1nc2c(N3CCCC3)nc(Cl)nc2[nH]1]

Step 2: 3-((2-(2-chloro-6-(pyrrolidin-1-yl)-9H-purin-8-yl)propan-2-yl)oxy)propan-1-ol To a solution of 2-(2-chloro-6-(pyrrolidin-1-yl)-9-(tetrahydro-2H-pyran-2-yl)-9H-purin-8-yl)propan-2-ol (500 mg, 1.367 mmol) in anhydrous dichloromethane (5 mL) was added sulfuryl dichloride (484 mg, 4.1 mmol) at 0° C. The reaction mixture was stirred at 0° C. for 30 min.

To a mixture of 1,3-propanediol (2.016 g, 26.5 mmol) in tetrahydrofuran (5 mL) and N,N-dimethylformaldehyde (5 mL) was added sodium hydride (548 mg, 60% in mineral oil, 13.7 mmol) at 0° C. and stirred for 10 min. The two reaction mixtures were added together immediately upon preparation and stirred at 0° C. for 25 min. Water (1 mL) was added and the mixture was concentrated to dryness in vacuo. The resulting mixture was diluted with water (20 mL) and extracted with ethyl acetate (2×200 mL). The combined organic layers were dried over sodium sulfate and concentrated to dryness in vacuo. The resulting residue was purified by RP-HPLC affording 3-((2-(2-chloro-6-(pyrrolidin-1-yl)-9H-purin-8-yl)propan-2-yl)oxy)propan-1-ol (205 mg, 44%): LCMS (ESI, 5-95AB/1.5 min): $R_T$=0.793 min, m/z 339.9 [M+H$^+$].

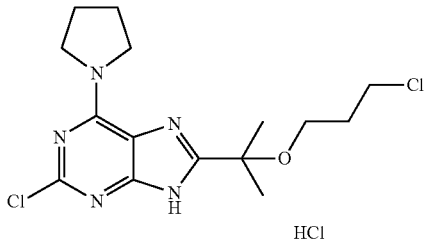 [SMILES: CC(C)(OCCCCl)c1nc2c(N3CCCC3)nc(Cl)nc2[nH]1 ; Cl]

HCl

Step 3: 2-chloro-8-(2-(3-chloropropoxy)propan-2-yl)-6-(pyrrolidin-1-yl)-9H-purine hydrochloride To a stirred solution of 3-((2-(2-chloro-6-(pyrrolidin-1-yl)-9H-purin-8-yl)propan-2-yl)oxy)propan-1-ol (80 mg, 0.235 mmol) in dichloromethane (2 mL) was added sulfuryl dichloride (84 mg, 0.708 mmol). The reaction mixture was stirred at room temperature for 1 h and subsequently concentrated to dryness in vacuo affording 2-chloro-8-(2-(3-chloropropoxy)propan-2-yl)-6-(pyrrolidin-1-yl)-9H-purine hydrochloride (103 mg, quantitive) as a yellow oil and used for the next step without any further purification: MS (ESI): m/z 358.1 [M+H$^+$].

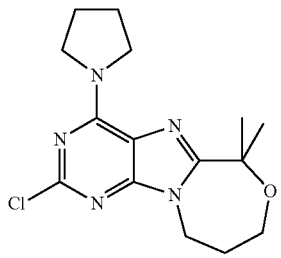 [SMILES: CC1(C)OCCCn2c1nc1c(N3CCCC3)nc(Cl)nc12]

Step 4: 2-chloro-6,6-dimethyl-4-(pyrrolidin-1-yl)-6,8,9,10-tetrahydro-[1,4]oxazepino[4,3-e]purine To a stirred solution of 2-chloro-8-(2-(3-chloropropoxy)propan-2-yl)-6-(pyrrolidin-1-yl)-9H-purine hydrochloride (61 mg, 0.155 mmol) in N,N-dimethylformaldehyde (2 mL) was added potassium carbonate (64 mg, 0.464 mmol). The reaction mixture was heated to 100° C. for 30 min and concentrated to dryness in vacuo. The resulting mixture was diluted with ethyl acetate (150 mL) and water (10 mL). The separated organic layer was dried over sodium sulfate and concentrated to dryness in vacuo to a 2-chloro-6,6-dimethyl-4-(pyrrolidin-1-yl)-6,8,9,10-tetrahydro-[1,4]oxazepino[4,3-e]purine (42 mg, 84%) used for the next step without any further purification: LCMS (ESI, 5-95AB/1.5 min): R$_T$=0.906 min, m/z 321.9 [M+H$^+$].

Step 5: 5-(6,6-dimethyl-4-(pyrrolidin-1-yl)-6,8,9,10-tetrahydro-[1,4]oxazepino[4,3-e]purin-2-yl)pyrimidin-2-amine 2-chloro-6,6-dimethyl-4-(pyrrolidin-1-yl)-6,8,9,10-tetrahydro-[1,4]oxazepino[4,3-e]purine (50 mg, 0.155 mmol) was dissolved in a mixed solvent of 1,4-dioxane/water (3:1, 2.5 mL) and transferred to a microwave vial equipped with a stirbar. To the solution was added 5-(4,4,5,5-tetramethyl-[1,3,2]dioxaborolan-2-yl)-pyrimidin-2-ylamine (34 mg, 0.155 mmol), potassium phosphate (100 mg, 0.472 mmol), 1,1'-bis(diphenylphosphino)ferrocene-palladium(II)dichloride (20 mg, 0.0283 mmol) and the mixture was microwaved at 110° C. for 30 min. The reaction mixture was diluted with 10 mL of water and extracted with ethyl acetate (3×15 mL). The combined organic extracts were dried over magnesium sulfate, filtered and concentrated to dryness in vacuo. This resulting residue was purified by RP-HPLC affording 5-(6,6-dimethyl-4-(pyrrolidin-1-yl)-6,8,9,10-tetrahydro-[1,4]oxazepino[4,3-e]purin-2-yl)pyrimidin-2-amine (8.2 mg, 14%): $^1$H NMR (400 MHz, Methanol-d4) δ 9.39 (s, 2H), 4.64-4.61 (m, 2H), 4.45-3.65 (m, 6H), 2.22-2.04 (m, 6H), 1.74 (s, 6H).

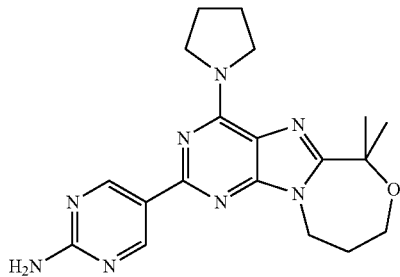

Example 135

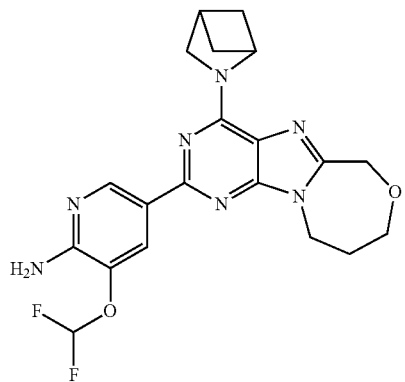

5-(4-(2-azabicyclo[2.1.1]hexan-2-yl)-6,8,9,10-tetrahydro-[1,4]oxazepino[4,3-e]purin-2-yl)-3-(difluoromethoxy)pyridin-2-amine 4-(2-azabicyclo[2.1.1]hexan-2-yl)-2-chloro-6,8,9,10-tetrahydro-[1,4]oxazepino[4,3-e]purine (50 mg, 0.1635 mmol) was dissolved in a mixed solvent of 1,4-dioxane/water (3:1, 2.0 mL) and transferred to a microwave vial equipped with a stirbar. To the solution was added 3-(difluoromethoxy)-5-(4,4,5,5-tetramethyl-1,3,2-dioxaborolan-2-yl)pyridin-2-amine (47 mg, 0.1635 mmol), potassium phosphate (104 mg, 0.492 mmol), 1,1'-bis(diphenylphosphino)ferrocene-palladium(II)dichloride (15 mg, 0.0212 mmol) and the mixture was microwaved at 110° C. for 30 min. The reaction mixture was diluted with 10 mL of water and extracted with ethyl acetate (3×20 mL). The combined organic extracts were dried over magnesium sulfate, filtered and concentrated to dryness in vacuo. This resulting residue was purified by RP-HPLC affording 5-(4-(2-azabicyclo[2.1.1]hexan-2-yl)-6,8,9,10-tetrahydro-[1,4]oxazepino[4,3-e]purin-2-yl)-3-(difluoromethoxy)pyridin-2-amine (17.8 mg, 25.4%): $^1$H NMR (400 MHz, DMSO-d6) δ 8.83 (s, 1H), 8.17 (s, 1H), 7.38-7.01 (m, 1H), 6.65-6.48 (m, 2H), 5.96-5.15 (m, 1H), 4.75 (s, 2H), 4.39-4.38 (m, 2H), 4.10-4.00 (m, 2H), 3.79-3.65 (m, 2H), 3.02-2.95 (m, 1H), 2.05-1.92 (m, 4H), 1.50-1.38 (m, 2H).

Example 136

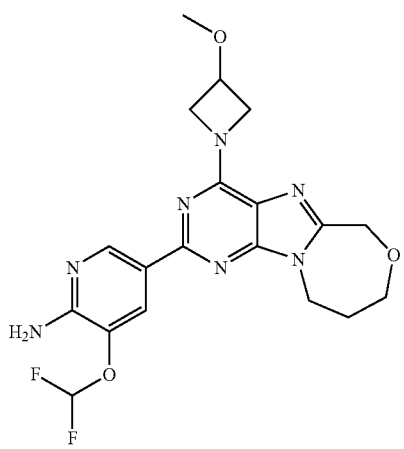 [SMILES: COC1CN(c2nc(-c3cnc(N)c(OC(F)F)c3)nc3c2nc2n3CCCOC2)C1]

3-(difluoromethoxy)-5-(4-(3-methoxyazetidin-1-yl)-
6,8,9,10-tetrahydro-[1,4]oxazepino[4,3-e]purin-2-yl)
pyridin-2-amine 2-chloro-4-(3-methoxyazetidin-1-yl)-6,8,9,10-tetrahydro-[1,4]oxazepino[4,3-e]purine (50 mg, 0.1614 mmol) was dissolved in a mixed solvent of 1,4-dioxane/water (3:1, 2.0 mL) and transferred to a microwave vial equipped with a stirbar. To the solution was added 3-(difluoromethoxy)-5-(4,4,5,5-tetramethyl-1,3,2-dioxaborolan-2-yl)pyridin-2-amine (46 mg, 0.1614 mmol), potassium phosphate (103 mg, 0.484 mmol), 1,1'-bis(diphenylphosphino)ferrocene-palladium(II)dichloride (15 mg, 0.0212 mmol) and the mixture was microwaved at 110° C. for 30 min. The reaction mixture was diluted with water (10 mL) and extracted with ethyl acetate (3×20 mL). The combined organic extracts were dried over magnesium sulfate, filtered and concentrated to dryness in vacuo. This resulting residue was purified by RP-HPLC affording 3-(difluoromethoxy)-5-(4-(3-methoxyazetidin-1-yl)-6,8,9,10-tetrahydro-[1,4]oxazepino[4,3-e]purin-2-yl)pyridin-2-amine (18 mg, 25.7%): $^1$H NMR (400 MHz, DMSO-d6) δ 8.85 (d, J=2.0 Hz, 1H), 8.16 (d, J=6.8 Hz, 2H), 7.39-7.02 (m, 1H), 6.49 (s, 2H), 4.78 (s, 2H), 4.68-4.52 (m, 2H), 4.43-4.41 (m, 3H), 4.19-4.17 (m, 2H), 4.06-4.03 (m, 2H), 3.29 (s, 3H), 2.00-1.90 (m, 2H).

Example 137

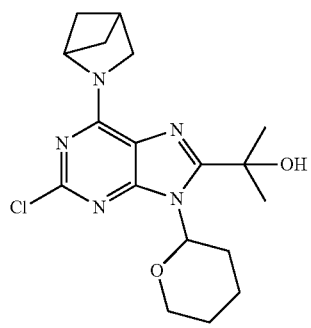 [SMILES: CC(C)(O)c1nc2c(N3CC4CC3C4)nc(Cl)nc2n1C1CCCCO1]

Step 1: 2-(6-(2-azabicyclo[2.1.1]hexan-2-yl)-2-chloro-9-(tetrahydro-2H-pyran-2-yl)-9H-purin-8-yl)propan-2-ol To a solution of 2-(2,6-dichloro-9-(tetrahydro-2H-pyran-2-yl)-9H-purin-8-yl)propan-2-ol (770 mg, 2.32 mmol) and N,N-diisopropylethylamine (899 mg, 6.97 mmol) in acetonitrile (10 mL) was added 2-azabicyclo[2.1.1]hexane hydrochloride (277 mg, 2.32 mmol). The resulting mixture was stirred at room temperature for 16 h and subsequently concentrated to dryness in vacuo. The resulting mixture was diluted with water and extracted with ethyl acetate (2×60 mL). The combined organic layers were dried over sodium sulfate and concentrated to dryness in vacuo. The resulting residue was purified by column chromatography (silica gel, 200-300 mesh, 30% ethyl acetate in petroleum ether) affording 2-(6-(2-azabicyclo[2.1.1]hexan-2-yl)-2-chloro-9-(tetrahydro-2H-pyran-2-yl)-9H-purin-8-yl)propan-2-ol (700 mg, 79.9%): LCMS (ESI, 5-95AB/1.5 min): $R_T$=0.834 min, m/z 378.1 [M+H$^+$].

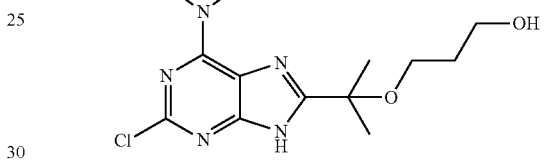

Step 2: 3-((2-(6-(2-azabicyclo[2.1.1]hexan-2-yl)-2-chloro-9H-purin-8-yl)propan-2-yl)oxy)propan-1-ol To a solution of 2-(6-(2-azabicyclo[2.1.1]hexan-2-yl)-2-chloro-9-(tetrahydro-2H-pyran-2-yl)-9H-purin-8-yl)propan-2-ol (1.0 g, 2.65 mmol) in dry dichloromethane (10 mL) was added sulfurous dichloride (0.6 mL, 7.94 mmol) at 0° C. The reaction mixture was stirred at 0° C. for 30 min. ii) To a mixture of 1,3-propanediol (2.016 g, 26.5 mmol) in tetrahydrofuran (10 mL) and N,N-dimethylformaldehyde (10 mL) was added sodium hydride (954 mg, 60% in mineral oil, 23.85 mmol) at 0° C. and stirred for 10 min. The two reaction mixtures were added together immediately upon preparation and stirred at 0° C. for 5 min. Water (1 mL) was added to and concentrated to dryness in vacuo. The resulting mixture was diluted with water (50 mL) and extracted with ethyl acetate (2×80 mL). The combined organic layers were dried over sodium sulfate and concentrated to dryness in vacuo. The resulting residue was purified by RP-HPLC affording 3-((2-(6-(2-azabicyclo[2.1.1]hexan-2-yl)-2-chloro-9H-purin-8-yl)propan-2-yl)oxy)propan-1-ol (110 mg, 11.8%): LCMS (ESI, 10-80AB/2.0 min): $R_T$=1.016 min, m/z 352.1 [M+H$^+$].

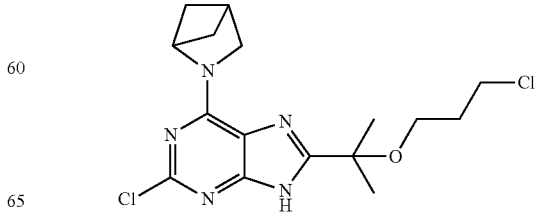

Step 3: 2-(2-chloro-8-(2-(3-chloropropoxy)propan-2-yl)-9H-purin-6-yl)-2-azabicyclo[2.1.1]hexane hydrochloride To a stirred solution of 3-((2-(6-(2-azabicyclo[2.1.1]hexan-2-yl)-2-chloro-9H-purin-8-yl)propan-2-yl)oxy)propan-1-ol (50 mg, 0.1421 mmol) in dichloromethane (5 mL) was added sulfuryl dichloride (51 mg, 0.43 mmol). The reaction mixture was stirred at room temperature for 1 h. The reaction mixture was concentrated to dryness in vacuo affording 2-(2-chloro-8-(2-(3-chloropropoxy)propan-2-yl)-9H-purin-6-yl)-2-azabicyclo[2.1.1]hexane hydrochloride (58 mg, quantitive) as a yellow oil and used for the next step without any further purification: LCMS (ESI, 5-95AB/1.5 min): $R_T$=0.797 min, m/z 369.9 [M+H$^+$].

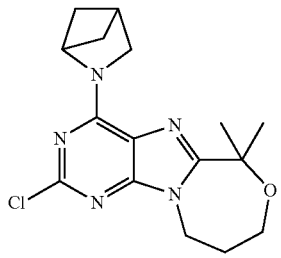 [SMILES: CC1(C)OCCCn2c1nc1c(N3CC4CC3C4)nc(Cl)nc12]

Step 4: 4-(2-azabicyclo[2.1.1]hexan-2-yl)-2-chloro-6,6-dimethyl-6,8,9,10-tetrahydro-[1,4]oxazepino[4,3-e]purine To a stirred solution of 2-(2-chloro-8-(2-(3-chloropropoxy)propan-2-yl)-9H-purin-6-yl)-2-azabicyclo[2.1.1]hexane hydrochloride (50 mg, 0.123 mmol) in N,N-dimethylformaldehyde (5 mL) was added potassium carbonate (51 mg, 0.369 mmol). The reaction mixture was heated to 100° C. for 30 min and concentrated to dryness in vacuo. The resulting mixture was diluted with ethyl acetate (60 mL) and water (20 mL). The separated organic layer was dried over sodium sulfate and concentrated to dryness in vacuo to afford 4-(2-azabicyclo[2.1.1]hexan-2-yl)-2-chloro-6,6-dimethyl-6,8,9, 10-tetrahydro-[1,4]oxazepino[4,3-e]purine (41 mg, quantitive) used for the next step without any further purification: LCMS (ESI): LCMS (ESI, 5-95AB/1.5 min): $R_T$=0.824 min, m/z 333.9 [M+H$^+$].

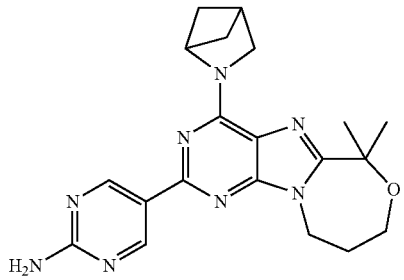 [SMILES: CC1(C)OCCCn2c1nc1c(N3CC4CC3C4)nc(-c3cnc(N)nc3)nc12]

Step 5: 5-(4-(2-azabicyclo[2.1.1]hexan-2-yl)-6,6-dimethyl-6,8,9,10-tetrahydro-[1,4]oxazepino[4,3-e]purin-2-yl)pyrimidin-2-amine 4-(2-azabicyclo[2.1.1]hexan-2-yl)-2-chloro-6,6-dimethyl-6,8,9,10-tetrahydro-[1,4]oxazepino[4,3-e]purine (45 mg, 0.135 mmol) was dissolved in a mixed solvent of 1,4-dioxane/water (3:1, 2.0 mL) and transferred to a microwave vial equipped with a stirbar. To the solution was added 5-(4,4,5,5-tetramethyl-1,3,2-dioxaborolan-2-yl)pyrimidin-2-amine (30 mg, 0.135 mmol), potassium phosphate (86 mg, 0.405 mmol), 1, 1'-bis(diphenylphosphino)ferrocene-palladium(II)dichloride (20 mg, 0.0283 mmol) and the mixture was microwaved at 110° C. for 45 min. The reaction mixture was diluted with water (10 mL) and extracted with ethyl acetate (3×15 mL). The combined organic extracts were dried over magnesium sulfate, filtered and concentrated to dryness in vacuo. The resulting residue was purified by RP-HPLC affording 5-(4-(2-azabicyclo[2.1.1]hexan-2-yl)-6,6-dimethyl-6,8,9,10-tetrahydro-[1,4]oxazepino[4,3-e]purin-2-yl)pyrimidin-2-amine (14 mg, 26.4%): $^1$H NMR (400 MHz, DMSO-d6) δ 9.12 (s, 2H), 6.99 (s, 2H), 6.03-5.33 (m, 1H), 4.45-4.44 (m, 2H), 3.89-3.69 (m, 4H), 3.05-2.95 (m, 1H), 2.08-1.95 (m, 4H), 1.62 (s, 6H), 1.48-1.43 (m, 2H).

Examples 138 and 139

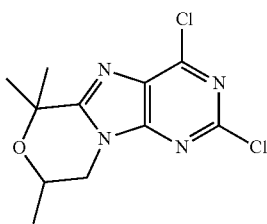 [SMILES: CC1Cn2c(nc3c(Cl)nc(Cl)nc32)C(C)(C)O1]

Step 1: 2,4-dichloro-6,6,8-trimethyl-8,9-dihydro-6H-[1,4]oxazino[4,3-e]purine To a suspension of 2-(2,6-dichloro-9-(tetrahydro-2H-pyran-2-yl)-9H-purin-8-yl)propan-2-ol (1.42 g, 4.29 mmol) in methanol (6.4 mL) was added p-toluenesulfonic acid (8.2 mg, 1 mol %) and the mixture was stirred vigorously for 18 h. The reaction mixture was concentrated to dryness in vacuo and the residue was dissolved in anhydrous N,N-dimethylformaldehyde (8.6 mL). To this solution was added potassium carbonate (900 mg, 6.44 mmol) and α-chloroacetone (430 μL, 5.2 mmol) and the mixture was heated in a sealed vial at 60° C. for 6 h. The mixture was diluted with dichloromethane, washed with brine and the organic layer was dried over magnesium sulfate. After concentration to dryness in vacuo, the residue was taken up in trifluoroacetic acid (8.6 mL) and triethylsilane was added (3.5 mL, 21 mmol). The reaction was stirred at 70° C. in an open flask for 1 h and then concentrated to dryness in vacuo. The residue was taken up in dichloromethane, washed with aqueous saturated sodium bicarbonate, dried over magnesium sulfate and concentrated to dryness in vacuo. The resulting residue was purified by column chromatography (silica gel, 100-200 mesh, 25% ethyl acetate in hexane) affording racemic 2,4-dichloro-6,6,8-trimethyl-8,9-dihydro-6H-[1,4]oxazino[4,3-e]purine as a white solid (604 mg, 49% over 3 steps): $^1$H NMR (400 MHz, DMSO-d6) δ 4.36 (dd, J=12.1, 3.0 Hz, 1H), 4.29 (m, 1H), 3.76 (dd, J=12.1, 10.3 Hz, 1H), 1.64 (s, 3H), 1.62 (s, 3H), 1.33 (d, J=6.1 Hz, 3H).

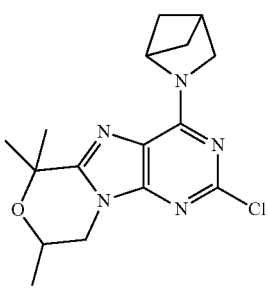 [SMILES: CC1Cn2c(nc3c(N4CC5CC4C5)nc(Cl)nc32)C(C)(C)O1]

Step 2: 4-(2-azabicyclo[2.1.1]hexan-2-yl)-2-chloro-6,6,8-trimethyl-8,9-dihydro-6H-[1,4]oxazino[4,3-e]purine To a solution of racemic 2,4-dichloro-6,6,8-trimethyl-8,9-dihydro-6H-[1,4]oxazino[4,3-e]purine (300 mg, 1.04 mmol) and 2-azabicyclo[2.1.1]hexane hydrochloride (180 mg, 1.46 mmol) in N,N-dimethylformaldehyde (4.2 mL) was added N,N-diisopropylethylamine (0.46 mL, 2.6 mmol) and the mixture was stirred at 50° C. for 43.5 h. The mixture was then diluted with dichloromethane, washed with saturated sodium bicarbonate, dried over magnesium sulfate and concentrated in vacuo. The resulting residue was purified by column chromatography (silica gel, 100-200 mesh, 25% ethyl acetate in hexane) affording racemic 4-(2-azabicyclo[2.1.1]hexan-2-yl)-2-chloro-6,6,8-trimethyl-8,9-dihydro-6H-[1,4]oxazino[4,3-e]purine as a white solid (287 mg, 82%); $^1$H NMR (400 MHz, Chloroform-d) δ 5.63 (br m, 1H), 4.29-4.11 (m, 2H), 3.84 (br m, 2H), 3.72-3.57 (m, 1H), 2.97 (m, 1H), 2.11 (m, 2H), 1.67 (s, 3H), 1.62 (s, 3H), 1.53 (m, 2H), 1.40 (d, J=6.1 Hz, 3H).

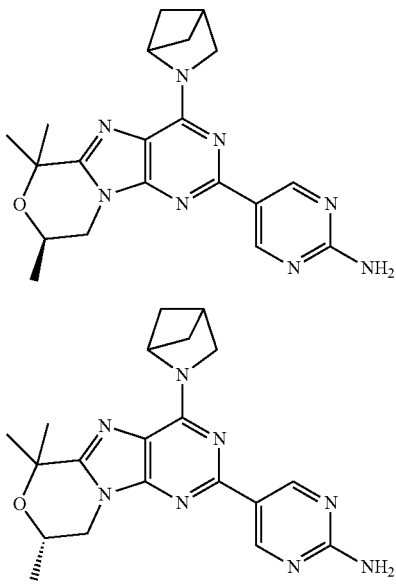

(R)-5-(4-(2-azabicyclo[2.1.1]hexan-2-yl)-6,6,8-trimethyl-8,9-dihydro-6H-[1,4]oxazino[4,3-e]purin-2-yl)pyrimidin-2-amine and (S)-5-(4-(2-azabicyclo[2.1.1]hexan-2-yl)-6,6,8-trimethyl-8,9-dihydro-6H-[1,4]oxazino[4,3-e]purin-2-yl)pyrimidin-2-amine Into a vial was weighed racemic 4-(2-azabicyclo[2.1.1]hexan-2-yl)-2-chloro-6,6,8-trimethyl-8,9-dihydro-6H-[1,4]oxazino[4,3-e]purine (285 mg, 0.854 mmol), bis(di-tert-butyl(4-dimethylaminophenyl)phosphine)dichloropalladium(II) (63.6 mg, 10 mol %), 2-aminopyrimidine-5-boronic acid pinacol ester (292 mg, 1.28 mmol), sodium carbonate (136 mg, 1.28 mmol), and potassium acetate (126 mg, 1.28 mmol). Under a flow of nitrogen, acetonitrile (4.3 mL) and distilled water (0.9 mL) were added and the vial was sealed. The reaction mixture was stirred at 110° C. for 18.5 h. After cooling to RT, the mixture was concentrated to dryness in vacuo and the resulting residue was purified by column chromatography (silica gel, 100-200 mesh, 10% methanol in dichloromethane) and then chiral SFC (Berger Cel-1, 21.2 mm×150 mm, 5 μm, 70 mL/min, 35% MeOH in 0.1% NH$_4$OH) affording arbitrarily assigned enantiomers (R)-5-(4-(2-azabicyclo[2.1.1]hexan-2-yl)-6,6,8-trimethyl-8,9-dihydro-6H-[1,4]oxazino[4,3-e]purin-2-yl)pyrimidin-2-amine and (S)-5-(4-(2-azabicyclo[2.1.1]hexan-2-yl)-6,6,8-trimethyl-8,9-dihydro-6H-[1,4]oxazino[4,3-e]purin-2-yl)pyrimidin-2-amine as a white solids (63.4 mg (t$_r$=0.930 min) and 55.3 mg (t$_r$=0.761 min), 35% total); $^1$H NMR (400 MHz, DMSO-d6) δ 9.10 (s, 2H), 6.97 (br s, 2H), 4.37-4.18 (m, 2H), 3.93-3.55 (m, 3H), 3.28-3.25 (m, 1H), 3.04-2.94 (m, 1H), 2.14-2.00 (m, 2H), 1.59 (s, 3H), 1.58 (s, 3H), 1.49-1.40 (m, 2H), 1.33 (d, J=6.0 Hz, 3H).

Examples 140 and 141

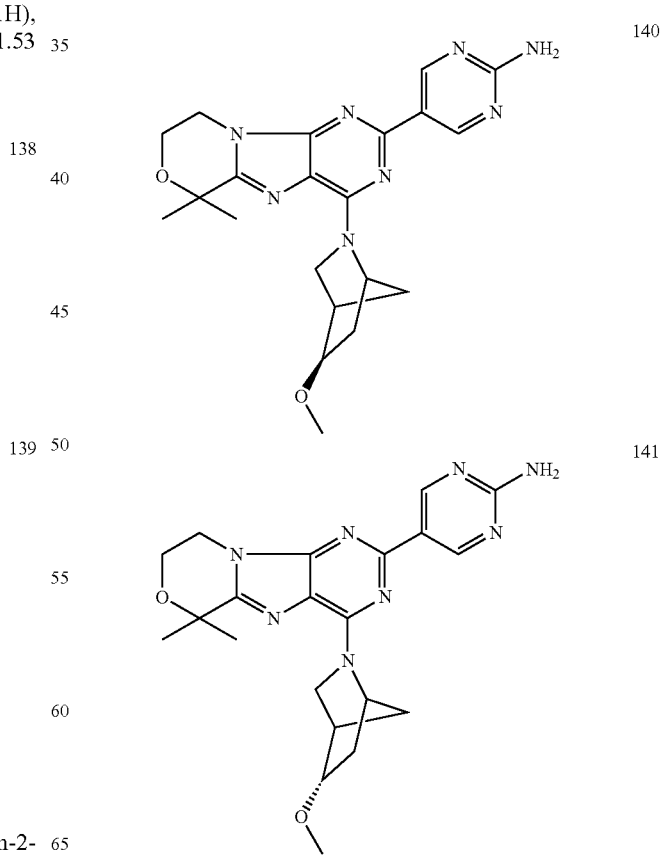

5-(4-((5R)-5-methoxy-2-azabicyclo[2.2.1]heptan-2-yl)-6,6-dimethyl-8,9-dihydro-6H-[1,4]oxazino[4,3-e]purin-2-yl)pyrimidin-2-amine and 5-(4-((5S)-5-methoxy-2-azabicyclo[2.2.1]heptan-2-yl)-6,6-dimethyl-8,9-dihydro-6H-[1,4]oxazino[4,3-e]purin-2-yl)pyrimidin-2-amine The title compounds were prepared by the procedure described in Example 1 by substituting 2-(methoxymethyl)pyrrolidine with 5-methoxy-2-azabicyclo[2.2.1]heptane in Step 5. The resulting racemic 5-(4-(5-methoxy-2-azabicyclo[2.2.1]heptan-2-yl)-6,6-dimethyl-8,9-dihydro-6H-[1,4]oxazino[4,3-e]purin-2-yl)pyrimidin-2-amine crude was purified by chiral SFC (MG II, 21.1 mm×150 mm, 5 μm, 70 mL/min, 15% MeOH in 0.1% NH$_4$OH) affording arbitrarily assigned enantiomers 5-(4-((5S)-5-methoxy-2-azabicyclo[2.2.1]heptan-2-yl)-6,6-dimethyl-8,9-dihydro-6H-[1,4]oxazino[4,3-e]purin-2-yl)pyrimidin-2-amine and 5-(4-((5R)-5-methoxy-2-azabicyclo[2.2.1]heptan-2-yl)-6,6-dimethyl-8,9-dihydro-6H-[1,4]oxazino[4,3-e]purin-2-yl)pyrimidin-2-amine as a white solids (10 mg (t$_r$=0.37 min) and 12.4 mg (t$_r$=0.46 min): $^1$H NMR (400 MHz, DMSO-d6) δ: 9.08 (s, 2H), 6.97 (s, 2H), 4.11 (s, 4H), 4.02-3.37 (m, 3H), 3.34 (s, 3H), 2.72-2.56 (m, 2H), 1.83-1.78 (m, 1H), 1.58 (s, 6H), 1.46-1.41 (m, 1H) and $^1$H NMR (400 MHz, DMSO-d6) δ: 9.08 (s, 2H), 6.97 (s, 2H), 4.14-4.09 (m, 4H), 4.04-3.42 (m, 4H), 3.34 (s, 3H), 2.61-2.56 (m, 1H), 1.83-1.78 (m, 2H), 1.58 (s, 6H), 1.45-1.40 (m, 1H)

5-(4-((5R)-5-fluoro-2-azabicyclo[2.2.1]heptan-2-yl)-6,6-dimethyl-8,9-dihydro-6H-[1,4]oxazino[4,3-e]purin-2-yl)pyrimidin-2-amine and 5-(4-((5S)-5-fluoro-2-azabicyclo[2.2.1]heptan-2-yl)-6,6-dimethyl-8,9-dihydro-6H-[1,4]oxazino[4,3-e]purin-2-yl)pyrimidin-2-amine The title compound were prepared by the procedure described in Example 1 by substituting 2-(methoxymethyl)pyrrolidine with 5-fluoro-2-azabicyclo[2.2.1]heptane in Step 5. The resulting racemic 5-(4-(5-fluoro-2-azabicyclo[2.2.1]heptan-2-yl)-6,6-dimethyl-8,9-dihydro-6H-[1,4]oxazino[4,3-e]purin-2-yl)pyrimidin-2-amine crude was purified by chiral SFC (MG II, 21.1 mm×150 mm, 5 μm, 70 mL/min, 20% MeOH in 0.1% NH$_4$OH) affording arbitrarily assigned enantiomers 5-(4-((5R)-5-fluoro-2-azabicyclo[2.2.1]heptan-2-yl)-6,6-dimethyl-8,9-dihydro-6H-[1,4]oxazino[4,3-e]purin-2-yl)pyrimidin-2-amine and 5-(4-((5S)-5-fluoro-2-azabicyclo[2.2.1]heptan-2-yl)-6,6-dimethyl-8,9-dihydro-6H-[1,4]oxazino[4,3-e]purin-2-yl)pyrimidin-2-amine as white solids (9.5 mg (t$_r$=0.34 min) and 9.1 mg (t$_r$=0.56 min): $^1$H NMR (400 MHz, DMSO-d6) δ: 9.09 (s, 2H), 6.98 (s, 2H), 4.14-4.09 (m, 4H), 4.02-3.46 (m, 2H), 2.41-1.65 (m, 4H), 1.58 (s, 6H) and $^1$H NMR (400 MHz, DMSO-d6) δ: 9.09 (s, 2H), 6.98 (s, 2H), 4.14-4.09 (m, 4H), 4.02-3.46 (m, 2H), 2.41-1.65 (m, 4H), 1.58 (s, 6H)

General HPLC Methods

The following general HPLC methods can be used to isolate the compounds of the invention.

Method A: LC-MS was performed on a Waters Acquity UPLC coupled to a Waters SQ mass spectrometer using an Acquity UPLC BEH C18 column (1.7 μm, 2.1×30 mm) with a linear gradient of 5-95% acetonitrile/water (with 0.1% formic acid in each mobile phase) within 1.4 minute and held at 95% for 0.3 minute.

Method B: LC-MS was performed on an Agilent 1200 Series LC coupled to an Agilent 6140 quadrupole mass spectrometer using an Agilent SD-C18 column (1.8 μm, 2.1×30 mm) with a linear gradient of 3-95% acetonitrile/water (with 0.05% trifluoroaceetic acid in each mobile phase) within 8.5 minutes and held at 95% for 2.5 minutes.

RP-HPLC: was generally carried out on a Prep Column: Gemini-NX (C18) 10 μm [100×30 mm] using the Gradient Basic Method (0.1% NH3OH): 30-70% ACN 9 min (70 mL/min).

Examples 142 and 143

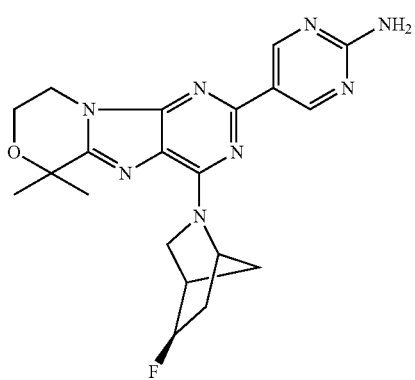

142

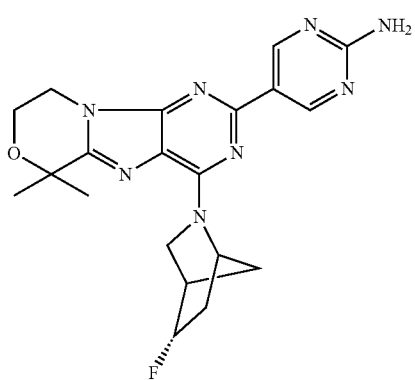

143

Examples 144-162

The following compounds were also prepared using a procedure similar to the procedure used in the Example that is referenced in column 3 below. Where no Example is referenced in column 3, the compound was prepared using modifications of procedures generally described herein. LCMS values were determined using either Method A or Method B.

| Example | Structure | Prepared as described in Example | LCMS |
|---|---|---|---|
| 144 | 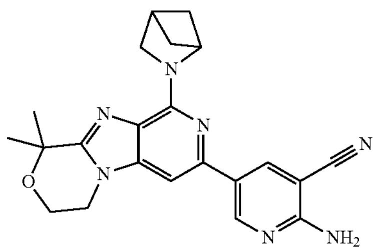 [SMILES: CC1(C)OCCn2c1nc1c(N3CC4CC3C4)nc(-c3cnc(N)c(C#N)c3)cc12] | | 402.2 |
| 145 | 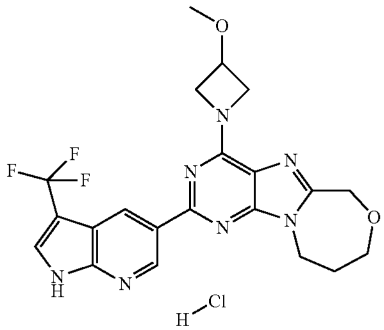 [SMILES: COC1CN(c2nc(-c3cnc4[nH]cc(C(F)(F)F)c4c3)nc3c2nc2n3CCCOC2)C1 ; Cl] | 93 | 460.1 |
| 146 | 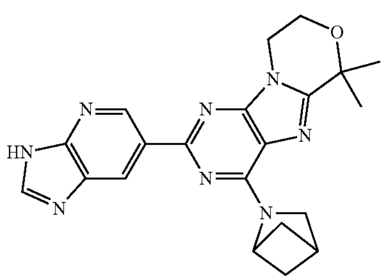 [SMILES: CC1(C)OCCn2c1nc1c(N3CC4CC3C4)nc(-c3cnc4[nH]cnc4c3)nc12] | 109 | 403.2 |
| 147 | 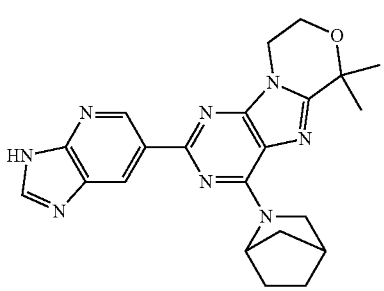 [SMILES: CC1(C)OCCn2c1nc1c(N3CC4CCC3C4)nc(-c3cnc4[nH]cnc4c3)nc12] | 109 | 417.2 |
| 148 | 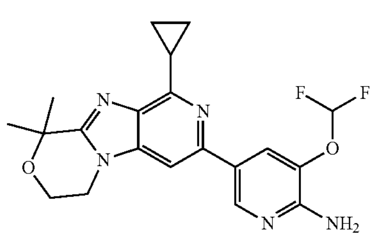 | | 402.2 |
| 149 | 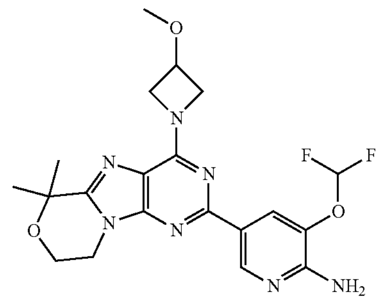 [SMILES: COC1CN(c2nc(-c3cnc(N)c(OC(F)F)c3)nc3c2nc2n3CCOC2(C)C)C1] | | 448.2 |
| 150 | 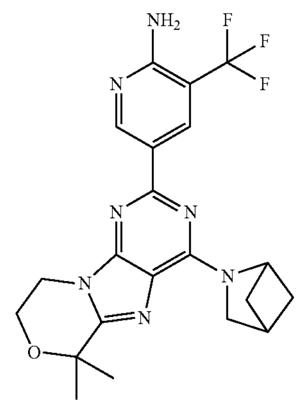 [SMILES: CC1(C)OCCn2c1nc1c(N3CC4CC3C4)nc(-c3cnc(N)c(C(F)(F)F)c3)nc12] | 127 | 446.2 |
| 151 | 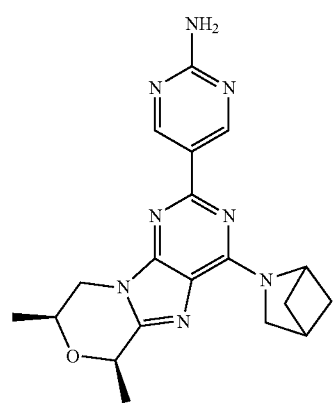 [SMILES: C[C@H]1Cn2c(nc3c(N4CC5CC4C5)nc(-c4cnc(N)nc4)nc32)[C@@H](C)O1] | 96, 107 | 379.2 |
| 152 | 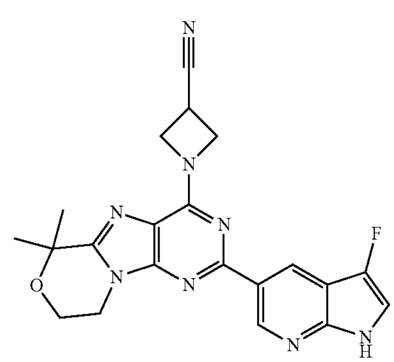 [SMILES: CC1(C)OCCn2c1nc1c(N3CC(C#N)C3)nc(-c3cnc4[nH]cc(F)c4c3)nc12] | 1 | 419.2 |

| Example | Structure | Prepared as described in Example | LCMS |
|---|---|---|---|
| 153 | 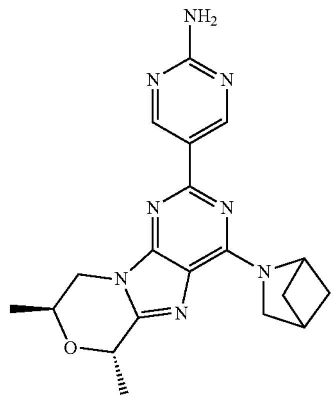 [SMILES: C[C@@H]1O[C@@H](C)Cn2c1nc1c(N3CC4CC3C4)nc(-c3cnc(N)nc3)nc12] | 96, 107 | 379.2 |
| 154 | 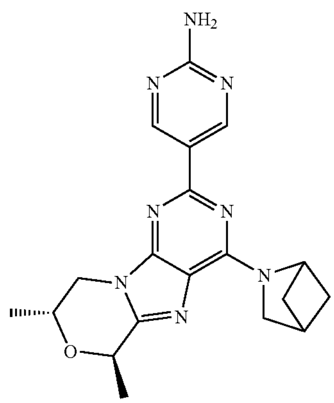 [SMILES: C[C@@H]1Cn2c(nc3c(N4CC5CC4C5)nc(-c4cnc(N)nc4)nc32)[C@@H](C)O1] | 96, 107 | 379.2 |
| 155 | 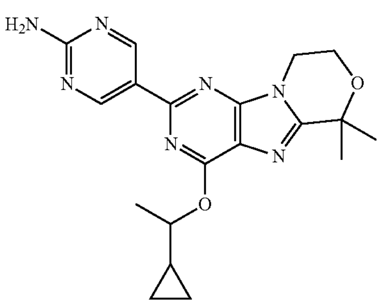 [SMILES: CC(Oc1nc(-c2cnc(N)nc2)nc2c1nc1n2CCOC1(C)C)C1CC1] | 84 | 382.2 |
| 156 | 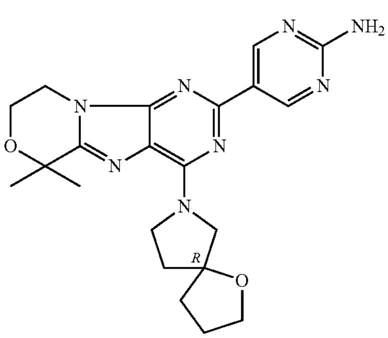 | 1 | 423.3 |

| Example | Structure | Prepared as described in Example | LCMS |
|---|---|---|---|
| 157 | | 20, 119 | 404.2 |
| 158 | | 20, 119 | 361.2 |
| 159 | | 116, 107 | 364.2 |
| 160 | | 116, 107 | 364.2 |

-continued

| Example | Structure | Prepared as described in Example | LCMS |
|---|---|---|---|
| 161 | (structure) | 1 | 462.2 |
| 162 | (structure) | 1 | 395.2 |

Example 163

DLK TR-FRET Inhibition Assay

DLK kinase reactions (20 μL) containing 5 nM N-terminally GST-tagged DLK (catalytic domain amino acid 1-520) (Carna Bioscience), 40 nM N-terminally HIS tagged MKK4 K131M substrate, and 30 μM ATP in kinase reaction buffer (50 mM HEPES, pH 7.5, 0.01% Triton X-100, 0.01% Bovine γ-Globulins, 2 mM DTT, 10 mM $MgCl_2$ and 1 mM EGTA), and testing compound 1:3 serial diluted starting at 20 uM were incubated at ambient temperature for 60 minutes in 384 well OptiPlate (Perkin Elmer). To quench kinase reactions and detect phosphorylated MKK4, 15 μL of TR-FRET antibody mixture containing 2 nM anti-phosphorylated MKK4 labeled with Europium cryptate (Cisbio) and 23 nM anti-HIS labeled with D2 (Cisbio) in detection buffer (25 mM Tris pH 7.5, 100 mM NaCl, 100 mM EDTA, 0.01% Tween-20, and 200 mM KF) was added to the reaction mixture. The detection mixture was incubated for 3 hours at ambient temperature and the TR-FRET was detected with an EnVision multilabel plate reader (Perkin-Elmer) using the LANCE/DELFIA Dual Enh label from Perkin-Elmer (excitation filter: UV2 (TRF) 320 and emission filters: APC 665 and Europium 615). Compounds of formula (I) as set forth in Table 1 inhibited the DLK kinase with the $K_i$s in micromolar (μM) as provided in Table 2 below.

TABLE 2

| Ex. | Structure | DLK HTRF $K_i$ (μm) |
|---|---|---|
| 1 | (structure) | 0.392 |
| 2 | (structure) | 0.391 |
| 3 | (structure) | 0.00492 |
| 4 | (structure) | 0.00974 |
| 5 | (structure) | 0.328 |

TABLE 2-continued

| Ex. | Structure | DLK HTRF K_i (μm) |
|---|---|---|
| 6 | 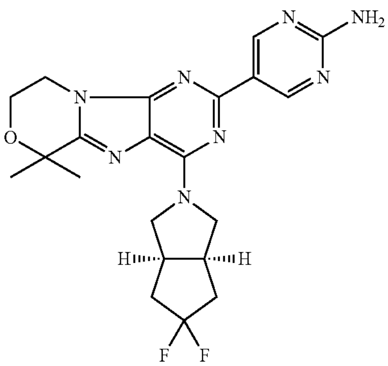 [SMILES: CC1(C)OCCn2c1nc1c(N3C[C@@H]4CC(F)(F)C[C@@H]4C3)nc(-c3cnc(N)nc3)nc12] | 0.727 |
| 7 | 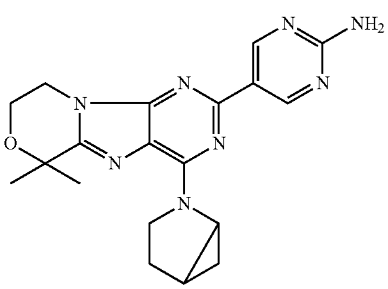 [SMILES: CC1(C)OCCn2c1nc1c(N3CCC4CC43)nc(-c3cnc(N)nc3)nc12] | 0.199 |
| 8 | 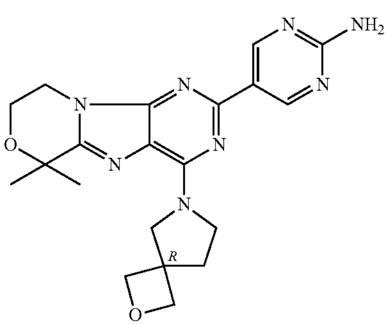 | 0.469 |
| 9 | 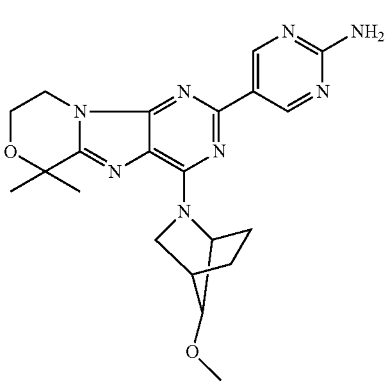 [SMILES: COC1C2CCC1N(c1nc(-c3cnc(N)nc3)nc3c1nc1n3CCOC1(C)C)C2] | 0.223 |
| 10 | | 0.157 |
| 11 | | 0.262 |
| 12 | | 0.584 |
| 13 | | 0.995 |

TABLE 2-continued
| Ex. | Structure | DLK HTRF $K_i$ (μm) |
|---|---|---|
| 14 | 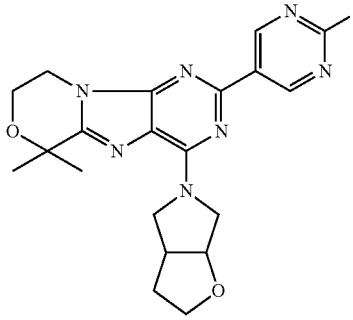 | 0.99 |
| 15 | 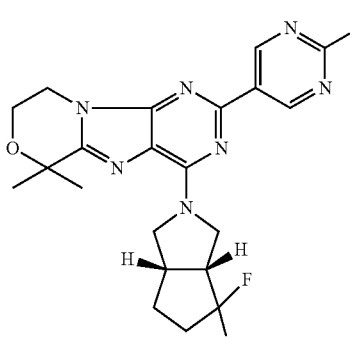 | 0.36 |
| 16 | 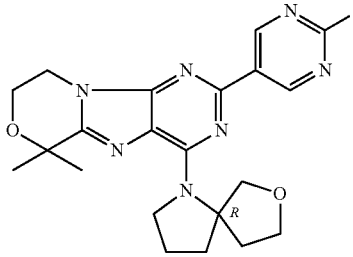 | 0.32 |
| 17 | 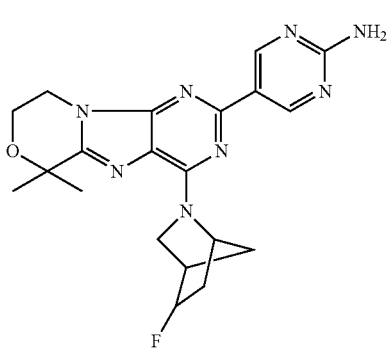 [SMILES: CC1(C)OCCn2c1nc1c(N3CC4CC3CC4F)nc(-c3cnc(N)nc3)nc12] | |
| 18 | 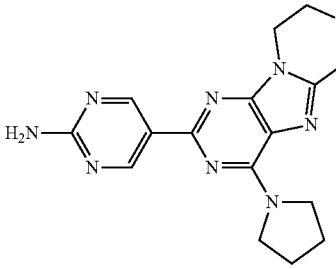 | 0.402 |
| 19 | 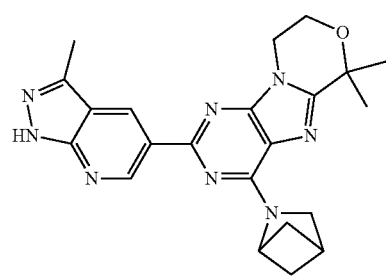 [SMILES: Cc1n[nH]c2ncc(-c3nc(N4CC5CC4C5)c4nc5n(c4n3)CCOC5(C)C)cc12] | 0.493 |
| 20 | 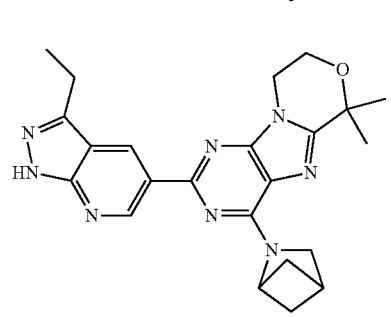 | 0.161 |
| 21 | 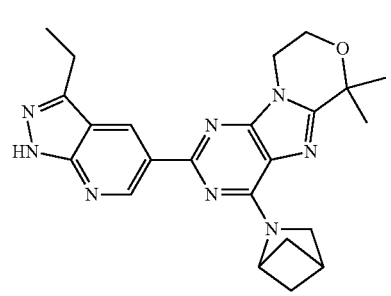 [SMILES: CCc1n[nH]c2ncc(-c3nc(N4CC5CC4C5)c4nc5n(c4n3)CCOC5(C)C)cc12] | 0.279 |
| 22 | 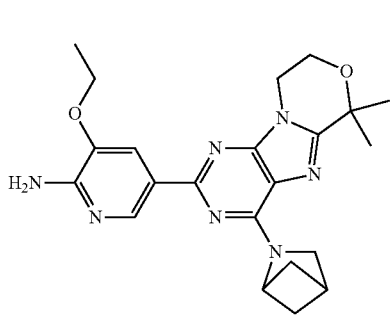 [SMILES: CCOc1cc(-c2nc(N3CC4CC3C4)c3nc4n(c3n2)CCOC4(C)C)cnc1N] | 0.406 |
| 23 | 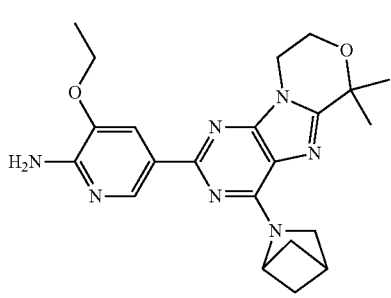 | 0.0577 |

TABLE 2-continued

| Ex. | Structure | DLK HTRF $K_i$ (μm) |
|---|---|---|
| 24 | 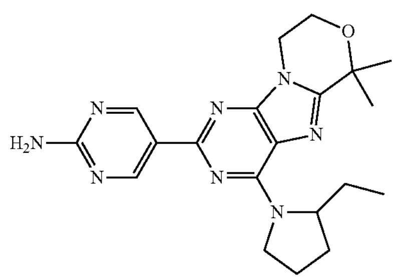 [SMILES: CCC1CCCN1c1nc(-c2cnc(N)nc2)nc2c1nc1n2CCOC1(C)C] | 0.294 |
| 25 | 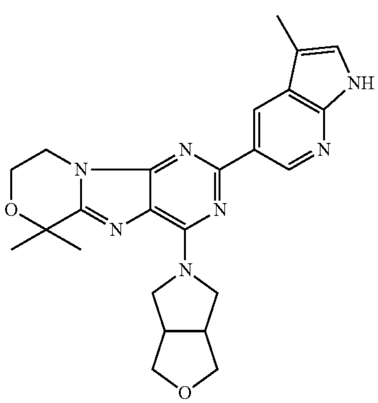 [SMILES: Cc1c[nH]c2ncc(-c3nc(N4CC5COCC5C4)c4nc5n(c4n3)CCOC5(C)C)cc12] | 0.0463 |
| 26 | 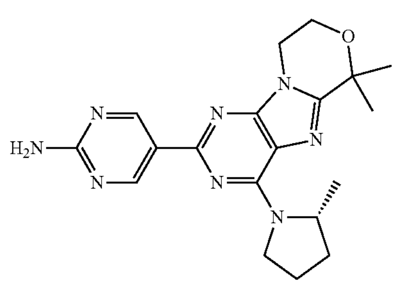 [SMILES: C[C@@H]1CCCN1c1nc(-c2cnc(N)nc2)nc2c1nc1n2CCOC1(C)C] | 0.21 |
| 27 | 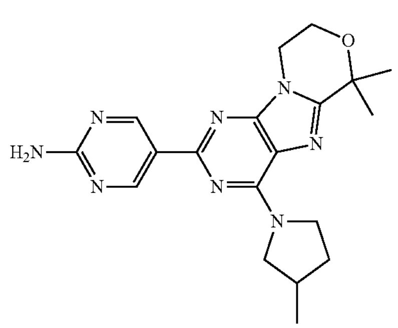 [SMILES: CC1CCN(c2nc(-c3cnc(N)nc3)nc3c2nc2n3CCOC2(C)C)C1] | 0.299 |
| 28 | 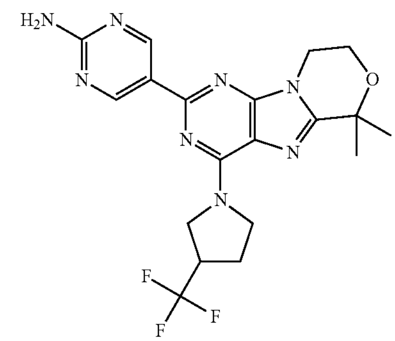 [SMILES: CC1(C)OCCn2c1nc1c(N3CCC(C(F)(F)F)C3)nc(-c3cnc(N)nc3)nc12] | 0.245 |
| 29 | 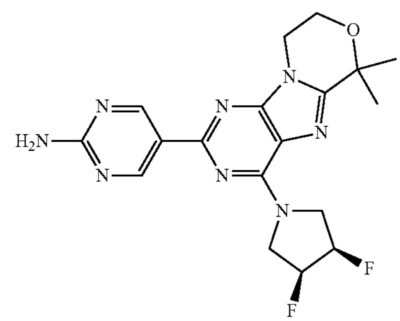 [SMILES: CC1(C)OCCn2c1nc1c(N3C[C@@H](F)[C@@H](F)C3)nc(-c3cnc(N)nc3)nc12] | 0.297 |
| 30 | 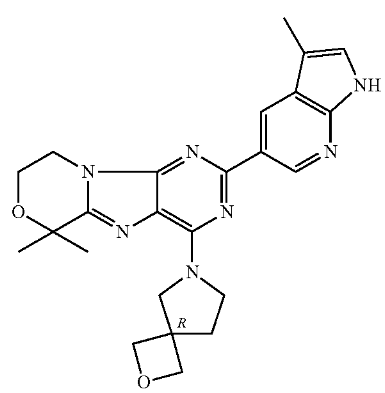 | 0.0102 |
| 31 | 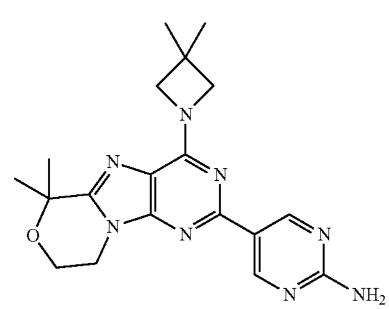 [SMILES: CC1(C)CN(c2nc(-c3cnc(N)nc3)nc3c2nc2n3CCOC2(C)C)C1] | 0.424 |

TABLE 2-continued

| Ex. | Structure | DLK HTRF K_i (μm) |
|---|---|---|
| 32 | 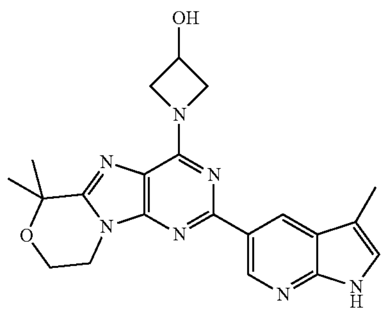 [SMILES: Cc1c[nH]c2ncc(-c3nc(N4CC(O)C4)c4nc5n(c4n3)CCOC5(C)C)cc12] | 0.0131 |
| 33 | 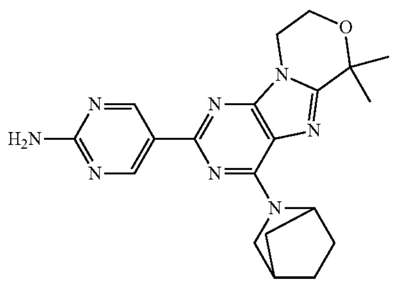 [SMILES: CC1(C)OCCn2c1nc1c(N3CC4CCC3C4)nc(-c3cnc(N)nc3)nc12] | 0.0903 |
| 34 | 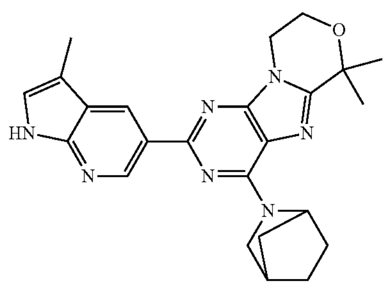 [SMILES: Cc1c[nH]c2ncc(-c3nc(N4CC5CCC4C5)c4nc5n(c4n3)CCOC5(C)C)cc12] | 0.0318 |
| 35 | 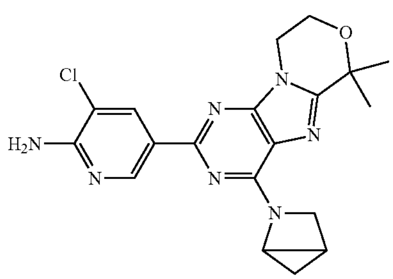 [SMILES: CC1(C)OCCn2c1nc1c(N3CC4CC43)nc(-c3cnc(N)c(Cl)c3)nc12] | 0.235 |
| 36 | 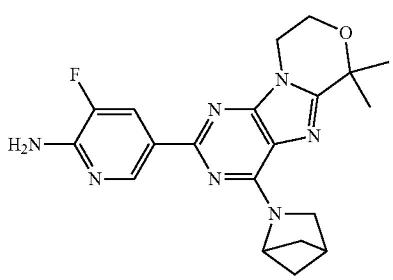 [SMILES: CC1(C)OCCn2c1nc1c(N3CC4CC3C4)nc(-c3cnc(N)c(F)c3)nc12] | 0.444 |
| 37 | | 0.663 |
| 38 | | 0.28 |
| 39 | | 0.00679 |
| 40 | | 0.00591 |
| 41 | | 0.0308 |

TABLE 2-continued

| Ex. | Structure | DLK HTRF K$_i$ (μm) |
|---|---|---|
| 42 | 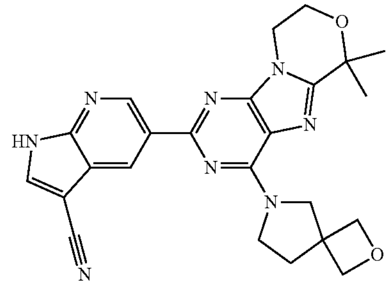 [SMILES: CC1(C)OCCn2c1nc1c(N3CCC4(COC4)C3)nc(-c3cnc4[nH]cc(C#N)c4c3)nc12] | 0.00497 |
| 43 | 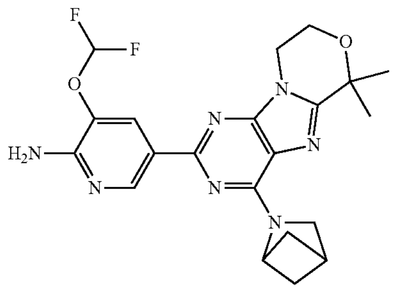 [SMILES: CC1(C)OCCn2c1nc1c(N3CC4CC3C4)nc(-c3cnc(N)c(OC(F)F)c3)nc12] | 0.0418 |
| 44 | 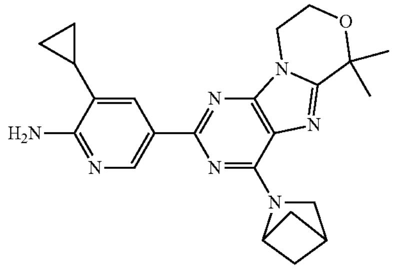 [SMILES: CC1(C)OCCn2c1nc1c(N3CC4CC3C4)nc(-c3cnc(N)c(C4CC4)c3)nc12] | 0.621 |
| 45 | 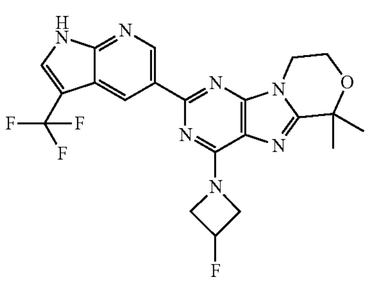 [SMILES: CC1(C)OCCn2c1nc1c(N3CC(F)C3)nc(-c3cnc4[nH]cc(C(F)(F)F)c4c3)nc12] | 0.00987 |
| 46 | 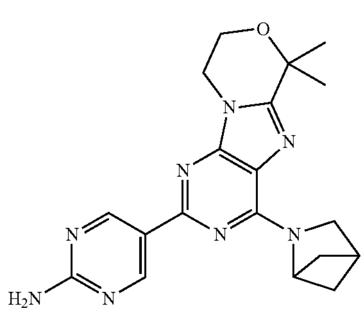 [SMILES: CC1(C)OCCn2c1nc1c(N3CC4CC3C4)nc(-c3cnc(N)nc3)nc12] | 0.13 |
| 47 | 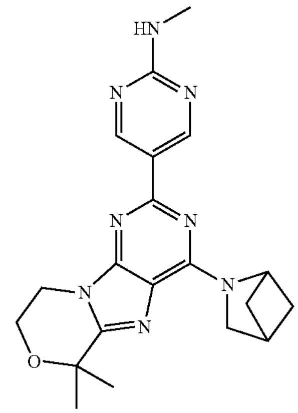 [SMILES: CNc1ncc(-c2nc(N3CC4CC3C4)c3nc4n(c3n2)CCOC4(C)C)cn1] | 1.3 |
| 48 | 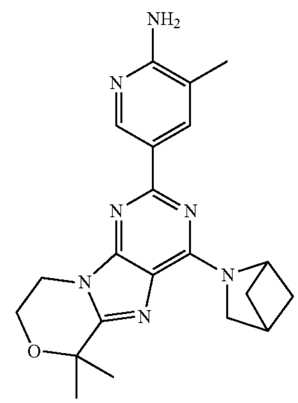 [SMILES: Cc1cc(-c2nc(N3CC4CC3C4)c3nc4n(c3n2)CCOC4(C)C)cnc1N] | 0.992 |
| 49 | 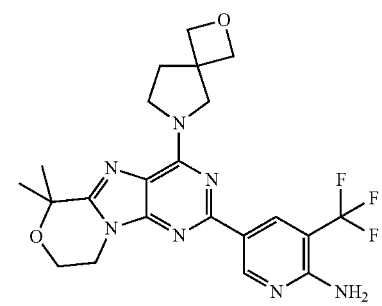 [SMILES: CC1(C)OCCn2c1nc1c(N3CCC4(COC4)C3)nc(-c3cnc(N)c(C(F)(F)F)c3)nc12] | 0.27 |
| 50 | 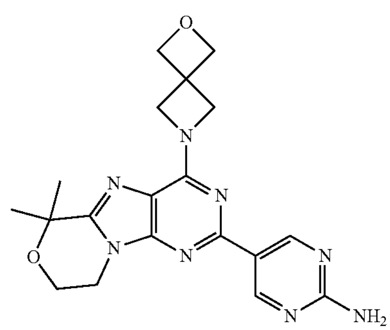 [SMILES: CC1(C)OCCn2c1nc1c(N3CC4(COC4)C3)nc(-c3cnc(N)nc3)nc12] | 0.49 |

TABLE 2-continued

| Ex. | Structure | DLK HTRF $K_i$ (μm) |
|---|---|---|
| 51 | 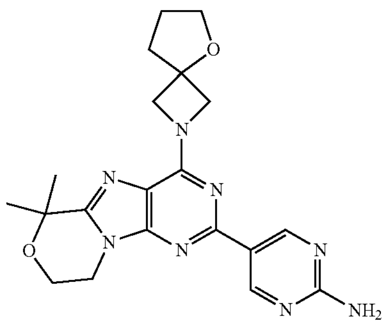 [SMILES: CC1(C)OCCn2c1nc1c(N3CC4(CCCO4)C3)nc(-c3cnc(N)nc3)nc12] | 0.907 |
| 52 | 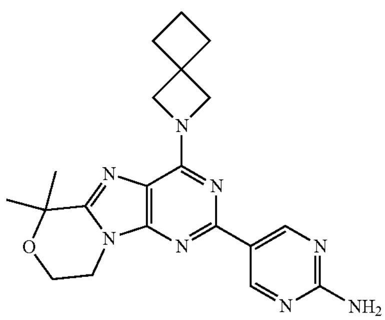 [SMILES: CC1(C)OCCn2c1nc1c(N3CC4(CCC4)C3)nc(-c3cnc(N)nc3)nc12] | 0.515 |
| 53 | 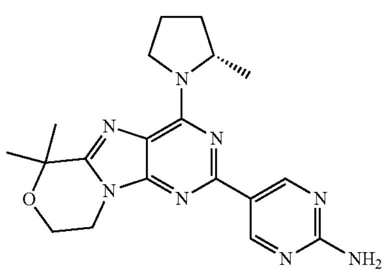 [SMILES: C[C@H]1CCCN1c1nc(-c2cnc(N)nc2)nc2c1nc1n2CCOC1(C)C] | 0.479 |
| 54 | 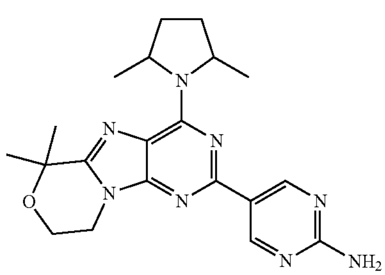 [SMILES: CC1CCC(C)N1c1nc(-c2cnc(N)nc2)nc2c1nc1n2CCOC1(C)C] | 0.284 |
| 55 | 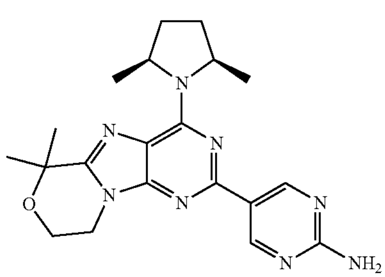 [SMILES: C[C@@H]1CC[C@H](C)N1c1nc(-c2cnc(N)nc2)nc2c1nc1n2CCOC1(C)C] | 0.371 |
| 56 | | 0.339 |
| 57 | | 0.2 |
| 58 | | 0.0877 |
| 59 | | 0.192 |
| 60 | | 0.207 |

TABLE 2-continued
| Ex. | Structure | DLK HTRF $K_i$ (μm) |
|---|---|---|
| 61 | 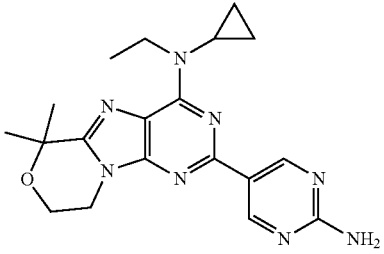 | 0.25 |
| 62 | 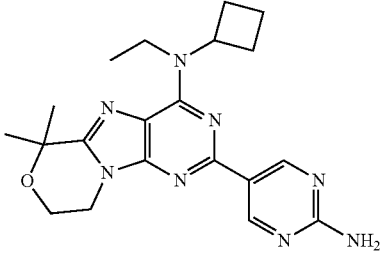 | 0.0867 |
| 63 | 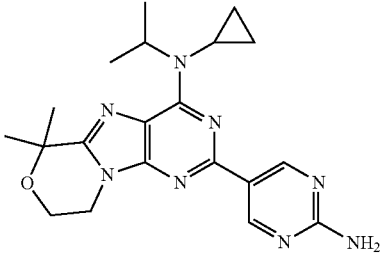 [SMILES: CC(C)N(c1nc(-c2cnc(N)nc2)nc2c1nc1n2CCOC1(C)C)C1CC1] | 0.558 |
| 64 | 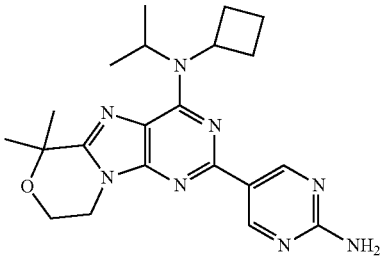 | 0.267 |
| 65 | 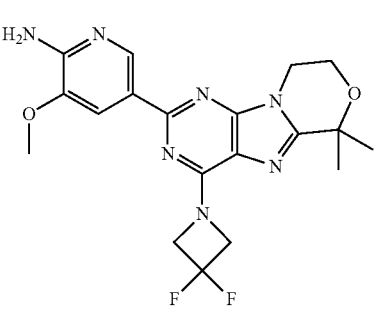 [SMILES: COc1cc(-c2nc(N3CC(F)(F)C3)c3nc4n(c3n2)CCOC4(C)C)cnc1N] | 0.86 |
| 66 | 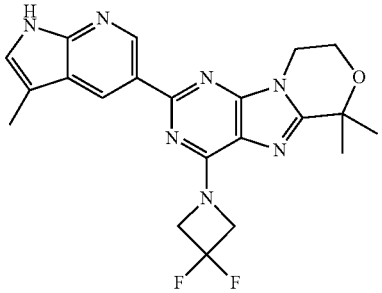 [SMILES: Cc1c[nH]c2ncc(-c3nc(N4CC(F)(F)C4)c4nc5n(c4n3)CCOC5(C)C)cc12] | 0.0119 |
| 67 | 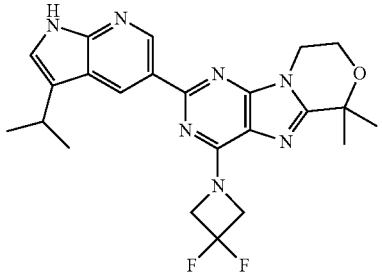 [SMILES: CC(C)c1c[nH]c2ncc(-c3nc(N4CC(F)(F)C4)c4nc5n(c4n3)CCOC5(C)C)cc12] | 0.0327 |
| 68 | 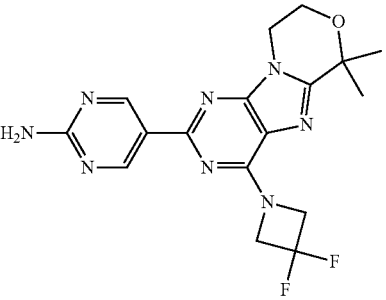 [SMILES: CC1(C)OCCn2c1nc1c(N3CC(F)(F)C3)nc(-c3cnc(N)nc3)nc12] | 0.48 |
| 69 | 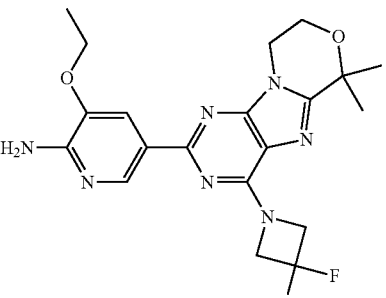 | 0.289 |
| 70 | 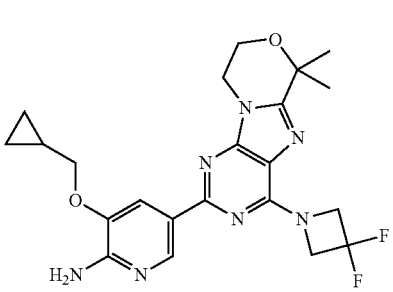 [SMILES: CC1(C)OCCn2c1nc1c(N3CC(F)(F)C3)nc(-c3cnc(N)c(OCC4CC4)c3)nc12] | 0.417 |

TABLE 2-continued

| Ex. | Structure | DLK HTRF K$_i$ (μm) |
|---|---|---|
| 71 | 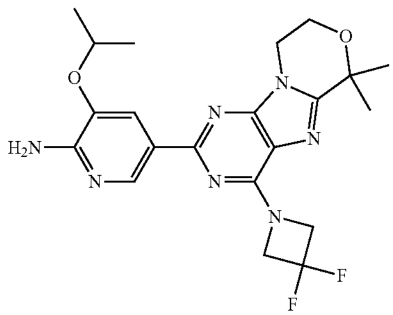 [SMILES: CC(C)Oc1cc(-c2nc(N3CC(F)(F)C3)c3nc4n(c3n2)CCOC4(C)C)cnc1N] | 0.104 |
| 72 | 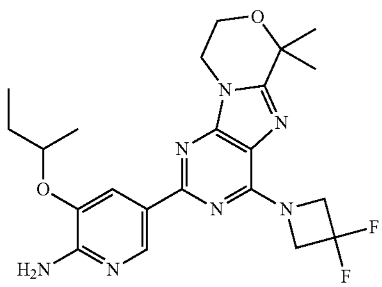 [SMILES: CCC(C)Oc1cc(-c2nc(N3CC(F)(F)C3)c3nc4n(c3n2)CCOC4(C)C)cnc1N] | 0.23 |
| 73 | 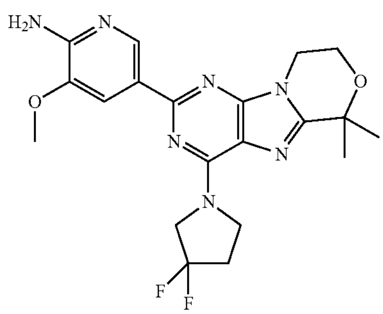 [SMILES: COc1cc(-c2nc(N3CCC(F)(F)C3)c3nc4n(c3n2)CCOC4(C)C)cnc1N] | 0.297 |
| 74 | 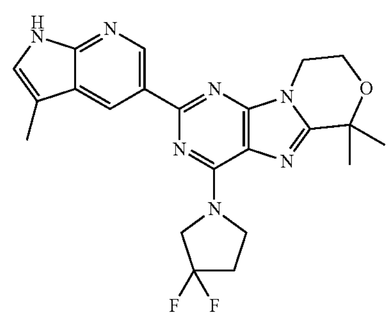 [SMILES: Cc1c[nH]c2ncc(-c3nc(N4CCC(F)(F)C4)c4nc5n(c4n3)CCOC5(C)C)cc12] | 0.0259 |
| 75 | 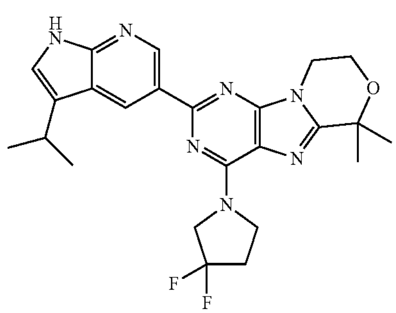 [SMILES: CC(C)c1c[nH]c2ncc(-c3nc(N4CCC(F)(F)C4)c4nc5n(c4n3)CCOC5(C)C)cc12] | 0.112 |
| 76 | | 0.0976 |
| 77 | | 0.588 |
| 78 | | 0.558 |
| 79 | | 0.269 |
| 80 | | 0.443 |

TABLE 2-continued

| Ex. | Structure | DLK HTRF K$_i$ (μm) |
|---|---|---|
| 81 | 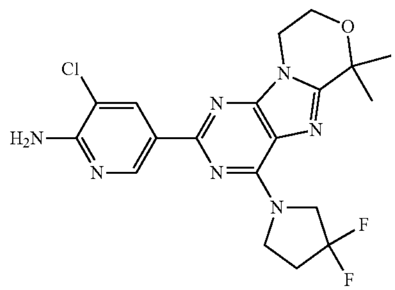 [SMILES: CC1(C)OCCn2c1nc1c(N3CCC(F)(F)C3)nc(-c3cnc(N)c(Cl)c3)nc12] | 0.272 |
| 82 | 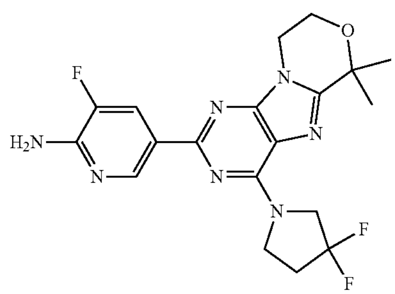 [SMILES: CC1(C)OCCn2c1nc1c(N3CCC(F)(F)C3)nc(-c3cnc(N)c(F)c3)nc12] | 0.28 |
| 83 | 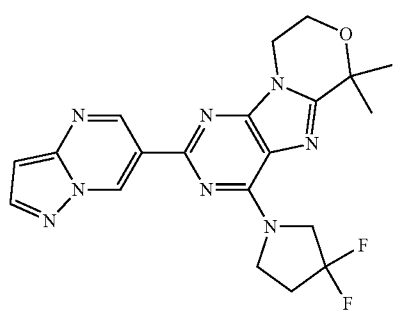 [SMILES: CC1(C)OCCn2c1nc1c(N3CCC(F)(F)C3)nc(-c3cnc4ccnn4c3)nc12] | 0.497 |
| 84 | 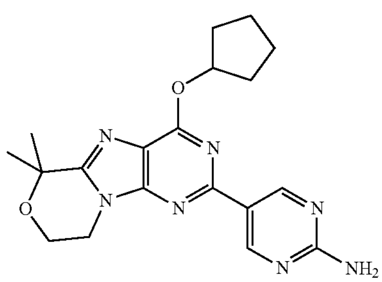 [SMILES: CC1(C)OCCn2c1nc1c(OC3CCCC3)nc(-c3cnc(N)nc3)nc12] | 0.357 |
| 85 | 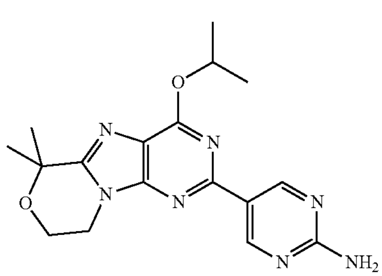 [SMILES: CC(C)Oc1nc(-c2cnc(N)nc2)nc2c1nc1n2CCOC1(C)C] | 0.571 |
| 86 | | 0.634 |
| 87 | | 0.014 |
| 88 | | 0.33 |
| 89 | | 0.551 |
| 90 | | 0.00598 |

TABLE 2-continued
| Ex. | Structure | DLK HTRF $K_i$ (μm) |
|---|---|---|
| 91 | 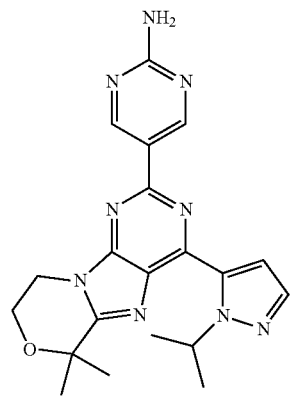 [SMILES: CC(C)n1nccc1-c1nc(-c2cnc(N)nc2)nc2c1nc1n2CCOC1(C)C] | 1.4 |
| 92 | 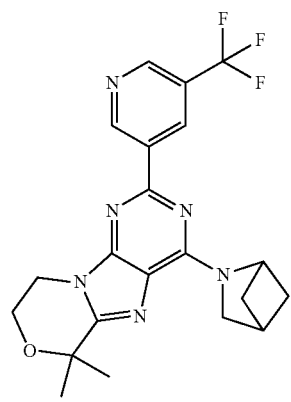 [SMILES: CC1(C)OCCn2c1nc1c(N3CC4CC3C4)nc(-c3cncc(C(F)(F)F)c3)nc12] | 0.478 |
| 93 | 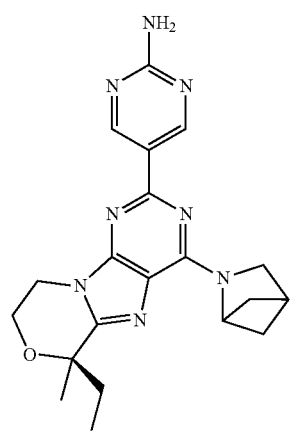 [SMILES: CC[C@@]1(C)OCCn2c1nc1c(N3CC4CC3C4)nc(-c3cnc(N)nc3)nc12] | 0.131 |
| 94 | 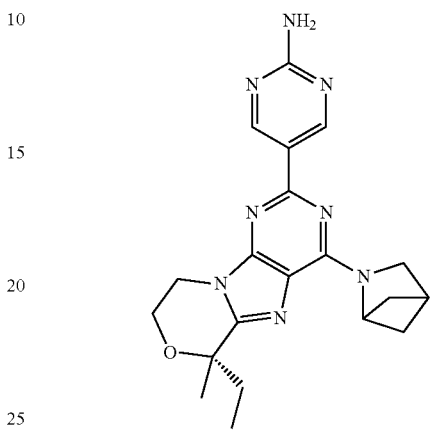 | 0.281 |
| 95 | 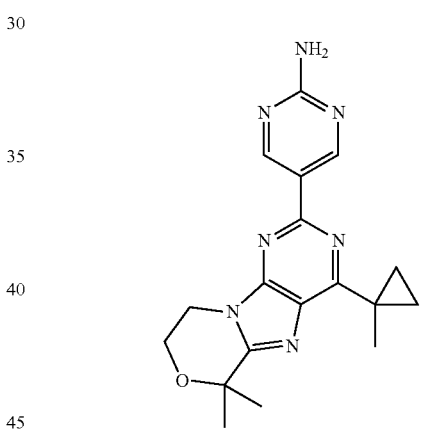 | 0.476 |
| 96 | 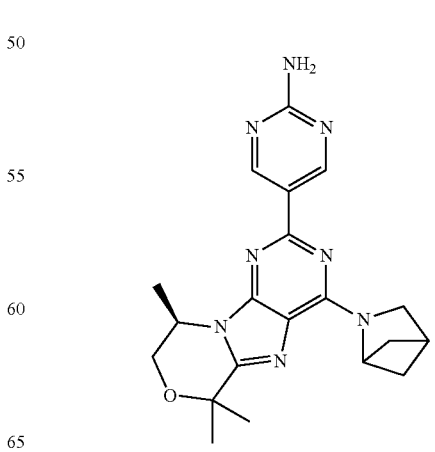 | 0.042 |

TABLE 2-continued

| Ex. | Structure | DLK HTRF $K_i$ (µm) |
|---|---|---|
| 97 | 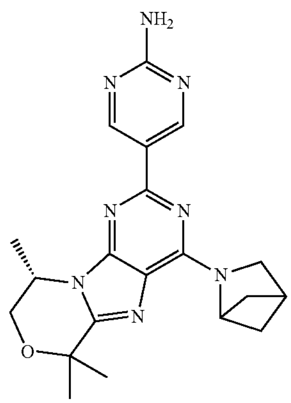 [SMILES: C[C@H]1COC(C)(C)c2nc3c(N4CC5CC4C5)nc(-c4cnc(N)nc4)nc3n21] | 0.062 |
| 98 | 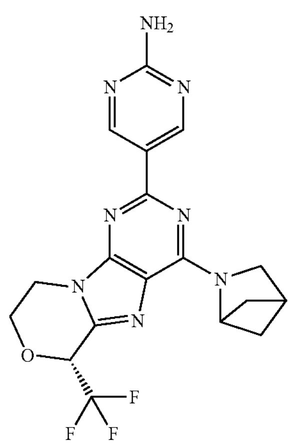 [SMILES: Nc1ncc(-c2nc(N3CC4CC3C4)c3nc4n(c3n2)CCO[C@H]4C(F)(F)F)cn1] | 0.0938 |
| 99 | 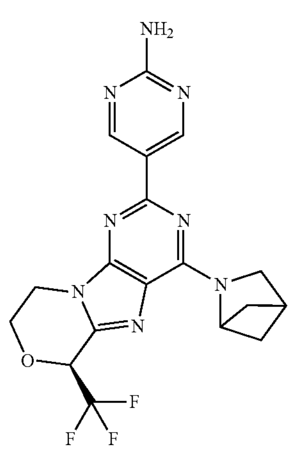 [SMILES: Nc1ncc(-c2nc(N3CC4CC3C4)c3nc4n(c3n2)CCO[C@@H]4C(F)(F)F)cn1] | 0.866 |
| 100 | | 0.225 |
| 101 | | 0.102 |
| 102 | | 0.157 |

TABLE 2-continued

| Ex. | Structure | DLK HTRF K$_i$ (μm) |
|---|---|---|
| 103 | | 1 |
| 104 | | 0.297 |
| 105 | | 0.211 |
| 106 | 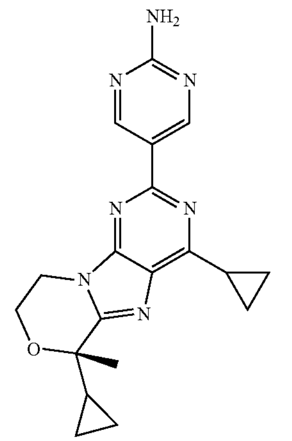 [SMILES: C[C@@]1(C2CC2)OCCn2c1nc1c(C3CC3)nc(-c3cnc(N)nc3)nc12] | 0.385 |
| 107 | 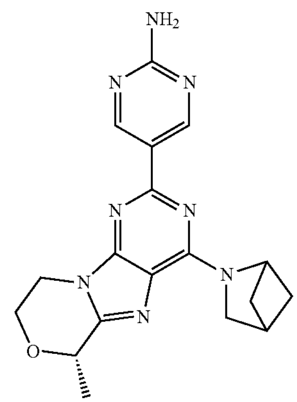 [SMILES: C[C@@H]1OCCn2c1nc1c(N3CC4CC3C4)nc(-c3cnc(N)nc3)nc12] | 0.0597 |
| 108 | 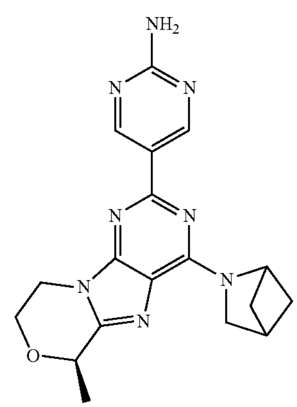 [SMILES: C[C@H]1OCCn2c1nc1c(N3CC4CC3C4)nc(-c3cnc(N)nc3)nc12] | 0.239 |
| 109 | 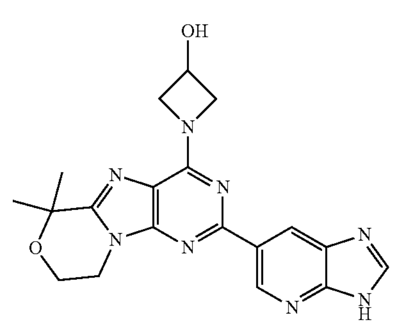 [SMILES: CC1(C)OCCn2c1nc1c(N3CC(O)C3)nc(-c3cnc4[nH]cnc4c3)nc12] | 0.379 |

TABLE 2-continued

| Ex. | Structure | DLK HTRF $K_i$ (μm) |
|---|---|---|
| 110 | | 0.00125 |
| 111 | | 0.885 |
| 112 | | 0.458 |
| 113 | | 0.521 |
| 114 | 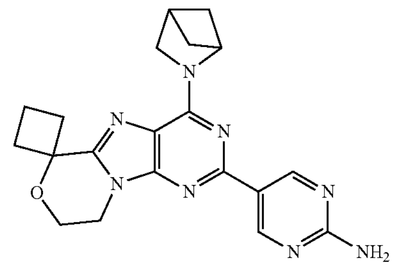 [SMILES: Nc1ncc(-c2nc(N3CC4CC3C4)c3nc4n(c3n2)CCOC42CCC2)cn1] | 0.0521 |
| 115 | 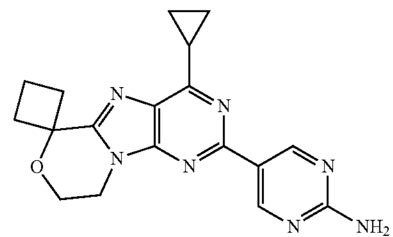 [SMILES: Nc1ncc(-c2nc(C3CC3)c3nc4n(c3n2)CCOC42CCC2)cn1] | 0.226 |
| 116 | 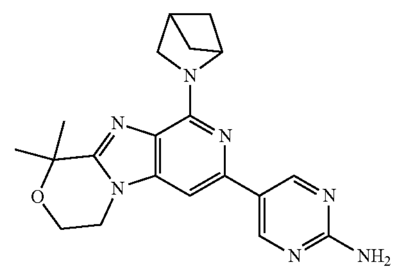 [SMILES: CC1(C)OCCn2c1nc1c(N3CC4CC3C4)nc(-c3cnc(N)nc3)cc12] | 0.0213 |
| 117 | 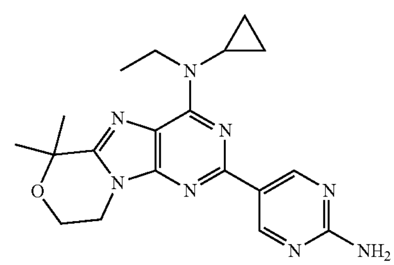 [SMILES: CCN(c1nc(-c2cnc(N)nc2)nc2c1nc1n2CCOC1(C)C)C1CC1] | 0.00039 |
| 118 | 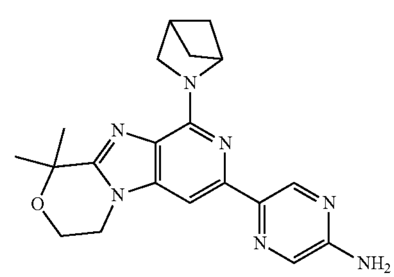 [SMILES: CC1(C)OCCn2c1nc1c(N3CC4CC3C4)nc(-c3cnc(N)cn3)cc12] | 1.2 |
| 119 | 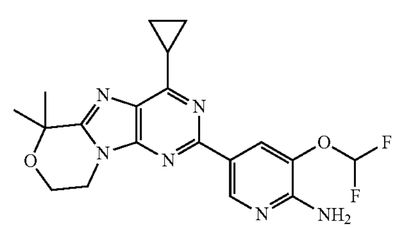 [SMILES: CC1(C)OCCn2c1nc1c(C3CC3)nc(-c3cnc(N)c(OC(F)F)c3)nc12] | 0.0343 |

TABLE 2-continued

| Ex. | Structure | DLK HTRF K$_i$ (μm) |
|---|---|---|
| 120 | 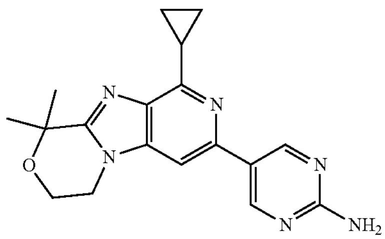 [SMILES: CC1(C)OCCn2c1nc1c(C3CC3)nc(-c3cnc(N)nc3)cc12] | 0.359 |
| 121 | 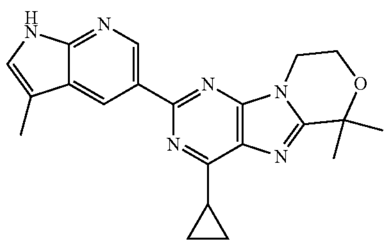 [SMILES: Cc1c[nH]c2ncc(-c3nc(C4CC4)c4nc5n(c4n3)CCOC5(C)C)cc12] | 0.00548 |
| 122 | 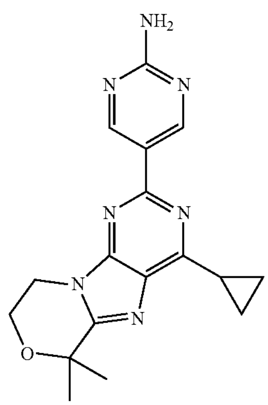 [SMILES: CC1(C)OCCn2c1nc1c(C3CC3)nc(-c3cnc(N)nc3)nc12] | 0.307 |
| 123 | 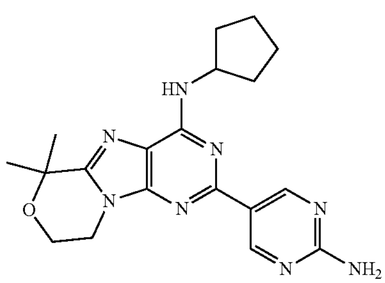 [SMILES: CC1(C)OCCn2c1nc1c(NC3CCCC3)nc(-c3cnc(N)nc3)nc12] | 0.0601 |
| 124 | 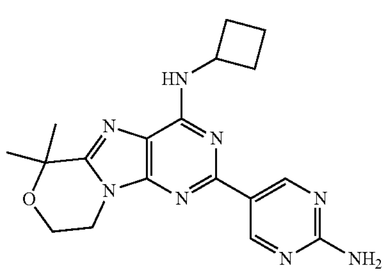 [SMILES: CC1(C)OCCn2c1nc1c(NC3CCC3)nc(-c3cnc(N)nc3)nc12] | 0.0739 |
| 125 | | 0.626 |
| 126 | | 0.264 |
| 127 | | 0.15 |
| 128 | | 0.0179 |

TABLE 2-continued

| Ex. | Structure | DLK HTRF $K_i$ (μm) |
|---|---|---|
| 129 | 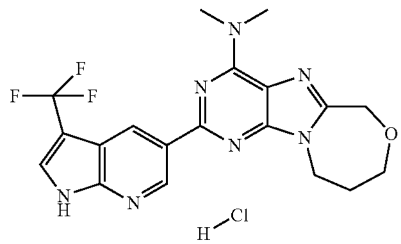 [SMILES: CN(C)c1nc(-c2cnc3[nH]cc(C(F)(F)F)c3c2)nc2c1nc1n2CCCOC1 ; Cl] | 0.00164 |
| 131 | 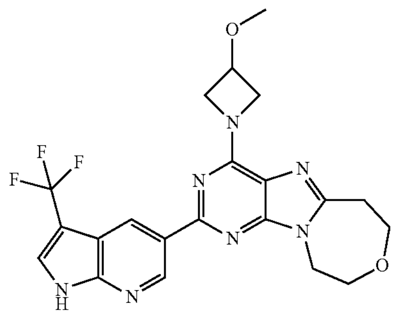 [SMILES: COC1CN(c2nc(-c3cnc4[nH]cc(C(F)(F)F)c4c3)nc3c2nc2n3CCOCC2)C1] | 0.0607 |
| 132 | 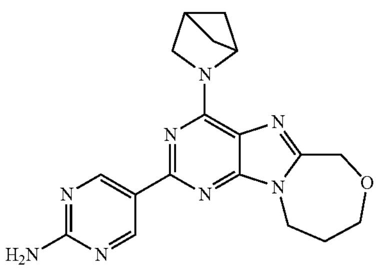 [SMILES: Nc1ncc(-c2nc(N3CC4CC3C4)c3nc4n(c3n2)CCCOC4)cn1] | 0.281 |
| 133 | 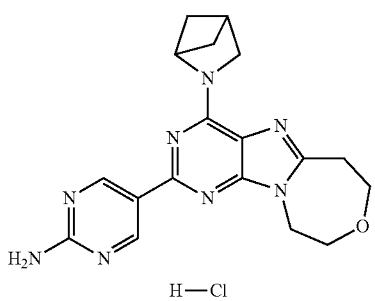 [SMILES: Nc1ncc(-c2nc(N3CC4CC3C4)c3nc4n(c3n2)CCOCC4)cn1 ; Cl] | 0.447 |
| 134 | 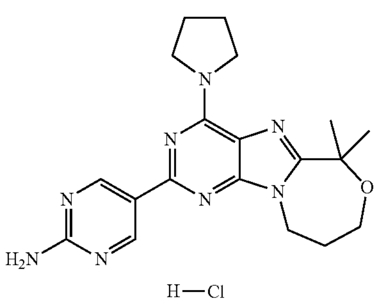 [SMILES: CC1(C)OCCCn2c1nc1c(N3CCCC3)nc(-c3cnc(N)nc3)nc12 ; Cl] | 0.21 |
| 135 | 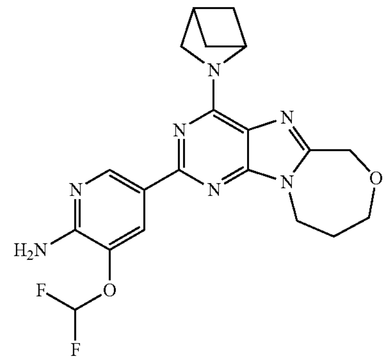 [SMILES: Nc1ncc(-c2nc(N3CC4CC3C4)c3nc4n(c3n2)CCCOC4)cc1OC(F)F] | 0.0308 |
| 136 | 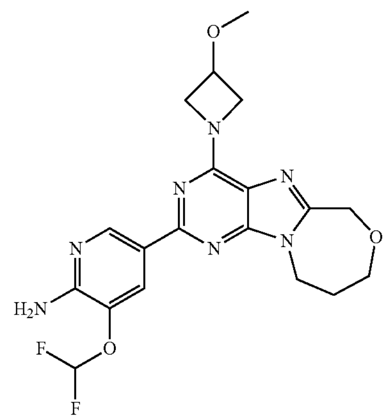 [SMILES: COC1CN(c2nc(-c3cnc(N)c(OC(F)F)c3)nc3c2nc2n3CCCOC2)C1] | 0.687 |
| 137 | 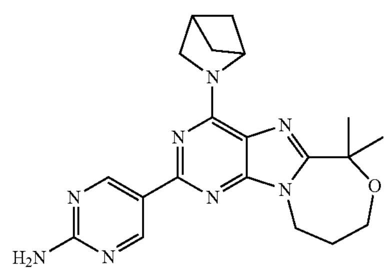 [SMILES: CC1(C)OCCCn2c1nc1c(N3CC4CC3C4)nc(-c3cnc(N)nc3)nc12] | 0.177 |
| 138 | 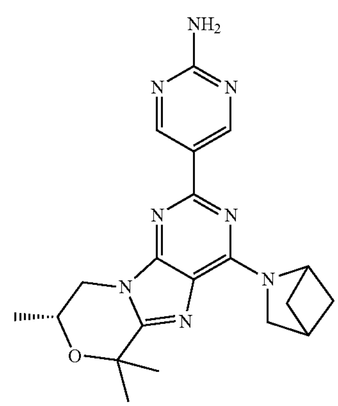 [SMILES: C[C@@H]1Cn2c(nc3c(N4CC5CC4C5)nc(-c4cnc(N)nc4)nc32)C(C)(C)O1] | 0.0825 |

TABLE 2-continued

| Ex. | Structure | DLK HTRF $K_i$ (μm) |
|---|---|---|
| 139 | | 0.149 |
| 140 | | 0.0727 |
| 141 | | 0.392 |
| 142 | | 0.216 |
| 143 | 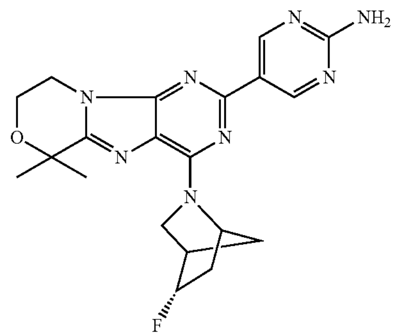 [SMILES: CC1(C)OCCn2c1nc1c(N3CC4CC3C[C@@H]4F)nc(-c3cnc(N)nc3)nc12] | 0.223 |
| 144 | 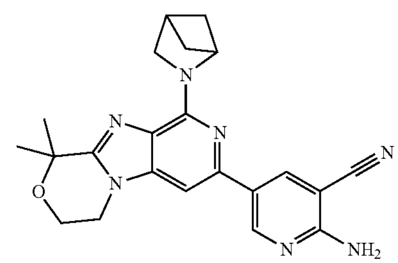 [SMILES: CC1(C)OCCn2c1nc1c(N3CC4CC3C4)nc(-c3cnc(N)c(C#N)c3)cc12] | 0.00223 |
| 145 | 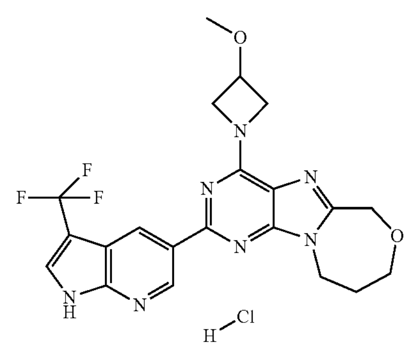 [SMILES: COC1CN(c2nc(-c3cnc4[nH]cc(C(F)(F)F)c4c3)nc3c2nc2n3CCCOC2)C1 ; Cl] | 0.00649 |
| 146 | 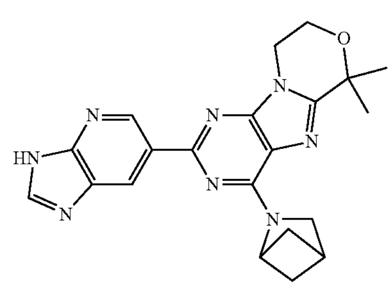 [SMILES: CC1(C)OCCn2c1nc1c(N3CC4CC3C4)nc(-c3cnc4[nH]cnc4c3)nc12] | 0.0322 |
| 147 | 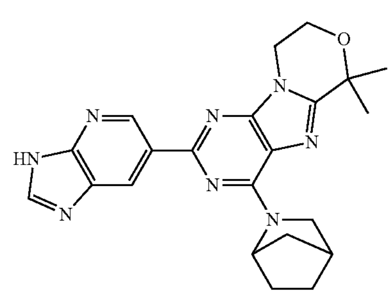 [SMILES: CC1(C)OCCn2c1nc1c(N3CC4CCC3C4)nc(-c3cnc4[nH]cnc4c3)nc12] | 0.0395 |

TABLE 2-continued

| Ex. | Structure | DLK HTRF K$_i$ (μm) |
|---|---|---|
| 148 | 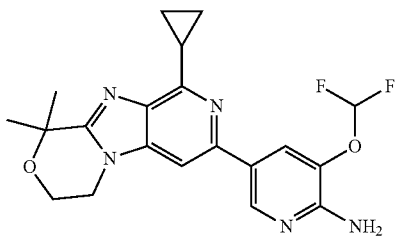 | 0.0569 |
| 149 | 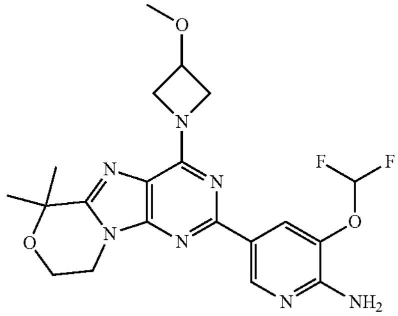 [SMILES: COC1CN(c2nc(-c3cnc(N)c(OC(F)F)c3)nc3c2nc2n3CCOC2(C)C)C1] | 0.0737 |
| 150 | 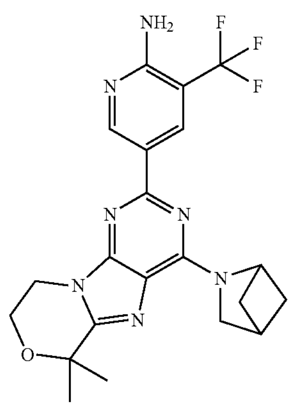 [SMILES: CC1(C)OCCn2c1nc1c(N3CC4CC3C4)nc(-c3cnc(N)c(C(F)(F)F)c3)nc12] | 0.112 |
| 151 | 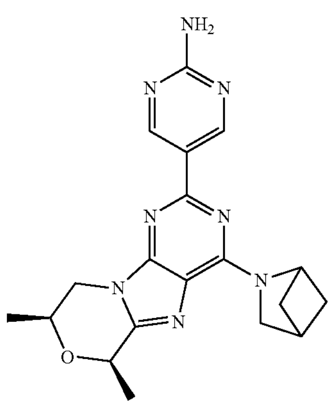 [SMILES: C[C@H]1Cn2c(nc3c(N4CC5CC4C5)nc(-c4cnc(N)nc4)nc32)[C@@H](C)O1] | 0.12 |
| 152 | 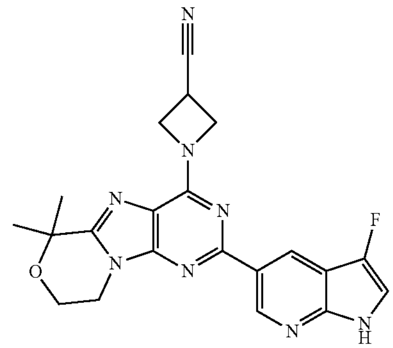 [SMILES: CC1(C)OCCn2c1nc1c(N3CC(C#N)C3)nc(-c3cnc4[nH]cc(F)c4c3)nc12] | 0.183 |
| 153 | 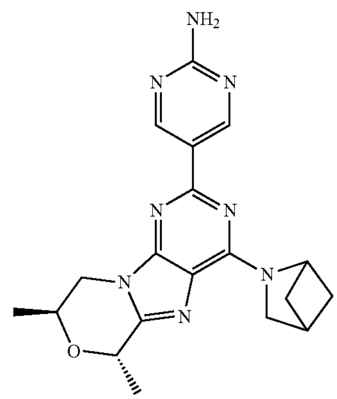 [SMILES: C[C@@H]1O[C@@H](C)Cn2c1nc1c(N3CC4CC3C4)nc(-c3cnc(N)nc3)nc12] | 0.261 |
| 154 | 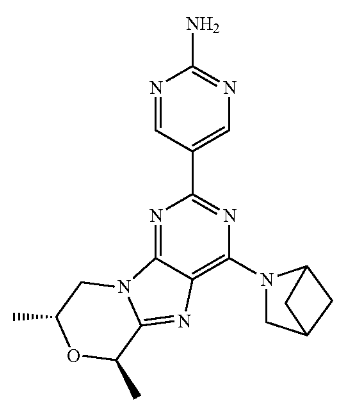 [SMILES: C[C@@H]1Cn2c(nc3c(N4CC5CC4C5)nc(-c4cnc(N)nc4)nc32)[C@@H](C)O1] | |
| 155 | 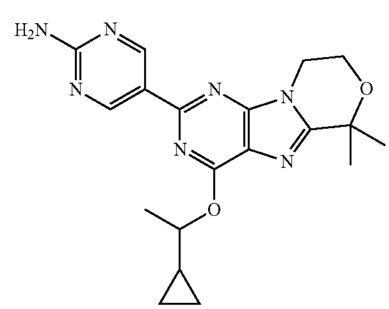 [SMILES: CC(Oc1nc(-c2cnc(N)nc2)nc2c1nc1n2CCOC1(C)C)C1CC1] | 1.2 |

TABLE 2-continued

| Ex. | Structure | DLK HTRF $K_i$ (μm) |
|---|---|---|
| 156 | 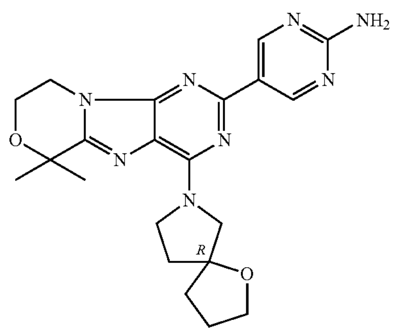 | 1.3 |
| 157 | 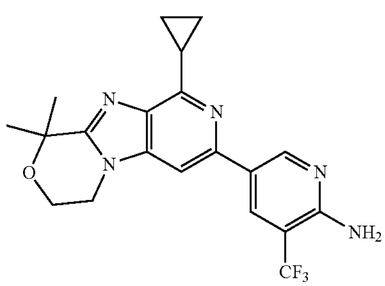 [SMILES: CC1(C)OCCn2c1nc1c(C3CC3)nc(-c3cnc(N)c(C(F)(F)F)c3)cc12] | |
| 158 | 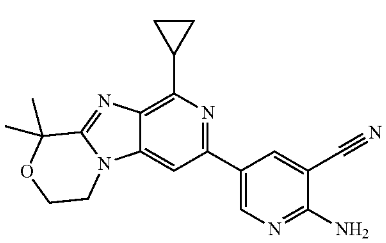 [SMILES: CC1(C)OCCn2c1nc1c(C3CC3)nc(-c3cnc(N)c(C#N)c3)cc12] | |
| 159 | 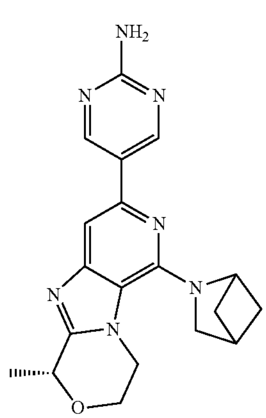 [SMILES: C[C@H]1OCCn2c1nc1cc(-c3cnc(N)nc3)nc(N3CC4CC3C4)c12] | |
| 160 | | |
| 161 | | |
| 162 | | |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I), or a pharmaceutically acceptable salt thereof:

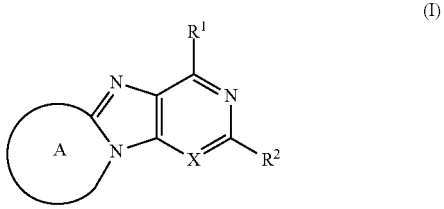

(I)

wherein:

A is a 6-10 membered heterocyclyl comprising one or more oxygen atoms, which heterocyclyl is optionally substituted with one or more groups independently selected from C$_{1-6}$alkyl, C$_{2-6}$alkenyl, C$_{2-6}$alkynyl, and C$_{3-6}$carbocyclyl, wherein any C$_{1-6}$alkyl, C$_{2-6}$alkenyl, C$_{2-6}$alkynyl, and C$_{3-6}$carbocyclyl is optionally substituted with one or more groups independently selected from halo, C$_{1-6}$alkyl, C$_{2-6}$alkenyl, C$_{2-6}$alkynyl, and C$_{3-6}$carbocyclyl;

X is N or CH;

R$^1$ is selected from the group consisting of hydrogen, —O—R$^d$, —N(R$^d$)$_2$, a 3-12 membered carbocyclyl, -continued

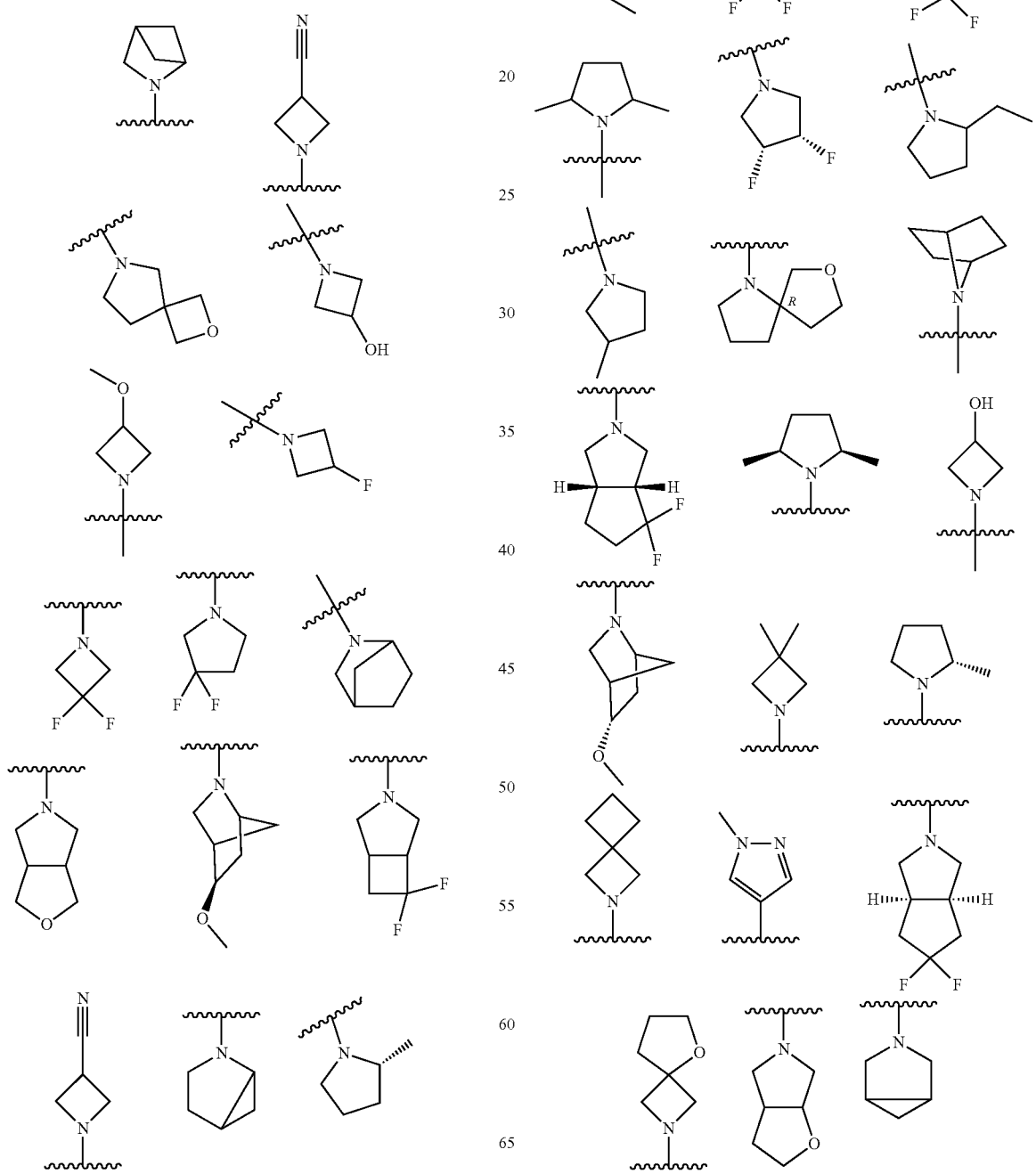

-continued

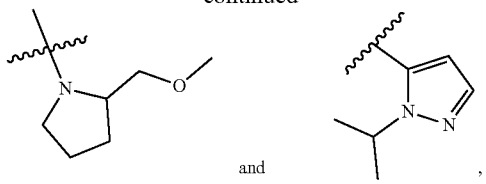

and which 3-12 membered carbocyclyl is optionally substituted with one or more groups independently selected from the group consisting of $C_{1-6}$alkyl, $C_{2-6}$alkenyl, $C_{2-6}$alkynyl, oxo, halo, —$NO_2$, —$N(R^b)_2$, —CN, —C(O)—$N(R^b)_2$, —O—$R^b$, —O—C(O)—$R^b$, —C(O) $R^b$, —C(O)—$OR^b$, and —$N(R^b)$—C(O)—$R^b$, wherein any $C_{1-6}$alkyl, $C_{2-6}$alkenyl, and $C_{2-6}$alkynyl, is optionally substituted with one or more groups independently selected from the group consisting of oxo, halo, —$NO_2$, —$N(R^b)_2$, —CN, —C(O)—$N(R^b)_2$, —O—$R^b$, —O—C(O)—$R^b$, —C(O)—$R^b$, —C(O)—$OR^b$, and —$N(R^b)$—C(O)—$R^b$;

each $R^b$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl is optionally substituted with one or more groups independently selected from the group consisting of oxo, halo, —$NO_2$, —$N(R^c)_2$, —CN, —C(O)—$N(R^c)_2$, —O—$R^c$, —O—C(O)—$R^c$, —C(O)—$R^c$, —C(O)—ORc, and —$N(R^c)$—C(O)—$R^c$; or two $R^b$ are taken together with the nitrogen to which they are attached to form a 3-8 membered heterocyclyl that is optionally substituted with one or more groups independently selected from the group consisting of oxo, halo and $C_{1-3}$alkyl that is optionally substituted with one or more groups independently selected from the group consisting of oxo and halo;

each $R^c$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl is optionally substituted with one or more groups independently selected from the group consisting of oxo, halo, amino, hydroxy, $C_{1-6}$alkoxy, 3-12 membered carbocyclyl, 3-12 membered heterocyclyl, and $C_{1-6}$alkyl that is optionally substituted with one or more groups independently selected from the group consisting of oxo and halo; or two $R^c$ are taken together with the nitrogen to which they are attached to form a 3-8 membered heterocyclyl that is optionally substituted with one or more groups independently selected from the group consisting of oxo, halo, and $C_{1-3}$alkyl that is optionally substituted with one or more groups independently selected from the group consisting of oxo and halo;

each $R^d$ is independently selected from the group consisting of hydrogen, $C_{1-6}$alkyl, $C_{2-6}$alkenyl, $C_{2-6}$alkynyl, 3-12 membered carbocyclyl, and 3-12 membered heterocyclyl, wherein each $C_{1-6}$alkyl, $C_{2-6}$alkenyl, $C_{2-6}$alkynyl, 3-12 membered carbocyclyl, and 3-12 membered heterocyclyl, is optionally substituted with one or more groups independently selected from the group consisting of oxo, halo, $C_{3-6}$carbocyclyl, —$NO_2$, —$N(R^c)_2$, —CN, —C(O)—$N(R^c)_2$, —O—$R^c$, —O—C(O)—$R^c$, —C(O) $R^c$, —C(O)—ORc, and —$N(R^c)$—C(O)—$R^c$;

$R^2$ is a 3-12 membered heterocyclyl, which 3-12 membered heterocyclyl is optionally substituted with one or more groups independently selected from the group consisting of $C_{1-6}$alkyl, $C_{2-6}$alkenyl, $C_{2-6}$alkynyl, $C_{3-6}$carbocyclyl, oxo, halo, —$NO_2$, —$N(R^e)_2$, —CN, —C(O)—$N(R^e)_2$, —O—$R^e$, —O—C(O)—$R^e$, —C(O)—$R^e$, —C(O)—$OR^e$, and —$N(R^e)$—C(O)—$R^e$, wherein any $C_{1-6}$alkyl, $C_{2-6}$alkenyl, $C_{3-6}$carbocyclyl, and $C_{2-6}$alkynyl, is optionally substituted with one or more groups independently selected from the group consisting of oxo, halo, —$NO_2$, —$N(R^e)_2$, —CN, —C(O)—$N(R^e)_2$, —O—$R^e$, —O—C(O)—$R^e$, —C(O)—$R^e$, —C(O)—ORe, and —$N(R^e)$—C(O)—$R^e$;

each $R^e$ is independently selected from the group consisting of hydrogen, $C_{1-6}$alkyl, $C_{2-6}$alkenyl, $C_{2-6}$alkynyl, $C_{1-6}$alkoxy, 3-12 membered carbocyclyl, and 3-12 membered heterocyclyl, wherein each $C_{1-6}$alkyl, $C_{2-6}$alkenyl, $C_{2-6}$alkynyl, $C_{1-6}$alkoxy, 3-12 membered carbocyclyl, and 3-12 membered heterocyclyl is optionally substituted with one or more groups independently selected from the group consisting of oxo, halo, —$NO_2$, —$N(R^f)_2$, —CN, —C(O)—$N(R^f)_2$, —O—$R^f$, —O—C(O)—$R^f$, —C(O)—$R^f$, —C(O)—$OR^f$, —$N(R^f)$—C(O)—$R^f$, and $C_{3-6}$carbocyclyl that is optionally substituted with one or more groups independently selected from the group consisting of oxo, halo and $C_{1-3}$alkyl that is optionally substituted with one or more groups independently selected from the group consisting of oxo and halo; or two $R^e$ are taken together with the nitrogen to which they are attached to form a 3-8 membered heterocyclyl that is optionally substituted with one or more groups independently selected from the group consisting of oxo, halo and $C_{1-3}$alkyl that is optionally substituted with one or more groups independently selected from the group consisting of oxo and halo; and each $R^f$ is independently selected from the group consisting of hydrogen, $C_{1-6}$alkyl, $C_{2-6}$alkenyl, $C_{2-6}$alkynyl, $C_{1-6}$alkoxy, 3-12 membered carbocyclyl, and 3-12 membered heterocyclyl, wherein each $C_{1-6}$alkyl, $C_{2-6}$alkenyl, $C_{2-6}$alkynyl, $C_{1-6}$alkoxy, 3-12 membered carbocyclyl, and 3-12 membered heterocyclyl is optionally substituted with one or more groups independently selected from the group consisting of oxo, halo, amino, hydroxy, $C_{1-6}$alkoxy, 3-12 membered carbocyclyl, 3-12 membered heterocyclyl, and $C_{1-6}$alkyl that is optionally substituted with one or more groups independently selected from the group consisting of oxo and halo; or two $R^f$ are taken together with the nitrogen to which they are attached to form a 3-8 membered heterocyclyl that is optionally substituted with one or more groups independently selected from the group consisting of oxo, halo and $C_{1-3}$alkyl that is optionally substituted with one or more groups independently selected from the group consisting of oxo and halo.

2. The compound of claim 1, which is selected from the group consisting of:

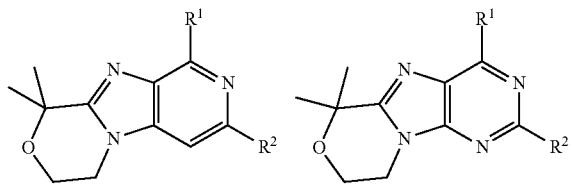

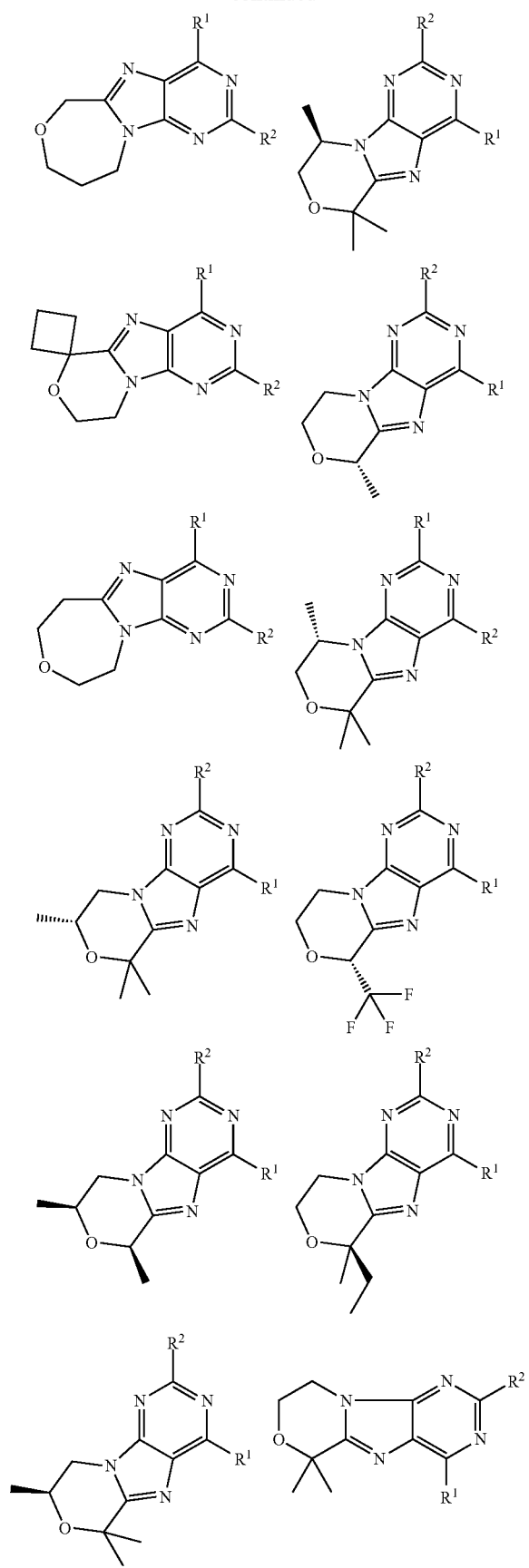
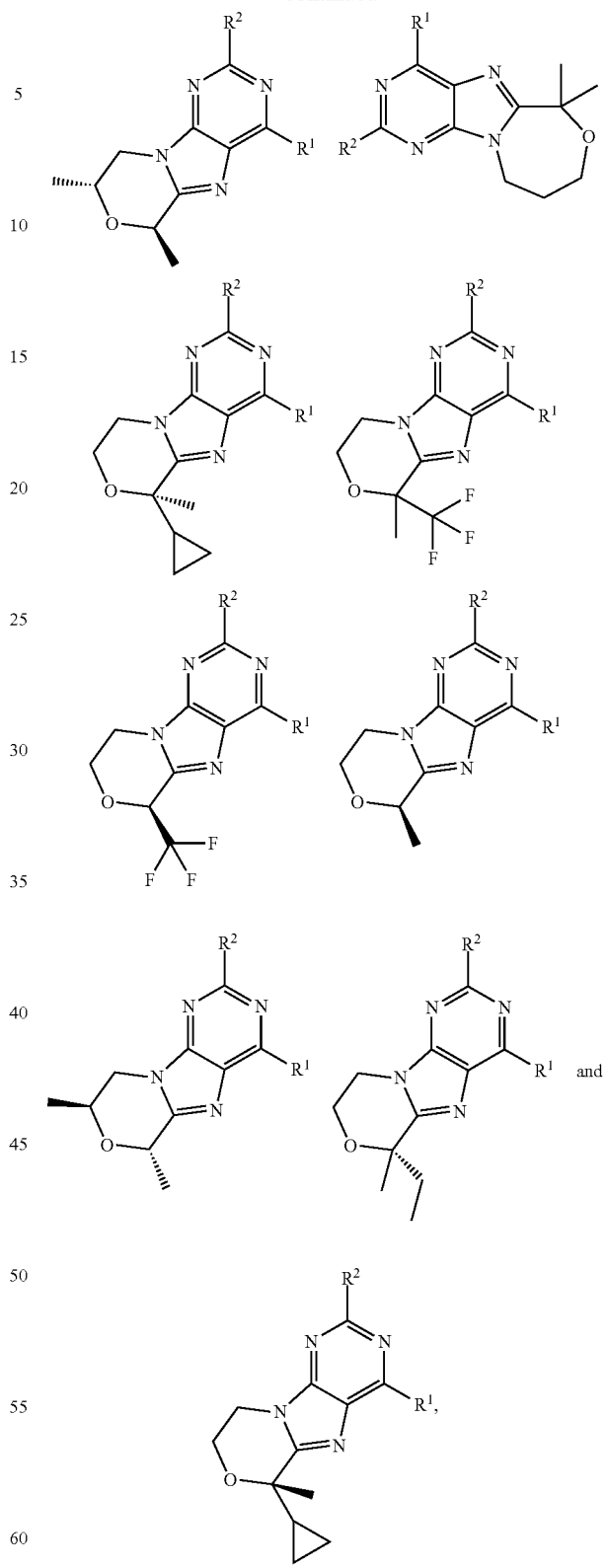
or a pharmaceutically acceptable salt thereof.
3. The compound of claim 1, or a pharmaceutically acceptable salt thereof, wherein R¹ is selected from the group consisting of:

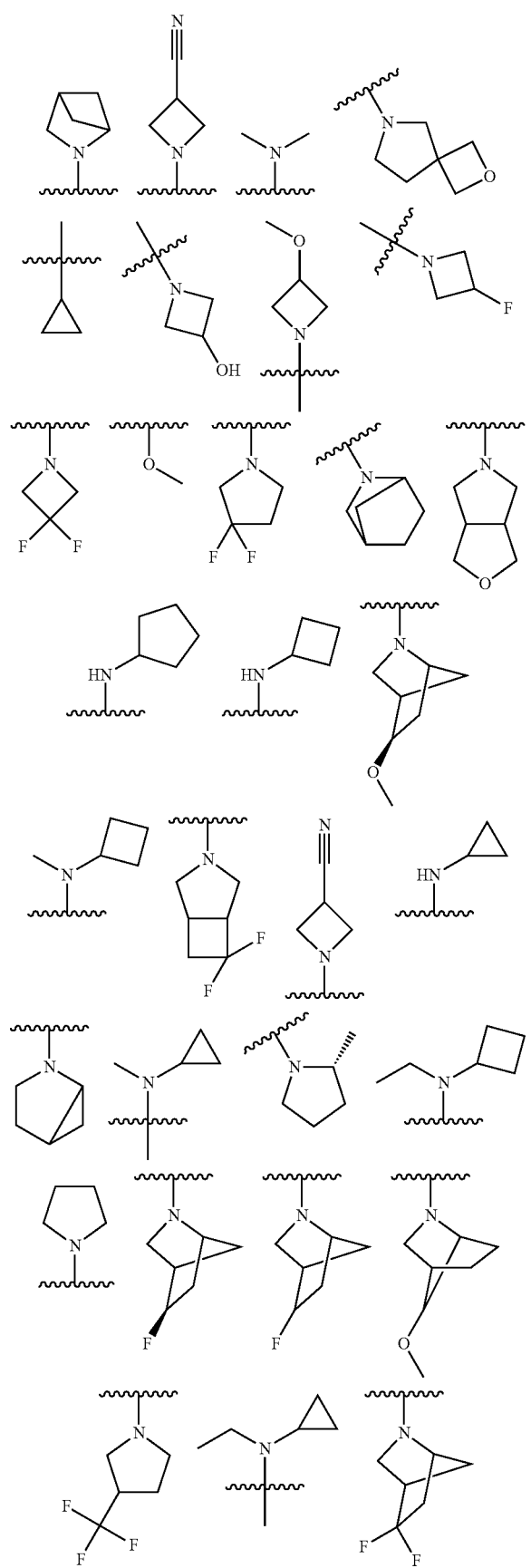
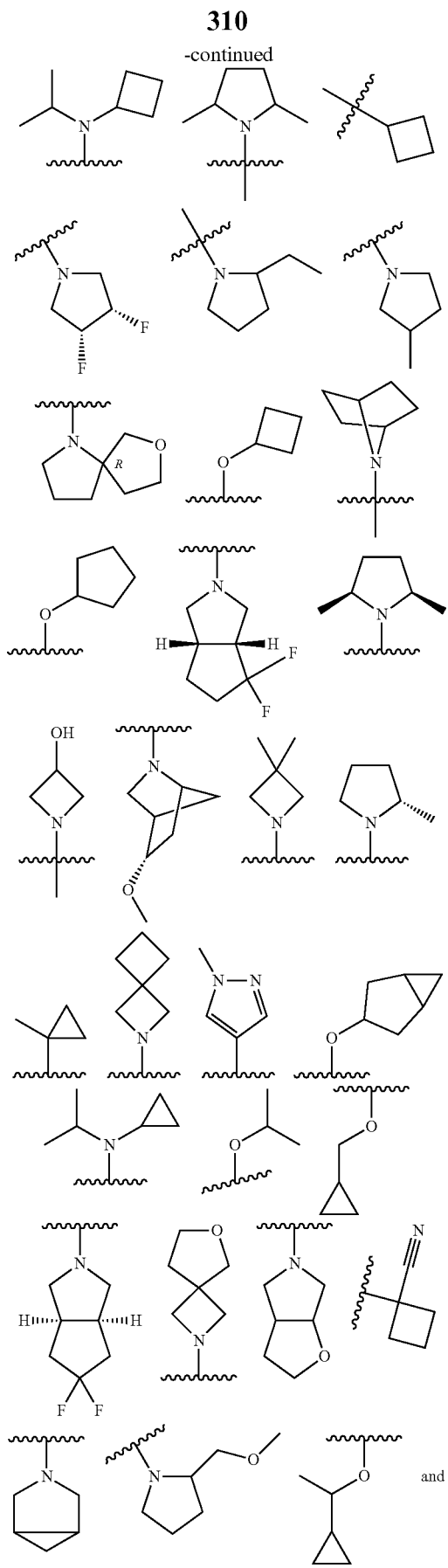

-continued
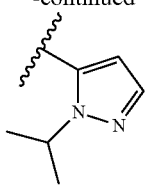
4. The compound of claim 1, or a pharmaceutically acceptable salt thereof, wherein R¹ is selected from the group consisting of:
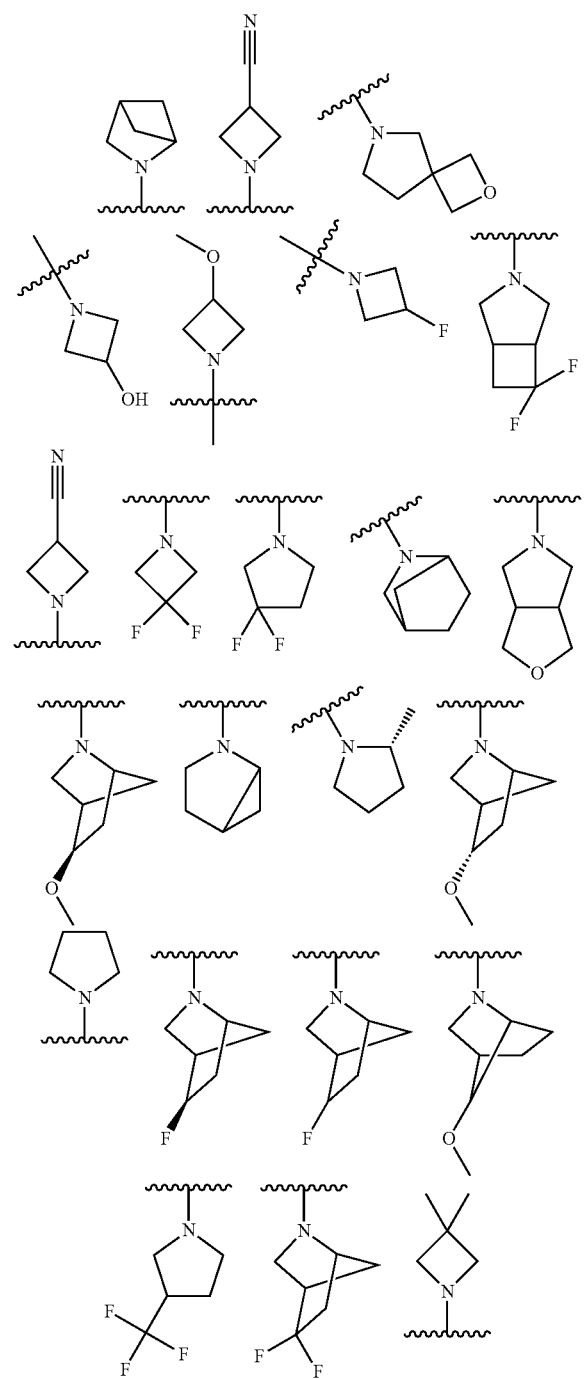
-continued
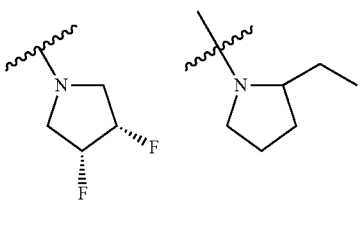
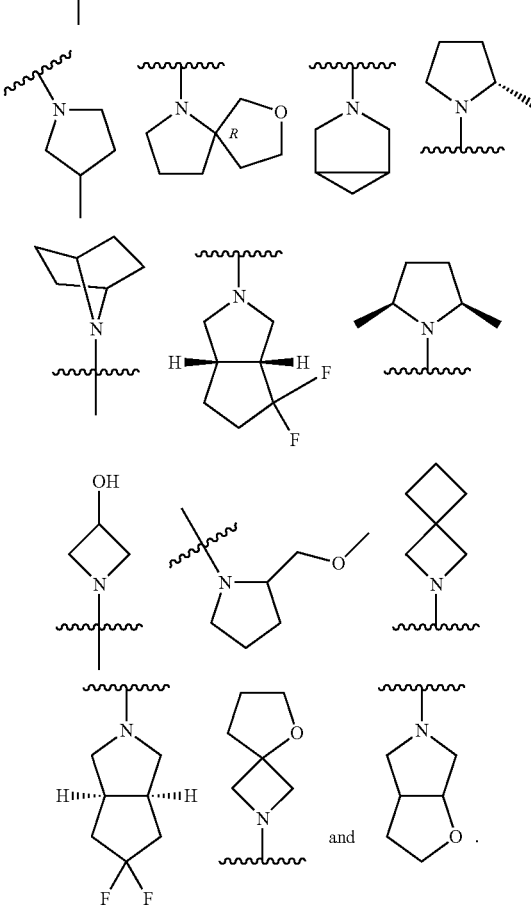
and
5. The compound of claim 1, or a pharmaceutically acceptable salt thereof, wherein R¹ is selected from the group consisting of:
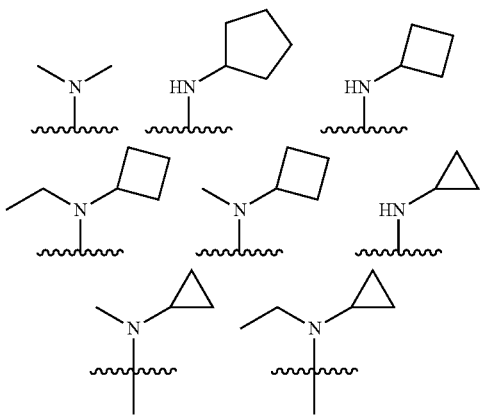

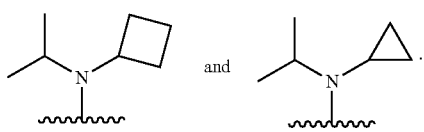
6. The compound of claim 1, or a pharmaceutically acceptable salt thereof, wherein R¹ is selected from the group consisting of:
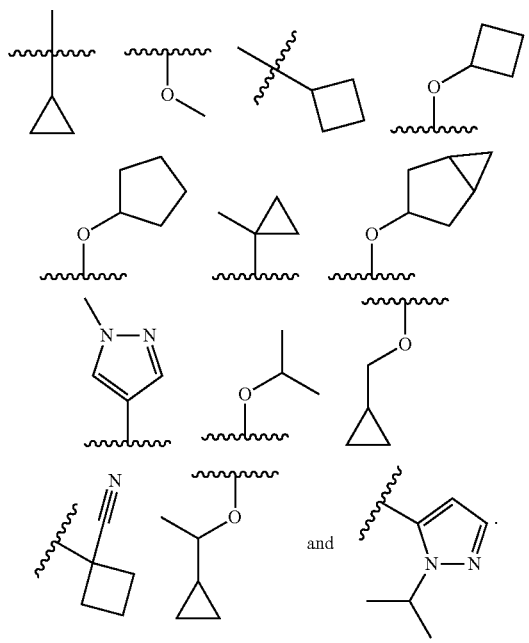
7. The compound of claim 1, or a pharmaceutically acceptable salt thereof, wherein R² is selected from the group consisting of:
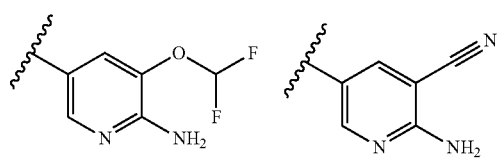
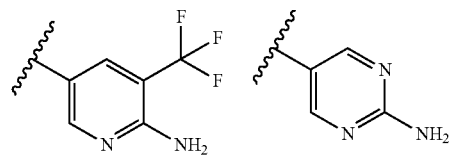
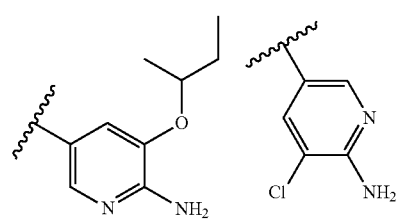
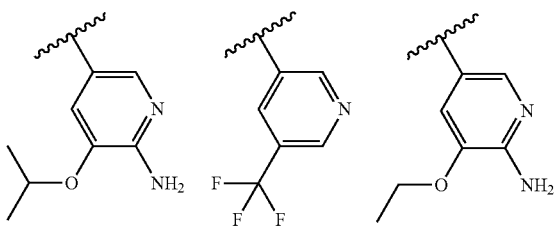
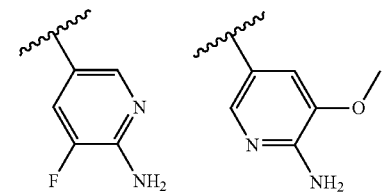
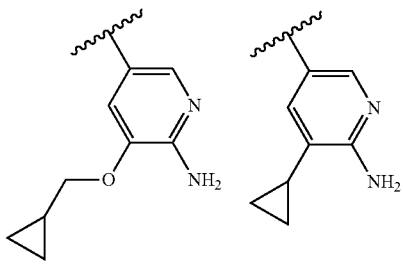
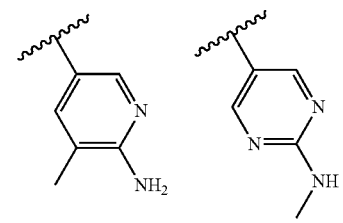
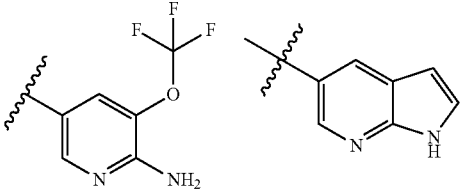
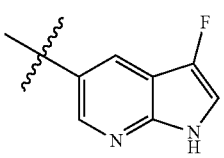
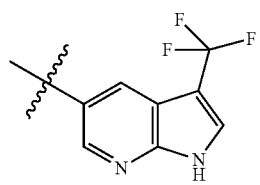
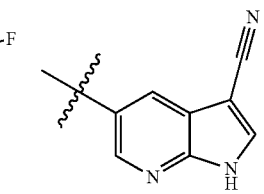
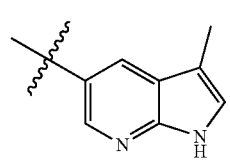
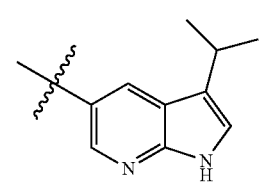

-continued

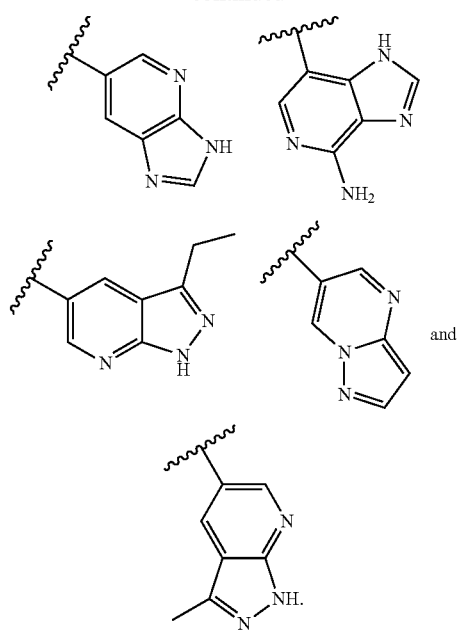

8. The compound of claim 1, or a pharmaceutically acceptable salt thereof, wherein R² is selected from the group consisting of:

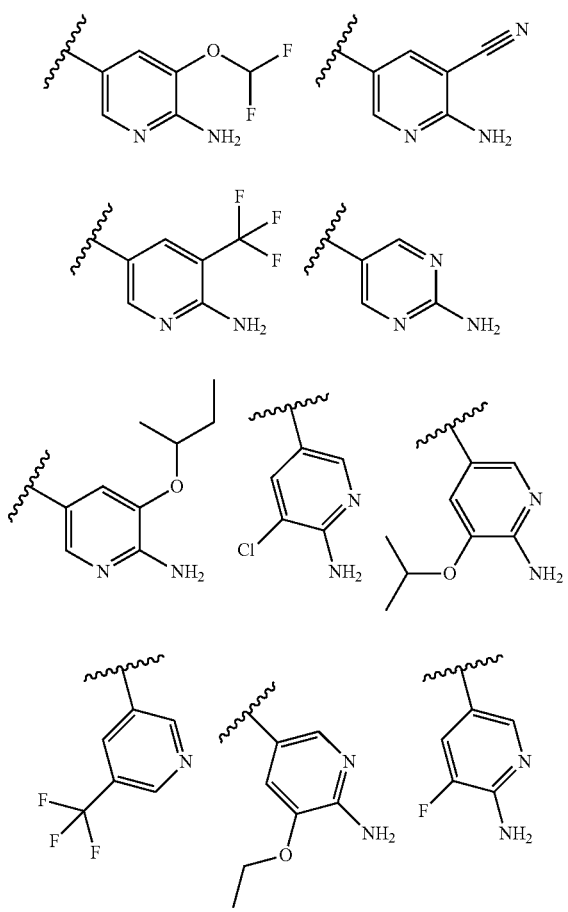

-continued

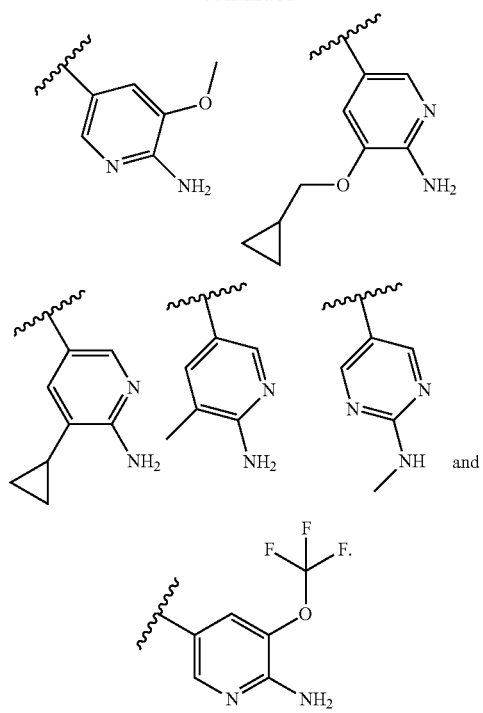

9. The compound of claim 1, or a pharmaceutically acceptable salt thereof, wherein R² is selected from the group consisting of:

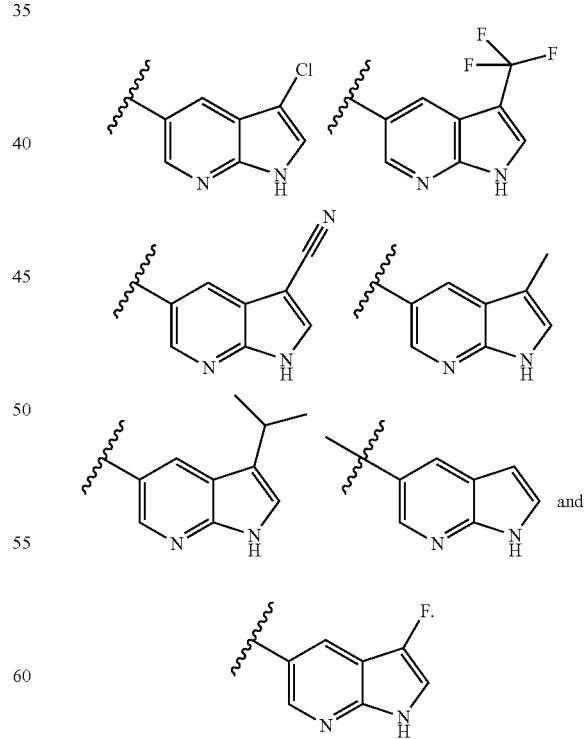

10. The compound of claim 1, or a pharmaceutically acceptable salt thereof, wherein R² is selected from the group consisting of:

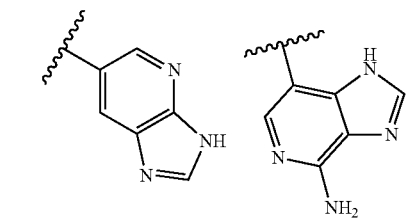

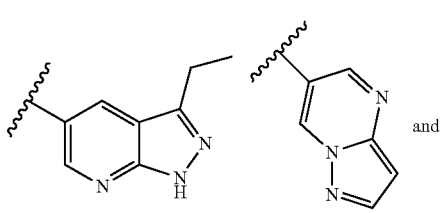 and

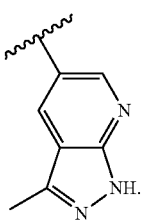

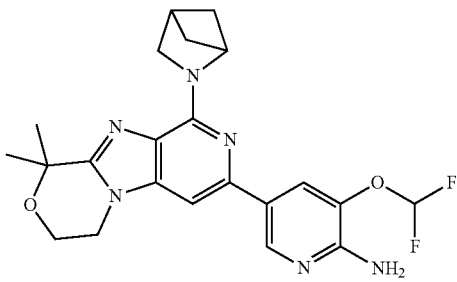

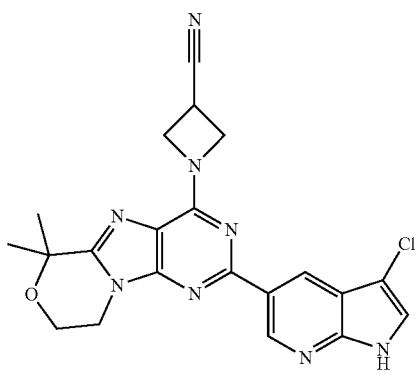

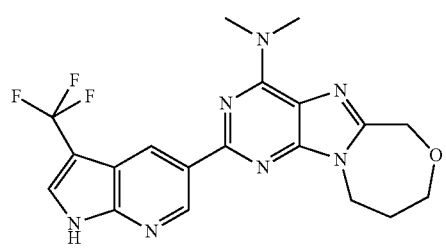

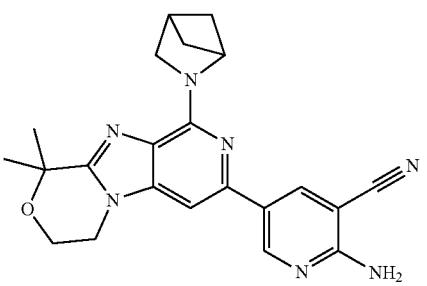

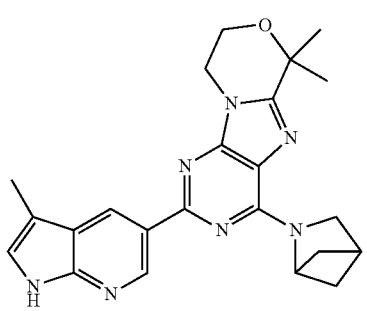

11. The compound of claim 1, or a pharmaceutically acceptable salt thereof, wherein A is a 6-, 7-, or 8-membered heterocyclyl comprising one oxygen atom, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-6}$alkenyl, $C_{2-6}$alkynyl, and $C_{3-6}$carbocyclyl.

12. The compound of claim 1, or a pharmaceutically acceptable salt thereof, wherein A is a 6-membered heterocyclyl comprising one oxygen atom, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-6}$alkenyl, $C_{2-6}$alkynyl, and $C_{3-6}$carbocyclyl.

13. The compound of claim 1, or a pharmaceutically acceptable salt thereof, wherein A is a 7-membered heterocyclyl comprising one oxygen atom, which heterocyclyl is optionally substituted with one or more groups independently selected from $C_{1-6}$alkyl, $C_{2-6}$alkenyl, $C_{2-6}$alkynyl, and $C_{3-6}$carbocyclyl, wherein any $C_{1-6}$alkyl, $C_{2-6}$alkenyl, $C_{2-6}$alkynyl, and $C_{3-6}$carbocyclyl is optionally substituted with one or more groups independently selected from halo, $C_{1-6}$alkyl, $C_{2-6}$alkenyl, $C_{2-6}$alkynyl, and $C_{3-6}$carbocyclyl.

14. The compound of claim 1 that is selected from the group consisting of:

319
-continued
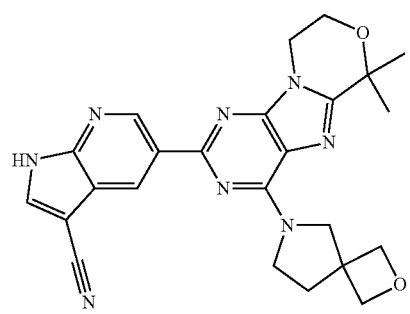
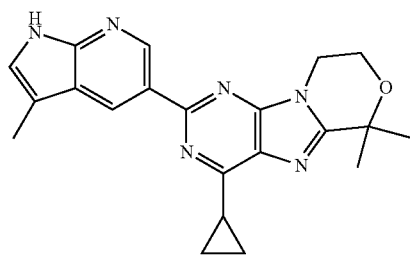
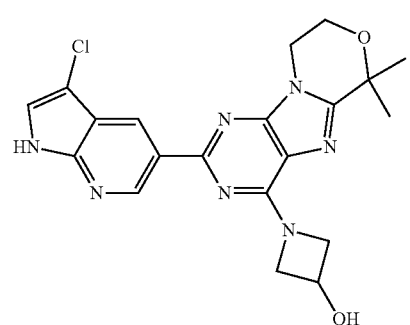
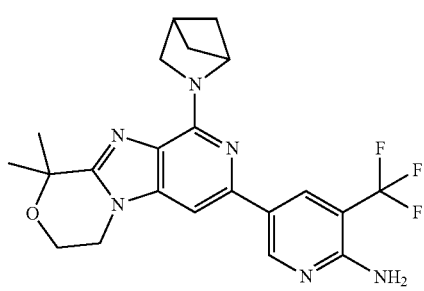
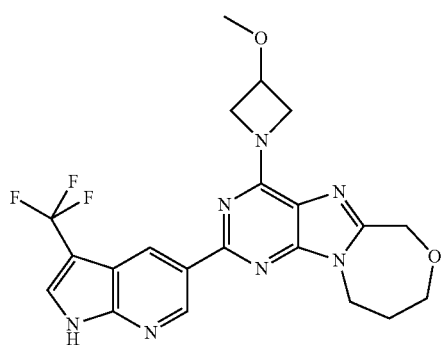
320
-continued
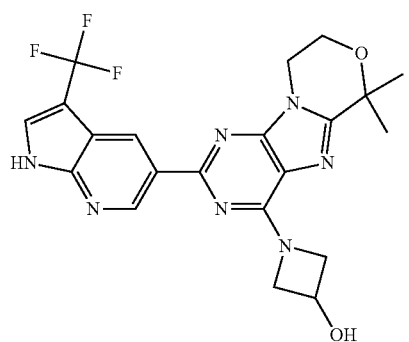
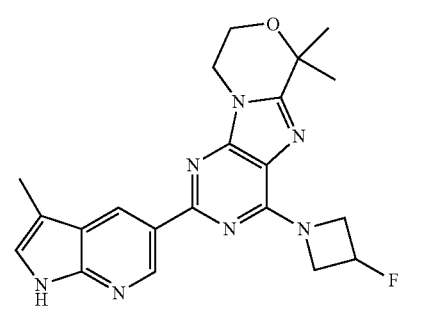
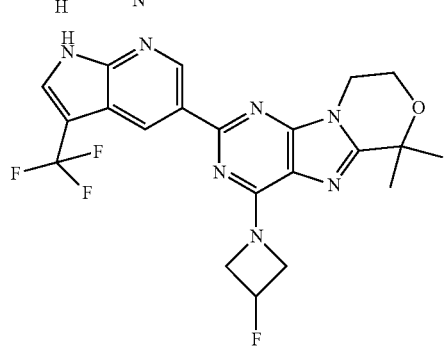
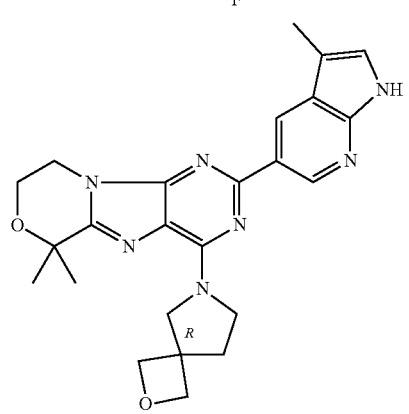
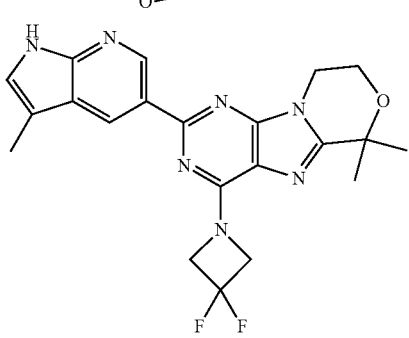

321
-continued
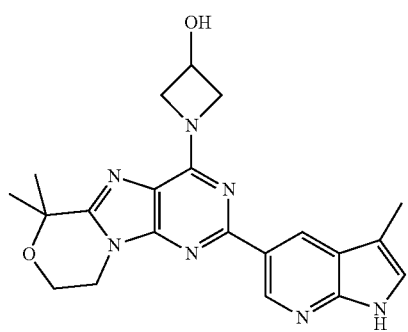
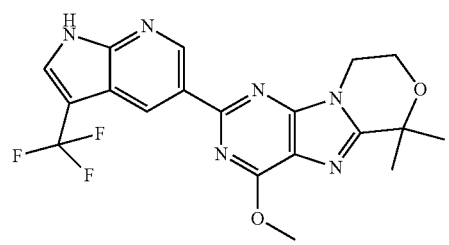
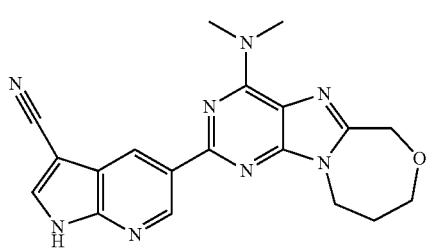
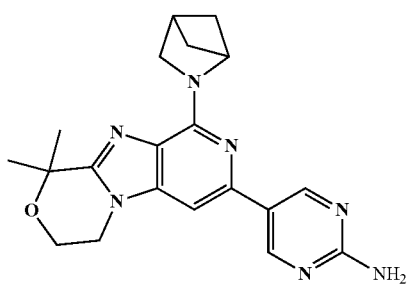
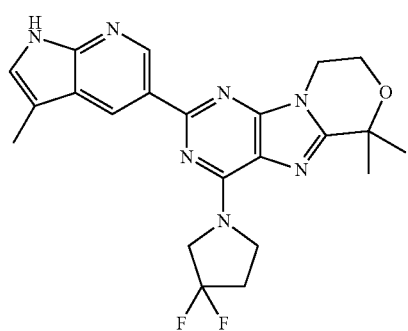
322
-continued
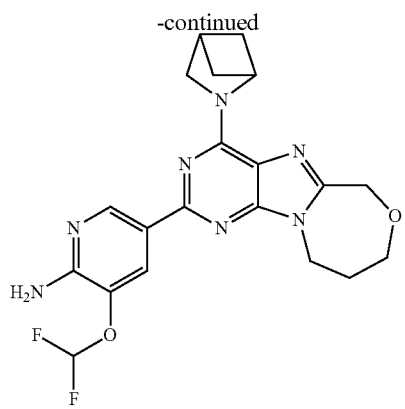
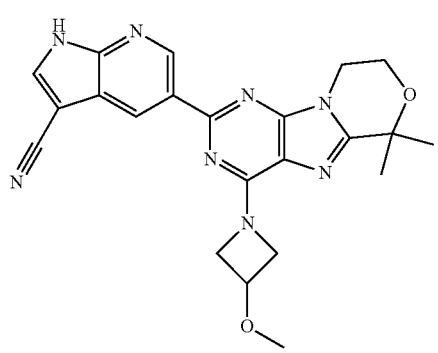
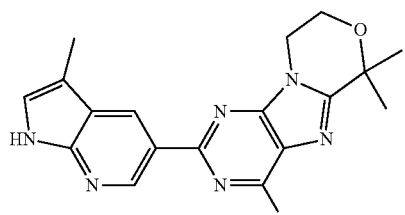
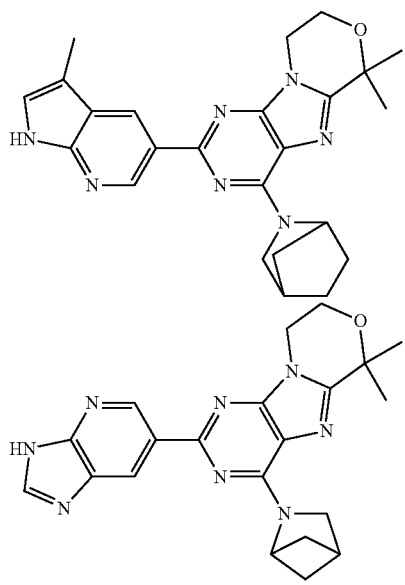
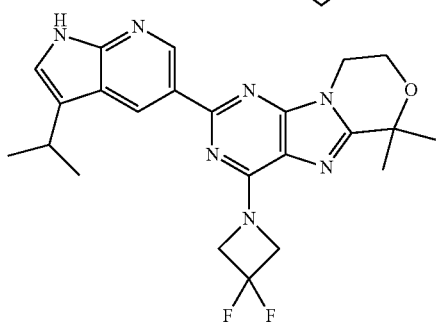

323
-continued
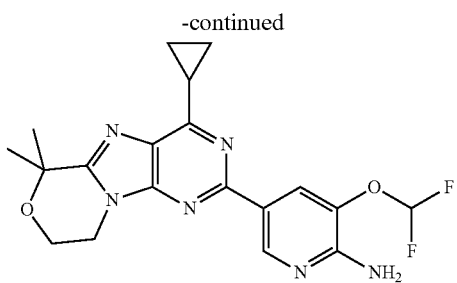
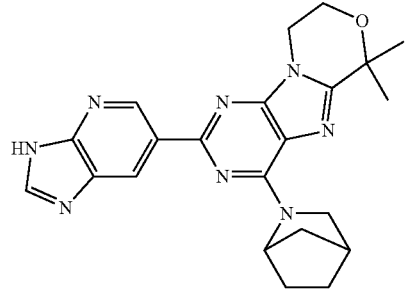
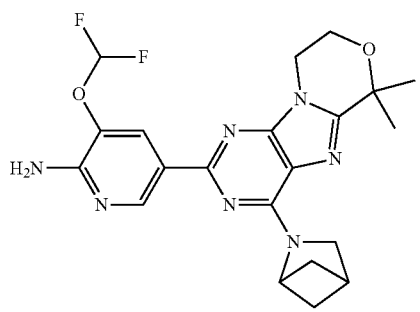
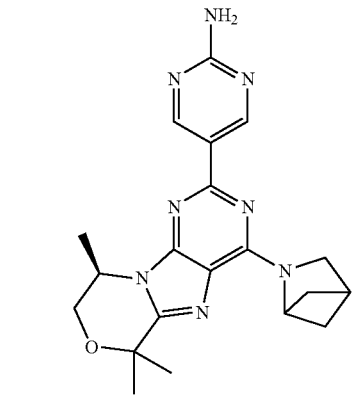
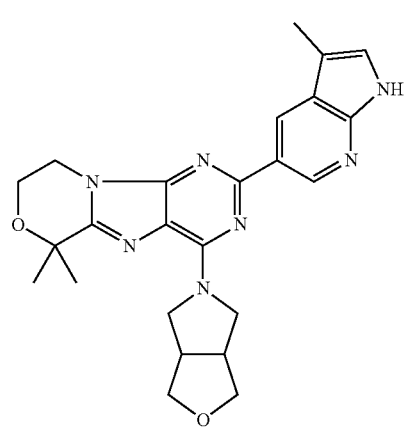
324
-continued
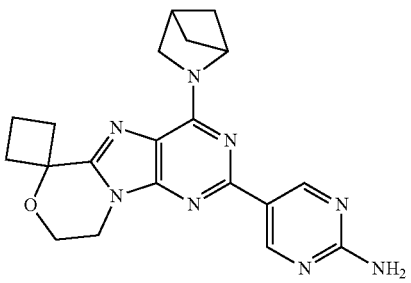
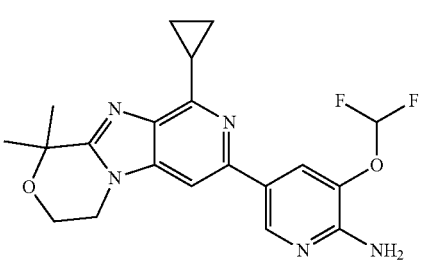
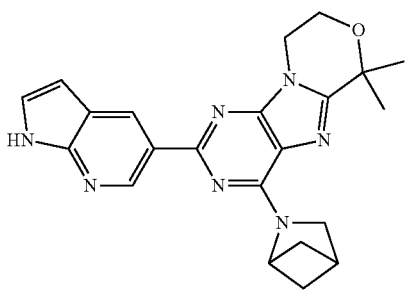
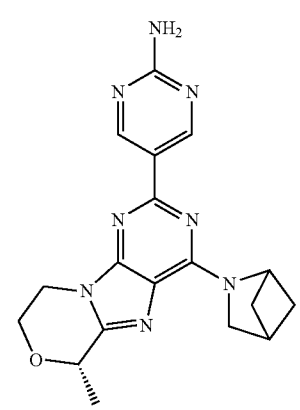
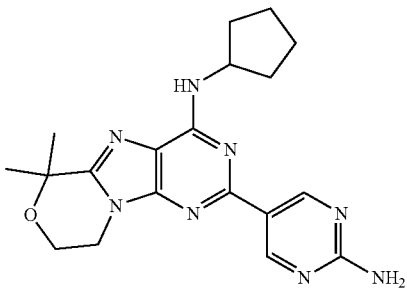

325
-continued
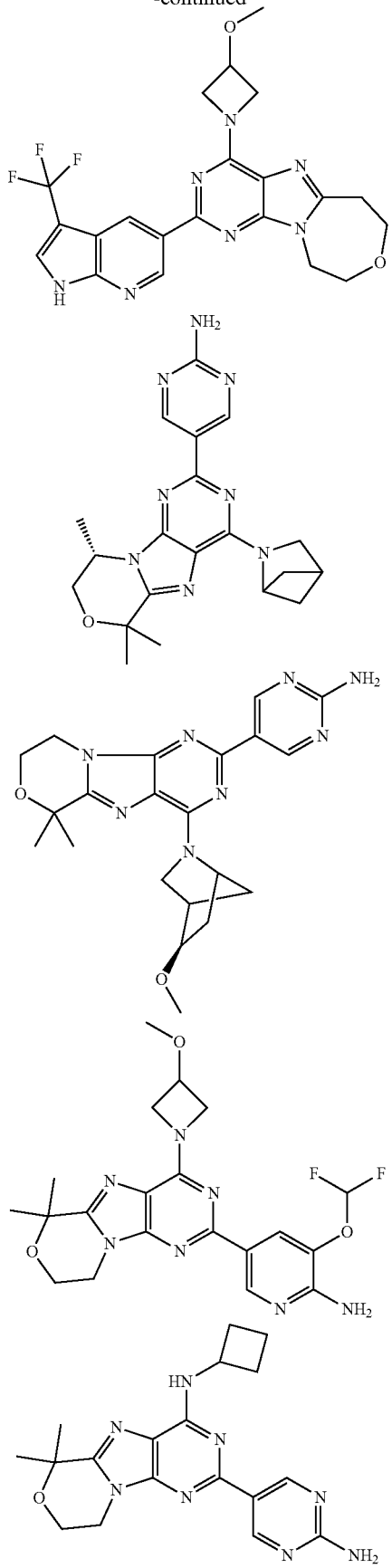
326
-continued
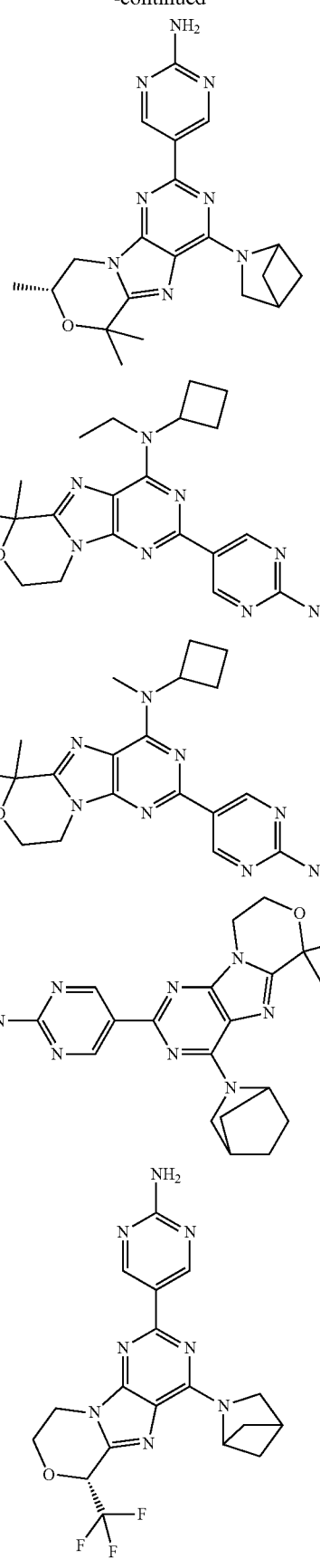

327
-continued
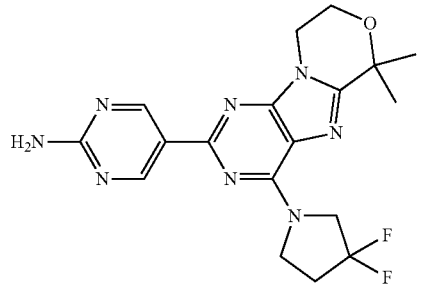
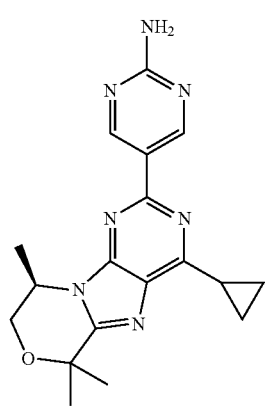
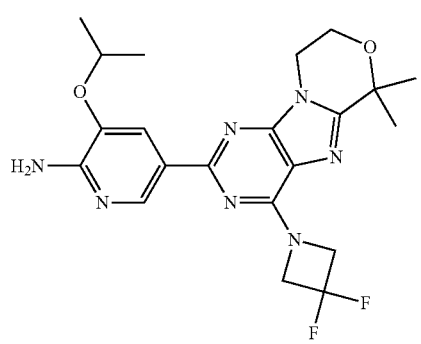
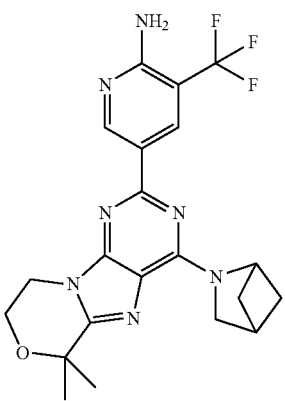
328
-continued
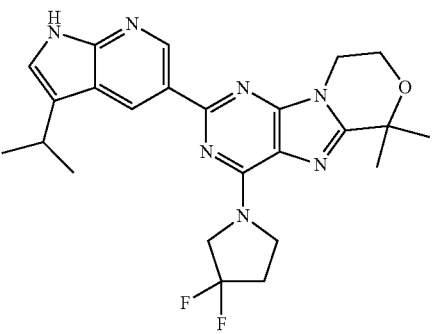
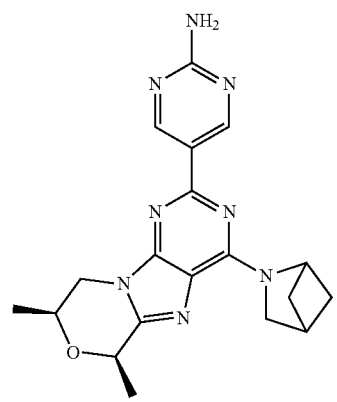
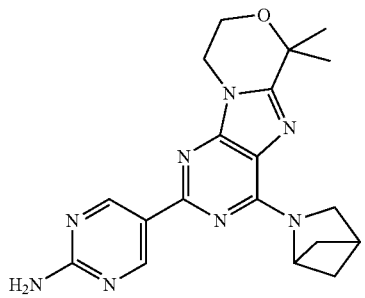
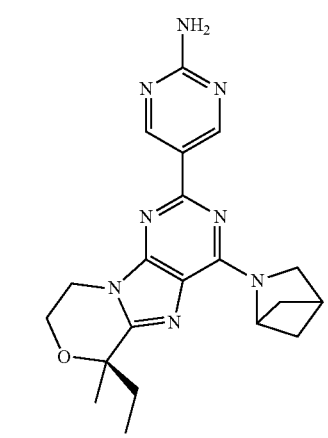

329
-continued
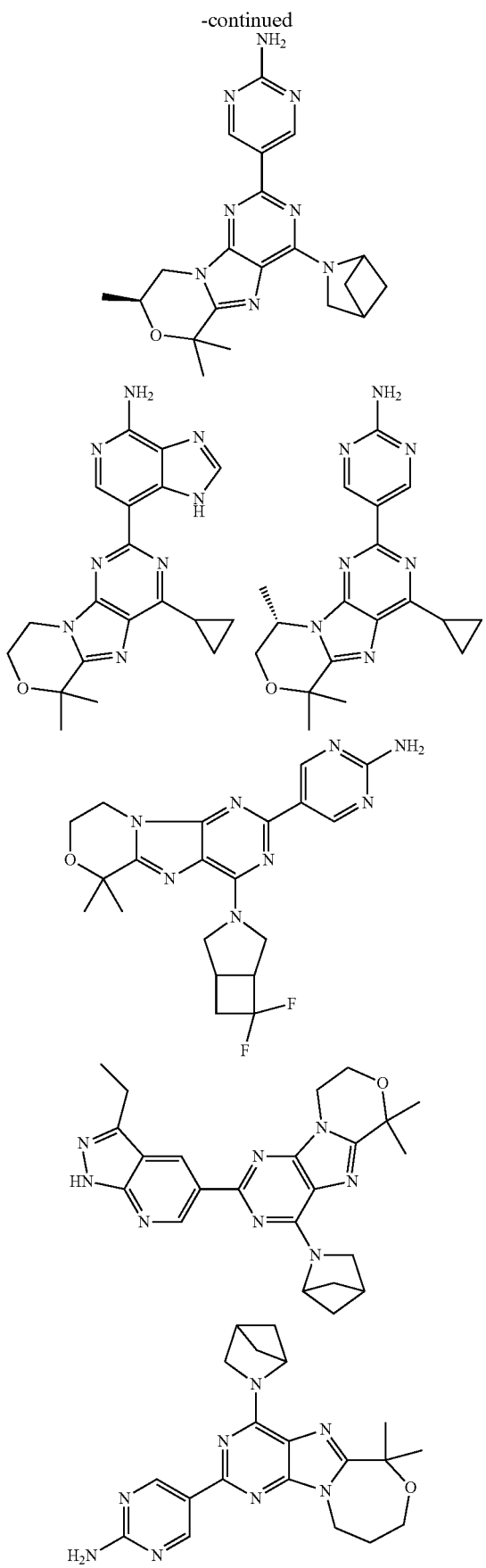
330
-continued
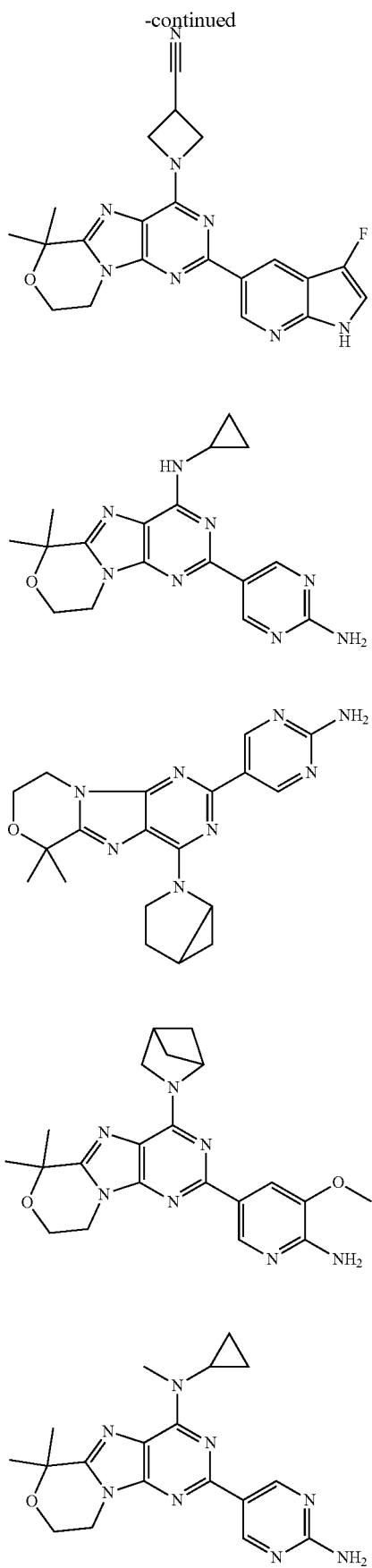

331
-continued
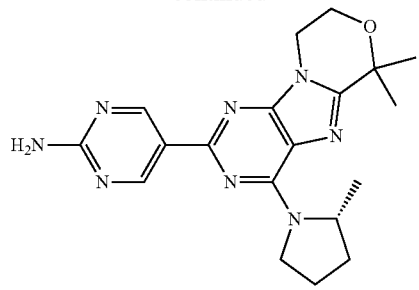
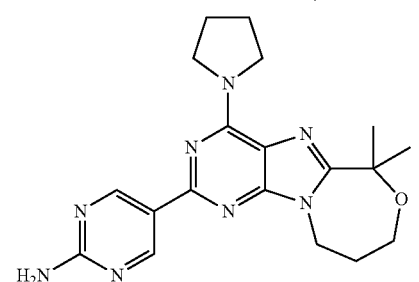
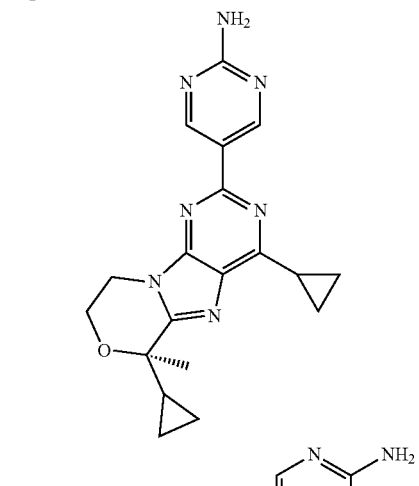
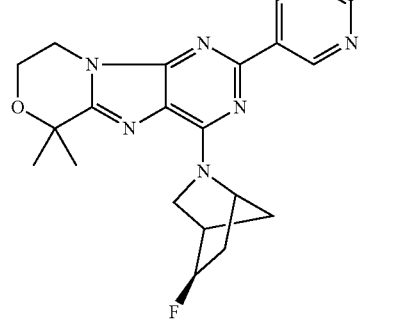
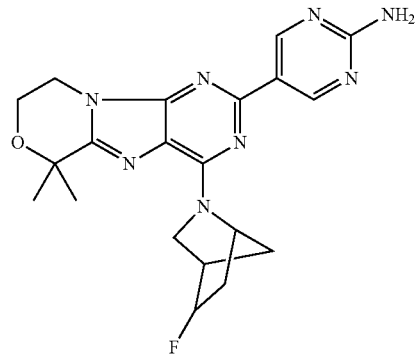
332
-continued
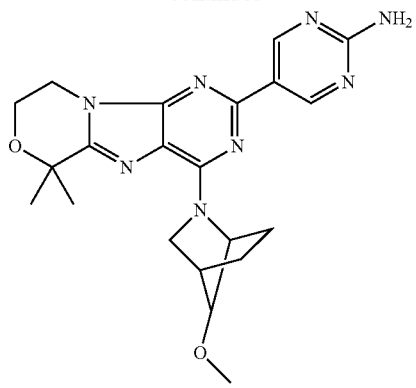
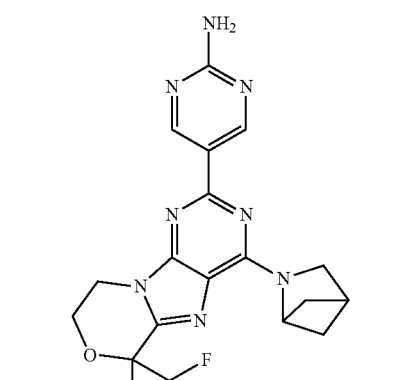
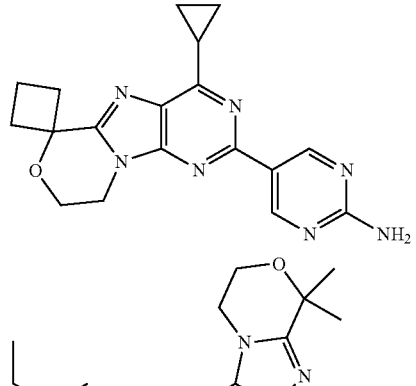
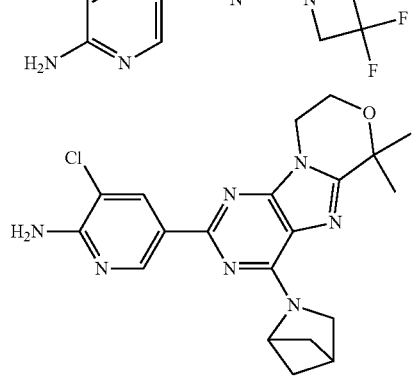
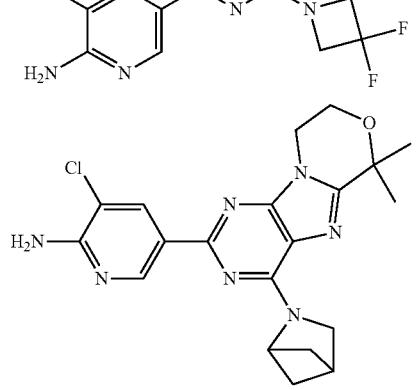

333
-continued
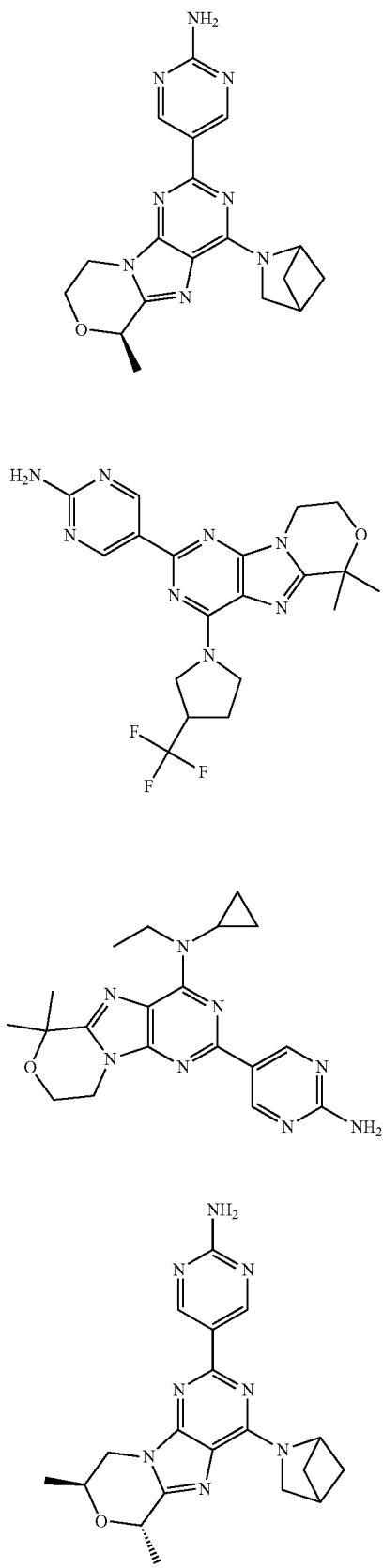
334
-continued
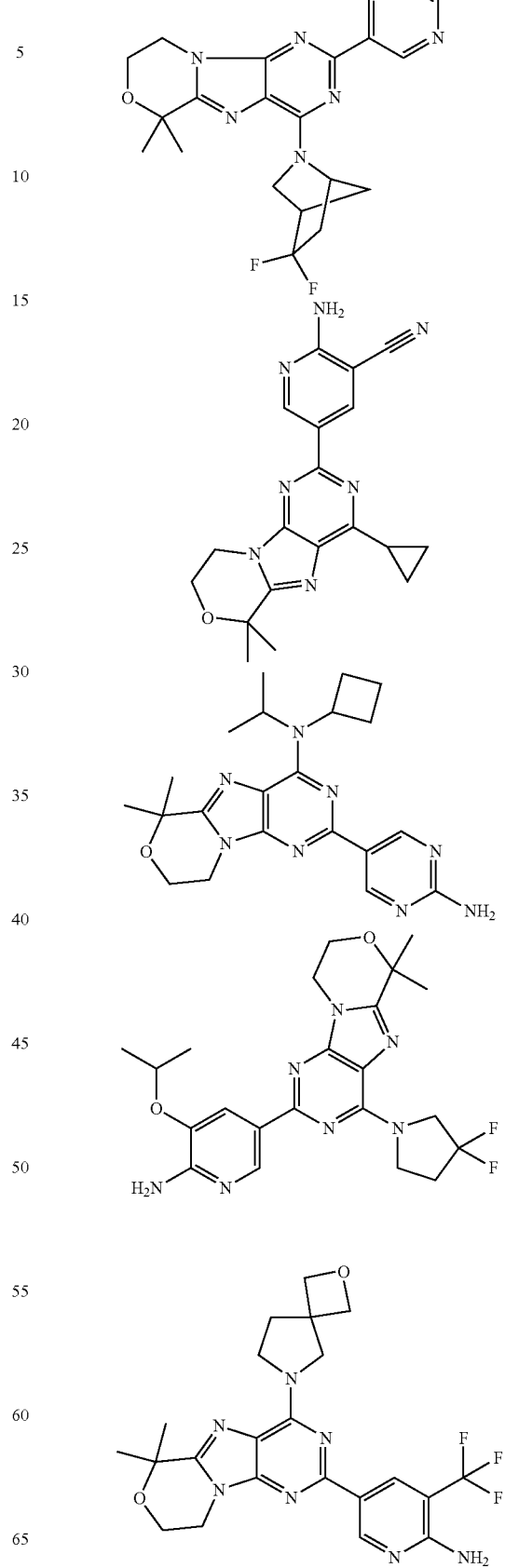

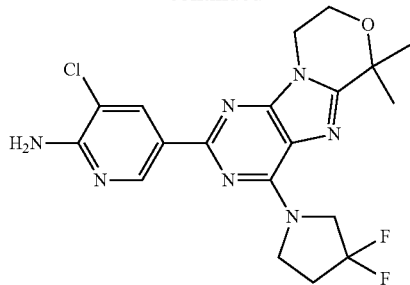
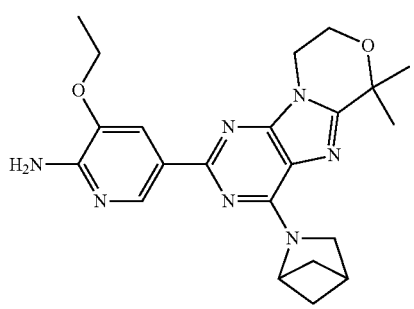
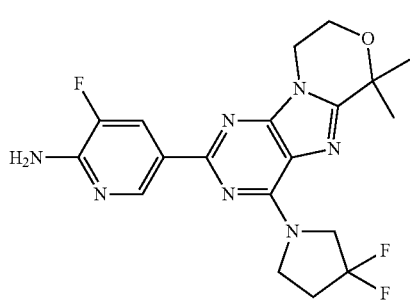
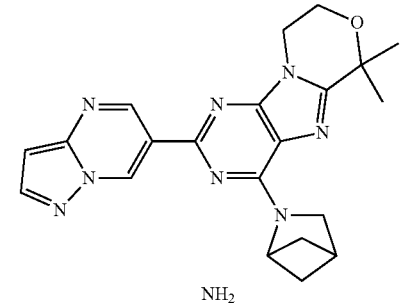
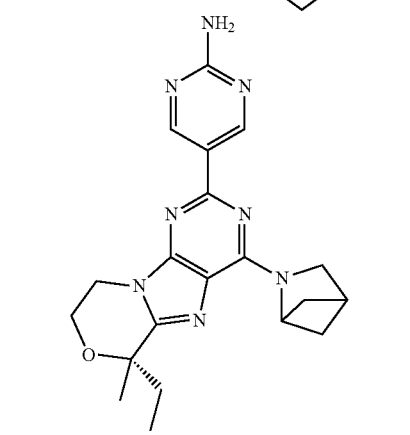
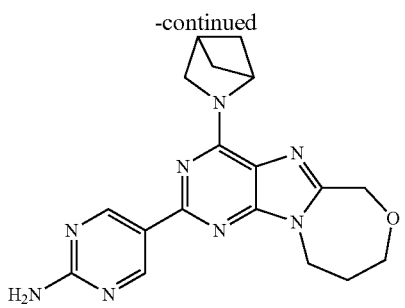
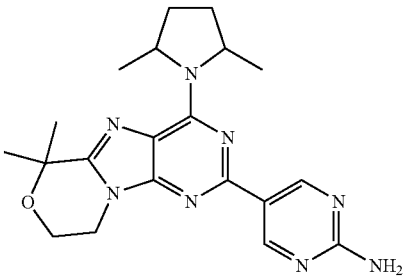
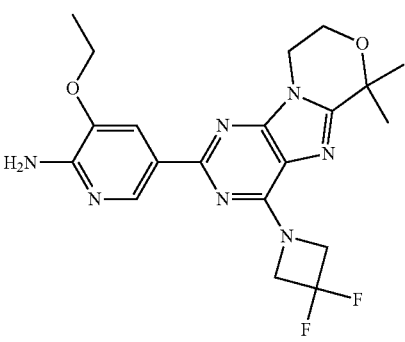
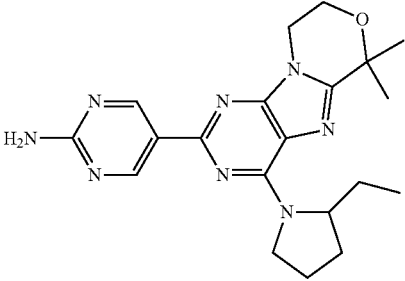
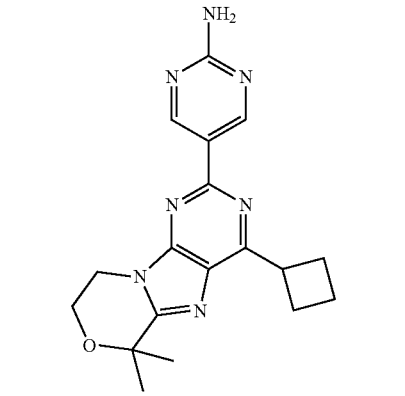

337
-continued
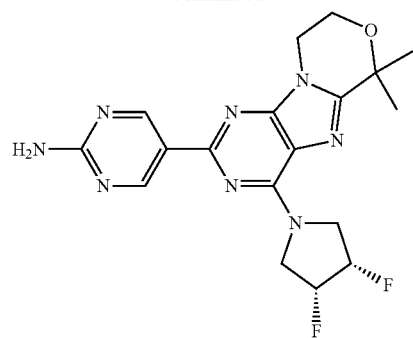
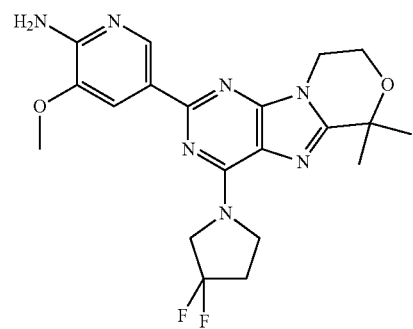
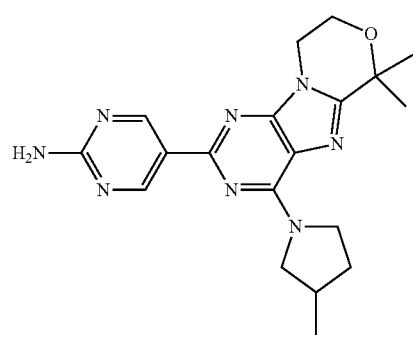
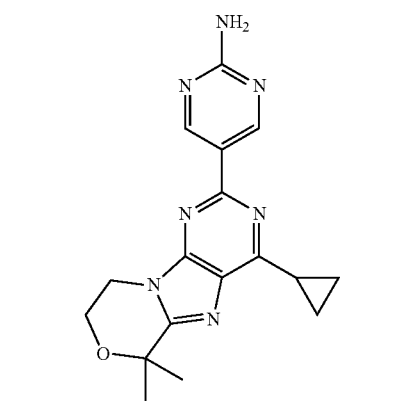
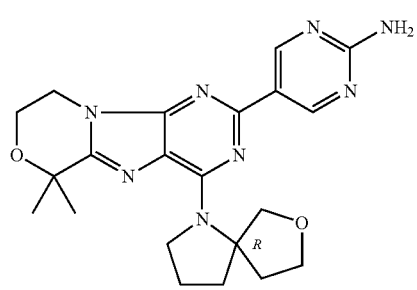
338
-continued
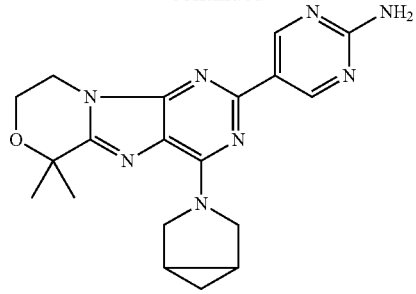
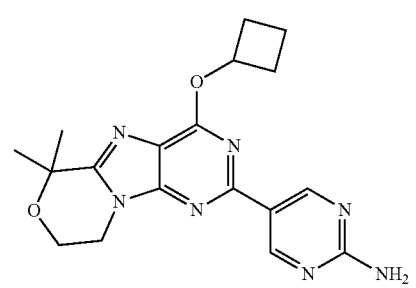
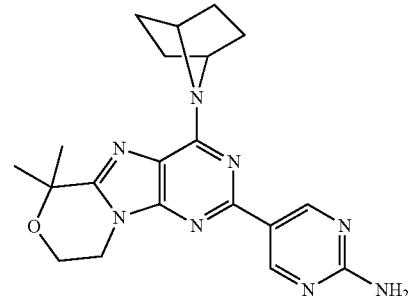
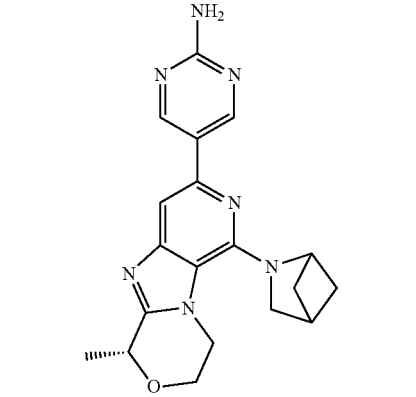
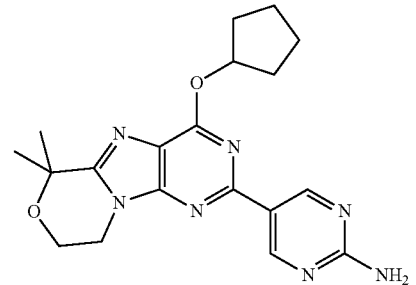

339
-continued
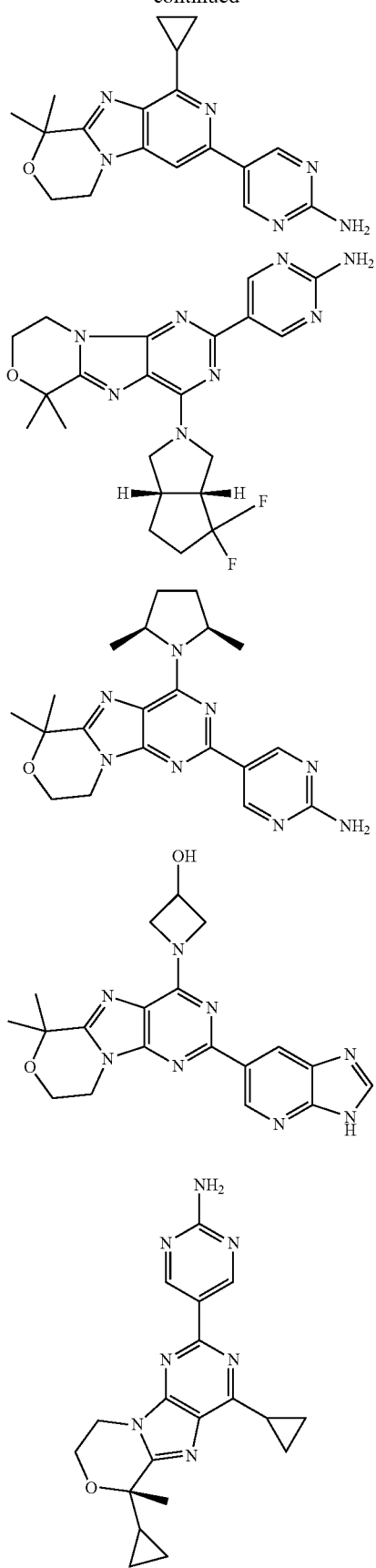
340
-continued
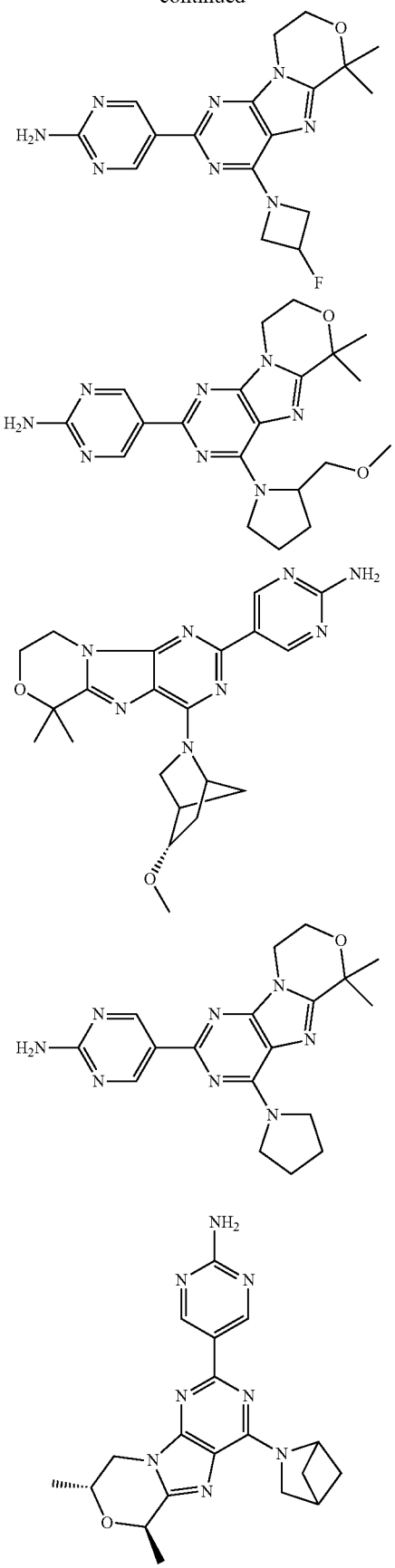

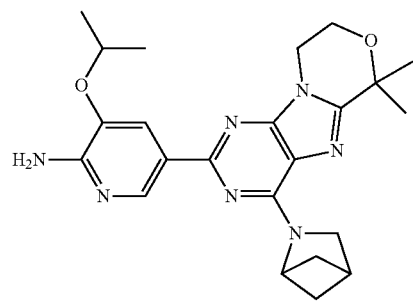
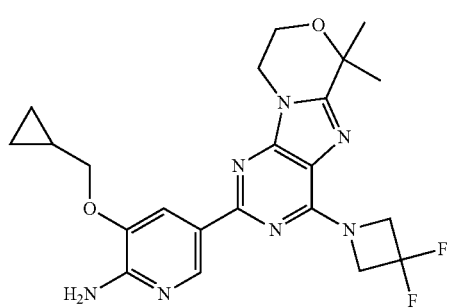
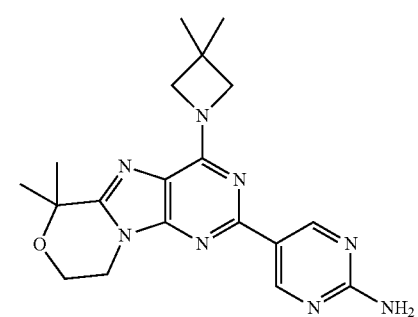
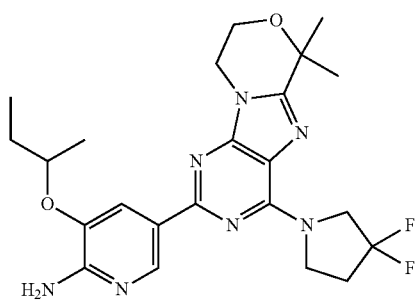
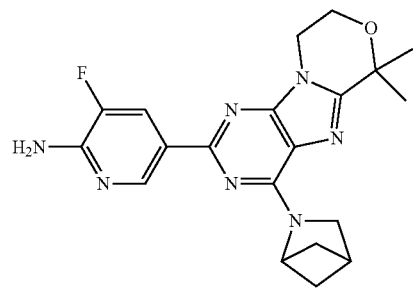
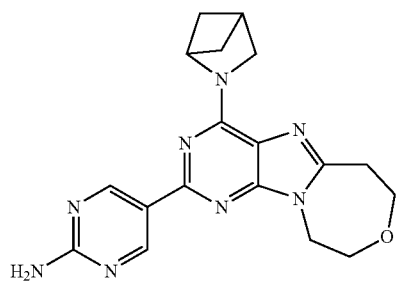
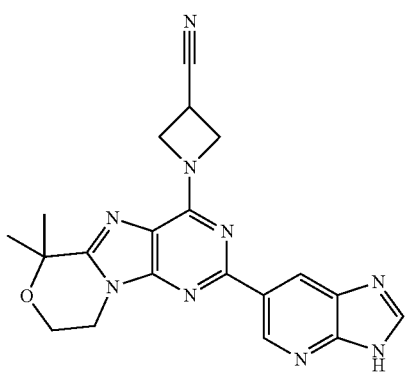
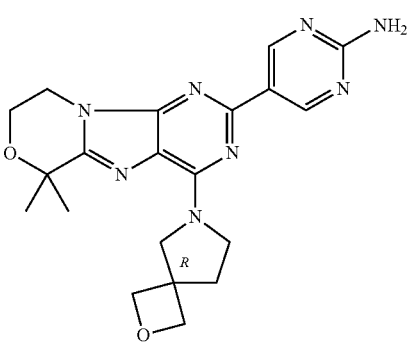
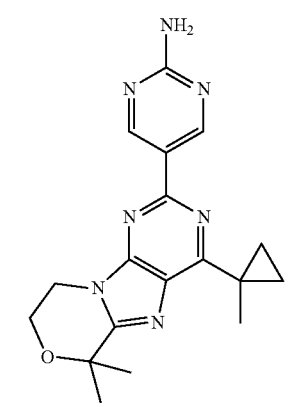

343
-continued
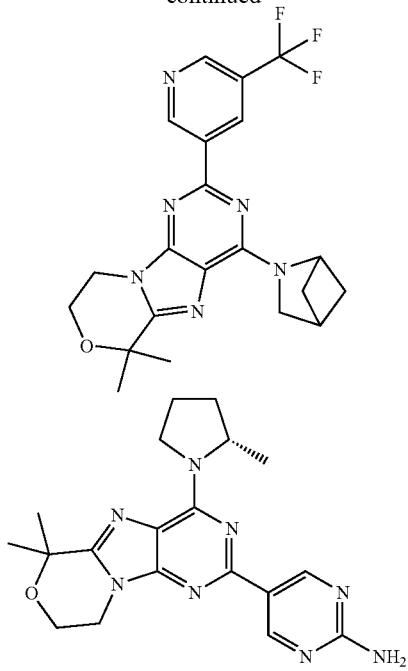
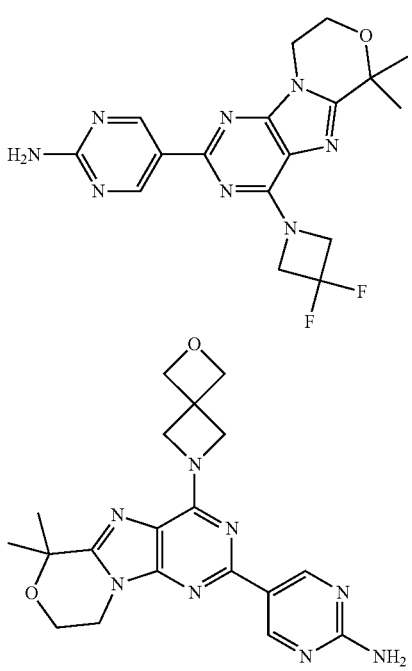
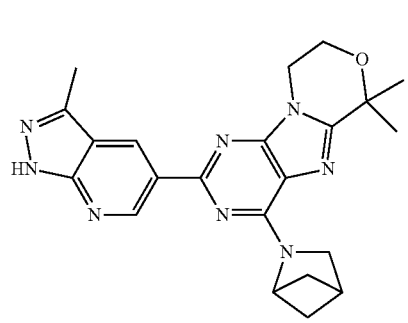
344
-continued
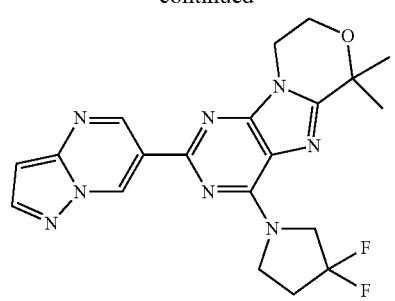
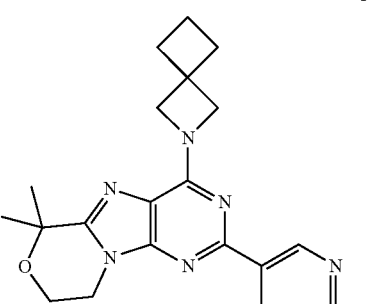
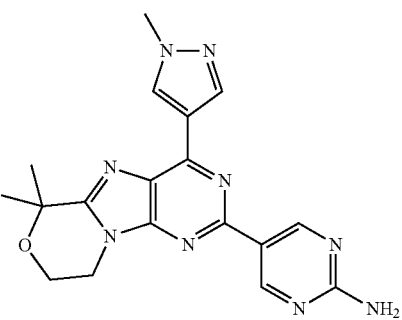
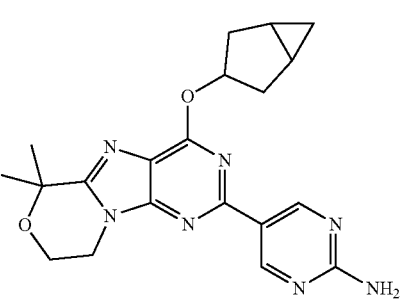
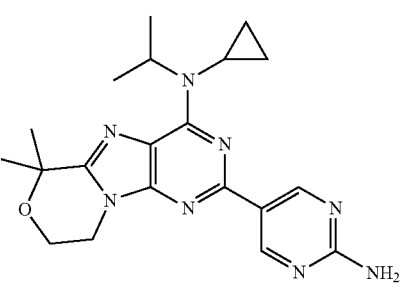

345
-continued
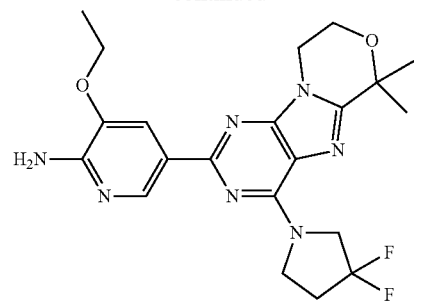
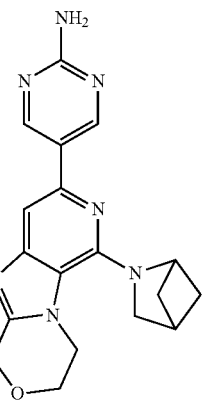
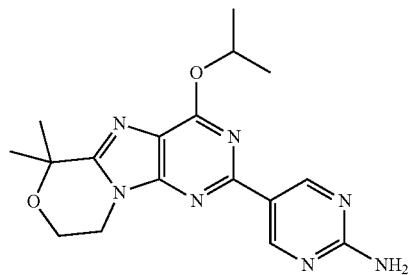
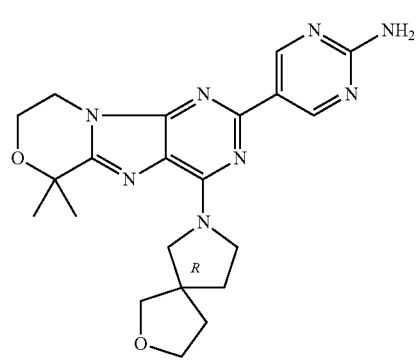
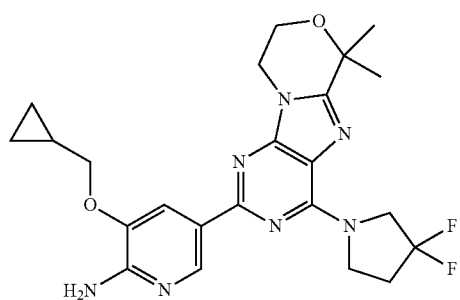
346
-continued
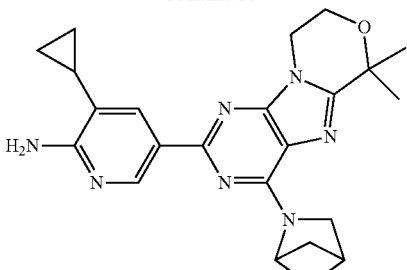
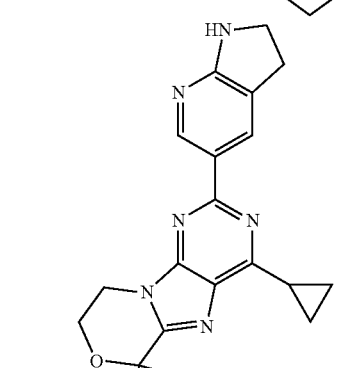
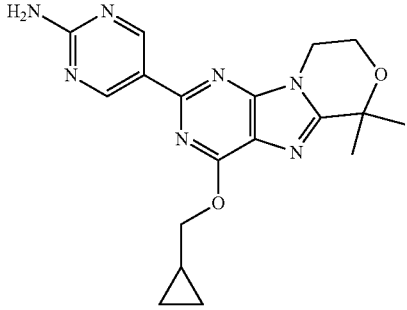
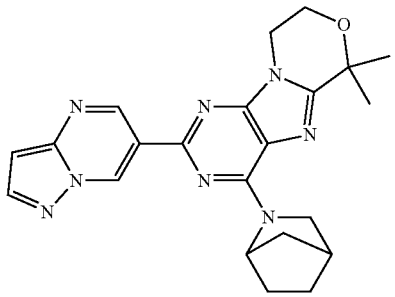
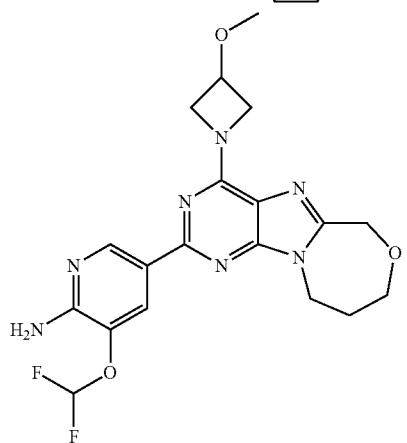

347
-continued
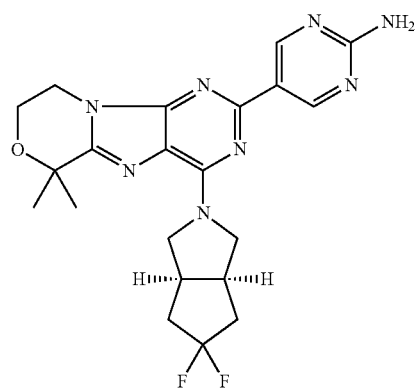
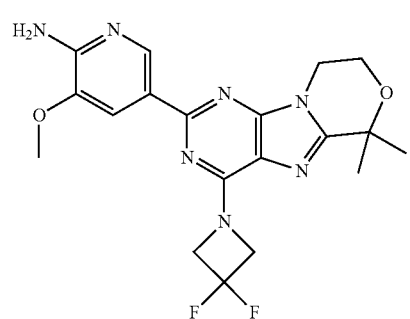
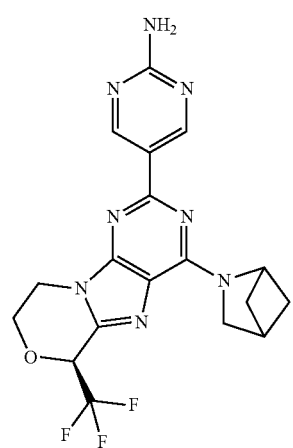
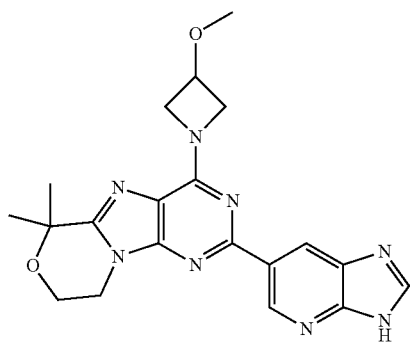
348
-continued
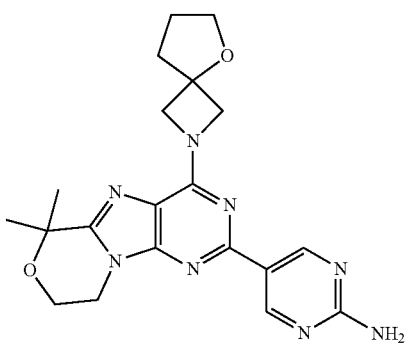
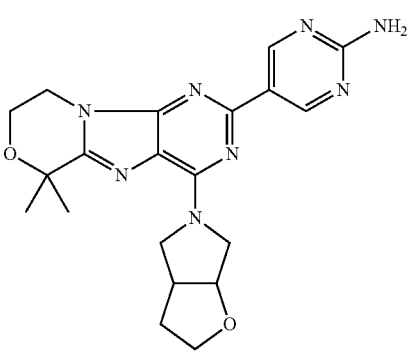
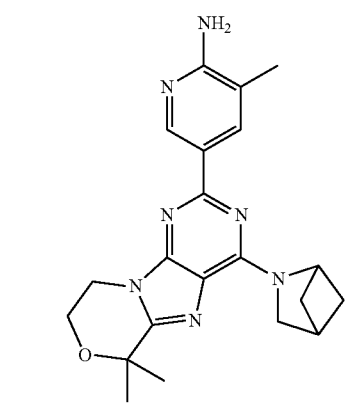
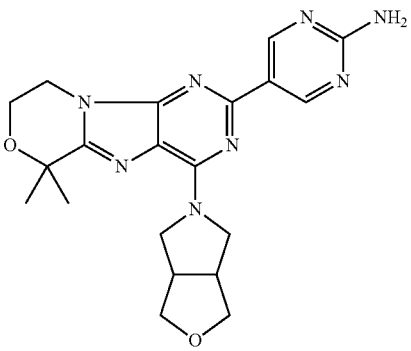

349
-continued
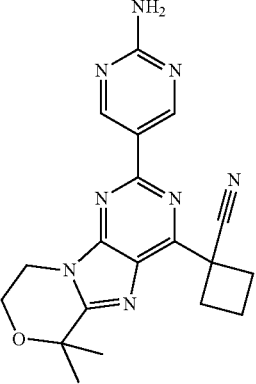
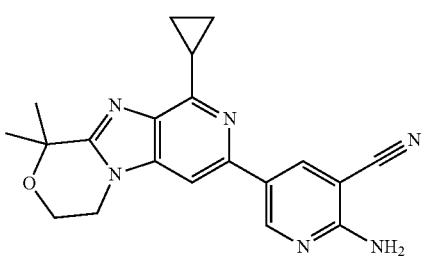
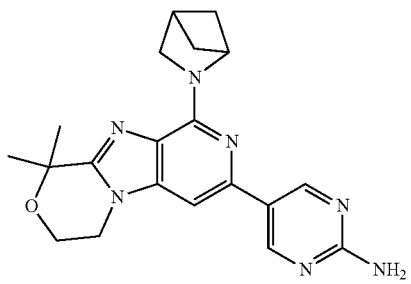
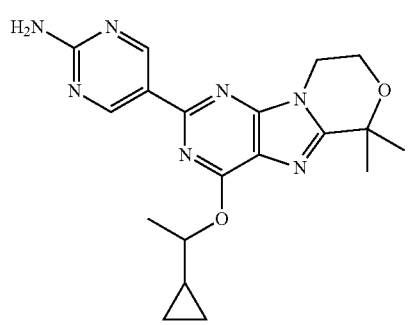
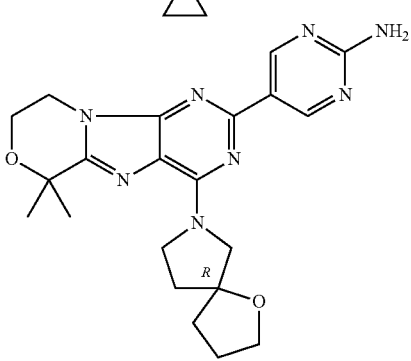
350
-continued
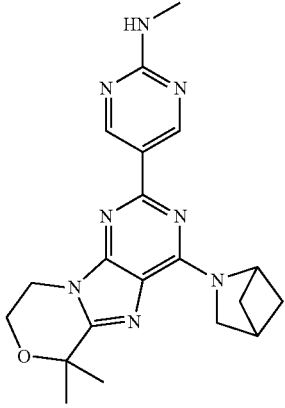
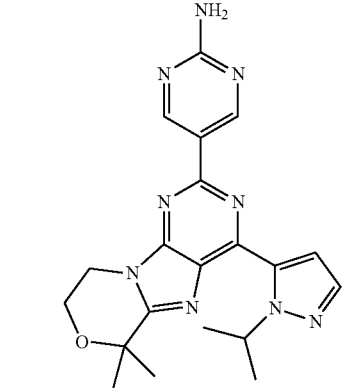
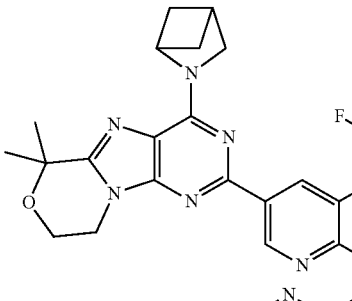
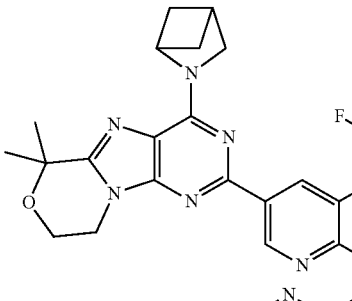
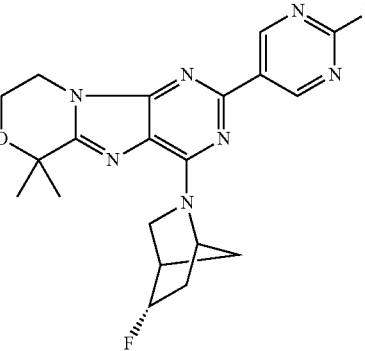
and

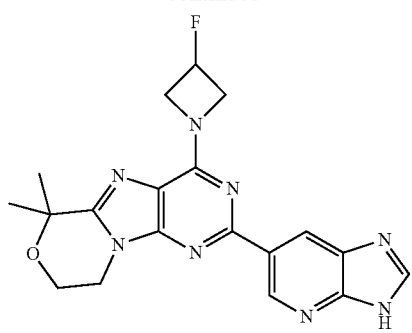
or a pharmaceutically acceptable salt thereof.
15. The compound of claim 1 that is selected from the group consisting of:
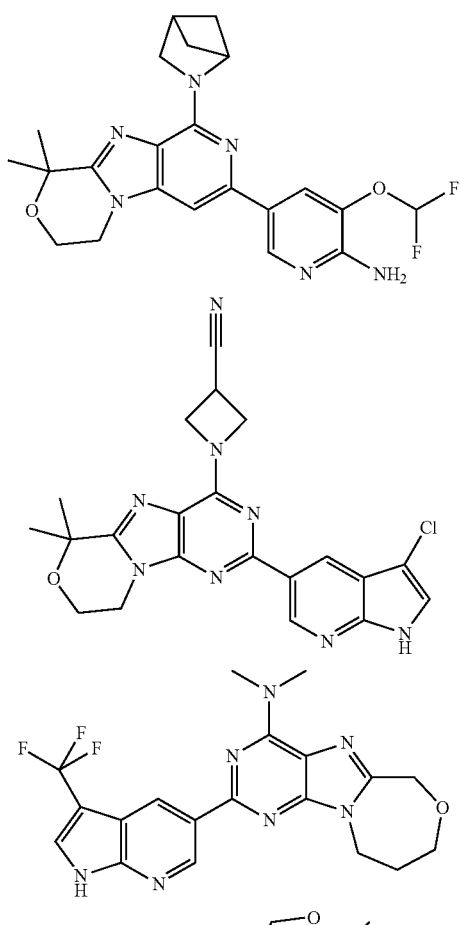
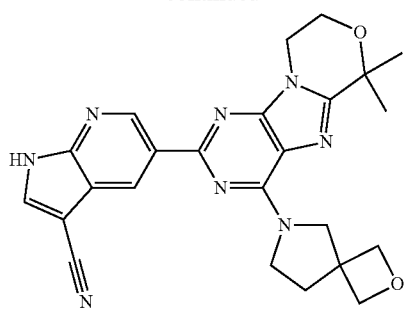
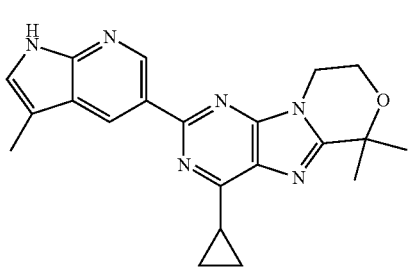
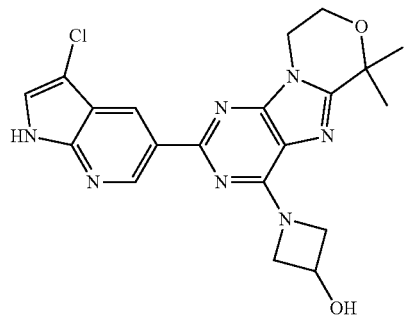
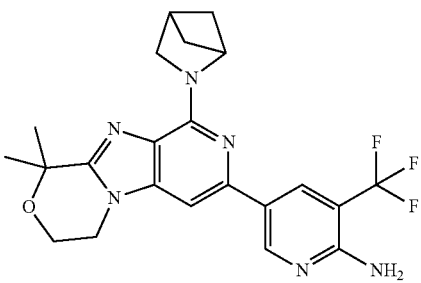
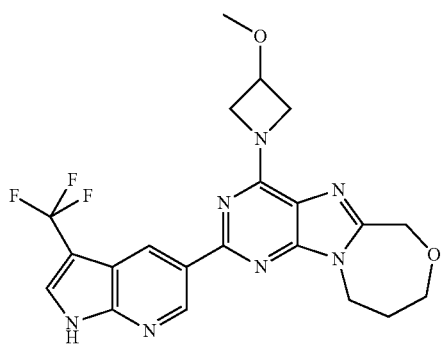

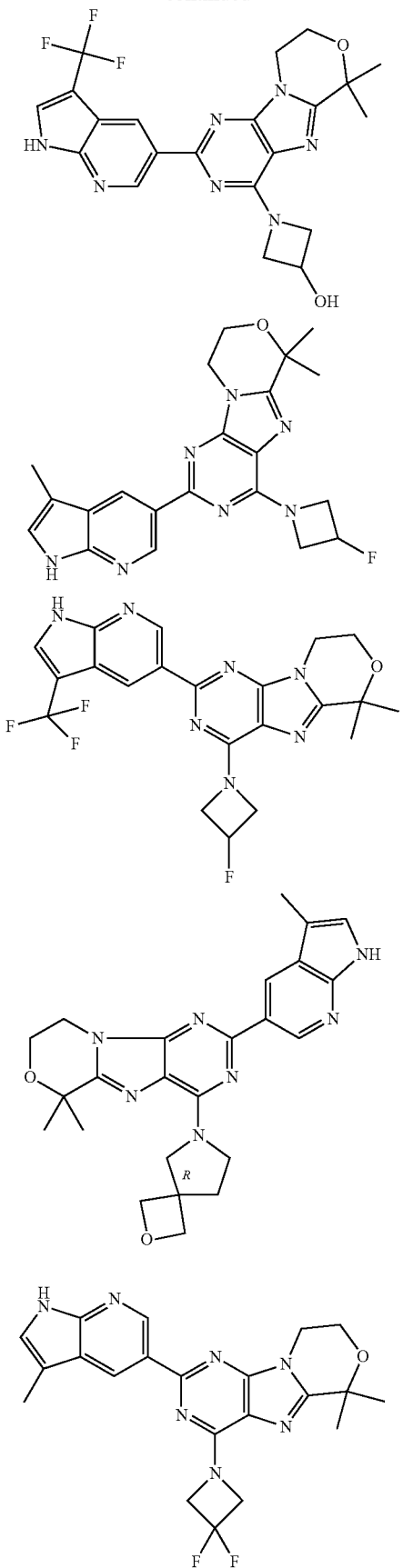
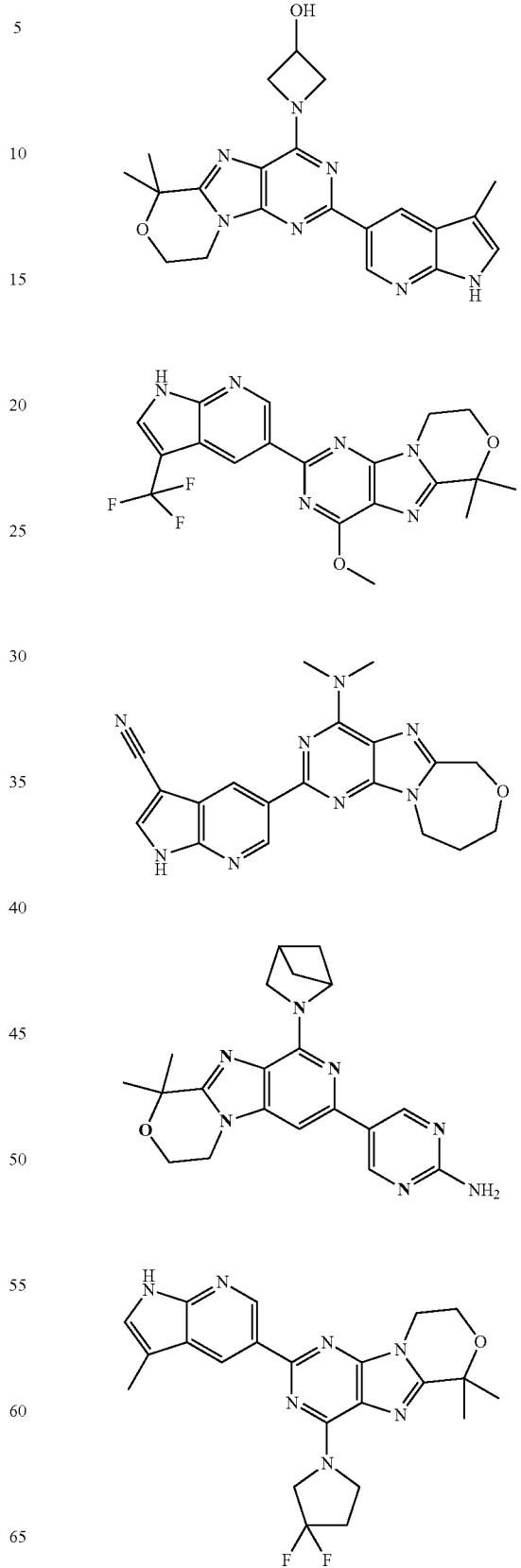

355 -continued
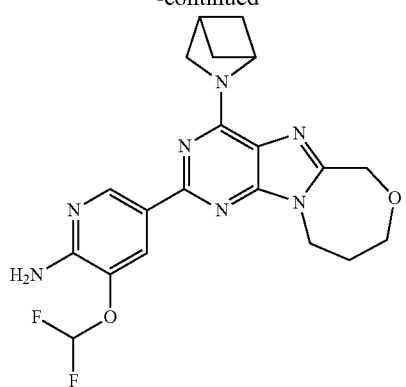
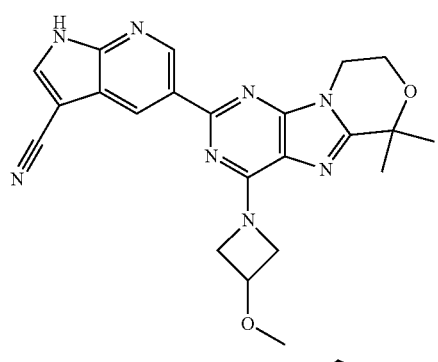
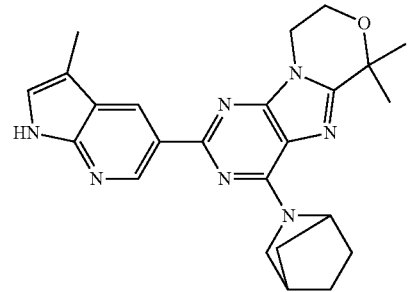
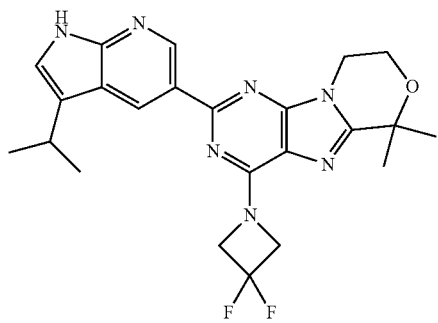
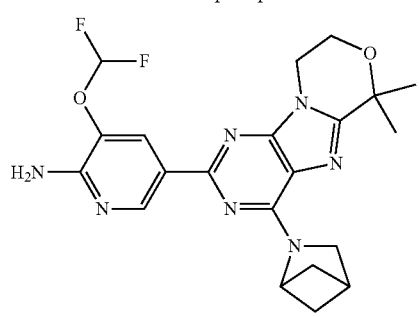
356 -continued
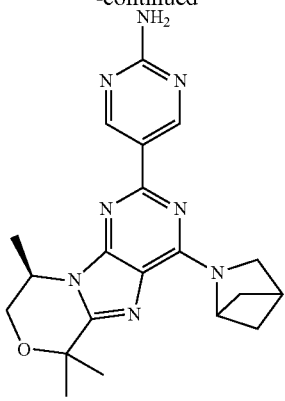
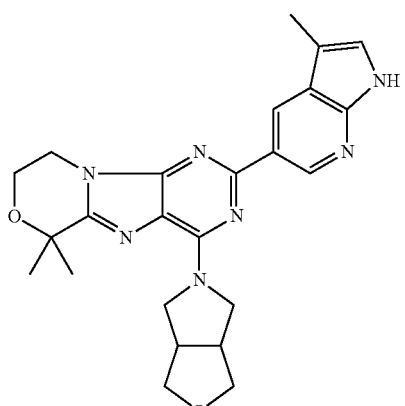
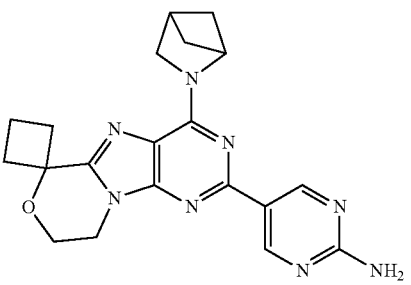
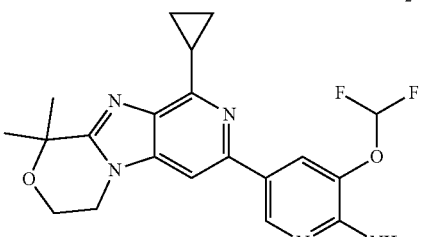
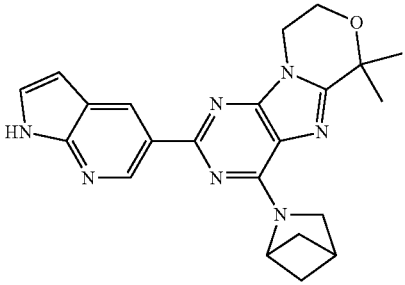

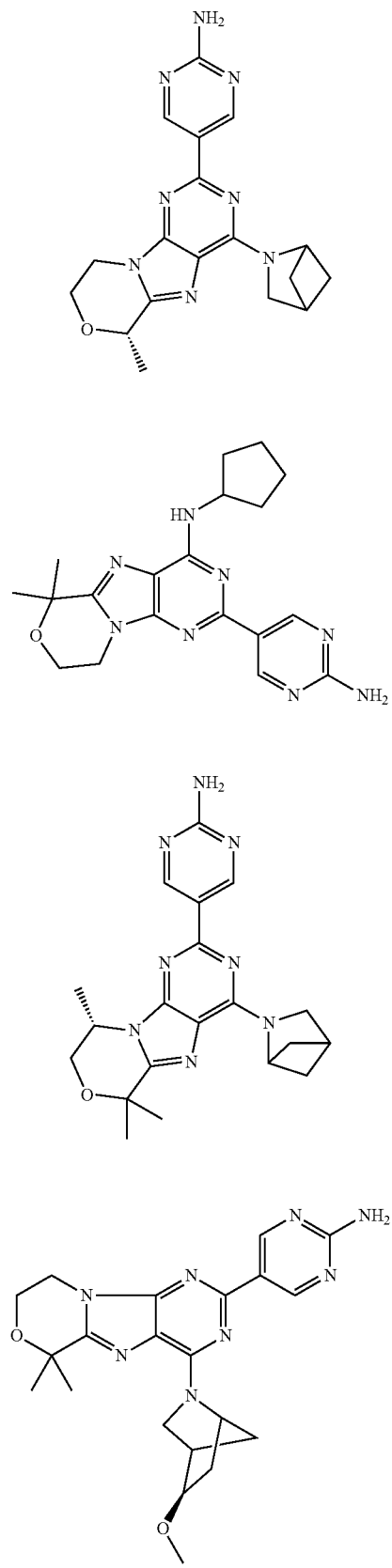
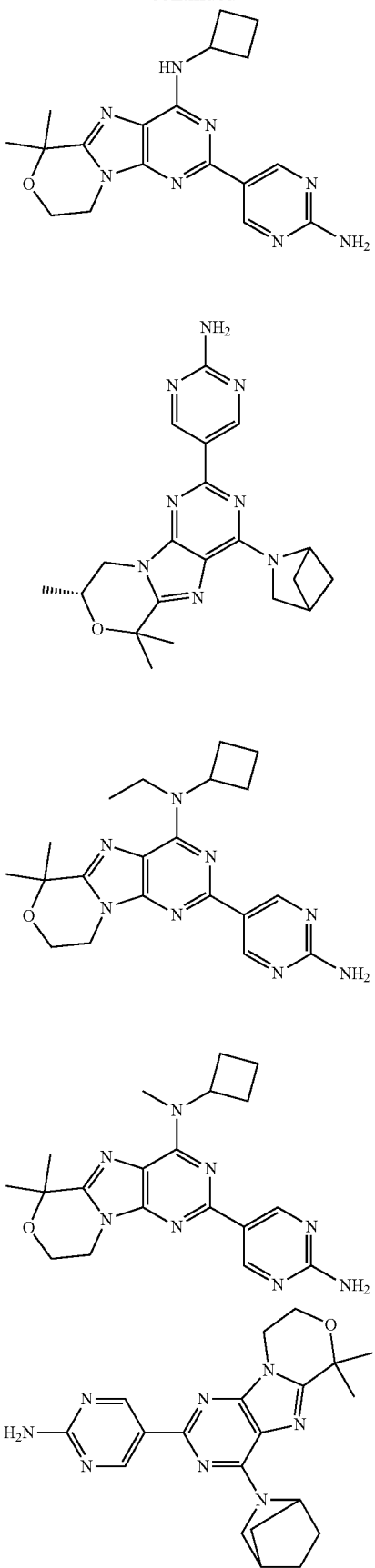

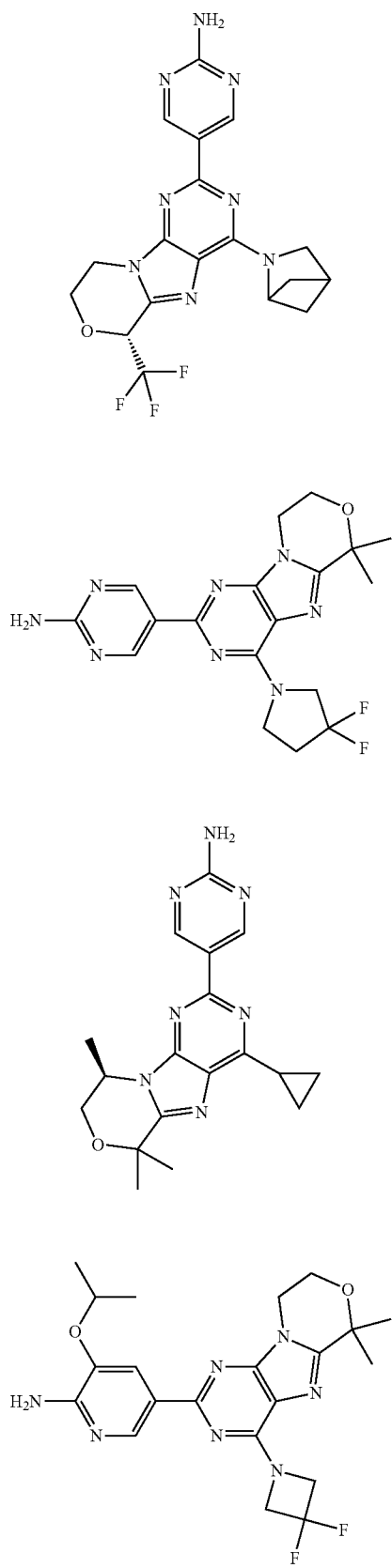
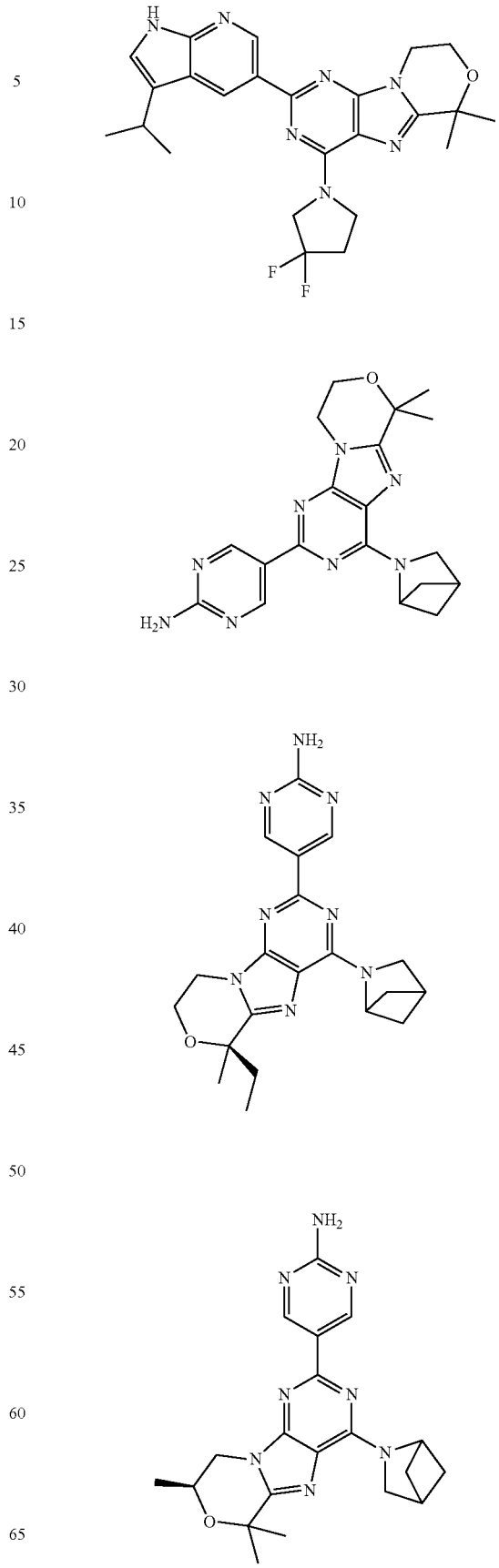

361
-continued
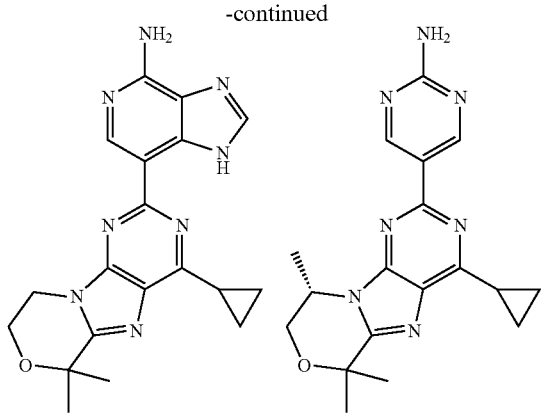
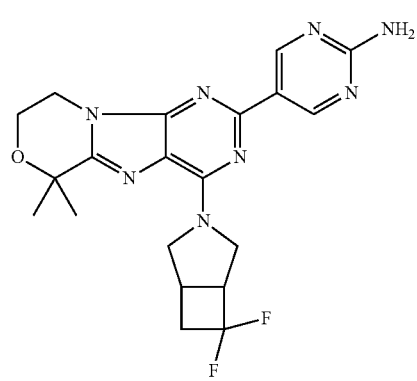
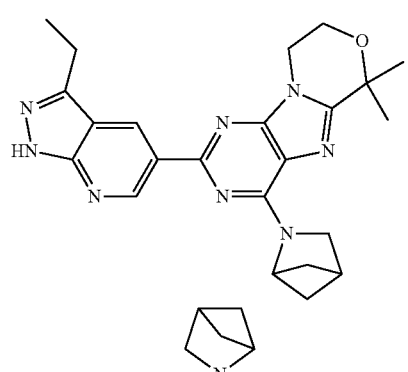
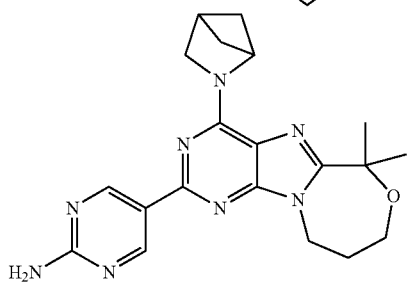
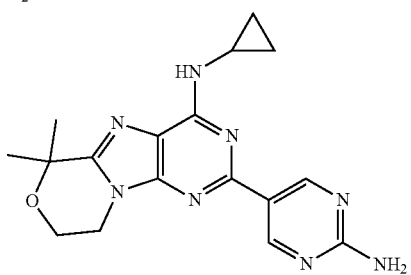
362
-continued
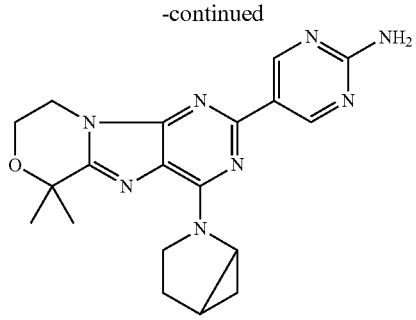
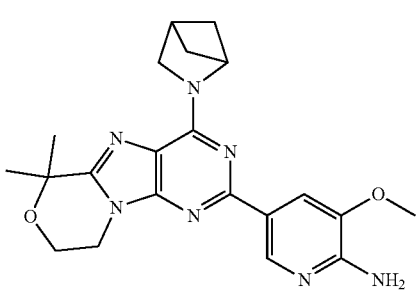
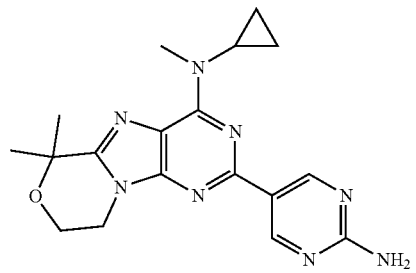
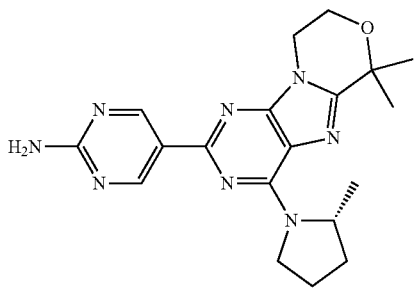
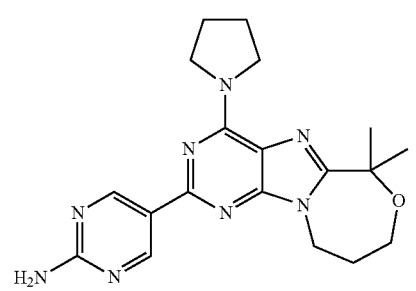

363
-continued
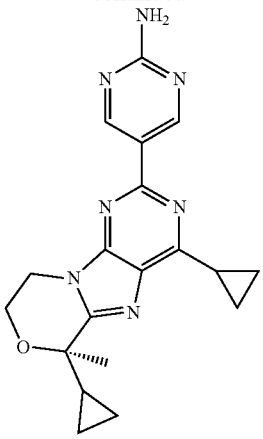
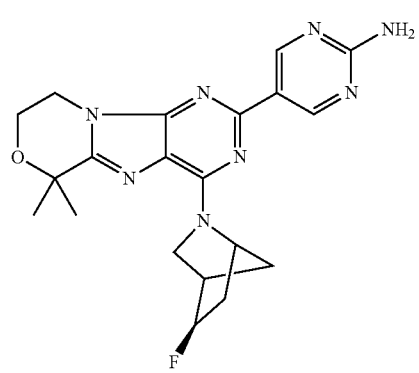
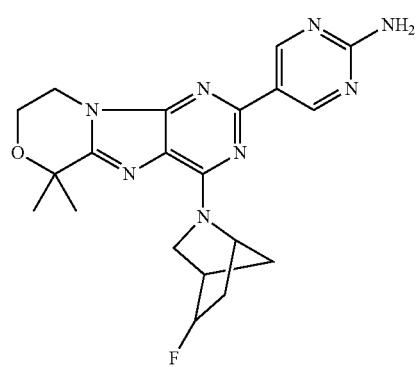
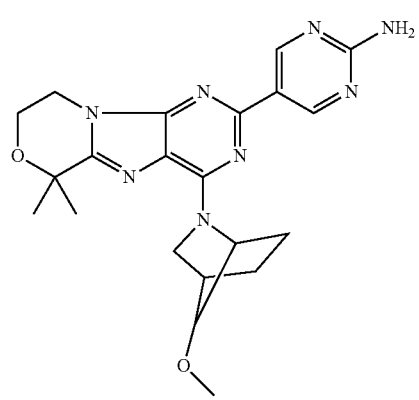
364
-continued
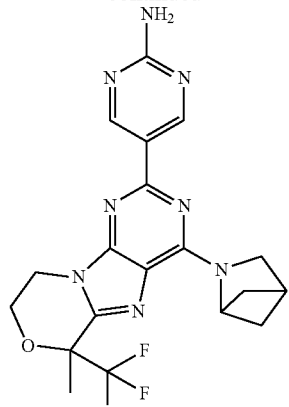
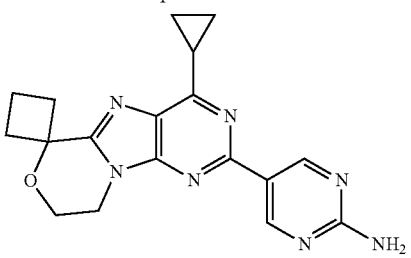
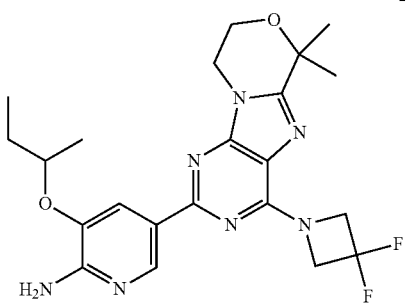
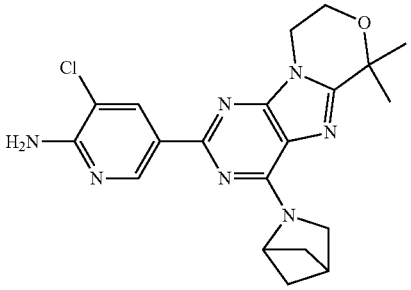
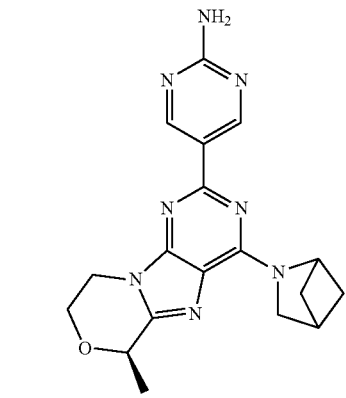

365
-continued
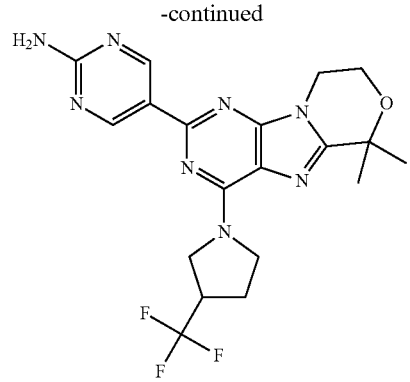
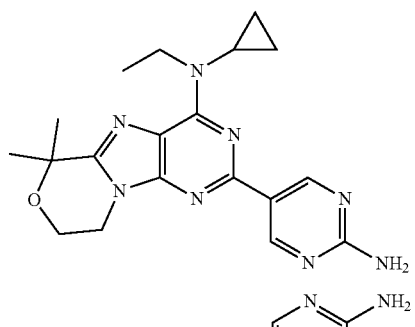
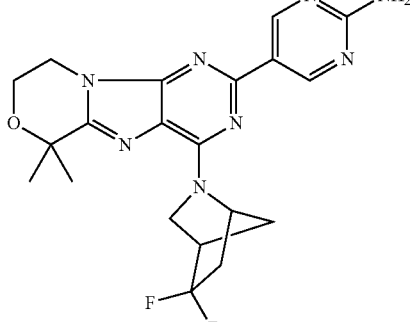
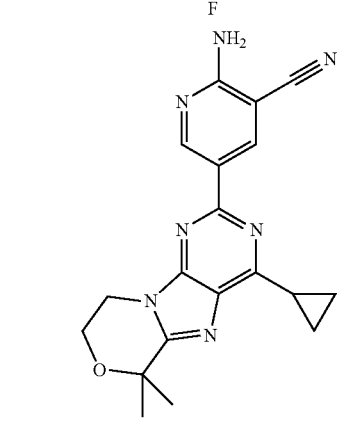
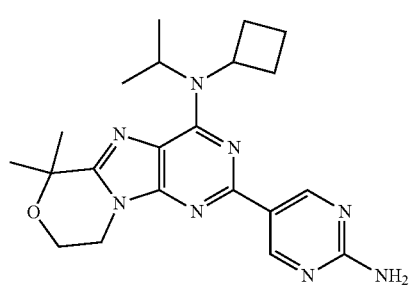
366
-continued
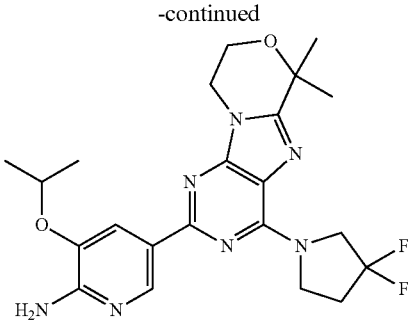
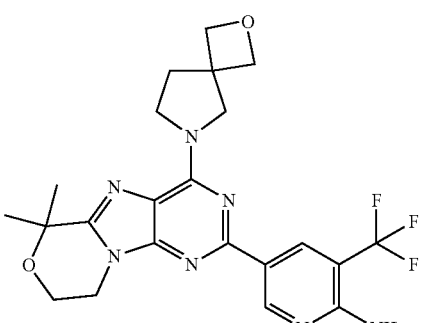
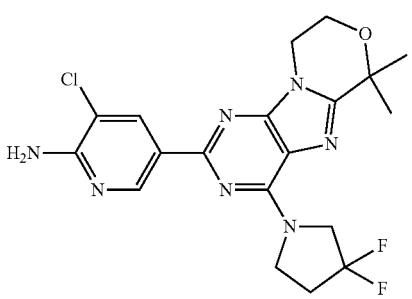
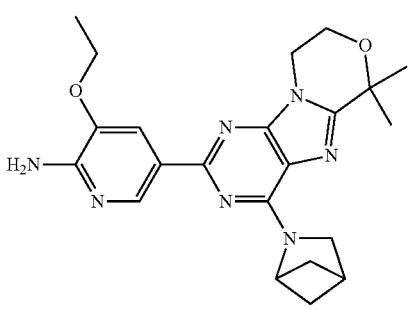
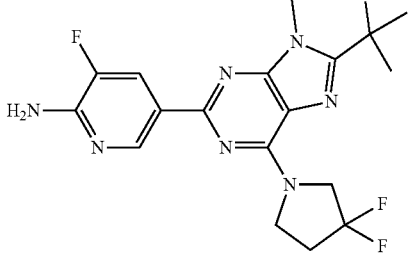

367
-continued
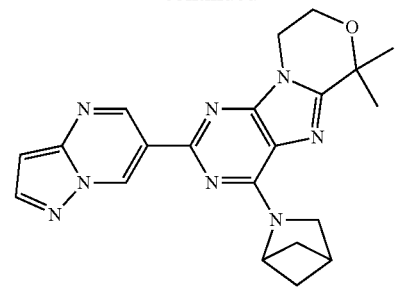
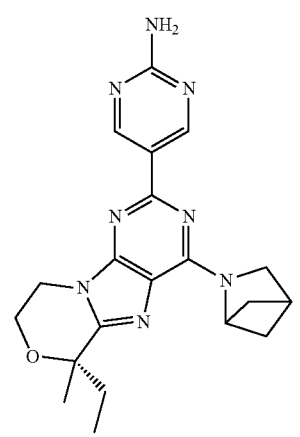
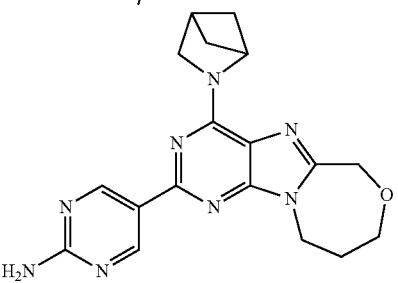
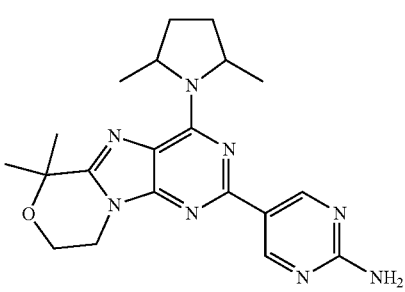
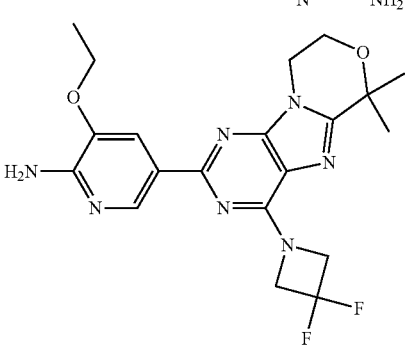
368
-continued
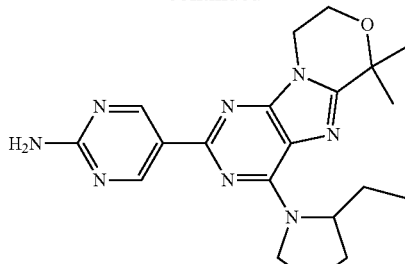
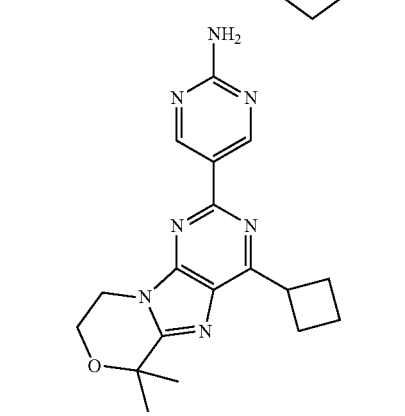
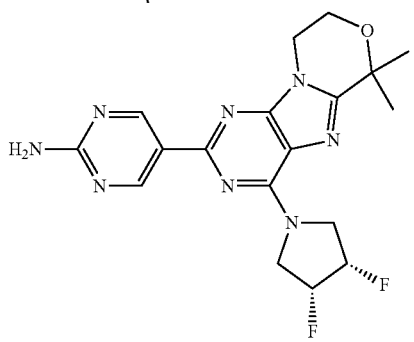
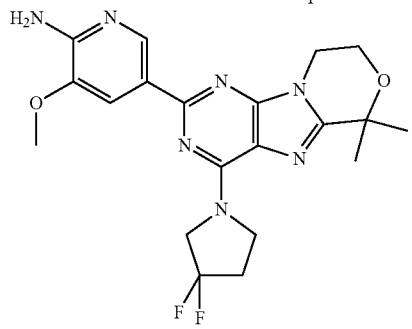
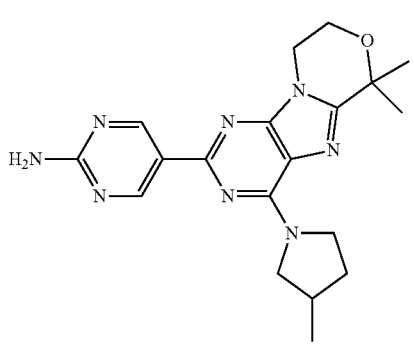

369
-continued
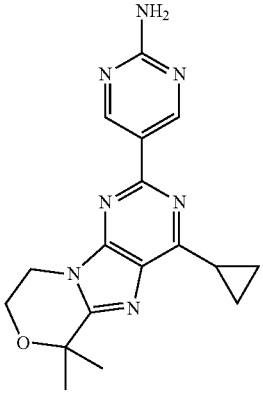
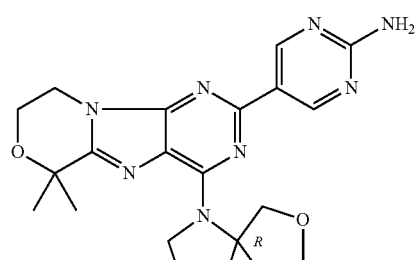
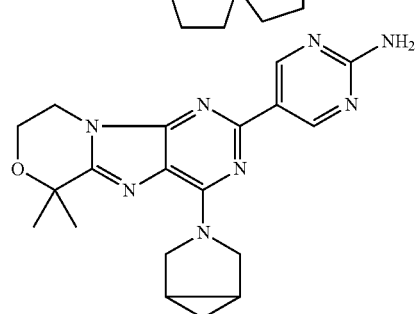
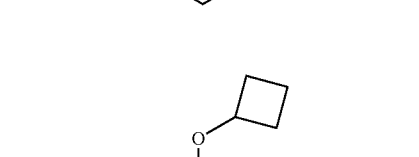
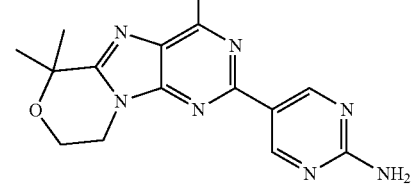
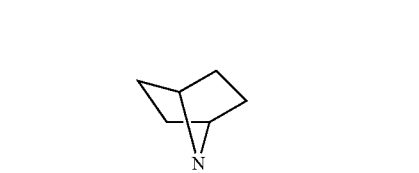
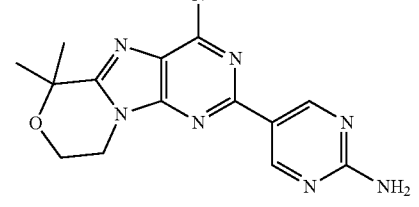
370
-continued
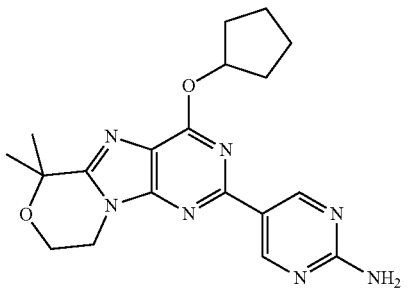
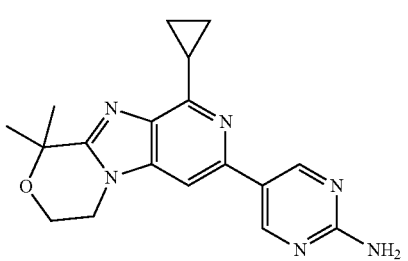
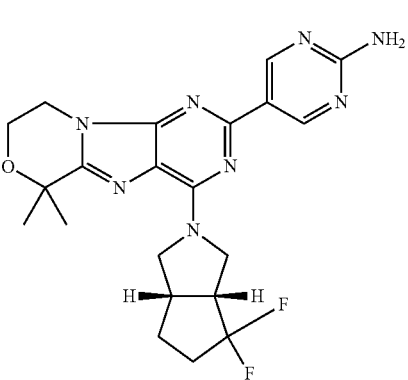
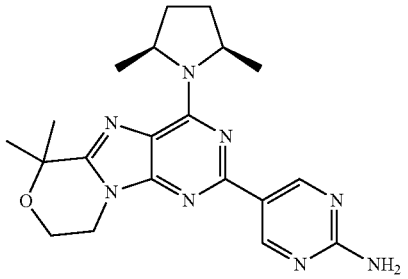
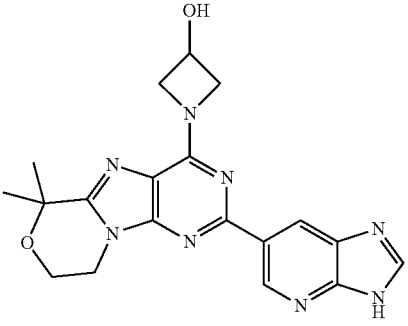

371
-continued
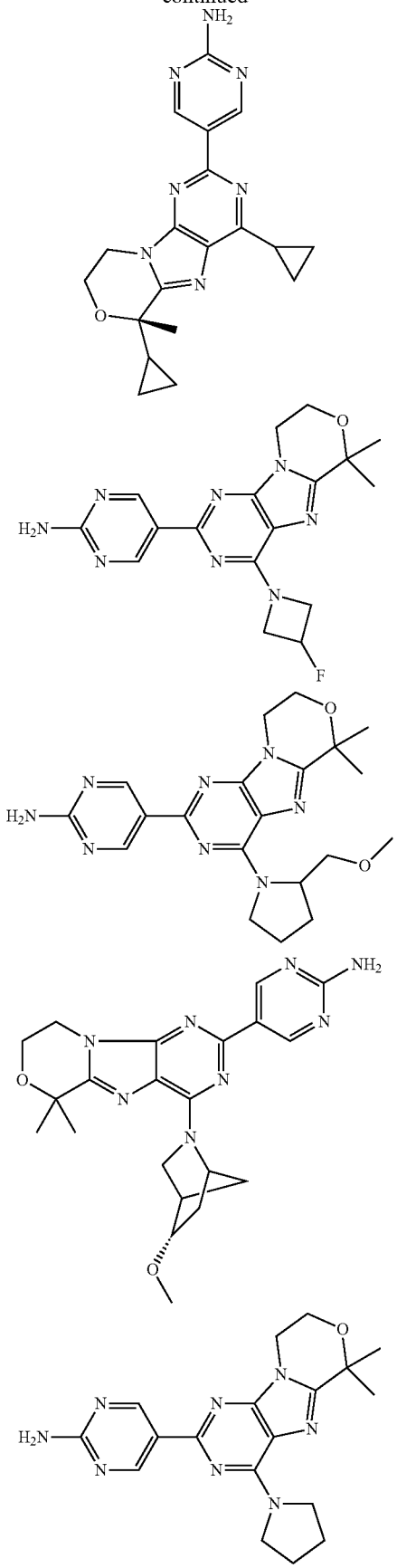
372
-continued
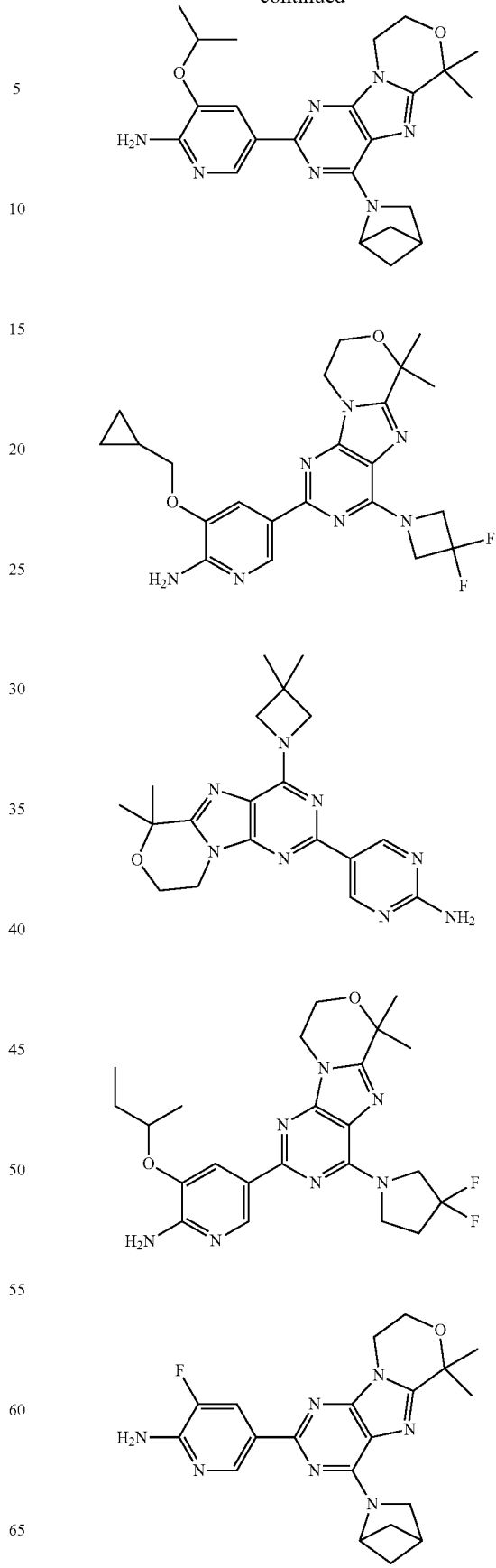

373
-continued
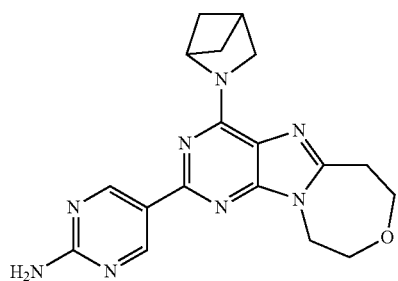
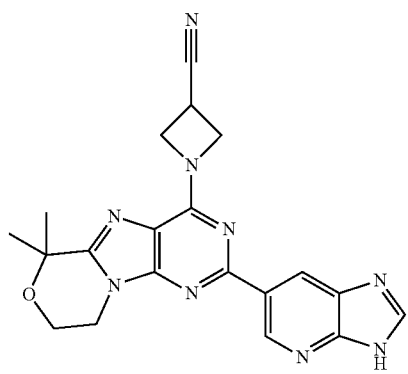
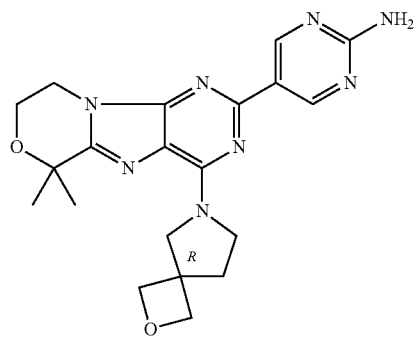
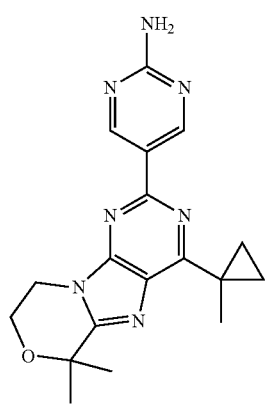
374
-continued
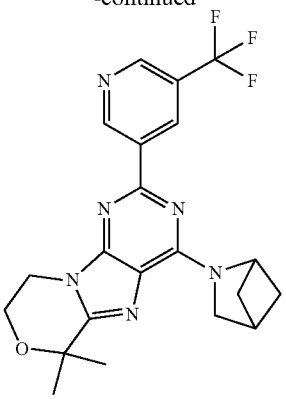
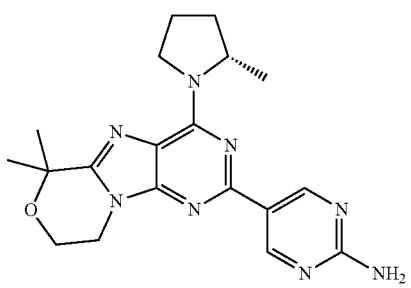
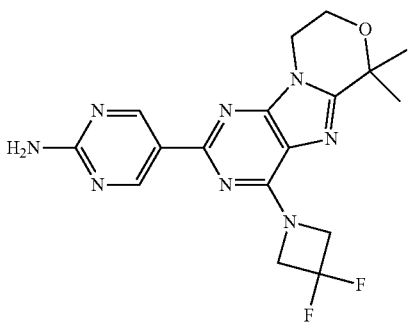
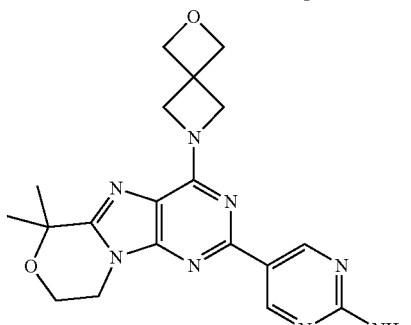
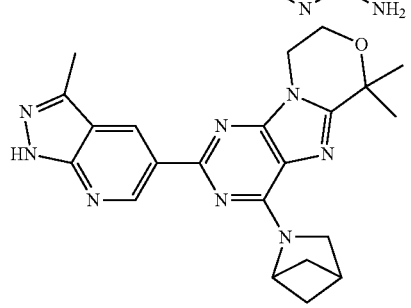

375
-continued
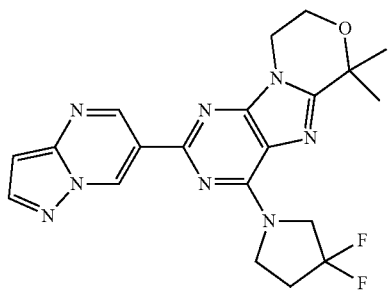
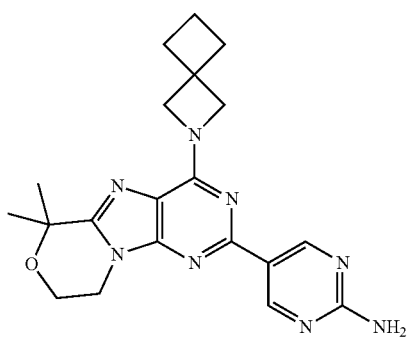
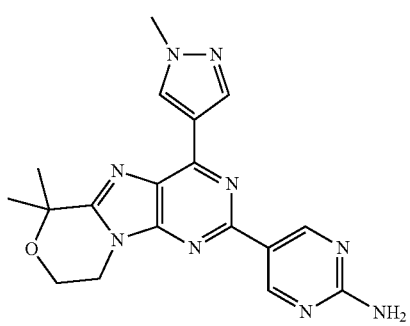
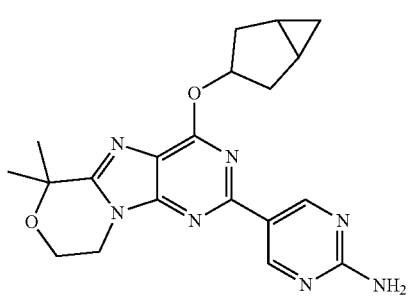
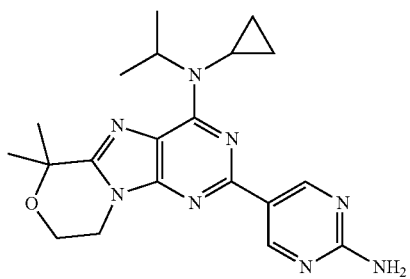
376
-continued
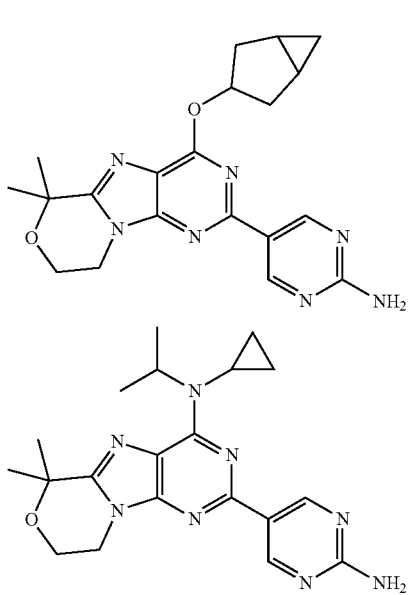

377
-continued
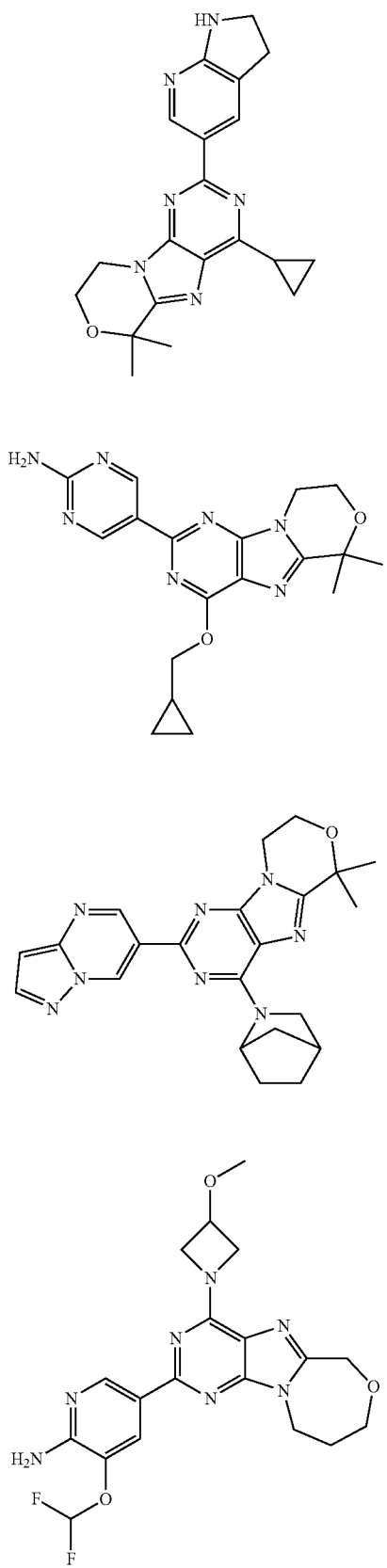
378
-continued
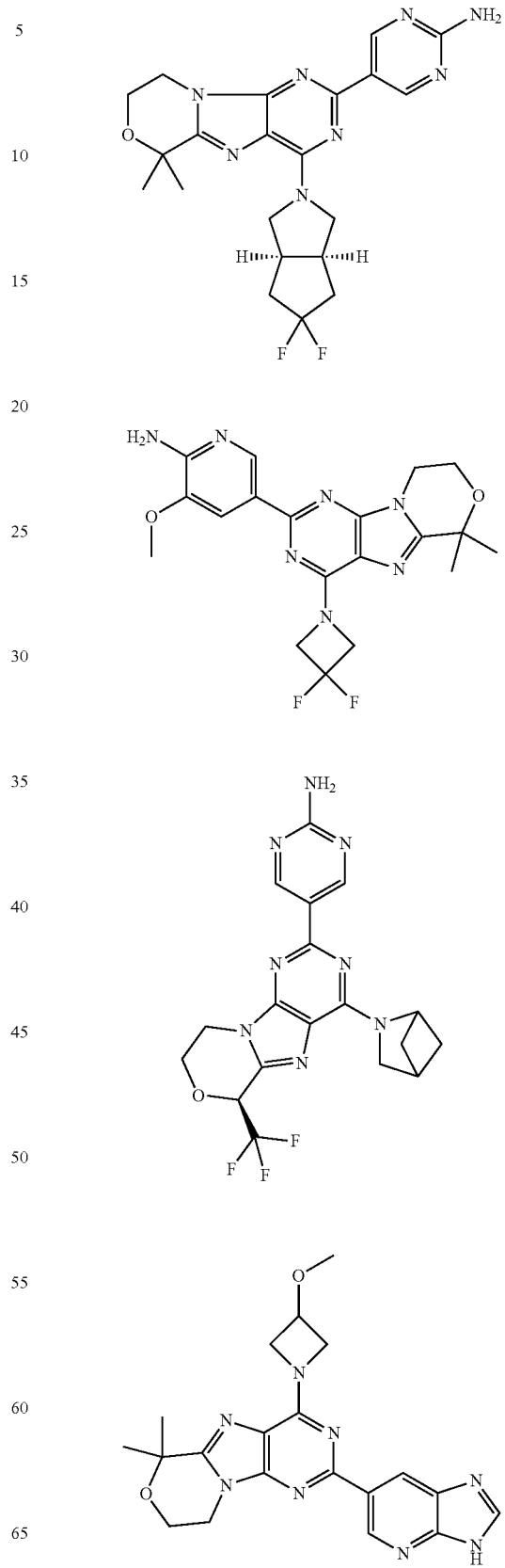

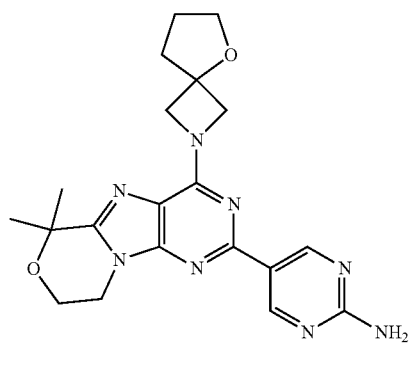
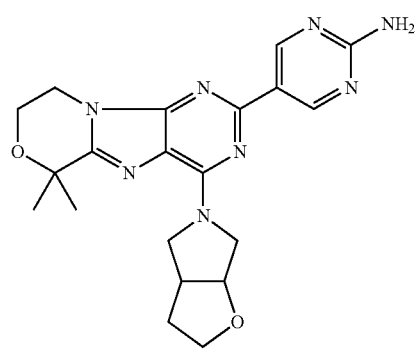
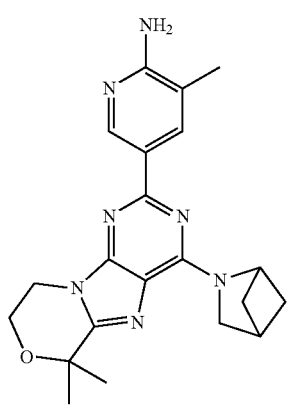
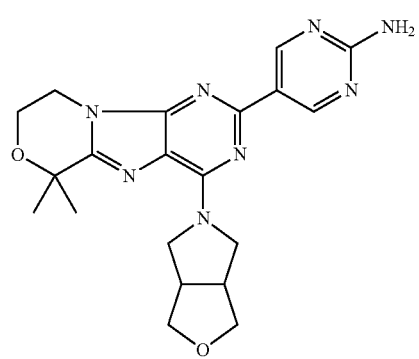
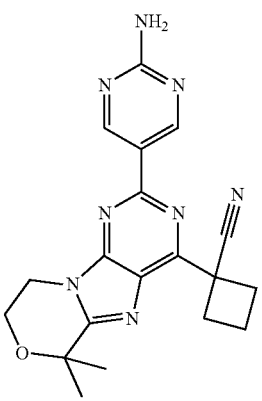
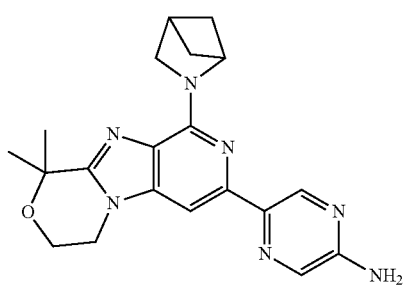
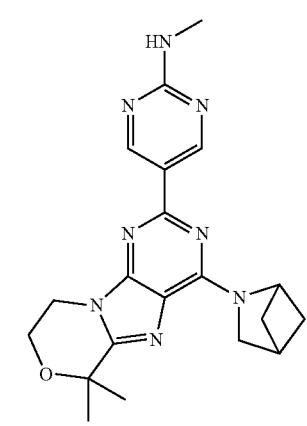
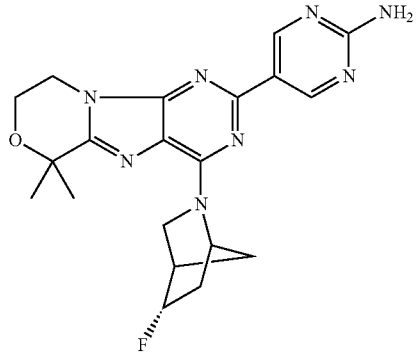
and -continued

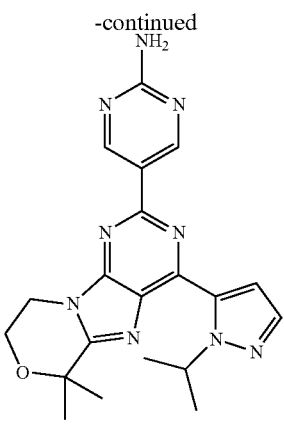

or a pharmaceutically acceptable salt thereof.

16. A pharmaceutical composition comprising a compound of claim 1, or a pharmaceutically acceptable salt thereof, and a pharmaceutically acceptable carrier, diluent or excipient.

17. The pharmaceutical composition of claim 16, in combination with an additional therapeutic agent.

18. The pharmaceutical composition of claim 17, wherein the additional therapeutic agent is a chemotherapeutic agent.

19. A method for inhibiting degeneration of a central nervous system (CNS) neuron or a portion thereof, the method comprising administering to the CNS neuron a compound of claim 1, or a pharmaceutically acceptable salt thereof.

20. The method of claim 19, wherein said administering to the CNS neuron is performed in vitro.

21. The method of claim 20, wherein the method further comprises grafting or implanting the CNS neuron into a human patient after administration of the agent.

22. The method of claim 19, wherein the CNS neuron is present in a human patient.

23. The method of claim 19, wherein said administering to the CNS neuron comprises administration of said compound, or a pharmaceutically acceptable salt thereof, in a pharmaceutically acceptable carrier, diluent or excipient.

24. The method of claim 19, wherein said administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

25. The method of claim 19 further comprising administering one or more additional pharmaceutical agents.

26. The method of claim 19, wherein said administering to the CNS neuron results in a decrease in JNK phosphorylation, JNK activity and/or JNK expression.

27. The method of claim 19, wherein said administering to the CNS neuron results in a decrease of cJun phosphorylation, cJun activity, and/or cJun expression.

28. The method of claim 19, wherein said administering to the CNS neuron results in a decrease in p38 phosphorylation, p38 activity, and/or p38 expression.

29. A method for inhibiting degeneration of a central nervous system (CNS) neuron in a patient having or at risk of developing a neurodegenerative disease or condition comprising administering to said patient a therapeutically effective amount of a compound of claim 1, or a pharmaceutically acceptable salt thereof.

30. A method for decreasing one or more symptoms of a neurodegenerative disease or condition in a patient suffering therefrom comprising administering to said patient a therapeutically effective amount of a compound of claim 1, or a pharmaceutically acceptable salt thereof.

31. A method for decreasing the progression of a neurodegenerative disease or condition in a patient suffering therefrom comprising administering to said patient a therapeutically effective amount of a compound of claim 1, or a pharmaceutically acceptable salt thereof.

32. The method of any one of claims 29-31, wherein said neurodegenerative disease or condition is selected from the group consisting of: Alzheimer's disease, Huntington's disease, Parkinson's disease, Parkinson's-plus diseases, amyotrophic lateral sclerosis (ALS), ischemia, stroke, intracranial hemorrhage, cerebral hemorrhage, trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie-Tooth disease, prion disease, Creutzfeldt-Jakob disease, Gerstmann-Strussler-Scheinker syndrome (GSS), fatal familial insomnia (FFI), bovine spongiform encephalopathy, Pick's disease, epilepsy, AIDS demential complex, nerve damage caused by exposure to toxic compounds selected from the group consisting of heavy metals, industrial solvents, drugs and chemotherapeutic agents; injury to the nervous system caused by physical, mechanical or chemical trauma, glaucoma, lattice dystrophy, retinitis pigmentosa, age-related macular degeneration (AMD), photoreceptor degeneration associated with wet or dry AMD, other retinal degeneration, optic nerve drusen, optic neuropathy and optic neuritis.

33. The method of any one of claims 29-31, wherein said neurodegenerative disease or condition is selected from the group consisting of: Alzheimer's disease, Parkinson's disease, and amyotrophic lateral sclerosis (ALS).

34. The method of any one of claims 29-31, wherein the compound, or a pharmaceutically acceptable salt thereof, is administered in combination with one or more additional pharmaceutical agents.

* * * * *